United States Patent
Stappenbeck et al.

(10) Patent No.: US 11,867,701 B2
(45) Date of Patent: Jan. 9, 2024

(54) METHODS FOR PROGNOSING CROHN'S DISEASE COMPRISING HUMAN DEFENSIN 5 (HD5)

(71) Applicants: Thaddeus Stappenbeck, St. Louis, MO (US); Ta-Chiang Liu, St. Louis, MO (US); Kelli VanDussen, St. Louis, MO (US)

(72) Inventors: Thaddeus Stappenbeck, St. Louis, MO (US); Ta-Chiang Liu, St. Louis, MO (US); Kelli VanDussen, St. Louis, MO (US)

(73) Assignee: Washington University, St. Louis, MO (US)

(*) Notice: Subject to any disclaimer, the term of this patent is extended or adjusted under 35 U.S.C. 154(b) by 751 days.

(21) Appl. No.: 16/097,104

(22) PCT Filed: Apr. 27, 2017

(86) PCT No.: PCT/US2017/029836
§ 371 (c)(1),
(2) Date: Oct. 26, 2018

(87) PCT Pub. No.: WO2017/189846
PCT Pub. Date: Nov. 2, 2017

(65) Prior Publication Data
US 2021/0223265 A1    Jul. 22, 2021

Related U.S. Application Data

(60) Provisional application No. 62/343,519, filed on May 31, 2016, provisional application No. 62/329,576, filed on Apr. 29, 2016, provisional application No. 62/328,386, filed on Apr. 27, 2016.

(51) Int. Cl.
*G01N 33/68* (2006.01)
*C07K 14/47* (2006.01)
*G01N 33/50* (2006.01)

(52) U.S. Cl.
CPC ..... *G01N 33/6893* (2013.01); *C07K 14/4723* (2013.01); *G01N 33/5091* (2013.01); *G01N 2800/065* (2013.01); *G01N 2800/52* (2013.01)

(58) Field of Classification Search
CPC ........... G01N 33/6893; G01N 33/5091; G01N 2800/065; G01N 2800/52; G01N 2800/54; C07K 14/4723; A61B 5/055; A61B 5/4255
See application file for complete search history.

(56) References Cited

U.S. PATENT DOCUMENTS

| | | | |
|---|---|---|---|
| 7,888,317 B2 | 2/2011 | Drucker | |
| 7,939,313 B2 | 5/2011 | Heyduk et al. | |
| 11,058,653 B2 | 7/2021 | Stappenbeck et al. | |
| 11,427,852 B2 * | 8/2022 | M'Koma | C12Q 1/6876 |
| 2004/0116504 A1 | 6/2004 | Elokdah et al. | |
| 2010/0081129 A1 | 4/2010 | Belouchi et al. | |
| 2013/0040835 A1 | 2/2013 | Harris | |
| 2013/0261058 A1 | 10/2013 | Schally et al. | |
| 2016/0069905 A1 | 3/2016 | Hains et al. | |
| 2016/0297861 A1 | 10/2016 | Poelstra et al. | |
| 2019/0274983 A1 | 9/2019 | Stappenbeck et al. | |
| 2020/0165677 A1 | 5/2020 | Stappenbeck et al. | |
| 2022/0082548 A1 | 3/2022 | Stappenbeck | |

FOREIGN PATENT DOCUMENTS

| | | | |
|---|---|---|---|
| WO | 2009117791 A2 | 10/2009 | |
| WO | 2012061620 A1 | 5/2012 | |
| WO | 2017189846 A1 | 11/2017 | |
| WO | 2018081388 A1 | 5/2018 | |
| WO | WO-2018175913 A1 * | 9/2018 | ............... C12Q 1/37 |
| WO | 2019018571 A1 | 1/2019 | |

OTHER PUBLICATIONS

Kelly et al., Paneth cell granule depletion in the human small intestine under infective and nutritional stress, Clin Exp Immunol, 135:303-309, 2004 (Year: 2004).*
Simms et al. Reduced-defensin expression is associated with inflammation and not NOD2 mutation status in ileal crohn's disease. Gut. (2008) 57:903-10. (Year: 2008).*
Elphick et al. Impaired luminal processing of human defensin-5 in crohn's disease. Am J Pathol. (2008) 172:702-13) (Year: 2008).*
Cunliffe R.N. Molecular Immunology 40 (2003) 463-467 (Year: 2003).*
Cadwell K, et al. A key role for autophagy and the autophagy gene Atg16l1 in mouse and human intestinal Paneth cells. Nature .2008;456(7219):259-263 (Year: 2008).*
Thachil et al. Abnormal activation of autophagy-induced crinophagy in paneth cells from patients with crohn's disease. Gastroenterology. (2012) 142:1097-9 (Year: 2012).*
Freeman H.J. World J Gastroenterol. Jan. 7, 2014; 20(1): 31-36 (Year: 2014).*
Wehkamp et al. FEBS Letters 580 (2006) 5344-5350 (Year: 2006).*
Tschurtschenthaler, M. et al., "Type I interferon signalling in the intestinal epithelium affects Paneth cells, microbial ecology and epithelial regeneration," Gut, 2014, pp. 1921-1931, vol. 63.
Uhlig, H. et al., "The Diagnostic Approach to Monogenic Very Early Onset Inflammatory Bowel Disease," Gastroenterol., 2014, pp. 990-1007, vol. 147, e1003.

(Continued)

*Primary Examiner* — Kimberly Ballard
*Assistant Examiner* — Stacey N Macfarlane
(74) *Attorney, Agent, or Firm* — Polsinelli PC

(57) ABSTRACT

The present disclosure provides methods for classifying a cell as abnormal based on HD5 protein detection as well as methods for predicting prognosis of a subject with Crohn's disease based on HD5 protein detection.

7 Claims, 76 Drawing Sheets
(71 of 76 Drawing Sheet(s) Filed in Color)
Specification includes a Sequence Listing.

(56) References Cited

OTHER PUBLICATIONS

Vacic, V. et al., "Genome-wide mapping of IBD segments in an Ashkenazi PD cohort identifies associated haplotypes," Hum. Mol. Genet., 2014, pp. 4693-4702, vol. 23, No. 17.

Van Hauwermeiren, F. et al., "TNFR1-induced lethal inflammation is mediated by goblet and Paneth cell dysfunction," Mucosal Immunol., Jul. 2015, pp. 828-840, vol. 8, No. 4.

Van Waveren, C. et al., "Transcriptional co-expression and co-regulation of genes coding for components of the oxidative phosphorylation system," BMC Genomics, 2008, pp. 1-15, vol. 9, No. 18.

Vandussen, K. et al., "Genetic Variant Synthesize to Produce Paneth Cell Phenotypes that Define Subtypes of Crohn's Disease," NIH Public Access Author Manuscript, available in PMC Jan. 1, 2015, pp. 1-19, Published in final form as: Gastroenterology, Jan. 2014, pp. 200-209, vol. 146, No. 1.

Vazquez-Baeza, Y. et al., "EMPeror: a tool for visualizing high-throughput microbial community data," Gigascience, 2013, pp. 1-4, vol. 2, No. 16.

Virgin, H. et al., "Metagenomics and Personalized Medicine," Cell, Sep. 30, 2011, pp. 44-56, vol. 147, Elsevier Inc.

Wehkamp, J. et al., "Reduced Paneth cell alpha-defensins in ileal Crohn's disease," PNAS, Dec. 13, 2005, pp. 18129-18134, vol. 102, No. 50.

Welsh, E. et al., "Iterative rank-order normalization of gene expression microarray data," BMC Bioinformatics, 2013, pp. 1-11, vol. 14, No. 153.

Willing, B. et al., "Twin Studies Reveal Specific Imbalances in the Mucosa-associated Microbiota of Patients with Ileal Crohn's Disease," Inflamm. Bowel Dis., May 2009, pp. 653-660, vol. 15, No. 5.

Wilson, C. et al., "Regulation of Intestinal alpha-Defensin Activation by the Metalloproteinase Matrilysin in Innate Host Defense," Sci., Oct. 1, 1999, pp. 113-117, vol. 286, No. 5437.

Yamazaki, K. et al., "Absence of mutation in the NOD2/CARD15 gene among 483 Japanese patients with Crohn's disease," J. Hum. Genet., 2002, pp. 469-472, vol. 47.

Yamazaki, K. et al., "Single nucleotide polymorphisms in TNFSF15 confer susceptibility to Crohn's disease," Hum. Mol. Genet., 2005, pp. 3499-3506, vol. 14, No. 22.

Yamazaki, K. et al., "A Genome-Wide Association Study Identifies 2 Susceptibility Loci for Crohn's Disease in a Japanese Population," Gastroenterol., 2013, pp. 781-788, vol. 144.

Yang, S-K. et al., "Genome—wide association study of Crohn's disease in Koreans revealed three new susceptibility loci and common attributes of genetic susceptibility across ethnic populations," Gut, 2014, pp. 80-87, vol. 63.

Yang, S-K. et al., "Immunochip Analysis Identification of 6 Additional Susceptibility Loci for Crohn's Disease in Koreans," NIH Public Access Author Manuscript, Jan. 1, 2016, pp. 1-14, published in final edited form as: Inflamm. Bowel Dis., Jan. 2015, pp. 1-7, vol. 21, No. 1.

Yatsunenko, T. et al., "Human gut microbiome viewed across age and geography," HHS Public Access Author Manuscript, Dec. 14, 2012, pp. 1-16, published in final edited form as: Nat., 2012, pp. 222-227, vol. 486, No. 7402.

Yilmaz, O. et al., "mTORC1 in the Paneth cell niche couples intestinal stem-cell function to calorie intake," Nat., 2012, pp. 490-495, vol. 486.

Zhang, Q. et al., "Commensal bacteria direct selective cargo sorting to promote symbiosis," Nat. Immunol., Sep. 2015, pp. 918-926, vol. 16, No. 9.

Zhou, Y. et al., "TSC2/mTORC1 signaling controls Paneth and goblet cell differentiation in the intestinal epithelium," Cell Death Dis., 2015, pp. 1-10, vol. 6, No. e1631, Macmillan Publishers Limited.

European Extended Search Report dated Apr. 1, 2021 from related European Patent Application No. 18834980.7; 8 pgs.

Gillespie, E. et al., "Plasminogen activator inhibitor-1 is increased in colonic epithelial cells from patients with colitis—associated cancer," J. Crohn's Colitis, 2013, pp. 403-411, vol. 7.

Lin, Q. et al., "Toll-Like Receptor 3 Ligand Polyinosinic:Polycytidylic Acid Promotes Wound Healing in Human and Murine Skin," J. Investigative Dermatology, 2012, pp. 2085-2092, vol. 132.

Notice of Allowance dated Mar. 10, 2021 from related U.S. Appl. No. 16/345,625; 5 pgs.

Office Action dated Sep. 18, 2020 from related U.S. Appl. No. 16/345,625; 14 pgs.

Quetglas, E. et al., "Update on pathogenesis and predictors of response of therapeutic strategies used in inflammatory bowel disease," World J. Gastroenterol., Nov. 2015, p. 12519-12543, vol. 22, No. 44.

Kobayashi, T. et al., "Dysbiosis and Staphylococcus aureus Colonization Drives Inflammation in Atopic Dermatitis," Immunity, Apr. 2015, pp. 756-766, vol. 42, Elsevier Inc.

Kolho, K-L. et al., "Fecal Microbiota in Pediatric Inflammatory Bowel Disease and Its Relation to Inflammation," Am. J. Gastroenterol., 2015, pp. 921-930, vol. 110.

Kostic, A. et al., "The Microbiome in Inflammatory Bowel Disease: Current Status and the Future Ahead," NIH Public Access Author Manuscript, May 1, 2015, pp. 1-19, published in final edited form as: Gastroenterol., May 2014, pp. 1489-1499, vol. 146, No. 6.

Koutroubakis, I. et al., "Genetic Risk Factors In Patients With Inflammatory Bowel Disease and Vascular Complications: Case-Control Study," Inflamm. Bowel Dis., Apr. 2007, pp. 410-415, vol. 13, No. 4, Wiley InterScience.

Lassen, K. et al., "Atg16L1 T300A variant decreases selective autophagy resulting in altered cytokine signaling and decreased antibacterial defense," PNAS, May 27, 2014, pp. 7741-7746, vol. 111, No. 21.

Lee, J. et al., "Genome-wide association study identifies distinct genetic contributions to prognosis and susceptibility in Crohn's disease," Europe PMC Funders Group Author Manuscript, Dec. 14, 2017, pp. 1-19, published in final edited form as: Nat Genet., Feb. 2017, pp. 262-268, vol. 49, No. 2.

Levine, A. et al., "Pediatric Modification of the Montreal Classification for Inflammatory Bowel Disease: The Paris Classification," Inflamm. Bowel Dis., Jun. 2011, pp. 1314-1321, vol. 17, No. 6.

Levine, B. et al., "Autophagy in immunity and inflammation," NIH Public Access Author Manuscript, Jul. 20, 2011, pp. 1-28, published in final edited form as: Nat., Jan. 20, 2011, pp. 323-335, vol. 469, No. 7330.

Lewis, J. et al., "Inflammation, Antibiotics, and Diet as Environmental Stressors of the Gut Microbiome in Pediatric Crohn's Disease," Cell Host Microbe, Oct. 2015, pp. 489-500, vol. 18.

Li, X. et al., "Risk of inflammatory bowel disease in first- and second-generation immigrants in Sweden: A nationwide follow-up study," Inflamm. Bowel Dis., Aug. 2011, pp. 1784-1791, vol. 17, No. 8.

Liu, B. et al., "Irgm1-deficient mice exhibit Paneth cell abnormalities and increased susceptibility to acute intestinal inflammation," Am. J. Physiol. Gastrointest. Liver Physiol., 2013, pp. G573-G584, vol. 305.

Liu, T-C. et al., "Spatial and Temporal Stability of Paneth Cell Phenotypes in Crohn's Disease: Implications for Prognostic Cellular Biomarker Development," NIH Public Access, Author Manuscript, Apr. 1, 2015, pp. 1-16, published In final edited form as: Inflamm. Bowel Dis., Apr. 2014, pp. 646-651, vol. 20, No. 4.

Liu, J. et al., "Association analyses identify 38 susceptibility loci for inflammatory bowel disease and highlight shared genetic risk across populations," Nat. Genet., Sep. 2015, pp. 979-986, vol. 47, No. 9.

Liu, T-C. et al., "Paneth cell defects in Crohn's disease patients promote dysbiosis," JCI Insight, 2016, pp. 1-15, vol. 1, No. 8, e86907.

Liu, T-C. et al., "LRRK2 but not ATG16L1 is associated with Paneth cell defect in Japanese Crohn's disease patients," JCI Insight, 2017, pp. 1-14, vol. 2, No. 6, e91917.

Lu, W. et al., "Functional intersection of Human Defensin 5 with the TNF receptor pathway," FEBS Lett., 2014, pp. 1906-1912, vol. 588.

(56) References Cited

OTHER PUBLICATIONS

Manichanh, C. et al., "Reduced diversity of faecal microbiota in Crohn's disease revealed by a metagenomic approach," Gut, 2006, pp. 205-211, vol. 55.
McDonald, D. et al., "An improved Greengenes taxonomy with explicit ranks for ecological and evolutionary analyses of bacteria and archaea," ISME J., 2012, pp. 610-618, vol. 6.
McGovern, D. et al., "Genetics of Inflammatory Bowel Diseases," HHS Public Access Author Manuscript, Oct. 1, 2016, pp. 1-28, published in final edited form as: Gastroenterol., Oct. 2015, pp. 1163-1176.e2, vol. 149, No. 5.
Mu, C. et al., "The Colonic Microbiome and Epithelial Transcriptome Are Altered in Rats Fed a High-Protein Diet Compared with a Normal-Protein Diet," J. Nutr., Mar. 2016, pp. 474-483, vol. 146, No. 3.
Murthy, A. et al., "A Crohn's disease variant in Atg16l1 enhances its degradation by caspase 3," Nat., Feb. 2014, pp. 456-462, vol. 506.
Nagasaki, M., et al., "Rare variant discovery by deep whole-genome sequencing of 1,070 Japanese individuals," Nat. Commun., 2015, pp. 1-13, vol. 6, No. 8018.
NCBI Geo Accession No. GSE90102, dated Nov. 21, 2016; 2 pgs.
Netzel-Arnett, S. et al., "The Role of Matriptase, Urokinase-Type Plasminogen Activator, and SERPINE1 in Colitis Pathogensis," Gastroenterology, AGA Abstracts, May 2011, p. S-650, vol. 140, No. 5, Suppl. 1, Elsevier Inc.
Palm, N. et al., "Immunoglobulin A Coating Identifies Colitogenic Bacteria in Inflammatory Bowel Disease," Cell, Aug. 2014, pp. 1000-1010, vol. 158, Elsevier, Inc.
"Paneth cell phenotype define a subtype of pediatric Crohn's disease through alterations in host-microbial interactions," Abstract presented at CCFA Annual Meeting, Dec. 10, 2015.
Perminow, G. et al., "Defective Paneth Cell-Mediated Host Defense in Pediatric Ileal Crohn's Disease," Am. J. Gastroenterol., Feb. 2010, pp. 452-459, vol. 105.
Pobezinsky, L. et al., "Let-7 miRNAs target the lineage-specific transcription factor PLZF to regulate terminal NKT cell differentiation and effector function," HHS Public Access Author Manuscript, Nov. 1, 2015, pp. 1-24, published in final edited form as: Nat. Immunol., May 2015, pp. 517-524, vol. 15, No. 5.
Probert, C. et al., "Epidemiological study of ulcerative proctocolitis in Indian migrants and the indigenous population of Leicestershire," Gut, 1992, pp. 687-693, vol. 33.
Pruim, R. et al., "LocusZoom: regional visualization of genome-wide association scan results," Bioinformatics, 2010, pp. 2336-2337, vol. 26, No. 18, Oxford University Press.
Purcell, S. et al., "PLINK: A Tool Set for Whole-Genome Association and Population-Based Linkage Analyses," Am. J. Hum. Genet., Sep. 2007, pp. 559-575, vol. 81.
Qi, W. et al., "Absence of Fer protein tyrosine kinase exacerbates endotoxin induced intestinal epithelial barrier dysfunction in vivo," Gut, 2005, pp. 1091-1097, vol. 54.
Rogler, G. et al., "Exposome in IBD: Recent Insights in Environmental Factors that Influence the Onset and Course of IBD," Inflamm. Bowel Dis., Feb. 2015, pp. 400-408, vol. 21, No. 2.
Roulis, M. et al., "Host and microbiota interactions are critical for development of murine Crohn's-like ileitis," Mucosal Immunol., May 2016, pp. 787-797, vol. 9, No. 3.
Round, J. et al., "The gut microbiota shapes intestinal immune responses during health and disease," Nat. Rev. Immunol., May 2009, pp. 313-323, vol. 9, with Erratum, 1 pg., Macmillan Publishers Limited.
Rutgeerts, P. et al., "Predictability of the Postoperative Course of Crohn's Disease," Gastroenterology, 1990, pp. 956-963, vol. 99.
Sadler, A. et al., "BTB-ZF transcriptional regulator PLZF modifies chromatin to restrain inflammatory signaling programs," PNAS, Feb. 3, 2015, pp. 1535-1540, vol. 112, No. 5.
Salzman, N. et al., "Protection against enteric salmonellosis in transgenic mice expressing a human intestinal defensin," Nat., Apr. 3, 2003, pp. 522-526, vol. 422.
Salzman, N. et al., "Enteric defensins are essential regulators of intestinal microbial ecology," HHS Publbic Access Author Manuscript, Jul. 1, 2010, pp. 1-22, published in final edited form as: Nat. Immunol., Jan. 2010, pp. 76-83, vol. 11, No. 1.
Sawdey, M. et al., "Regulation of murine type 1 plasminogen activator inhibitor gene expression in vivo. Tissue specificity and induction by lipopolysaccharide, tumor necrosis factor-alpha, and transforming growth factor-beta," J. Clin. Invest., Oct. 1991, pp. 1346-1353, vol. 88, No. 4.
Schaubeck, M. et al., "Dysbiotic gut microbiota causes transmissible Crohn's disease-like ileitis independent of failure in antimicrobial defence," Gut, 2016, pp. 225-237, vol. 65.
Schwiertz, A. et al., "Microbiota in Pediatric Inflammatory Bowel Disease," J. Pediatr., Aug. 2010, pp. 240-244.e1, vol. 157, No. 2.
Segata, N. et al., "Metagenomic biomarker discovery and explanation," Genome Biol., 2011, pp. 1-18, vol. 12, No. R60.
Shanware, N. et al., "The PI3K, Metabolic, and Autophagy Networks: Interactive Partners in Cellular Health and Disease," Annu. Rev. Pharmacol. Toxicol., Jan. 2013, pp. 89-106, vol. 53.
Shanahan, M. et al., "Mouse Paneth cell antimicrobial function is independent of Nod2," Gut, 2014, pp. 903-910, vol. 63.
Sokol, H. et al., "Faecalibacterium prausnitzii is an anti-inflammatory commensal bacterium identified by gut microbiota analysis of Crohn disease patients," PNAS, Oct. 28, 2008, pp. 16731-16736, vol. 105, No. 43.
Sorrentino, D., "State-of-the-art medical prevention of postoperative recurrence of Crohn's disease," Nat. Rev. Gastroenterol. Hepatol., Jul. 2013, pp. 413-422, vol. 10.
Soucie, E. et al., "Lineage-specific enhancers activate self-renewal genes in macrophages and embryonic stem cells," Sci., Feb. 12, 2016, pp. 680 and aad5510-1 to aad5510-13, vol. 351, No. 6274.
Takagi, S. et al., "Effectiveness of an 'half elemental diet' as maintenance therapy for Crohn's disease: a randomized-controlled trial," Aliment. Pharmacol. Ther., 2006, pp. 1333-1340, vol. 24.
Trabzuni, D. et al., "Fine-Mapping, Gene Expression and Splicing Analysis of the Disease Associated LRRK2 Locus," PLOS One, Aug. 2013, pp. 1-9, vol. 8, No. 8, e70724.
Abt, M. et al., "Commensal Bacteria Calibrate the Activation Threshold of Innate Antiviral Immunity," Immunity, Jul. 27, 2012, pp. 158-170, vol. 37.
Arimori, Y. et al., "Type I interferon limits influenza virus-induced acute lung injury by regulation of excessive inflammation in mice," Antiviral Res., 2013, pp. 230-237, vol. 99, No. 3.
Billiau, A., "Anti-inflammatory properties of Type I interferons," Antiviral Res., 2006, pp. 108-116, vol. 71.
Boon, A. et al., "Host Genetic Variation Affects Resistance to Infection with a Highly Pathogenic H5N1 Influenza A Virus in Mice," J. Virol., Oct. 2009, pp. 10417-10426, vol. 83, No. 20.
Byrne, A. et al., "Pulmonary macrophages: key players in the innate defence of the airways," Thorax, 2015, pp. 1189-1196, vol. 70.
Davidson, S. et al., "Pathogenic potential of interferon alphabeta in acute influenza infection," Nat. Commun., 2014, pp. 1-15, vol. 5, No. 3864.
Gonzalez-Navajas, J. et al., "Immunomodulatory functions of type I interferons," Nat. Rev. Immunol., Feb. 2012, pp. 125-135, vol. 12.
Guarda, G. et al., "Type I Interferon Inhibits Interleukin-1 Production and Inflammasome Activation," Immunity, Feb. 25, 2011, pp. 213-223, vol. 34.
Hogner, K. et al., "Macrophage-expressed IFN-beta Contributes to Apoptotic Alveolar Epithelial Cell Injury in Severe Influenza Virus Pneumonia," PLOS Pathog., Feb. 2013, pp. 1-16, vol. 9, No. 2, e1003188.
Honda, K. et al., "IRF-7 is the master regulator of type-I interferon-dependent immune responses," Nature, Apr. 2005, pp. 772-777, vol. 434.
Ichinohe, T. et al., "Microbiota regulates immune defense against respiratory tract influenza A virus infection," PNAS, Mar. 29, 2011, pp. 5354-5359, vol. 108, No. 13.
International Search Report and Written Opinion dated Feb. 12, 2018 from related Patent Application No. PCT/US2017/058478; 8 pgs.

(56) References Cited

OTHER PUBLICATIONS

Kaiko, G. et al., "The Colonic Crypt Protects Stem Cells from Microbiota—Derived Metabolites," Cell, 2016, pp. 1708-1720, vol. 165.
Kernbauer, E. et al., "An enteric virus can replace the beneficial function of commensal bacteria," Europe PMC Funders Group Public Access Author Manuscript, Jun. 4, 2015, pp. 1-32, Published in final edited form as: Nature, Dec. 4, 2014, pp. 94-98, vol. 516, No. 7529.
Koerner, I. et al., "Protective Role of Beta Interferon in Host Defense against Influenza A Virus," J. Virol, Feb. 2007, pp. 2025-2030, vol. 81, No. 4.
Kolumam, G. et al., "Type I interferons act directly on CD8 T cells to allow clonal expansion and memory formation in response to viral infection," J. Exp. Med., Sep. 5, 2005, pp. 637-650, vol. 202, No. 5.
Matsumoto, M. et al., "Impact of Intestinal Microbiota on Intestinal Luminal Metabolome," Sci. Rep., 2012, pp. 1-10, vol. 2, No. 233.
Newby, C. et al., "The RNA Binding Domain of Influenza A Virus NS1 Protein Affects Secretion of Tumor Necrosis Factor Alpha, Interleukin-6, and Interferon in Primary Murine Tracheal Epithelial Cells," J. Virol., Sep. 2007, pp. 9469-9480, vol. 81, No. 17.
Nguyen, K. et al., "Coordinated and Distinct Roles for IFN-alpha beta, IL-12, and IL-15 Regulation of NK Cell Responses to Viral Infection," J. Immunol., 2002, pp. 4279-4287, vol. 169.
Patel, D. et al., "High Throughput Screening for Small Molecule Enhancers of the Interferon Signaling Pathway to Drive Next-Generation Antiviral Drug Discovery," PLOS One, May 2012, pp. 1-12, vol. 7, No. 5, e36594.
Platanias, L., "Mechanisms of Type-I- and Type-II-Interferon-Mediated Signalling," Nat. Rev. Immunol., May 2005, pp. 375-386, vol. 5.
Ryu, S. et al., "Gut-Pancreatic Axis AMPlified in Islets of Langerhans," Immunity, Aug. 18, 2015, pp. 216-218, vol. 43.
Schoefer, L. et al., "Anaerobic Degradation of Flavonoids by Clostridium orbiscindens," Appl. Environ. Microbiol., Oct. 2003, pp. 5849-5854, vol. 69, No. 10.
Smith, P. et al., "The Microbial Metabolites, Short-Chain Fatty Acids, Regulate Colonic Treg Cell Homeostasis," Sci., Aug. 2, 2013, pp. 569-573, vol. 341, No. 6145.
Steed, A. et al., "The microbial metabolite desaminotyrosine protects from influenza through type I interferon," Sci., Aug. 4, 2017, pp. 498-502, vol. 357.
Stevens, V. et al., "Comparative Effectiveness of Vancomycin and Metronidazole for the Prevention of Recurrence and Death in Patients With Clostridium difficile Infection," JAMA Intern. Med., 2017, pp. 546-553, vol. 177, No. 4.
Sun, L. et al., "Type I Interferons Link Viral Infection to Enhanced Epithelial Turnover and Repair," Cell Host Microbe, Jan. 14, 2015, pp. 85-97, vol. 17.
Trompette, A. et al., "Gut microbiota metabolism of dietary fiber influences allergic airway disease and hematopoiesis," Nat. Med., Feb. 2014, pp. 159-166, vol. 20, No. 2.
Van Rooijen, N. et al., "Elimination of phagocytic cells in the spleen after intravenous injection of liposome—encapsulated dichloromethylene diphosphonate," Cell Tissue Res., 1984, pp. 355-358, vol. 238, No. 2.
Wang, J. et al., "Bacterial colonization dampens influenza-mediated acute lung injury via induction of M2 alveolar macrophages," Nat. Commun., 2013, pp. 1-10, vol. 4, No. 2106.
Zhang, Z. et al., "Isolation and Identification of Quercetin Degrading Bacteria from Human Fecal Microbes," PLoS One, Mar. 2014, pp. 1-5, vol. 9, No. 3, e90531.
Kohoutova, D. et al., "Prevalence of hypercoagulable disorders in inflammatory bowel disease," Scand. J. Gastro., 2014, pp. 287-294, vol. 49, No. 3.
UniProt Accession No. P00750, "Tissue-type plasminogen activator," Jul. 21, 1986; 21 pgs.
UniProt Accession No. P05121, "Plasminogen activator inhibitor 1," Aug. 13, 1987; 12 pgs.

Adolph, T. et al., "Paneth cells as a site of origin for intestinal inflammation," HHS Public Access Author Manuscript, May 14, 2014, pp. 1-19, published in final edited form as: Nature, Nov. 14, 2013, pp. 272-276, vol. 503, No. 7475.
Albenberg, L. et al., "Diet and the Intestinal Microbiome: Associations, Functions, and Implications for Health and Disease," NIH Public Access Author Manuscript, May 1, 2015, pp. 1-16, published in final edited form as: Gastroenterol., May 2014, pp. 1564-1572, vol. 146, No. 6.
Arijs, I. et al., "Mucosal gene signatures to predict response to infliximab in patients with ulcerative colitis," Gut, Aug. 20, 2009, pp. 1612-1619, vol. 58, No. 12, BMJ Publishing Group Ltd.
Avitzur, Y. et al., "Mutations in Tetratricopeptide Repeat Domain 7A Result in a Severe Form of Very Early Onset Inflammatory Bowel Disease," Gastroenterol., Apr. 2014, pp. 1028-1039, vol. 146, No. 4.
Aziz, A. et al., "MafB/c-Maf Deficiency Enables Self-Renewal of Differentiated Functional Macrophages," Sci., Nov. 6, 2009, pp. 867-871, vol. 326, No. 5954.
Baxt, L. et al., "Role of Autophagy in the Maintenance of Intestinal Homeostasis," HHS Public Access Author Manuscript, Sep. 1, 2016, pp. 1-19, published in final edited form as: Gastroenterol., Sep. 2015, pp. 553-562, vol. 149, No. 3.
Belkaid, Y. et al., "Role of the Microbiota in Immunity and Inflammation," Cell, Mar. 27, 2014, pp. 121-141, vol. 157, Elsevier Inc.
Bernstein, C. et al., "World Gastroenterology Organization Practice Guidelines for the Diagnosis and Management of IBD in 2010," Inflamm. Bowel Dis., Jan. 2010, pp. 112-124, vol. 16, No. 1, Wiley InterScience.
Bevins, C. et al., "Paneth cells, antimicrobial peptides and maintenance of intestinal homeostasis," Nat. Rev. Microbiol., May 2011, pp. 356-368, No. 9.
Bloom, S. et al., "Commensal Bacteroides Species Induce Colitis in Host-Genotype-Specific Fashion in a Mouse Model of Inflammatory Bowel Disease," Cell Host Microbe, May 19, 2011, pp. 390-403, vol. 9, Elsevier Inc.
Cadwell, K. et al., "A key role for autophagy and the autophagy gene Atg16l1 in mouse and human intestinal Paneth cells," Nat., Nov. 13, 2008, pp. 259-263, vol. 456, Macmillan Publishers Limited.
Cadwell, K. et al., "Virus-Plus-Susceptibility Gene Interaction Determines Crohn's Disease Gene Atg16L1 Phenotypes in Intestine," Cell, Jun. 25, 2010, pp. 1135-1145, vol. 141, Elsevier Inc.
Caporaso, J. et al., "QIIME allows analysis of high-throughput community sequencing data," NIH Public Access Author Manuscript, Aug. 16, 2011, pp. 1-4, published in final edited form as: Nat. Methods, May 2010, pp. 335-336, vol. 7, No. 5.
Caporaso, J. et al., "Ultra-high-throughput microbial community analysis on the Illumina HiSeq and MiSeq platforms," ISME J., 2012, pp. 1621-1624, vol. 6.
Carr, I. et al., "The effects of migration on ulcerative colitis: a three-year prospective study among Europeans and first- and second-generation South Asians in Leicester (1991-1994)," Am. J. Gastroenterol., Oct. 1999, pp. 2918-2922, vol. 94, No. 10.
Chassaing, B. et al., "The Commensal Microbiota and Enteropathogens in the Pathogenesis of Inflammatory Bowel Diseases," Gastroenterol., 2011, pp. 1720-1728, vol. 140, AGA Institute.
Chen, P. et al., "Autophagy-mediated regulation of macrophages and its applications for cancer," Autophagy, Feb. 2014, pp. 192-200, vol. 10, No. 2, Landes Bioscience.
Chuang, L-S. et al., "A Frameshift in CSF2RB Predominant Among Ashkenazi Jews Increases Risk for Crohn's Disease and Reduces Monocyte Signaling via GM-CSF," Gastroenterol., Oct. 2016, pp. 710-723, vol. 151, No. 4.
Conte, M. et al., "Gut-associated bacterial microbiota in paediatric patients with inflammatory bowel disease," Gut, 2006, pp. 1760-1767, vol. 55.
Dalal, S. et al., "The microbial basis of inflammatory bowel diseases," J. Clin. Invest., Oct. 2014, pp. 4190-4196, vol. 124, No. 10.

(56) References Cited

OTHER PUBLICATIONS

Deuring, J. et al., "Genomic ATG16L1 risk allele-restricted Paneth cell ER stress in quiescent Crohn's disease," Gut, 2013, pp. 1081-1091, vol. 63.
Dinh, D. et al., "Intestinal Microbiota, Microbial Translocation, and Systemic Inflammation in Chronic HIV Infection," J. Infect. Dis., Jan. 2015, pp. 19-27, vol. 211.
Donohoe, D. et al., "The Microbiome and Butyrate Regulate Energy Metabolism and Autophagy in the Mammalian Colon," Cell Metab., May 4, 2011, pp. 517-526, vol. 13, Elsevier Inc.
Faith, D. et al., "Phylogenetic diversity (PD) and biodiversity conservation: some bioinformatics challenges," Evol. Bioinform. Online, 2006, pp. 121-128, vol. 2.
Fava, V. et al., "A Missense LRRK2 Variant is a Risk Factor for Excessive Inflammatory Responses in Leprosy," PLoS Negl. Trop. Dis., Feb. 2016, pp. 1-14, vol. 10, No. 2, e0004412.
Franke, A. et al., "Genome-wide meta-analysis increases to 71 the No. of confirmed Crohn's disease susceptibility loci," Nat. Genet., Dec. 2010, pp. 1118-1125, vol. 42, No. 12.
Fuyuno, Y. et al., "Genetic characteristics of inflammatory bowel disease in a Japanese population," J. Gastroenterol., Jul. 2016, pp. 672-681, vol. 51, No. 7.
Gevers, D. et al., "The Treatment-Naive Microbiome in New-Onset Crohn's Disease," Cell Host Microbe, Mar. 12, 2014, pp. 382-392, vol. 15, Elsevier Inc.
Gunther, C. et al., "Caspase-8 regulates TNF-alpha-induced epithelial necroptosis and terminal ileitis," Nat., Sep. 15, 2011, pp. 335-339, vol. 477, Macmillan Publishers Limited.
Haberman, Y. et al., "Pediatric Crohn disease patients exhibit specific ileal transcriptome and microbiome signature," J. Clin. Invest., 2014, pp. 3617-3633, vol. 124, No. 8.
Hampe, J. et al., "A genome-wide association scan of nonsynonymous SNPs identifies a susceptibility variant for Crohn disease in ATG16L 1," Nat. Genet., Feb. 2007, pp. 207-211, vol. 39, No. 2.
Hansen, R. et al., "Microbiota of De-Novo Pediatric IBD: Increased Faecalibacterium Prausnitzii and Reduced Bacterial Diversity in Crohn's But Not in Ulcerative Colitis," Am. J. Gastroenterol., Dec. 2012, pp. 1913-1922, vol. 107.
Hirano, A. et al., "Association Study of 71 European Crohn's Disease Susceptibility Loci in a Japanese Population," Inflamm. Bowel Dis., Mar. 1, 2013, pp. 526-533, vol. 19, No. 3.
Hodin, C. et al., "Reduced Paneth cell antimicrobial protein levels correlate with activation of the unfolded protein response in the gut of obese individuals," J. Pathol., Oct. 2011, pp. 276-284, vol. 225, No. 2.
Hong, S. et al., "Deep resequencing of 131 Crohn's disease associated genes in pooled DNA confirmed three reported variants and identified eight novel variants," Gut, 2016, pp. 788-796, vol. 65.
Huttenhower, C. et al., "Inflammatory Bowel Disease as a Model for Translating the Microbiome," Immunity, Jun. 19, 2014, pp. 843-854, vol. 40, Elsevier Inc.
Igarashi, M. et al., "mTORC1 and SIRT1 Cooperate to Foster Expansion of Gut Adult Stem Cells during Calorie Restriction," Cell, Jul. 2016, pp. 436-450, vol. 166.
Inoue, N. et al., "Lack of Common NOD2 Variants in Japanese Patients With Crohn's Disease," Gastroenterol., Jul. 2002, pp. 86-91, vol. 123, No. 1.
International Search Report and Written Opinion dated Dec. 3, 2018 from related International Patent Application No. PCT/US2018/042761; 18 pgs.
International Search Report and Written Opinion dated Jul. 31, 2017 from related International Patent Application No. PCT/US2017/029836; 11 pgs.
Jostins, L. et al., "Host-microbe interactions have shaped the genetic architecture of inflammatory bowel disease," HHS Public Access Author Manuscript, May 1, 2013, pp. 1-18, published in final edited form as: Nat., Nov. 1, 2012, pp. 119-124, vol. 491, No. 7422.
Jung, C. et al., "mTOR regulation of autophagy," FEBS Lett., 2010, pp. 1287-1295, vol. 584.
Kanayama, M. et al., "Autophagy enhances NFKB activity in specific tissue macrophages by sequestering A20 to boost antifungal immunity," Nat. Commun., 2015, pp. 1-14, vol. 6, No. 5779.
Kaser, A. et al., "XBP1 Links ER Stress to Intestinal Inflammation and Confers Genetic Risk for Human Inflammatory Bowel Disease," Cell, Sep. 5, 2008, pp. 743-756, vol. 134, Elsevier Inc.
Kawai, Y. et al., "Japonica array: improved genotype imputation by designing a population-specific SNP array with 1070 Japanese individuals," J. Hum. Genet., 2015, pp. 581-587, vol. 60.
Khajah, M. et al., "Fer Kinase Limits Neutrophil Chemotaxis toward End Target Chemoattractants," J. Immunol., 2013, pp. 2208-2216, vol. 190.
Khor, B. et al., "Genetics and pathogenesis of inflammatory bowel disease," NIH Public Access Author Manuscript, Dec. 16, 2011, pp. 1-25, published in final edited form as: Nat., Jun. 16, 2011, pp. 307-317, vol. 474, No. 7351.
Knights, D. et al., "Supervised classification of microbiota mitigates mislabeling errors," ISME J., 2011, pp. 570-573, vol. 5.
Knights, D. et al., "Bayesian community-wide culture-independent microbial source tracking," Nat. Methods, Sep. 2011, pp. 761-763, vol. 8, No. 9.
Ko, Y. et al., "Epidemiological studies of migration and environmental risk factors in the inflammatory bowel diseases," World J. Gastroenterol., Feb. 7, 2014, pp. 1238-1247, vol. 20, No. 5, Baishideng Publishing Group Co., Limited, Hong Kong.
Danese, S. et al., "PAI-1 and TAFI in inflammatory bowel disease: the yin and yang of the fibrinolytic system," Eur. J. Gastroenterol. Hepatol., 2008, pp. 826-828, vol. 20.
Restriction Requirement dated Sep. 23, 2021 from related U.S. Appl. No. 16/631,980; 10 pgs.
Arijs, I. et al., "Predictive Value of Epithelial Gene Expression Profiles for Response to Infliximab in Chron's Disease," Inflamm. Bowel Dis., Dec. 2010, pp. 2090-2098, vol. 16, No. 12.
Baggerly, K. et al., "Driving Chemosensitivity From Cell Lines: Forensic Bioinformatics and Reproducible Research in High-Throughput Biology," Annals of Applied Statistics, 2009, pp. 1309-1334, vol. 3.
Benner, S. et al., "Evolution, language and analogy in functional genomics," Trends in Genetics, Jul. 2001, pp. 414-418, vol. 17, No. 7.
Cheung, V. et al., "Natural variation in human gene expression assessed in lymphoblastoid cells," Nat. Genetics, Mar. 2003, pp. 422-425, vol. 33.
Couzin-Frankel, J., "As Questions Grow, Duke Halts Trials, Launches Investigation," Sci., Aug. 6, 2010, pp. 614-615, vol. 329.
Gyorffy, A. et al., "Validation of Biomarkers in Gene Expression Datasets of Inflammatory Bowel Disease: IL13RA2, PTGS2 and WNT5A as Predictors of Responsiveness to Infliximab Therapy," J. Proteomics Bioinform., 2014, pp. 272-277, vol. 7, No. 9.
Office Action dated Feb. 10, 2022 from related U.S. Appl. No. 16/631,980; 21 pgs.
Saito-Hisaminato, A. et al., "Genome-Wide Profiling of Gene Expression in 29 Normal Human Tissues with a CDNA Microarray," DNA Res., 2002, pp. 35-45, vol. 9, No. 2.

\* cited by examiner

METHODS FOR PROGNOSING CROHN'S DISEASE COMPRISING HUMAN DEFENSIN 5 (HD5)

CROSS REFERENCE TO RELATED APPLICATIONS

This application claims the benefit of PCT Application PCT/US2017/029836, filed Apr. 27, 2017, which claims priority from U.S. Provisional Application No. 62/328,386, filed Apr. 27, 2016; U.S. Provisional Application No. 62/329,576, filed Apr. 29, 2016; and U.S. Provisional Application No. 62/343,519, filed May 31, 2016, each of the disclosures of which is herein incorporated by reference in its entirety.

GOVERNMENTAL RIGHTS

This invention was made with government support under AI084887 and DK095820 awarded by the National Institutes of Health. The government has certain rights in the invention.

FIELD OF THE INVENTION

The present disclosure provides methods for classifying a cell as abnormal based on HD5 protein detection as well as methods for predicting prognosis of a subject with Crohn's disease based on HD5 protein detection.

BACKGROUND OF THE INVENTION

Crohn's disease (CD) is a form of inflammatory bowel disease (IBD) rooted in environmental triggers of immune dysregulation that occur in genetically susceptible hosts. CD involves a complex network of etiologic factors, including genetic susceptibility, immune dysregulation, and environmental triggers. Therefore, it is challenging to study the pathogenesis and prognosis using simple genotype-phenotype correlation models. Accordingly, new approaches are needed that focus on a CD-associated cell type that can synthesize the impact of genetic and potential environmental factors and facilitate prognosis determination.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) Pediatric CD patients have a significantly higher prevalence of Type I Paneth cell phenotype than adult CD patients (P<0.001 by ANOVA). (FIG. 1B) Flow chart of the recruitment and exclusion of the Milwaukee pediatric CD cohort. (FIG. 1C) Representative Paneth cell staining by lysozyme immunofluorescence. Red: lysozyme; blue: DAPI. Dashed circle: intestinal crypts. D0: normal Paneth cells; D1, D3: abnormal Paneth cells. Bar: 1 µm.

(FIG. 2A and FIG. 2B) Alpha diversity of mucosal microbial composition in pediatric CD and non-IBD patients. Shown here with Shannon diversity index (FIG. 2A; P=0.1106, Mann-Whitney test) and Faith's phylogenetic diversity index FIG. 2B; P=0.0241, Mann-Whitney test). (FIG. 2C and FIG. 2D) Unweighted (FIG. 2C; Kruskal-Wallis test P<0.0001, Dunn's multiple comparisons test P<0.0001) and weighted (FIG. 2D; Kruskal-Wallis test P=0.0011, Dunn's multiple comparisons test P<0.01) beta-diversity comparison within and between each group (Milwaukee cohort). *: P<0.05; ****: P<0.0001.

(FIG. 3A, FIG. 3B, FIG. 3C, and FIG. 3D) Alpha diversity (Shannon and Faith's phylogenetic diversity by Mann-Whitney test) of Type I versus Type II Paneth cell phenotype in CD (n=44) and non-IBD (n=62). (FIG. 3E and FIG. 3F) Unweighted and weighted beta-diversity comparison (by Kruskal-Wallis and Dunn's tests) within and between CD patients with Type I versus Type II Paneth cell phenotype. *: P<0.05; : P<0.01; *: P<0.001.

(FIG. 4A and FIG. 4B) Microbes that are significantly more abundant in CD patients with Type I Paneth cell phenotype identified by Differential Feature analysis (LEfSe). (FIG. 4A) *Corynebacterium*. (FIG. 4B) *Erysipeloctrichaceae*. (FIG. 4C, FIG. 4D, FIG. 4E, FIG. 4F, FIG. 4G, FIG. 4H, FIG. 4I, and FIG. 4J) Selected microbes whose abundance is reduced in CD patients with Type I Paneth cell phenotype but not in non-IBD patients with either Paneth cell phenotype identified by Differential Feature analysis (LEfSe). (FIG. 4C) *Faecalibacterium*. (FIG. 4D) *Blautia*. (FIG. 4E) *Ruminococcaceae*. (FIG. 4F) *Porphyromonas*. (FIG. 4G) *Lachnospira*. (FIG. 4H) *Peptostreptococcus*. (FIG. 4I) *Anaerostipes*. (FIG. 4J) *Odoribacteraceae*. *: P<0.05; : P<0.01; *: P<0.001 (Mann-Whitney test).

(FIG. 5A) Heat map based on hierarchical clustering (Pearson with complete linkage) of gene expression profiles of Type I and Type II Paneth CD patients. Blue and red indicate lower and higher levels of expression, respectively. The cluster region containing the oxidative phosphorylation genes is labeled. (FIG. 5B, FIG. 5C, and FIG. 5D) Expression of selected nuclear-encoded oxidative phosphorylation genes is associated with Paneth cell phenotype in CD patients, including COX6B1 (FIG. 5B), ATP5J2 (FIG. 5C), and NDUFA8 (FIG. 5D). Data analyzed by one-way ANOVA. (FIG. 5E) Expression level of oxidative phosphorylation gene COX6A1 correlates with the percentage of normal Paneth cells (D0) by Pearson's correlation test. (FIG. 5F) Selected bacterial taxa that are significantly more abundant in CD patients with high expression level of oxidative phosphorylation genes (*Faecalibacterium, Actinomyces, Verrrucomicrobiaceae*) identified by Differential Feature analysis (LEfSe). (FIG. 5G) Reduced abundance of *Faecalibacterium* in CD patients with low oxidative phosphorylation expression level (by Mann-Whitney test). *: P<0.05; **: P<0.01.

(FIG. 7A) Saint Louis adult CD. (FIG. 7B) Los Angeles adult CD. (FIG. 7C) Saint Louis pediatric CD. (FIG. 7D) Milwaukee pediatric CD.

(FIG. 8A) No significant difference was seen between the numbers of ATG16L1 T300A risk alleles and the actual percentage of normal Paneth cells. P=0.4284 by T test. (FIG. 8B) No significant difference was seen between the numbers of NOD2 risk alleles and the actual percentage of normal Paneth cells. P=0.8982 by ANOVA. (FIG. 8C) No significant difference was seen between the total sum numbers of ATG16L1 T300A and NOD2 risk alleles and the actual percentage of normal Paneth cells. P=0.0888 by ANOVA.

(FIG. 9A) Differential feature analysis for CD patients versus non-IBD patients by LEfSe. Red bars represent taxa with a significantly higher relative abundance in CD patients. Blue bars represent taxa with a significantly higher relative abundance in non-IBD patients. (FIG. 9B) Stacked bar plots of phylum-level compositions of mucosal microbiome between CD and non-IBD patients. Each bar represents one patient. (FIG. 9C) Cladogram of differential taxa between CD and non-IBD patients analyzed by LEfSe.

(FIG. 10A) Unweighted beta-diversity of microbiome between CD and non-IBD patients by principal coordinate analysis (P=0.137). Red: CD patients with Type I Paneth cell phenotype. Blue: CD patients with Type II Paneth cell phenotype. (FIG. 10B) Stacked bar plots of phylum-level compositions of mucosal microbiome between Type I and Type II Paneth cell phenotypes. Each bar represents one patient.

(FIG. 11A and FIG. 11B) Unweighted and weighted beta-diversity comparison in and between non-IBD patients with Type I and II Paneth cell phenotypes. *: $P<0.05$; ****: $P<0.0001$. (FIG. 11C) The cladogram of mucosal microbiome in non-IBD patients stratified by Paneth cell phenotype.

(FIG. 12A) Differential feature analysis for CD patients with Type I versus Type II Paneth cell phenotypes by LEfSe. Red bars represent taxa with a significantly higher relative abundance in CD patients with Type I Paneth cell phenotype. Blue bars represent taxa with a significantly higher relative abundance in CD patients with Type II Paneth cell phenotype. (FIG. 12B) Cladogram of differential taxa between CD patients with Type I and Type II Paneth cell phenotype analyzed by LEfSe.

(FIG. 14A) DEFA6; (FIG. 14B) PLA2G2A; (FIG. 14C) REG3A. (FIG. 14D) Selected bacterial taxa that are significantly more abundant in CD patients with high expression level of Paneth cell genes identified by Differential Feature analysis (LEfSe). **: $P<0.01$.

(FIG. 20A) Representative images of Defensin-5 immunofluorescence on Japanese CD resection specimens. Scale bar: 10 µm. (FIG. 20B) The distribution of percentage of normal Paneth cells in North American (n=164) and Japanese CD (n=110). P=0.87 by unpaired T test. Error bars represent ±SEM.

(FIG. 21B) Percentage of disordered (D1) Paneth cells (P=0.1249); (FIG. 21C) Percentage of diminished (D2) Paneth cells (P=0.0506); (FIG. 21D) Percentage of diffuse (D3) Paneth cells (P=0.0992); (FIG. 21E) Percentage of excluded (D4) Paneth cells (P=0.7152); (FIG. 21F) Percentage of enlarged (D5) Paneth cells (P=0.5396). Statistical analysis was performed using Fisher's exact test.

(FIG. 23A) The numbers of ATG16L1 T300A risk allele did not correlate with the percentage of normal Paneth cells ($R^2=0.01717$ and P=0.20 by linear regression) in Japanese CD, while (FIG. 23B) in North American CD without common CD-associated NOD2 risk alleles, the numbers of ATG16L1 T300A risk allele correlated with the percentage of normal Paneth cells ($R^2=0.04387$ and P=0.0395 by linear regression). In contrast, (FIG. 23C) the numbers of LRRK2 M2397T risk alleles negatively correlated with the percentage of normal Paneth cells in Japanese CD ($R^2=0.247$, $P=3.62\times10^{-4}$ by linear regression). (FIG. 23D) However, in North American CD, the numbers of LRRK2 M2397T risk alleles did not correlate with the percentage of normal Paneth cells ($R^2=0.02054$, $P=0.76$ by linear regression). Error bars represent ±SEM.

(FIG. 26B, FIG. 26D, and FIG. 26F) corresponding normal Paneth cells-numbers of risk alleles correlation. Error bars represent ±SEM. (B) $P=2.74\times10^{-6}$; (D) $P=5.11\times10^{-7}$; (F) $P=7.22\times10^{-7}$ (FIG. 26B, FIG. 26D, and FIG. 26F by linear regression).

(FIG. 33A) Prophylactic therapy; (FIG. 33B) Smoking. Patients who received postoperative prophylaxis showed a significantly longer recurrence-free survival than those who did not (24 vs. 12 months; $P=0.0369$). never smokers also have significantly longer recurrence-free survival than active/ex smokers (32 vs. 12 months; $P=0.0151$).

DETAILED DESCRIPTION OF THE INVENTION

Figure 1A:
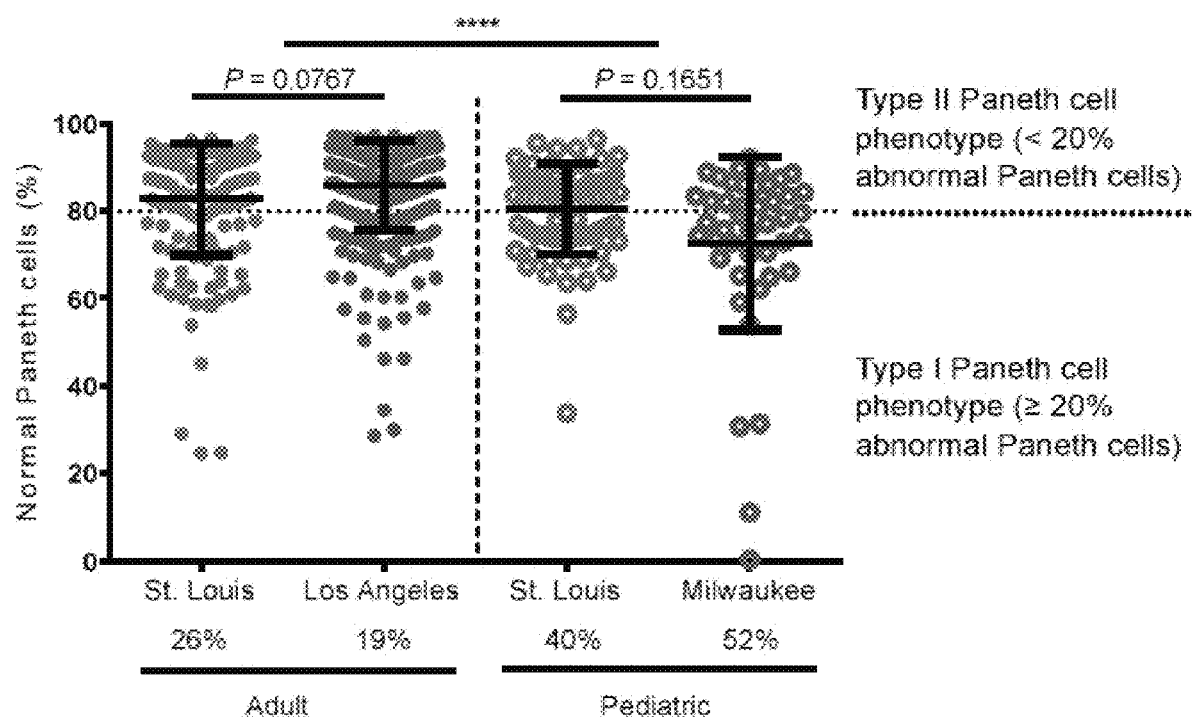
FIG. 1A, FIG. 1B, and FIG. 1C depicts a graph, flowchart and image showing the high prevalence of Type I Paneth cell phenotype in pediatric CD patients.

Disclosed herein are methods to classify a subject based on HD5 protein detection. Currently there are no methods to accurately predict the prognosis and/or response to treatment for Crohn's disease that both use minimal tissue and that can be automated. The inventors have discovered that immunofluorescence staining of biopsied tissue for HD5 results in a more specific marker for Paneth cells than previous methods. Interactions between Paneth cells and gut microbiota has been postulated to be one of the key elements of CD pathogenesis. Further, it is suggested that defects in Paneth cells could lead to reduced antimicrobial peptide production, which could result in dysbiosis and ultimately IBD. Paneth cell granule morphology may be used as an indicator of Crohn's disease. Staining for HD5 has better resolution, stronger signal and minimal to no background when compared to prior art methods of Paneth cell staining. Accordingly, a method comprising detecting HD5 allows for more accurate prediction of Paneth cell phenotype while using less tissue sample and has the potential to be automated based on absence of background staining and intensity of Paneth cell staining. The inventors have shown that the methods disclosed herein may be used to predict disease recurrence after surgery (e.g., resection) in subjects with Crohn's disease.

Various aspects of the methods are disclosed in detail below.

I. Methods

In an aspect, the disclosure provides a method to classify a cell in a biological sample. The method generally comprises: (a) detecting HD5 protein in the biological sample; and (b) identifying an HD5 positive cell as normal or abnormal based on the granule morphology of the HD5 positive cell, wherein abnormal granule morphology is selected from the group consisting of disordered, diminished, diffuse, excluded and enlarged granule morphology. In an embodiment, the cell is a Paneth cell. In another embodiment, the HD5 protein is detected using immunofluorescence. In still another embodiment, the HD5 protein is detected using automated detection. In a further embodiment, the HD5 protein is detected using an autostainer. In yet still another embodiment, the biological sample is a tissue biopsy. As used herein, "HD5" refers to human defensin 5 encoded by the DEFA5 gene and comprising the sequence set forth in SEQ ID NO:3 (ATCYCRHGRCATRESLSGV-CEISGRLYRLCCR).

In another aspect, the disclosure provides a method to classify a subject with Crohn's disease as having a Type I or Type II phenotype. The method generally comprises: (a) detecting HD5 protein in the biological sample from the subject; (b) identifying the number of HD5 positive cells in the biological sample with normal or abnormal granule morphology, wherein abnormal granule morphology is selected from the group consisting of disordered, diminished, diffuse, excluded and enlarged granule morphology; and (c) classifying the subject as having a Type II phenotype if <20% of HD5 positive cells in the biological sample have abnormal granule morphology or having a Type I phenotype if 20% of HD5 positive cells in the biological sample have abnormal granule morphology. In an embodiment, the HD5 protein is detected using immunofluorescence. In still another embodiment, the HD5 protein is detected using automated detection. In a further embodiment, the HD5 protein is detected using an autostainer. In still yet another embodiment, the biological sample is a tissue biopsy. The method to classify a subject with Crohn's disease as having a Type I or Type II phenotype provides improved accuracy of classification relative to methods of the prior art. Specifically, reduced background, better resolution, and enhanced signal strength with HD5 straining relative to methods of the prior art (i.e., lysozyme staining) improves classification. These features also allow for automation of the method to classify a subject based on HD5 protein and reduced amount of tissue (i.e., biopsy vs. resection) needed for the method to classify a subject based on HD5 protein. In an embodiment, the method to classify a subject with Crohn's disease as having a Type I or Type II phenotype based on HD5 protein in a biological sample from the subject is about 25% more accurate than previous methods of classifying a subject. For example, the method to classify a subject with Crohn's disease as having a Type I or Type II phenotype based on HD5 protein in a biological sample from the subject is about 25%, about 24%, about 23%, about 23%, about 21%, about 20%, about 19%, about 18%, about 17%, about 16%, or about 15% more accurate than previous methods of classifying a subject. In certain embodiments, the previous method of classifying a subject comprises detecting lysozyme.

In still yet another aspect, the disclosure provides a method to predict the likelihood that a subject will have a reoccurrence of Crohn's disease following surgery. The method generally comprises: (a) detecting an HD5 protein in the biological sample; (b) identifying the number of cells in the biological sample with normal or abnormal granule morphology, wherein abnormal includes disordered, diminished, diffuse, excluded and enlarged granule morphology; (c) classifying the subject as having a Type II phenotype if <20% of cells have abnormal granule morphology or having a Type I phenotype if ≥20% of cells have abnormal granule morphology; and (d) identifying the subject as more likely to recur following surgery if the Type I phenotype is detected. In an embodiment, the subject having the Type I phenotype is about 40% more likely to recur 30 months following surgery relative to a subject having the Type II phenotype. In still another embodiment, the HD5 protein is detected using automated detection. In a further embodiment, the HD5 protein is detected using an autostainer. In still another embodiment, the biological sample is a tissue biopsy.

In other aspects, the disclosure provides a method of determining treatment of a subject with Crohn's disease. The method generally comprises: (a) detecting HD5 protein in the biological sample; (b) identifying the number of cells in the biological sample with normal or abnormal granule morphology, wherein abnormal includes disordered, diminished, diffuse, excluded and enlarged granule morphology; (c) classifying the subject as having a Type II phenotype if <20% of cells have abnormal granule morphology or having a Type I phenotype if ≥20% of cells have abnormal granule morphology; and (d) treating a Type I phenotype subject more aggressively. In an embodiment, the cells are Paneth cells. In another embodiment, HD5 protein is detected using immunofluorescence. In still another embodiment, the HD5 protein is detected using automated detection. In a further embodiment, the HD5 protein is detected using an autostainer. In still another embodiment, the biological sample is a tissue biopsy. Non-limiting examples of treatment for Crohn's disease include the use of medications such as oral 5-aminosalicylates including sulfasalazine (Azulifidine) and mesalamine (Asacol, Delzicol, Pentasa, Lialda, Apriso), corticosteroids such as prednisone, budesonide (Entocort EC), immune system suppressors such as azathioprine (Imuran), mercaptopurine (Purinethol), infliximab (Remicade), adalimumab (Humira), certolizumab pegol (Cimzia), methotrexate (Rehumatrex), cyclosporine (Gengraf, Neoral, Sandimmune), tacrolimus (Astagraf XL, Hecoria), Natalizumab (Tysabri), vedolizumab (Entyvio), and ustekinumab (Stelara), antibiotics such as metronidazole (Flagyl) and ciprofloxacin (Cipro), and other medications such as anti-diarrheals, pain relievers, iron supplements, vitamin B-12 shots and calcium and vitamin D supplements, alterations in diet and nutrition including enteral nutrition and parenteral nutrition, and/or surgical procedures to repair or remove affected portions of the GI tract.

In another aspect, the disclosure provides a method for monitoring Crohn's disease in a subject. In such an embodiment, a method to classify a subject is performed at one point in time. Then, at a later time, the method to classify a subject may be performed to determine the change in Type I and Type II phenotype over time. For example, the method to classify a subject may be performed on the same subject days, weeks, months, or years following the initial use of the method to classify a subject. Accordingly, the method to classify a subject may be used to follow a subject over time to determine when the risk of progressing to more severe disease is high thereby requiring more aggressive treatment. Additionally, the method to classify a subject may be used to measure the rate of disease progression. For example, a progression from Type II phenotype to Type I phenotype may indicate disease progression. Early assessment of the risk of disease progression in the subject may reduce the development and/or progression of symptoms associated with Crohn's disease by enabling improved interventions or enabling earlier interventions.

Additionally, a method for monitoring Crohn's disease in a subject may be used to determine the response to treatment. As used herein, subjects who respond to treatment are said to have benefited from treatment. For example, a method to classify a subject may be performed on the biological sample of the subject prior to initiation of treatment. Then, at a later time, a method to classify a subject may be used to determine the response to treatment over time. For example, a method to classify a subject may be performed on the biological sample of the same subject days, weeks, months, or years following initiation of treatment. Accordingly, a method to classify a subject may be used to follow a subject receiving treatment to determine if the subject is responding to treatment. If the subject progresses from Type II phenotype to Type I phenotype, then the subject may not be responding to treatment. If subject remains at Type II phenotype or improves from Type I phenotype to Type II phenotype, then the subject may be responding to treatment. These steps may be repeated to determine the response to therapy over time.

In any of the foregoing embodiments, the subject may or may not be diagnosed with Crohn's disease. In certain embodiments, the subject may not be diagnosed with Crohn's disease but is suspected of having Crohn's disease based on symptoms. Non-limiting examples of symptoms of Crohn's disease that may lead to a diagnosis include diarrhea, fever and fatigue, abdominal pain and cramping, bloody stool, mouth sores, reduced appetite and weight loss, perianal disease, inflammation of skin, eyes and joints, inflammation of the liver or bile ducts, and/or delayed growth or sexual development (in children). In other embodiments, the subject may not be diagnosed with Crohn's disease but is at risk of having Crohn's disease. Non-limiting examples of risk factors for Crohn's disease include age (i.e., young), ethnicity (i.e., white and Eastern European Jewish descent), family history, smoking, non-steroidal anti-inflammatory medication (i.e., ibuprofen, naproxen sodium, diclofenac sodium), and/or residence (i.e., urban area, industrialized country). In other embodiment, the subject has no symptoms and/or no risk factors for Crohn's disease. Methods of diagnosing Crohn's disease are known in the art. Non-limiting examples of methods of diagnosing Crohn's disease include blood tests for anemia or infection, fecal occult blood test, colonoscopy or endoscopy with biopsy, flexible sigmoidoscopy, computerized tomography (CT), magnetic resonance imaging (MRI), capsule endoscopy, double-balloon endoscopy, and/or small bowel imaging.

Suitable subjects include, but are not limited to, a human, a livestock animal, a companion animal, a lab animal, and a zoological animal. In one embodiment, the subject may be a rodent, e.g., a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In an embodiment, the animal is a laboratory animal. Non-limiting examples of a laboratory animal may include rodents, canines, felines, and non-human primates. In certain embodiments, the animal is a rodent. In a preferred embodiment, the subject is human.

(a) Biological Sample

As used herein, the term "biological sample" refers to a sample obtained from a subject. Any biological sample containing tissue from the small intestine or colon is suitable. Numerous types of biological samples are known in the art. Suitable biological samples may include, but are not limited to, tissue samples. In some embodiments, the biological sample is a tissue sample such as a tissue biopsy. In other embodiments, the biological sample is a tissue sample such as resected tissue. The tissue may be fixed, embedded in paraffin or plastic, and sectioned, or the tissue may be frozen and cryosectioned. In a specific embodiment, the tissue is from the small intestine.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that the HD5 protein can be accurately detected and the amount measured according to the disclosure.

In some embodiments, a single sample is obtained from a subject to detect HD5 protein in the sample. Alternatively, HD5 protein may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time.

When more than one sample is collected from a subject over time, samples may be collected every 1, 2, 3, 4, 5, 6, 7, 8, 9, 10, 11, 12 or more days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days. In still other embodiments, samples are collected a month apart, 3 months apart, 6 months apart, 1 year apart, 2 years apart, 5 years apart, 10 years apart or more.

(b) Detecting HD5 Protein

Once a sample is obtained, it is processed in vitro to detect and determine the pattern of HD5 protein expression. All suitable methods for detecting and determining the pattern of HD5 protein expression known to one of skill in the art are contemplated within the scope of the invention. Non-limiting examples of suitable methods to detect and determine the pattern of protein expression may include epitope binding agent-based methods. The pattern of HD5 protein expression is used to determine granule morphology in Paneth cells. Based on the granule morphology, the Paneth cell may be classified as normal or abnormal.

In some embodiments, the method to detect an amount of protein expression is an epitope binding agent-based method. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of binding to a target gene protein. Nucleic acids may include RNA, DNA, and naturally occurring or synthetically created derivative.

As used herein, the term "antibody" generally means a polypeptide or protein that recognizes and can bind to an epitope of an antigen. An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody and a humanized antibody. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; which is herein incorporated by reference in its entirety).

As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in it binding to a polypeptide, may be synthesized and/or identified by in vitro evolution methods. Means for preparing and characterizing aptamers, including by in vitro evolution methods, are well known in the art (See, e.g., U.S. Pat. No. 7,939,313; which is herein incorporated by reference in its entirety).

In general, an epitope binding agent-based method of detecting and determining the amount of protein expression comprises contacting a sample comprising a polypeptide with an epitope binding agent specific for the polypeptide under conditions effective to allow for formation of a complex between the epitope binding agent and the polypeptide.

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen present. After this time, the complex will be washed and the complex may be detected by any method well known in the art. Methods of detecting the epitope binding agent-polypeptide complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, and luciferase). In a specific embodiment, an HD5 epitope binding agent comprises a fluorophore.

Alternatively, an HD5 epitope binding agent do not comprise a label, but instead is contacted with a secondary epitope binding agent that specifically recognizes the HD5 epitope binding agents and comprises a label. For example, an HD5 antibody is contacted with a secondary antibody conjugated to a fluorophore that specifically recognizes the constant region of the HD5 antibody.

Methods of detecting an epitope binding agent-polypeptide complex based on the detection of a label or marker are well known in the art.

In a specific embodiment, the epitope binding agent-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art. In a specific embodiment, the IHC is immunofluorescence.

A benefit of detecting HD5 via immunofluorescence is that the detection of HD5 may be automated. For example, an autostainer may be used to automatically detect HD5. Non-limiting examples of commercially available autostainers include Leica, Lab Vision, Dako, and Ventana. The use of an autostainer allows for the detection of HD5 in a CLIA-certified laboratory.

In addition to HD5, a control marker may be detected. For example, nuclei may be detected. More specifically, a nuclear pore protein may be detected. The inventors have shown that cells comprising HD5 (i.e., abnormal cells) do not have a defect in the morphologic pattern of the nuclei. Thus detection of nuclei may facilitate cell counting to aid in determining the percentage of abnormal cells.

(c) Classifying Based on HD5

Figure 16:
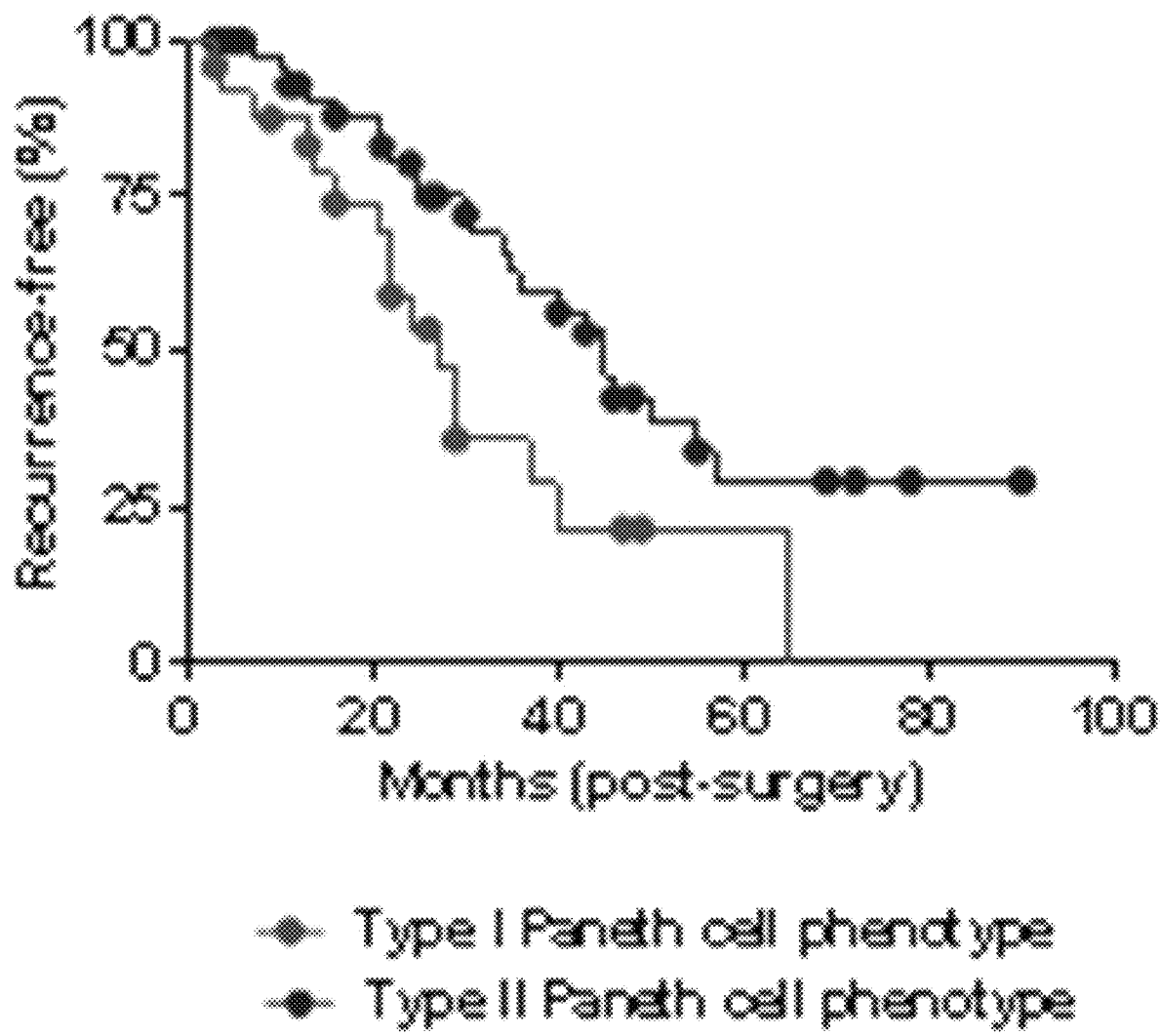
FIG. 16 depicts a diagram of Paneth cell cytoplasmic antimicrobial granule morphology classification under HD5 immunofluorescence. The Paneth cell HD5 classification can be categorized into normal (D0) and 5 abnormal (D1-D5) categories. D1: disordered; D2: diminished; D3: diffuse; D4: excluded; and D5: enlarged.

In certain embodiments, a cell is classified as normal or abnormal based on granule morphology. The pattern of HD5 protein expression is used to determine granule morphology in cells. Specifically, a cell is a Paneth cell. A cell is classified as normal if HD5 protein demonstrates normal granule morphology or abnormal if HD5 protein demonstrates one of 5 abnormal granule morphologies. See, for example, FIG. 16 where D0 is normal and disordered (D1), diminished (D2), diffuse (D3), excluded (D4), and enlarged (D5) are abnormal. A cell may be classified as disordered (also referred to as D1) if there is abnormal distribution and size of the HD5 granules. Additionally, a cell may be classified as diminished (also referred to as D2) if there are less than or equal to ten HD5 granules. Further, a cell may be classified as diffuse (also referred to as D3) if there is a smear of HD5 within the cytoplasm with no recognizable granules. Still further, a cell may be classified as excluded (also referred to as D4) if the majority of HD5 granules do not contain stainable material. Lastly, a cell may be classified as enlarged (also referred to as D5) which are HD5 megagranules. Any one of the 5 abnormal categories may be used to classify a cell as abnormal.

In other embodiments, a subject is classified as having a Type I phenotype or Type II phenotype based on the number of cells detected with abnormal granule morphology. The phenotype is determined by the percentage of total abnormal cells in the biological sample. A subject is classified as having a Type I phenotype if 20% of cells have abnormal granule morphology. Alternatively, a subject is classified as having a Type II phenotype if <20% of cells have abnormal granule morphology.

In further embodiments, a subject is classified as having a poor prognosis or good prognosis based on the phenotype detected. A subject is classified as having a poor prognosis if the Type I phenotype is detected. Alternatively, a subject is classified as having a good prognosis if the Type II phenotype is detected. A subject with a poor prognosis has an increased likelihood of disease recurrence after surgery. In an embodiment, a subject with a poor prognosis may have about a 100% likelihood of recurrence within 70 months after surgery. For example, a subject with a poor prognosis may have about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% likelihood of recurrence within about 70 months after surgery. In another embodiment, a subject with a poor prognosis may have about a 75% likelihood of recurrence within about 40 months after surgery. For example, a subject with a poor prognosis may have about a 74%, 73%, 72%, 71%, 70%, 69%, 68%, 67%, 66%, 65%, 64%, 63%, 62% 61%, 60%, 59%, 58%, 57%, 56%, 55%, 54%, 53%, 52%, 51% or 50% likelihood of recurrence within about 40 months after surgery. In still another embodiment, a subject with a poor prognosis may have about a 50% likelihood of recurrence within about 30 months after surgery. For example, a subject with a poor prognosis may have about a 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, or 25% likelihood of recurrence within about 30 months after surgery. In still yet another embodiment, a subject with a poor prognosis may have about a 25% likelihood of recurrence within about 20 months after surgery. For example, a subject with a poor prognosis may have about a 24%, 23%, 22%, 21%, 20%, 19%, 18%, 17%, 16%, 15%, 14%, 13%, 12%, 11%, or 10% likelihood of recurrence within about 20 months after surgery.

In additional embodiments, a subject is classified as having an increased likelihood of recurrence or a reduced likelihood of recurrence based on the phenotype detected. A subject is classified as having an increased likelihood of recurrence if the Type I phenotype is detected. Alternatively, a subject is classified as having a reduced likelihood of recurrence if the Type II phenotype is detected. In an embodiment, a subject having the Type I phenotype may be about 15% more likely to recur 20 months following surgery relative to a subject having the Type II phenotype. For example, a subject having the Type I phenotype may be about 10%, 11%, 12%, 13%, 14%, 15%, 16%, 17%, 18%, 19%, or 20% more likely to recur 20 months following surgery relative to a subject having the Type II phenotype. In another embodiment, a subject having the Type I phenotype may be about 40% more likely to recur 30 months following surgery relative to a subject having the Type II phenotype. For example, a subject having the Type I phenotype may be about 30%, 31%, 32%, 33%, 34%, 35%, 36%, 37%, 38%, 39%, 40%, 41%, 42%, 43%, 44%, 45%, 46%, 47%, 48%, 49%, or 50% more likely to recur 30 months following surgery relative to a subject having the Type II phenotype. In still another embodiment, a subject having the Type I phenotype may be about 35% more likely to recur 40 months following surgery relative to a subject having the Type II phenotype. For example, a subject having the Type I phenotype may be about 25%, 26%, 27%, 28%, 29%, 30%, 31%, 32%, 33%, 34%, 35%, 36%, 37%, 38%, 39%, 40%, 41%, 42%, 43%, 44%, or 45% more likely to recur 40 months following surgery relative to a subject having the Type II phenotype. In still yet another embodiment, a subject having the Type I phenotype may be about 35% more likely to recur 60 months following surgery relative to a subject having the Type II phenotype. For example, a subject having the Type I phenotype may be about 25%, 26%, 27%, 28%, 29%, 30%, 31%, 32%, 33%, 34%, 35%, 36%, 37%, 38%, 39%, 40%, 41%, 42%, 43%, 44%, or 45% more likely to recur 60 months following surgery relative to a subject having the Type II phenotype.

A skilled artisan would be able to determine which surgical method is the most appropriate course of action for treatment of Crohn's disease. Non-limiting examples of surgery for Crohn's disease include strictureplasty, resection, and proctocolectomy and colectomy. In a preferred embodiment, the surgical method is resection.

The determination of Paneth cell phenotype may be used to select treatment for subjects. As explained herein, HD5 protein can be used to classify a subject as having a Type I phenotype or Type II phenotype and into groups that might benefit from more aggressive therapy or determine the appropriate treatment for the subject. In an embodiment, a subject classified as having a Type I phenotype may be more aggressively treated. A skilled artisan would be able to determine standard treatment for Crohn's disease versus aggressive treatment for Crohn's disease. Accordingly, the methods disclosed herein may be used to select treatment for subjects with Crohn's disease. The term "treatment" or "therapy" as used herein means any treatment suitable for the treatment of Crohn's disease. Non-limiting examples of treatment for Crohn's disease include the use of medications such as oral 5-aminosalicylates including sulfasalazine (Azulifidine) and mesalamine (Asacol, Delzicol, Pentasa, Lialda, Apriso), corticosteroids such as prednisone, budesonide (Entocort EC), immune system suppressors such as azathioprine (Imuran), mercaptopurine (Purinethol), infliximab (Remicade), adalimumab (Humira), certolizumab pegol (Cimzia), methotrexate (Rehumatrex), cyclosporine (Gengraf, Neoral, Sandimmune), tacrolimus (Astagraf XL, Hecoria), Natalizumab (Tysabri), vedolizumab (Entyvio), and ustekinumab (Stelara), antibiotics such as metronidazole (Flagyl) and ciprofloxacin (Cipro), and other medications such as anti-diarrheals, pain relievers, iron supplements, vitamin B-12 shots and calcium and vitamin D supplements, alterations in diet and nutrition including enteral nutrition and parenteral nutrition, and/or surgical procedures to repair or remove affected portions of the GI tract.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction for Examples 1-5

Crohn's disease (CD) is a form of inflammatory bowel disease (IBD) rooted in environmental triggers of immune dysregulation that occur in genetically susceptible hosts. There is mounting clinical evidence that environmental factors are critical in CD pathogenesis. While environmental factors may play a more significant role in patients who harbor common variants of susceptible genes than those with rare variants, in vivo models have shown that environmental factors are still required to trigger disease even in the case of Mendelian inheritance. However, the exposure and impact of potential environmental factors, and their interplay with host genetics, are difficult to quantify. Therefore, the development of a cellular readout that synthesizes the impact from host genetics and environmental exposures will improve our understanding of pathogenesis and functionally sub-classify CD.

Small intestinal Paneth cells are a candidate biomarker. Paneth cells are secretory epithelial cells important in innate immunity. Their proper function limits enteric pathogens and prevents commensal microbe translocations through the production of a diverse array of antimicrobial peptides and proteins. For example, deletion of Mmp7, which encodes the enzyme critical for processing Paneth cell α-defensins in mice, increases susceptibility to S. typhimurium while engineered expression of human defensin HD5 in mice is protective. In addition, alteration of defensin expression in mouse Paneth cells is associated with alterations in the small intestinal microbiota and subsequent modulation of mucosal immune response. In humans, reduced mRNA expression of alpha defensins have been shown in CD patients with ileal disease, suggesting that the microbiome compositions between CD and non-IBD patients may be different. The interaction between Paneth cells and gut microbiota has been postulated to be one of the key elements of CD pathogenesis. Indeed, several studies have shown that there is reduced microbiome diversity and changes in abundance in certain phyla in CD. In a large cohort of treatment-naive pediatric CD patients, the microbiome contained an increased abundance in specific bacterial families including Enterobacteriaceae, Pasteurellacaea, Veillonellaceae, and Fusobacteriaceae, and decreased abundance in Erysipelotrichales, Bacteroidales, and Clostridiales. Together, these studies suggest that defects in Paneth cells could lead to reduced antimicrobial peptide production, which could result in dysbiosis and ultimately IBD. However, an alternative mechanism has recently been postulated that dysbiosis may precede intestinal inflammation and subsequent Paneth cell dysfunction in genetically susceptible hosts. In a TNFΔARE mouse model, gut dysbiosis led to chronic intestinal inflammation that resulted in loss of Paneth cells. Thus, it is likely that there is a complex cross talk between Paneth cells and the gut microbiota.

Localization and distribution of cytoplasmic granules containing anti-microbial proteins within Paneth cells can be used to subtype CD. Abnormal localization and distribution of antimicrobial peptide-containing cytoplasmic granules within Paneth cells has been observed in association with autophagy defects in mouse models and humans with CD. A subset of adult CD patients with mutations in autophagy-associated CD susceptible genes ATG16L1 and NOD2 has alterations in anti-microbial protein distribution in Paneth cells. These alterations are similar to that seen in mice engineered for decreased expression of the autophagy protein Atg16l1 and infected with murine norovirus. These mice also showed worsened injury in a dextran sodium sulfate-colitis model. Additional candidate genes that are identified as CD susceptible genes that may affect Paneth cells include Xbp1 and Irgm1. Mice deficient in Xbp1 not only showed defective Paneth cells but also intestinal inflammation.

In adult CD patients, the abnormal Paneth cell-enriched phenotype (defined as ≥20%, total Paneth cells showing morphologic defects; herein classified as Type I Paneth cell phenotype) shows an immune activation gene expression signature, consistent with a role of these cells in the initiation of inflammation. Importantly, in adult CD patients, Paneth cell phenotypes strongly correlate with early disease recurrence after resection for CD.

Given the role of Paneth cells in gut homeostasis, we address the central question of whether Paneth cell phenotypes may be associated with specific aspects of mucosal microbiome composition in CD patients. Herein, we report that a CD subtype characterized by enrichment for abnormal Paneth cells correlates with alterations in the mucosal microbiome. The abnormal Paneth cell phenotype and microbiome composition alterations were both associated with profound changes in the expression of a unique set of genes involved in oxidative phosphorylation, suggesting the later as a potential underlying mechanism in the host-microbial interaction in CD.

Figure 1B:
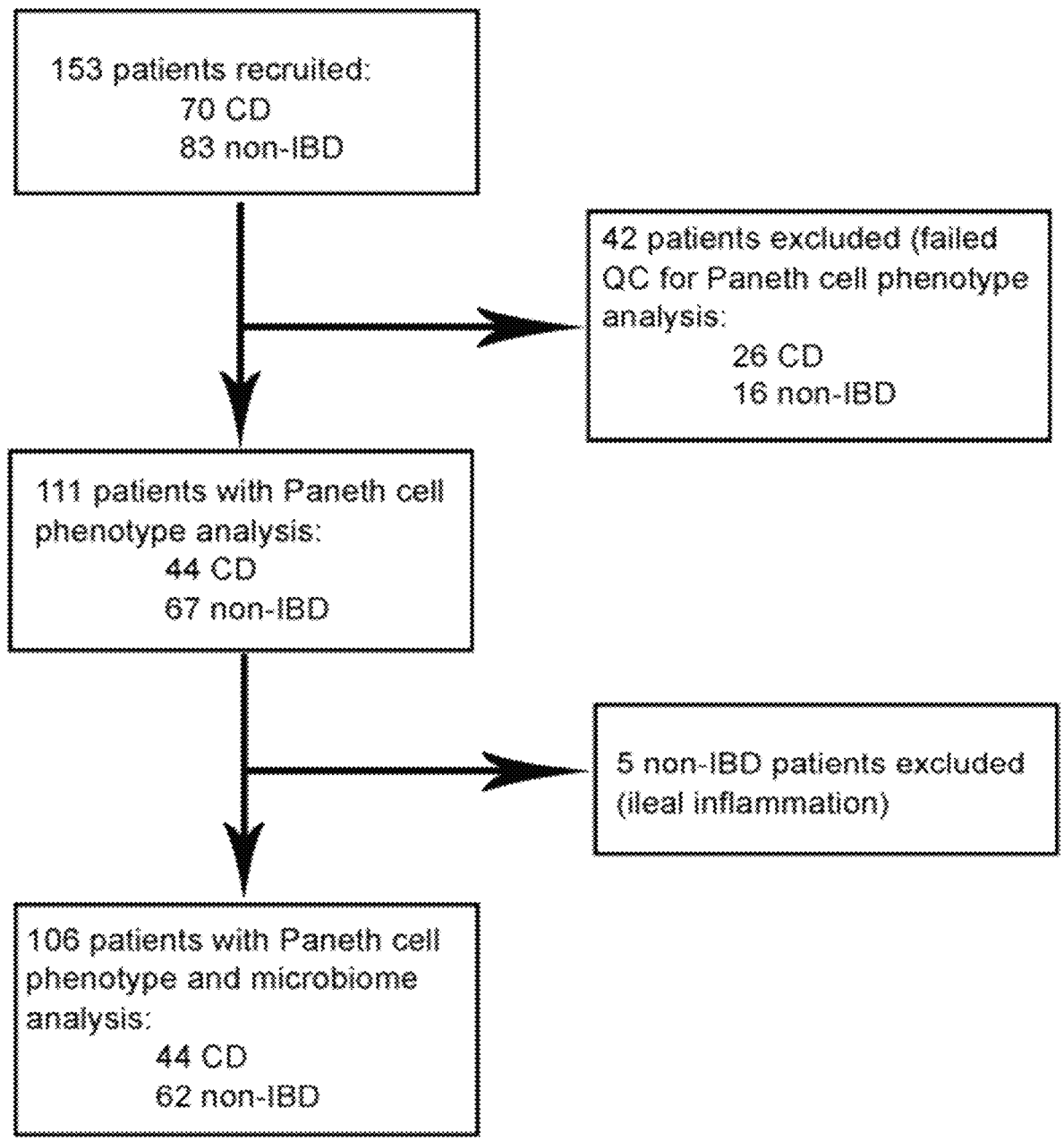
Figure 1C:
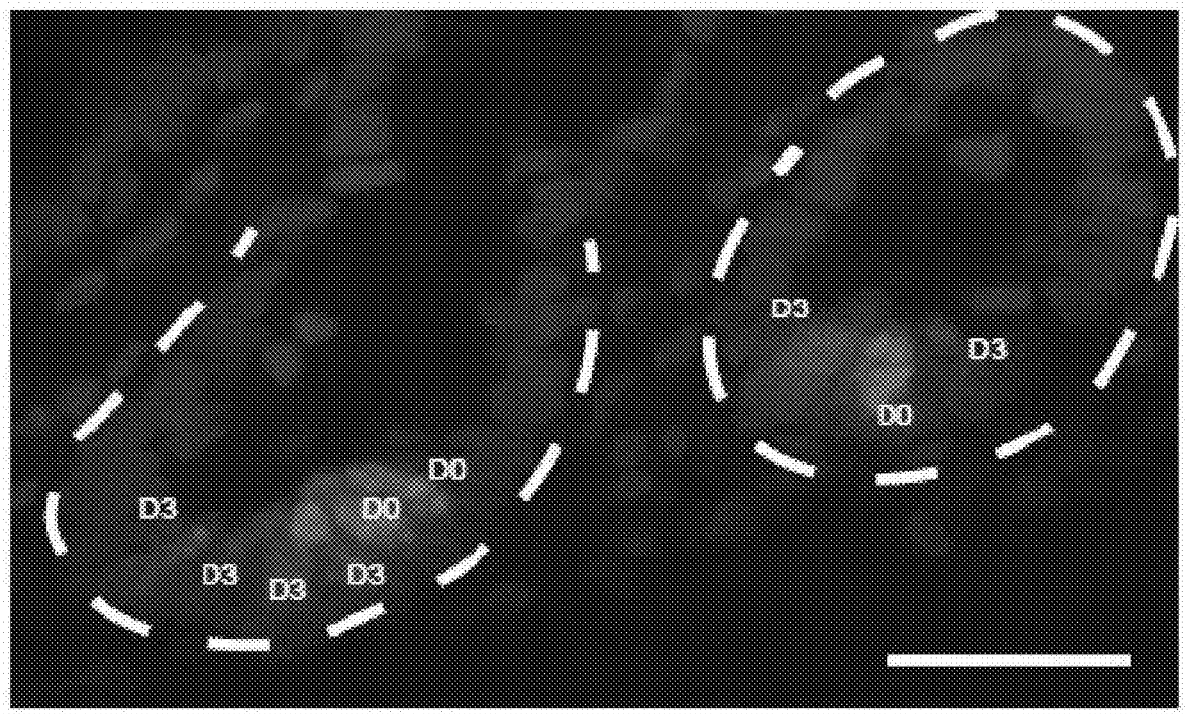
Figure 7A:
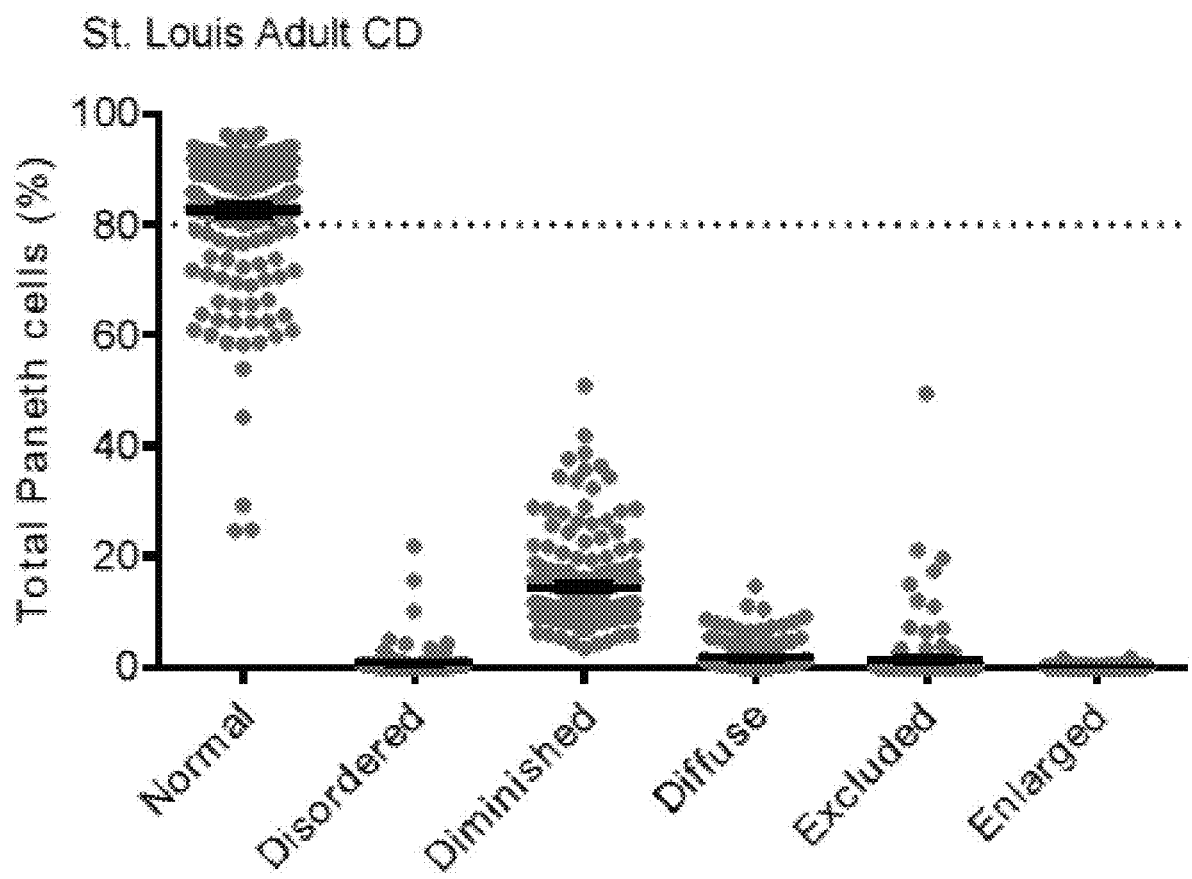
FIG. 7A, FIG. 7B, FIG. 7C and FIG. 7D depicts graphs showing the detailed Paneth cell morphologic classifications of 4 independent CD cohorts.
Figure 7B:
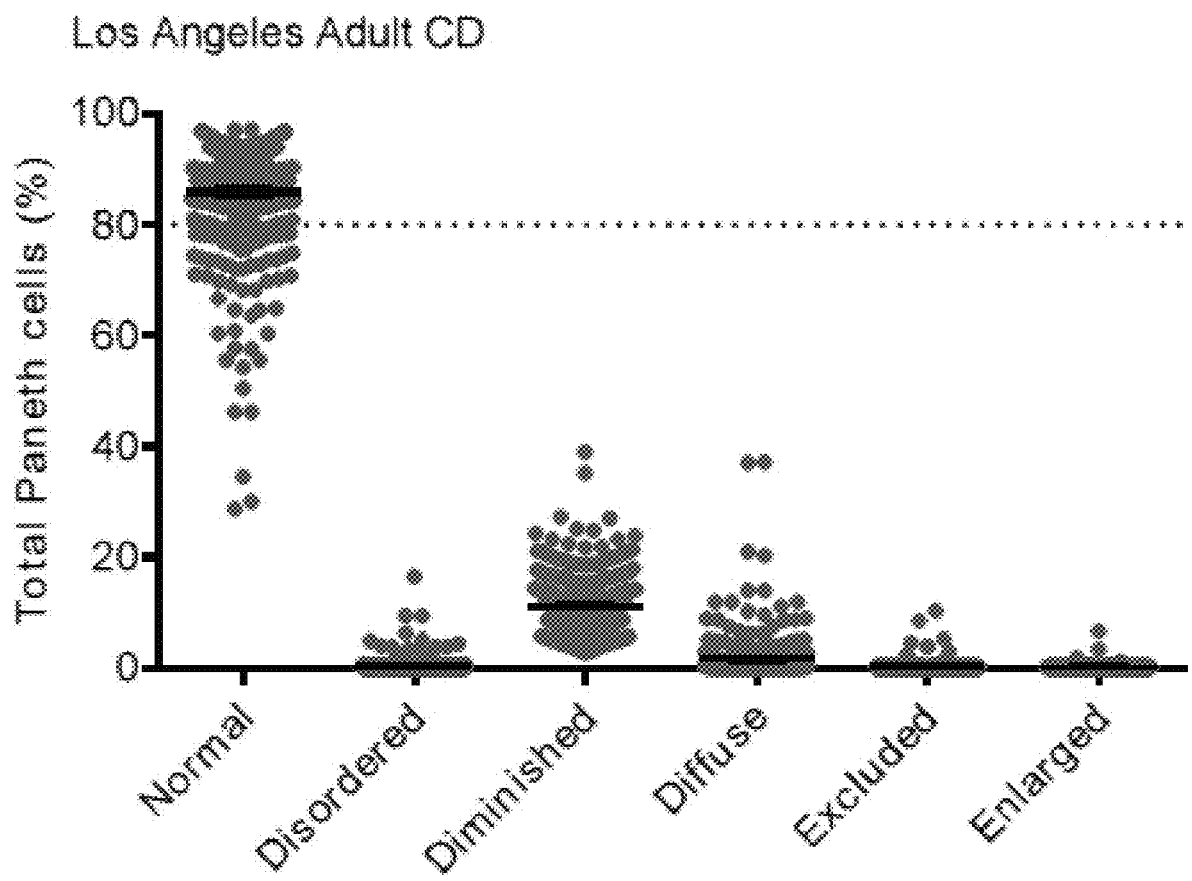
Figure 7C:
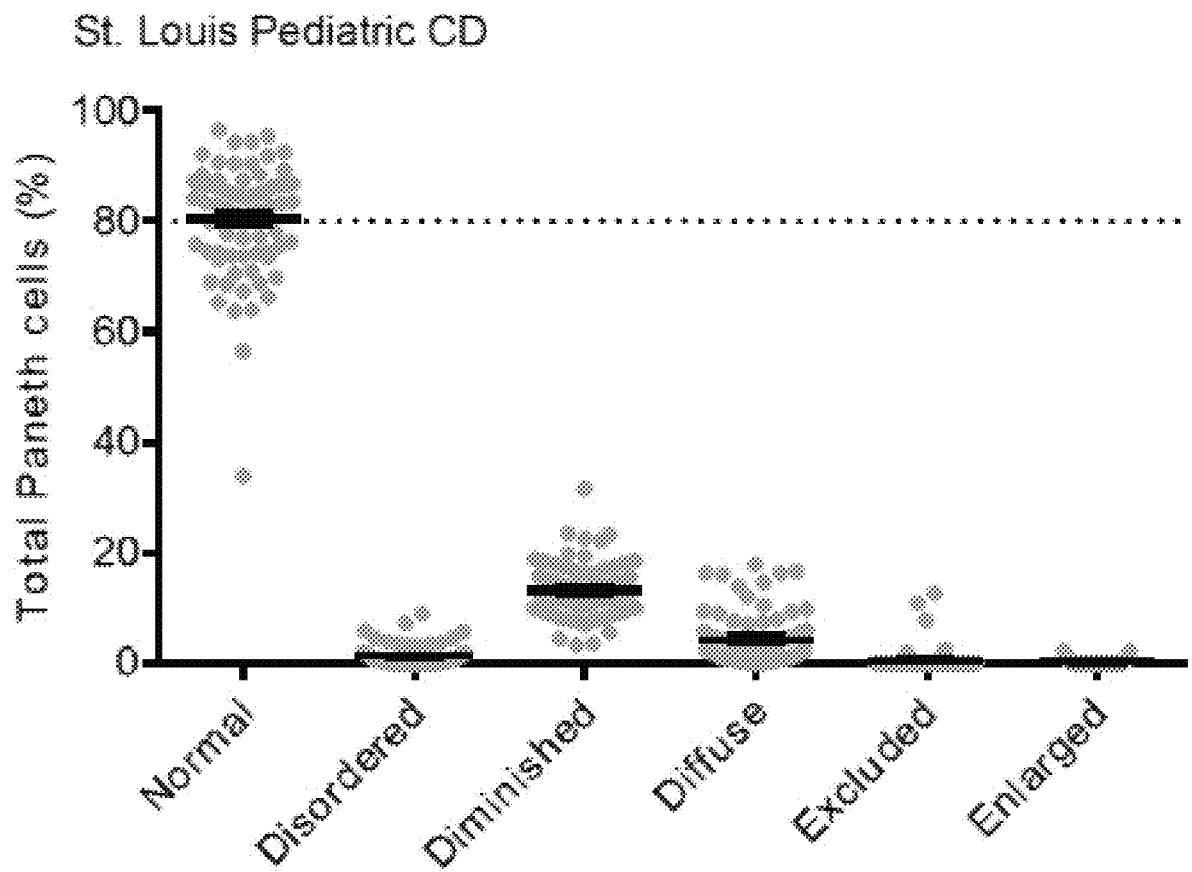
Figure 7D:
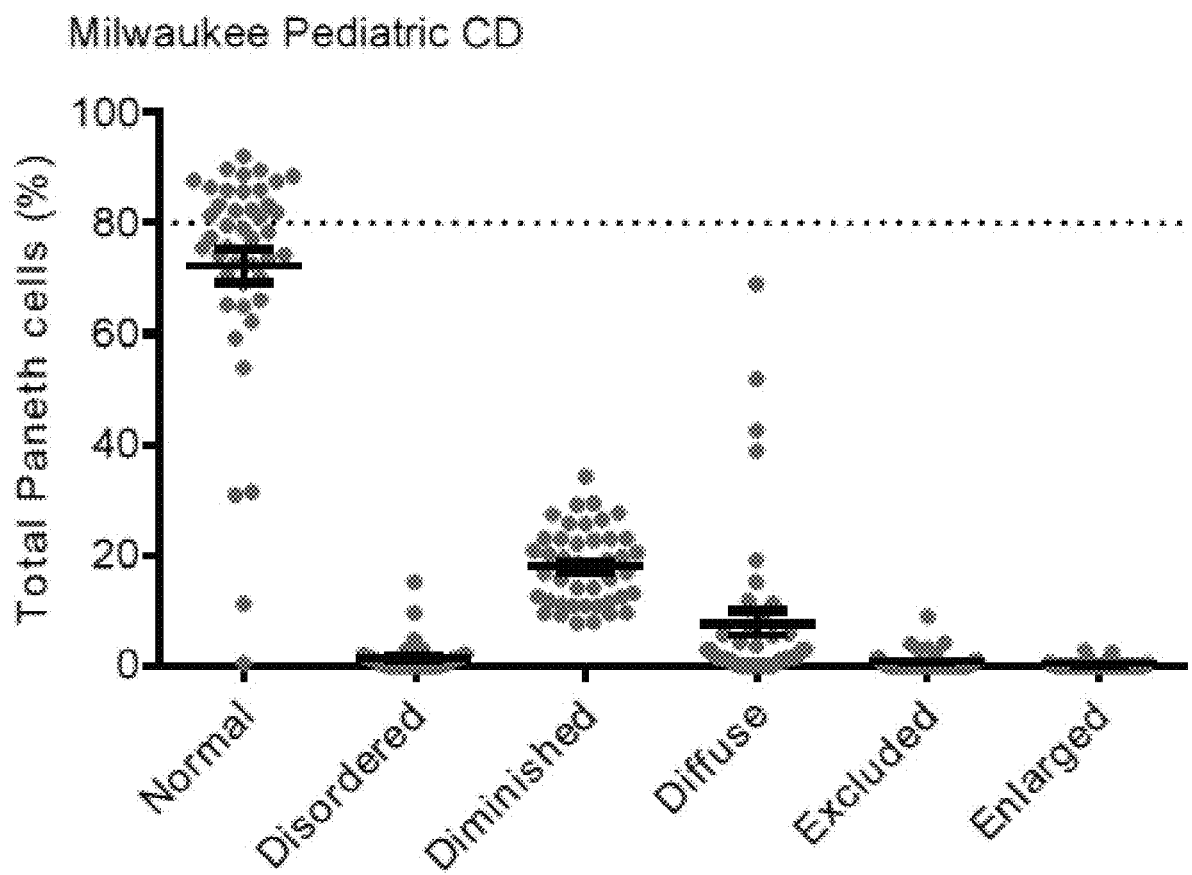

Example 1. Pediatric CD Patients Showed Higher Prevalence of Type I Paneth Cell Phenotype than Adult CD Patients We previously analyzed two cohorts of adult CD resection cases from St. Louis (n=170) and Los Angeles (n=361) (FIG. 1A and FIG. 7A). Prevalence of the Type I Paneth cell phenotype (defined as ≥20%, abnormal Paneth cells) was 26% and 19%, respectively (FIG. 1A, FIG. 7A, and FIG. 7B). In addition, we also analyzed a cohort of pediatric resection cases from St. Louis (n=73) and found that the prevalence of the Type I Paneth cell phenotype in this cohort was much higher (40%; FIG. 1A and FIG. 7C). To investigate the biological relevance of the Paneth cell phenotype in pediatric CD, we recruited and analyzed an independent, prospectively-collected pediatric cohort (Milwaukee; FIG. 1A and FIG. 1B, and Table 1). For this part of the study, multiple mucosal biopsies were obtained for analysis of Paneth cell phenotype, microbiome and host mucosal transcriptome. We previously showed that biopsy samples can be used to accurately determine Paneth cell phenotypes independent of active inflammation. The prevalence of the Type I Paneth cell phenotype in CD patients was 52% in this cohort (n=44; FIG. 1A and FIG. 7D). The combined pediatric cohorts showed a significantly higher percentage of Type I Paneth cell phenotype as compared to the combined adult cohorts (P<0.0001). The approximately 50:50 split of Paneth cell phenotypes in the Milwaukee cohort facilitated additional analysis of microbiome and transcriptome. A representative Paneth cell lysozyme immunofluorescence is shown in FIG. 1C.

Figure 8A:
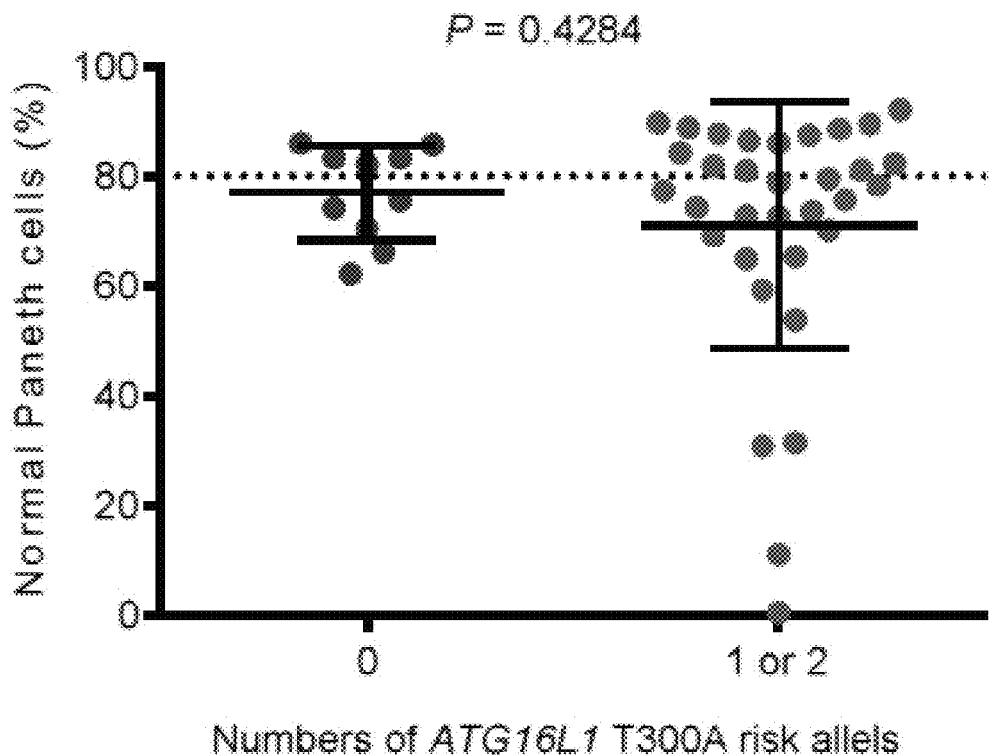
FIG. 8A, FIG. 8B and FIG. 8C depict graphs showing that ATG16L1 T300A and NOD2 risk alleles did not correlate with Paneth cell phenotype in pediatric CD patients.
Figure 8B:
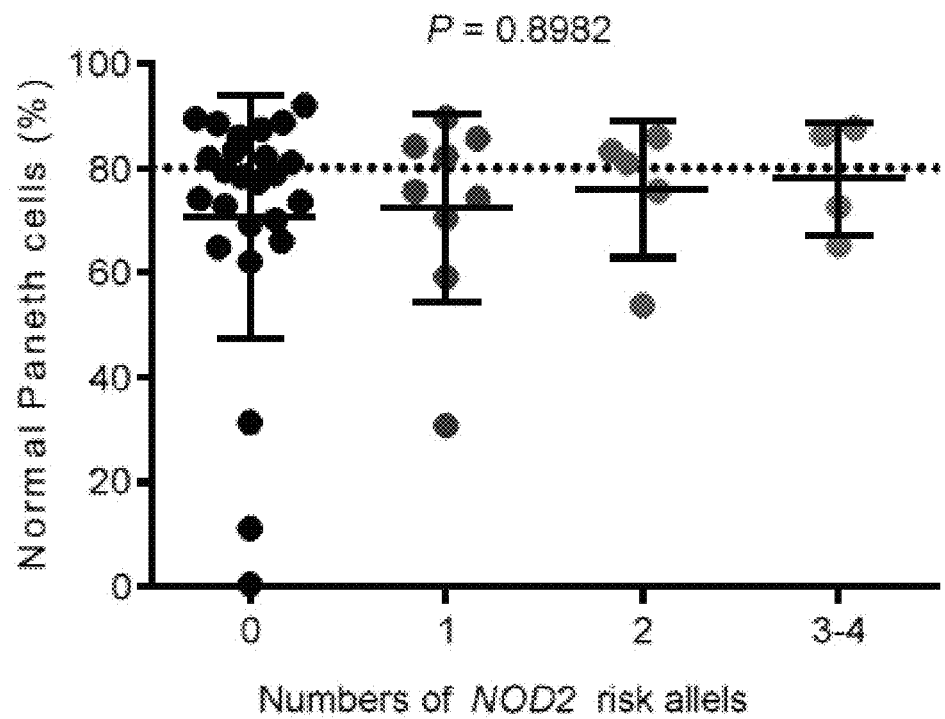
Figure 8C:
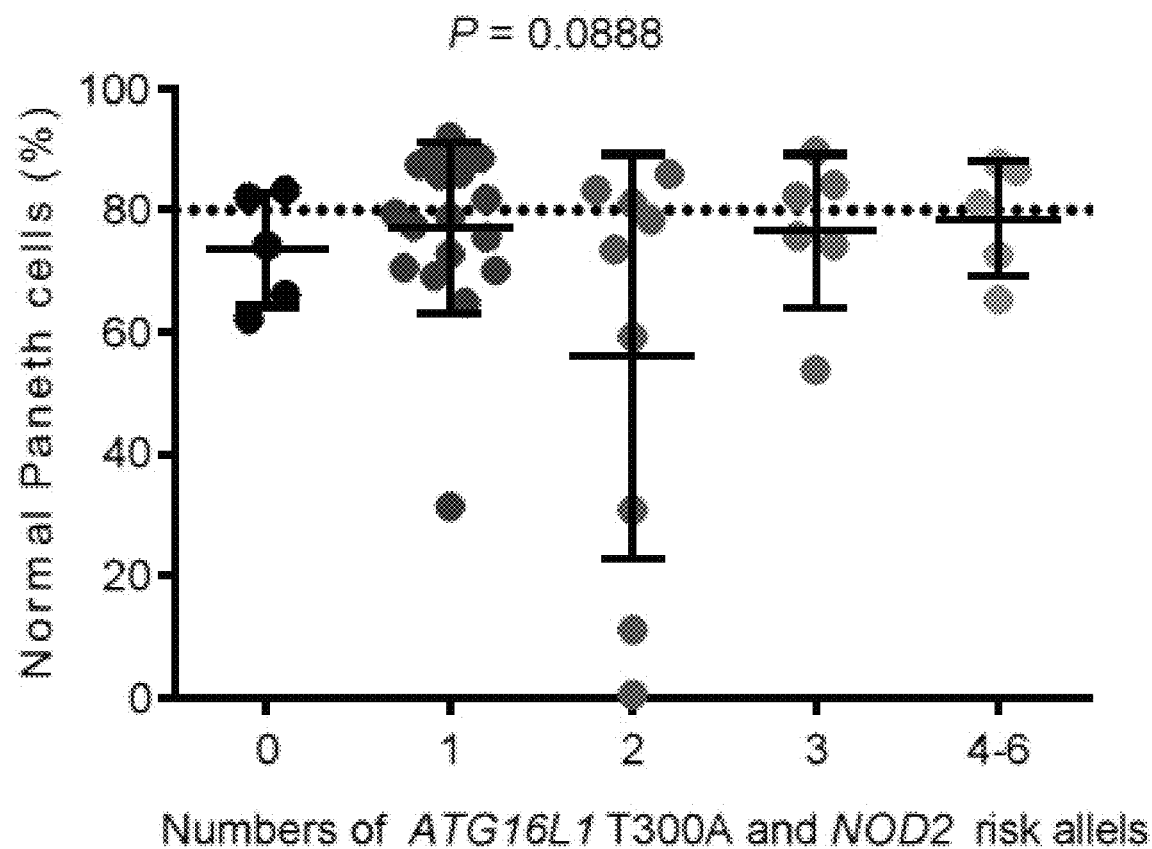

Example 2. Paneth Cell Phenotype Did not Correlate with Genotypes in Pediatric CD We correlated the degree of Paneth cell defect (percentage of Paneth cells with normal morphology) with numbers of ATG16L1 T300A or NOD2 risk alleles. As shown in FIG. 8A and FIG. 8B, neither the numbers of risk alleles of ATG16L1 T300A nor NOD2 correlated with Paneth cell phenotype. Likewise, neither the sum total of ATG16L1 T300A nor NOD2 risk alleles correlated with Paneth cell phenotype (FIG. 8C). This suggests that in this population of pediatric CD patients, environmental factor(s) may play a more significant role in modulating Paneth cell function.

Figure 2A:
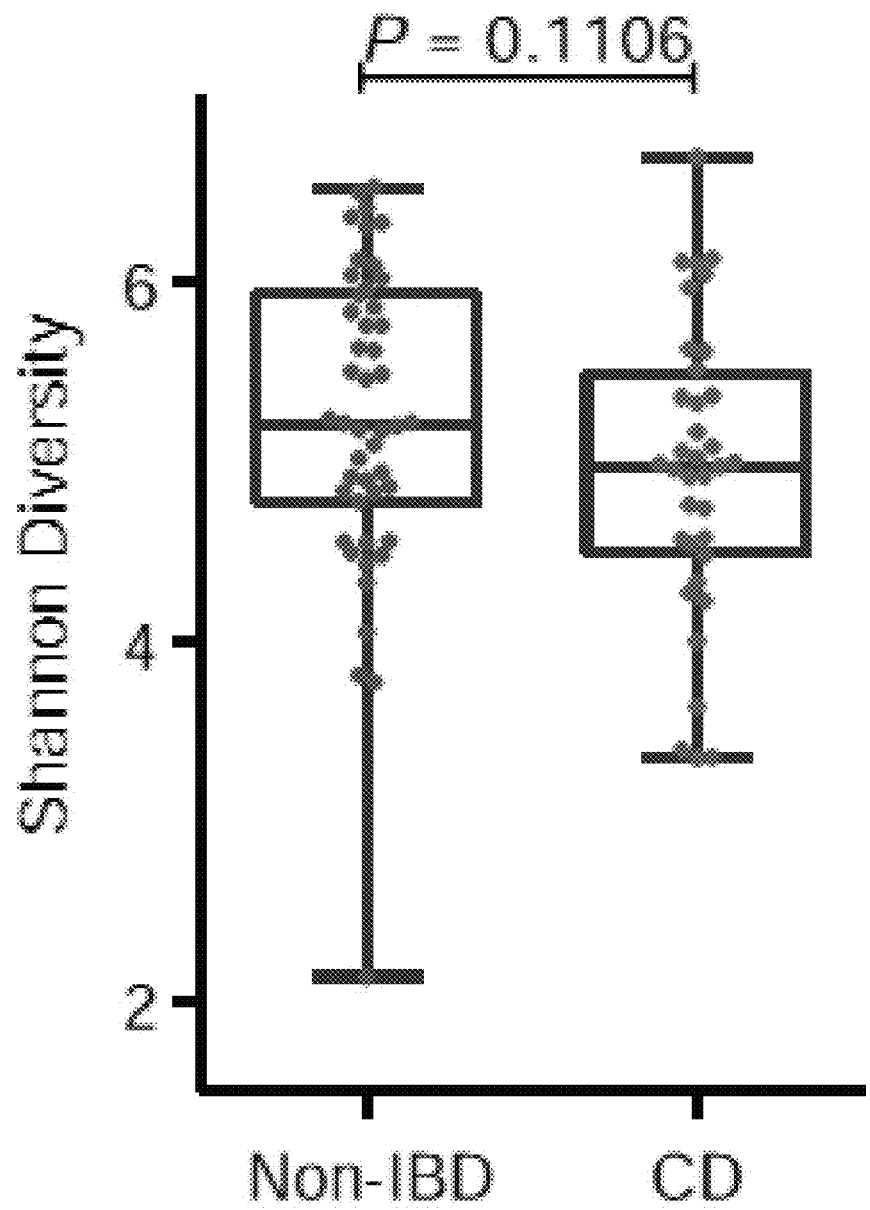
FIG. 2A, FIG. 2B, FIG. 2C, and FIG. 2D depict graphs showing the mucosal microbiome of pediatric CD and non-IBD patients (Milwaukee cohort).
Figure 2B:
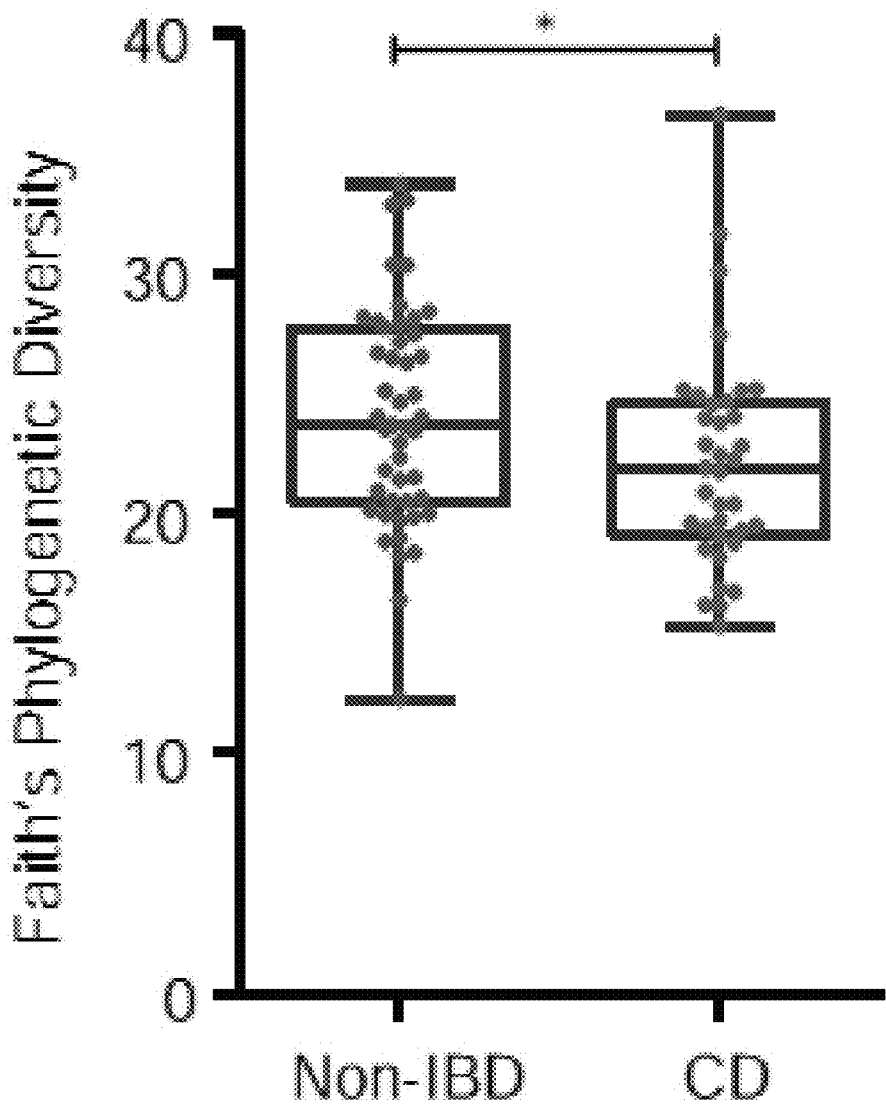
Figure 2C:
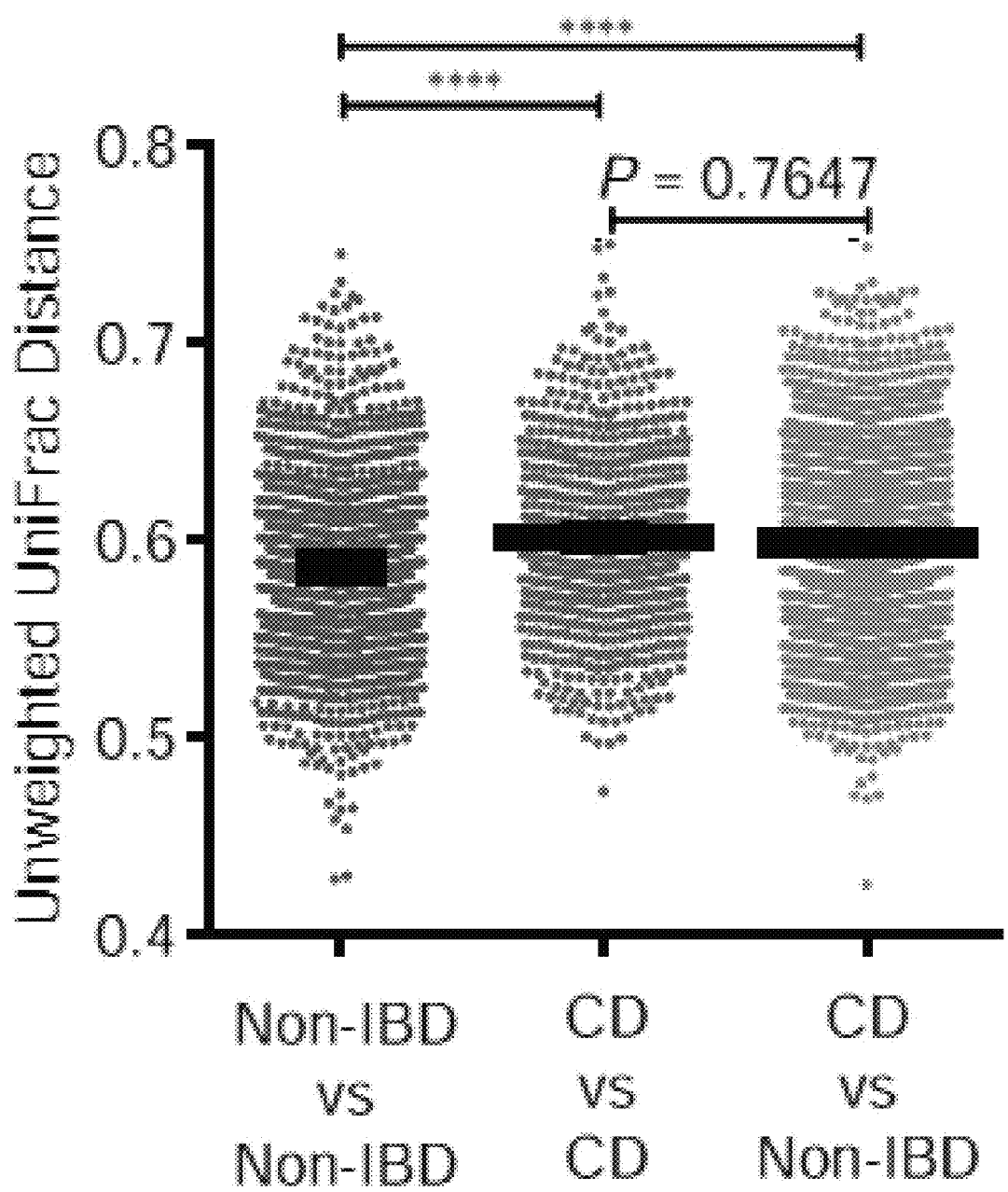
Figure 2D:
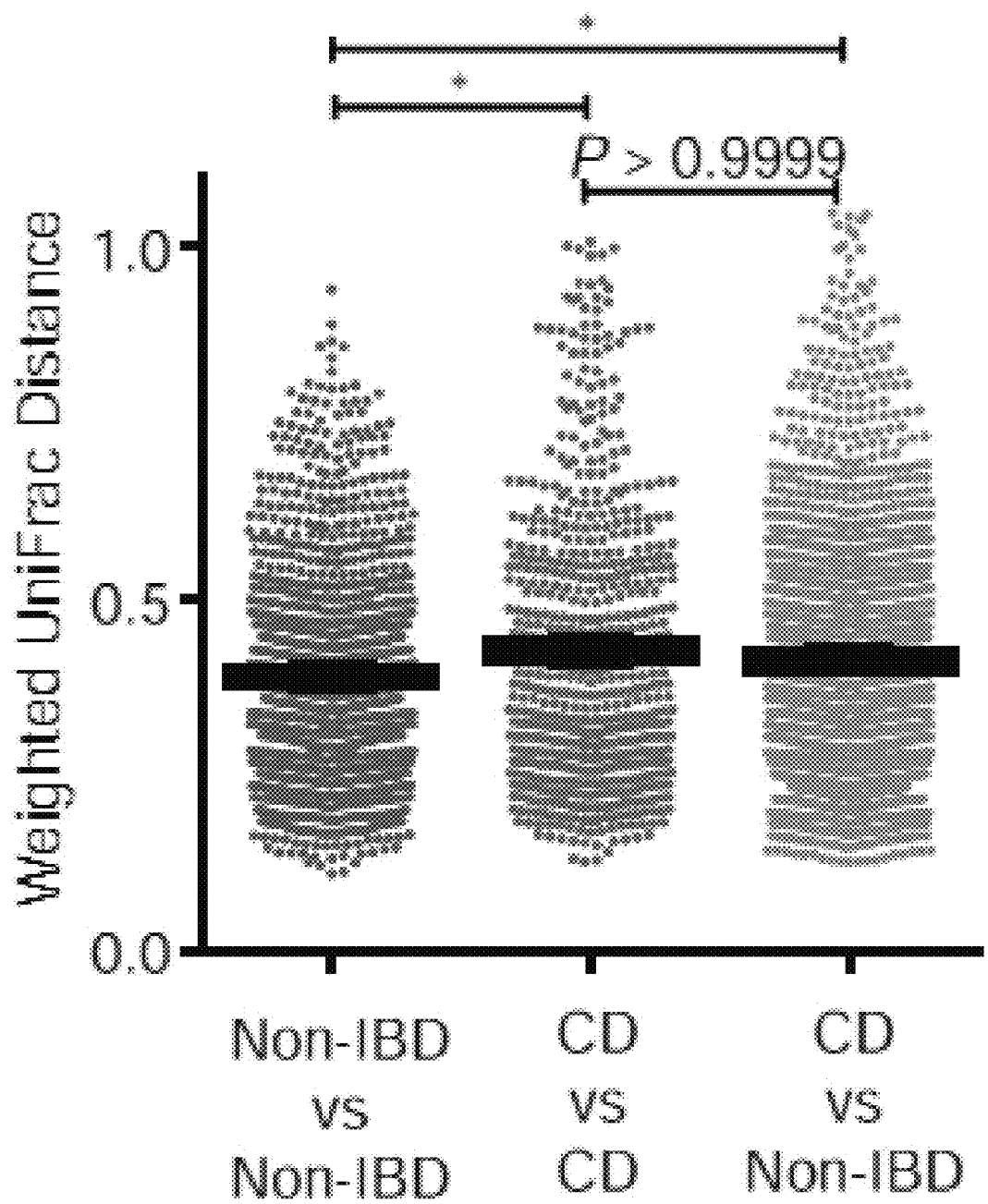
Figure 9A:
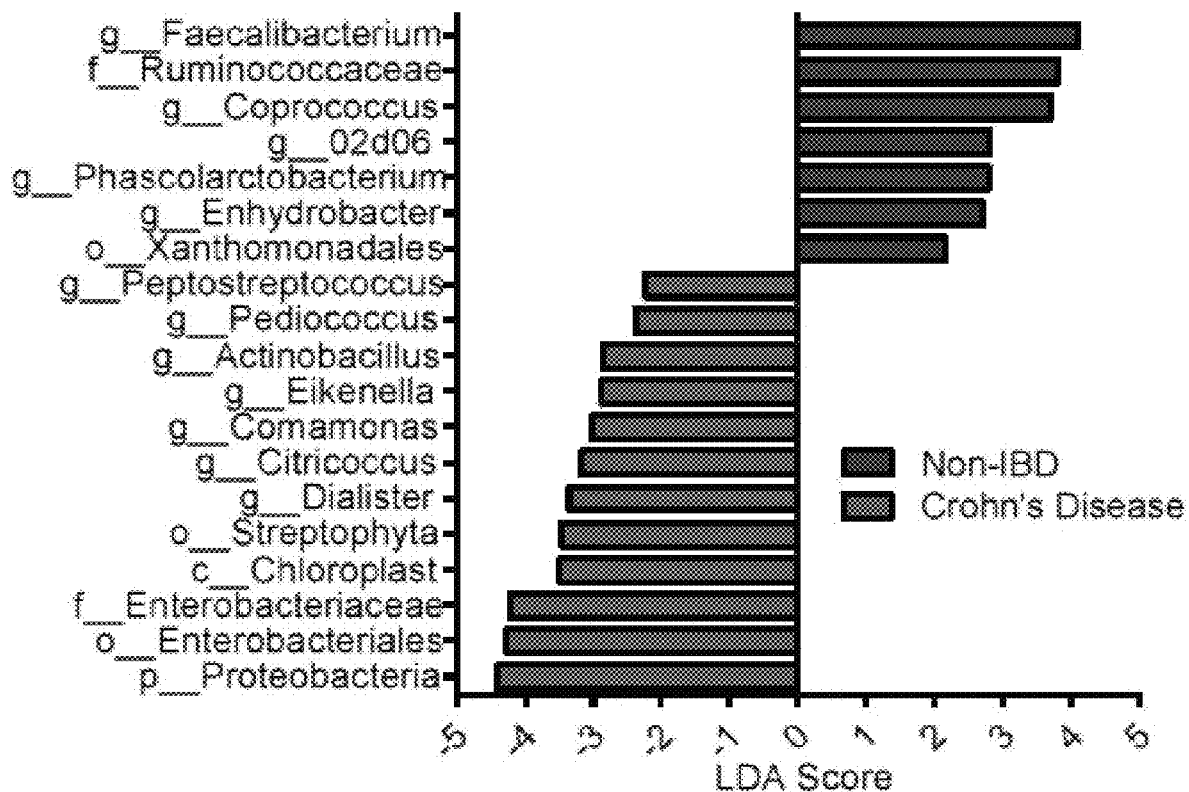
FIG. 9A, FIG. 9B, and FIG. 9C depict graphs and a cladograph showing that different microbial compositions between CD and non-IBD patients.
Figure 9B:
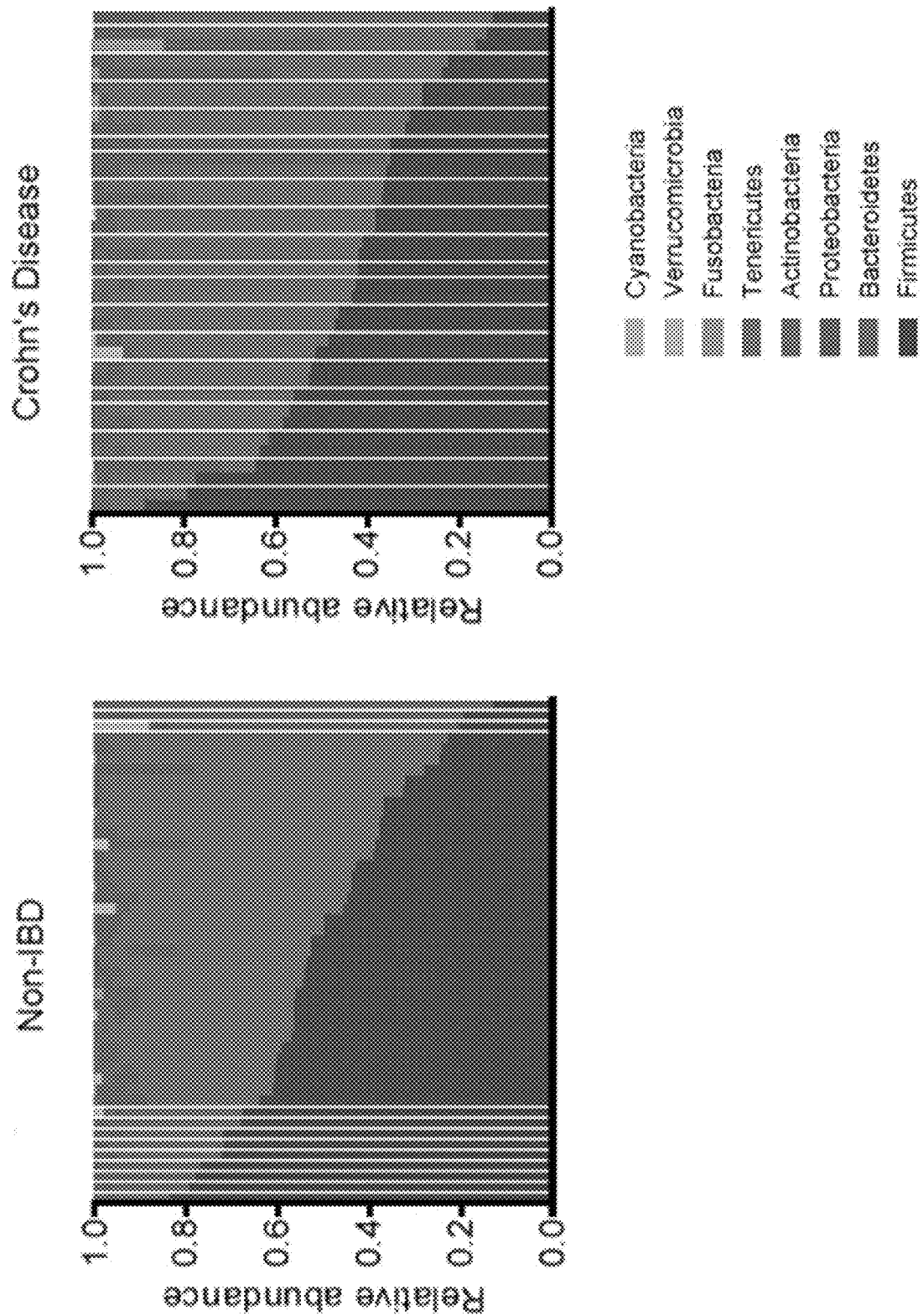
Figure 9C:
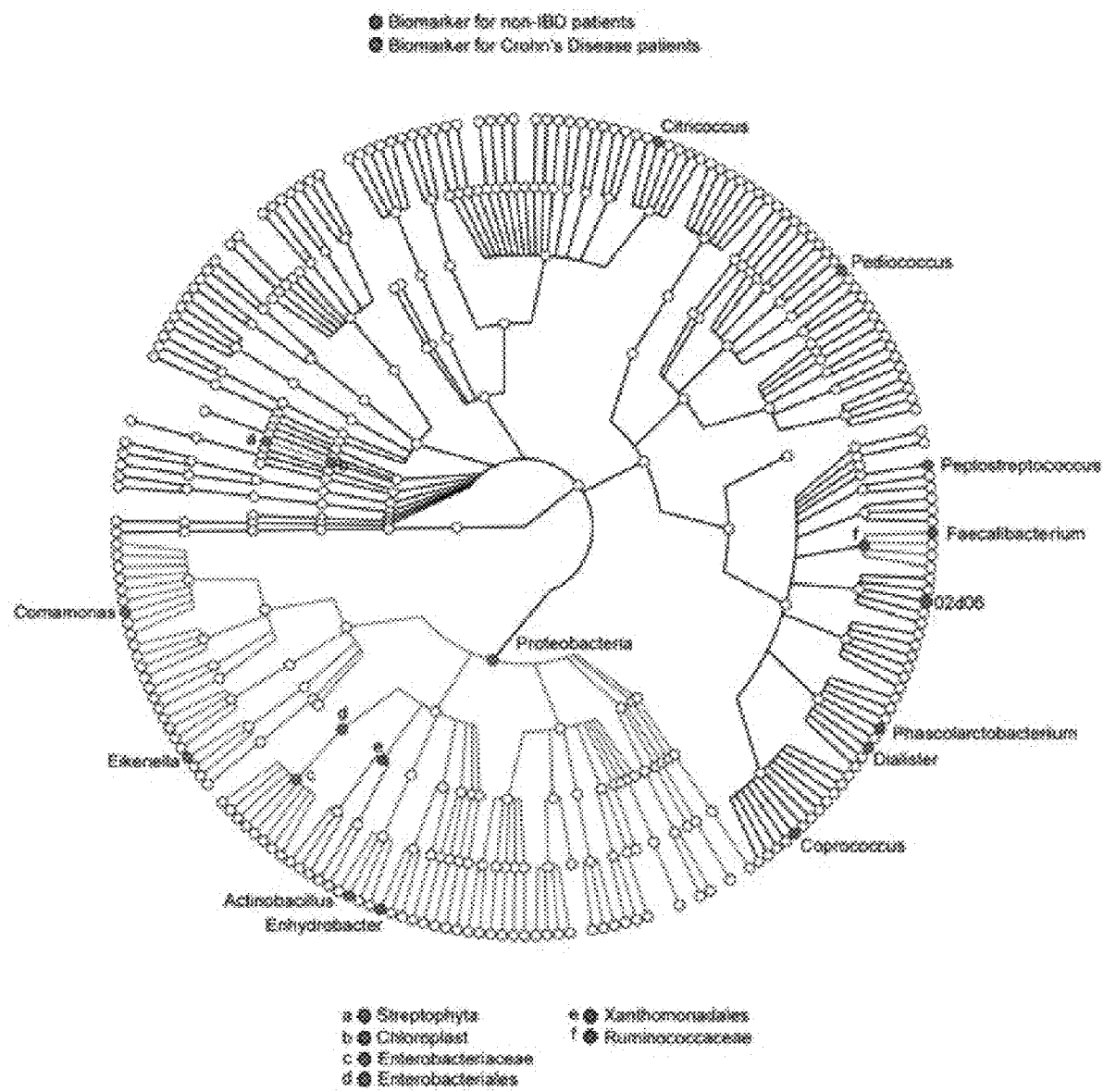

Example 3. Characterization of the Ileal Mucosal Microbiome in Pediatric CD Patients 16S rRNA sequencing of ileal biopsies showed that the mucosally-associated bacteria from pediatric CD patients had reduced alpha diversity (Faith's phylogenetic diversity) compared to non-IBD patients (FIG. 2A and FIG. 2B). In addition, by examining the beta diversity, we found that microbial communities were more dissimilar among CD patients than a separately recruited, slightly younger non-IBD patient cohort (FIG. 2C and FIG. 2D). In the pediatric population, healthy volunteers are not available. The non-IBD controls were culled from pediatric patients with abdominal pain, who had no evidence of intestinal inflammation by histology, and were primarily comprised of individuals with functional abdominal pain and irritable bowel syndrome. Analysis of the bacterial composition of CD and non-IBD patients revealed distinguishing taxa between non-IBD and CD patients (FIG. 9A, FIG. 9B and FIG. 9C). These results suggested that the non-IBD controls in this study, while slightly younger on average and exhibiting GI complaints without evidence of inflammation were nevertheless more homogeneous and maintained an overall diverse microbial community.

Figure 3A:
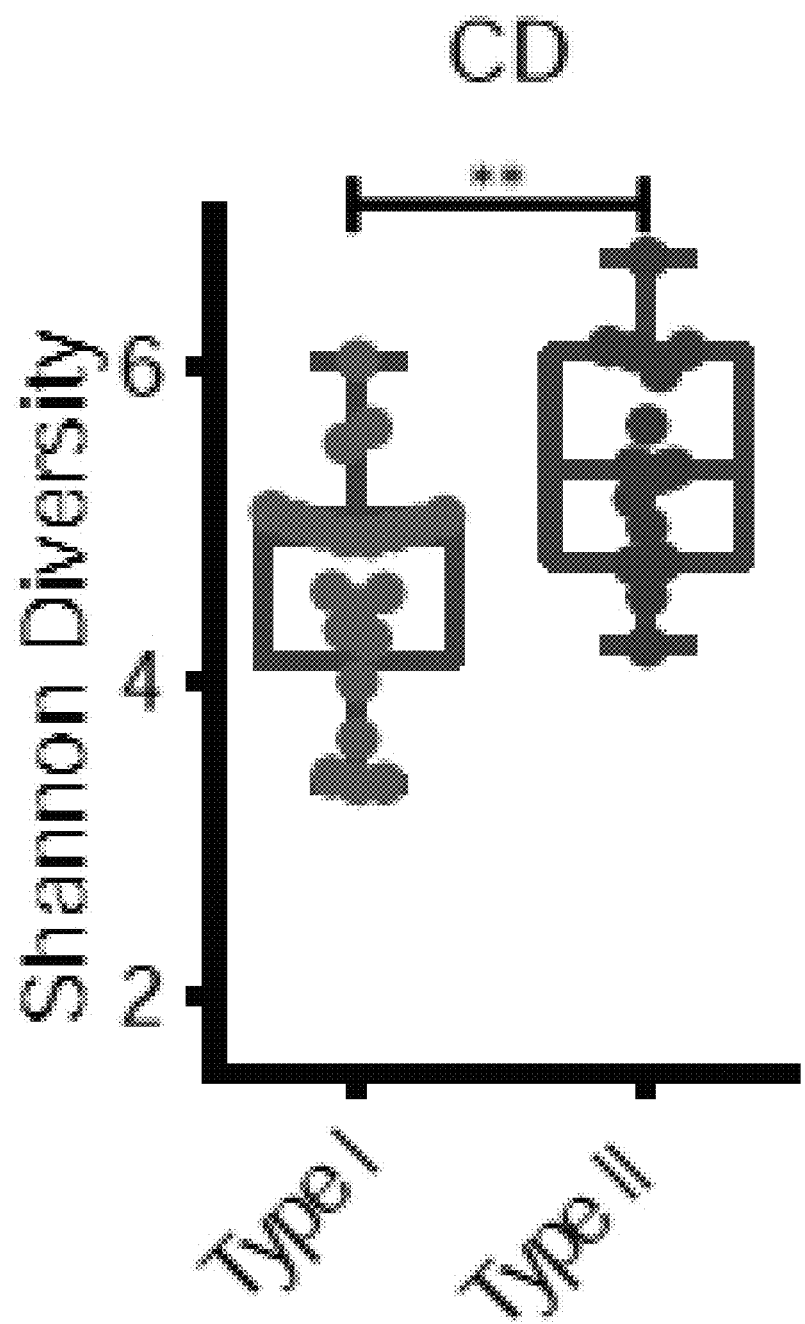
FIG. 3A, FIG. 3B, FIG. 3C, FIG. 3D, FIG. 3E, and FIG. 3F depict graphs showing that stratifying pediatric CD patients by Paneth cell phenotype reveals differences in alpha and beta diversity in CD patients with Type I Paneth cell phenotype.
Figure 3B:
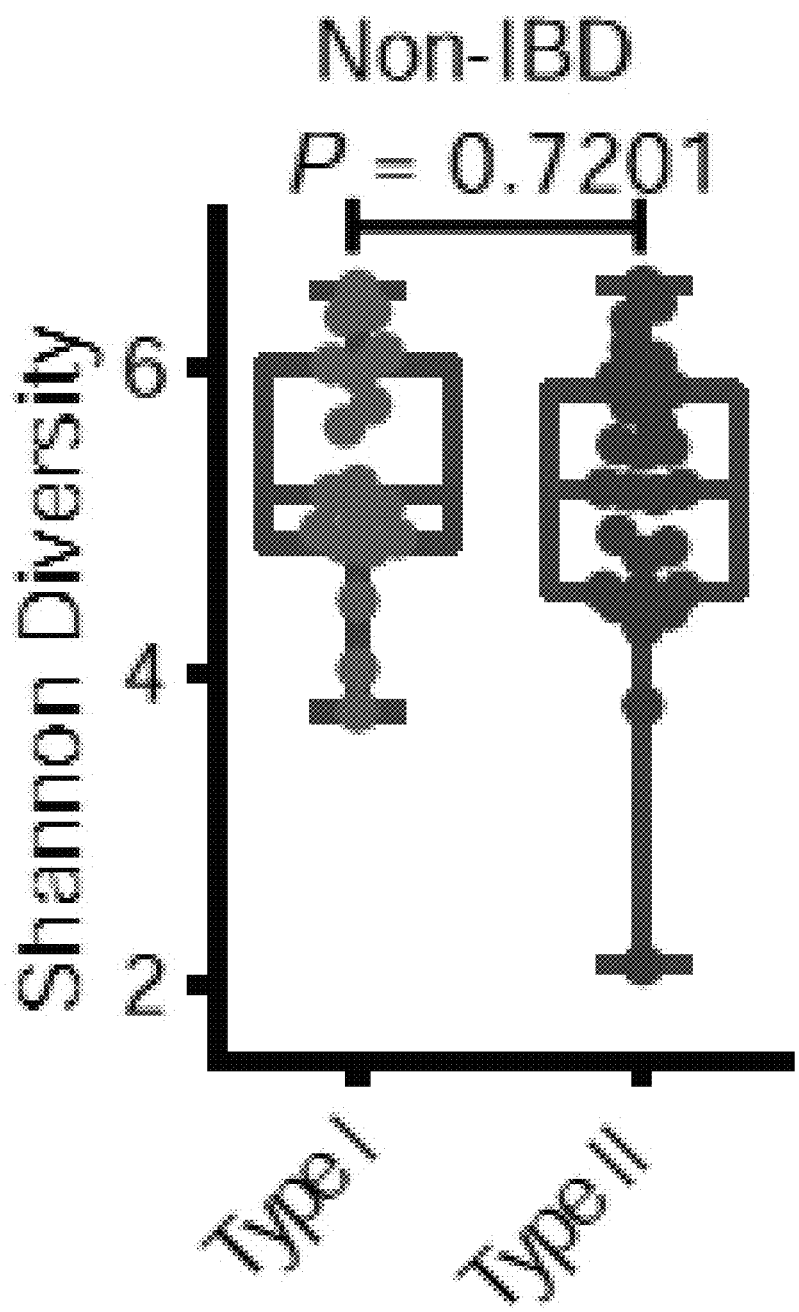
Figure 3C:
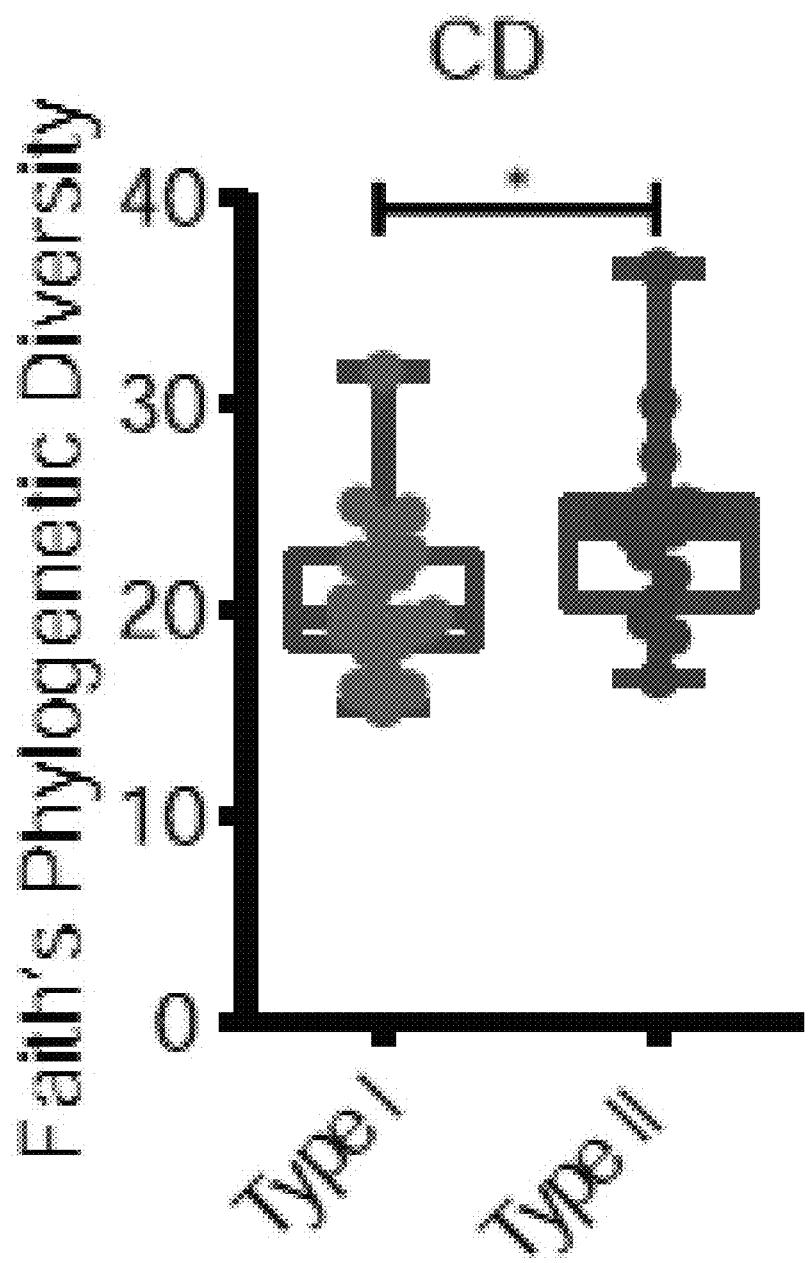
Figure 3D:
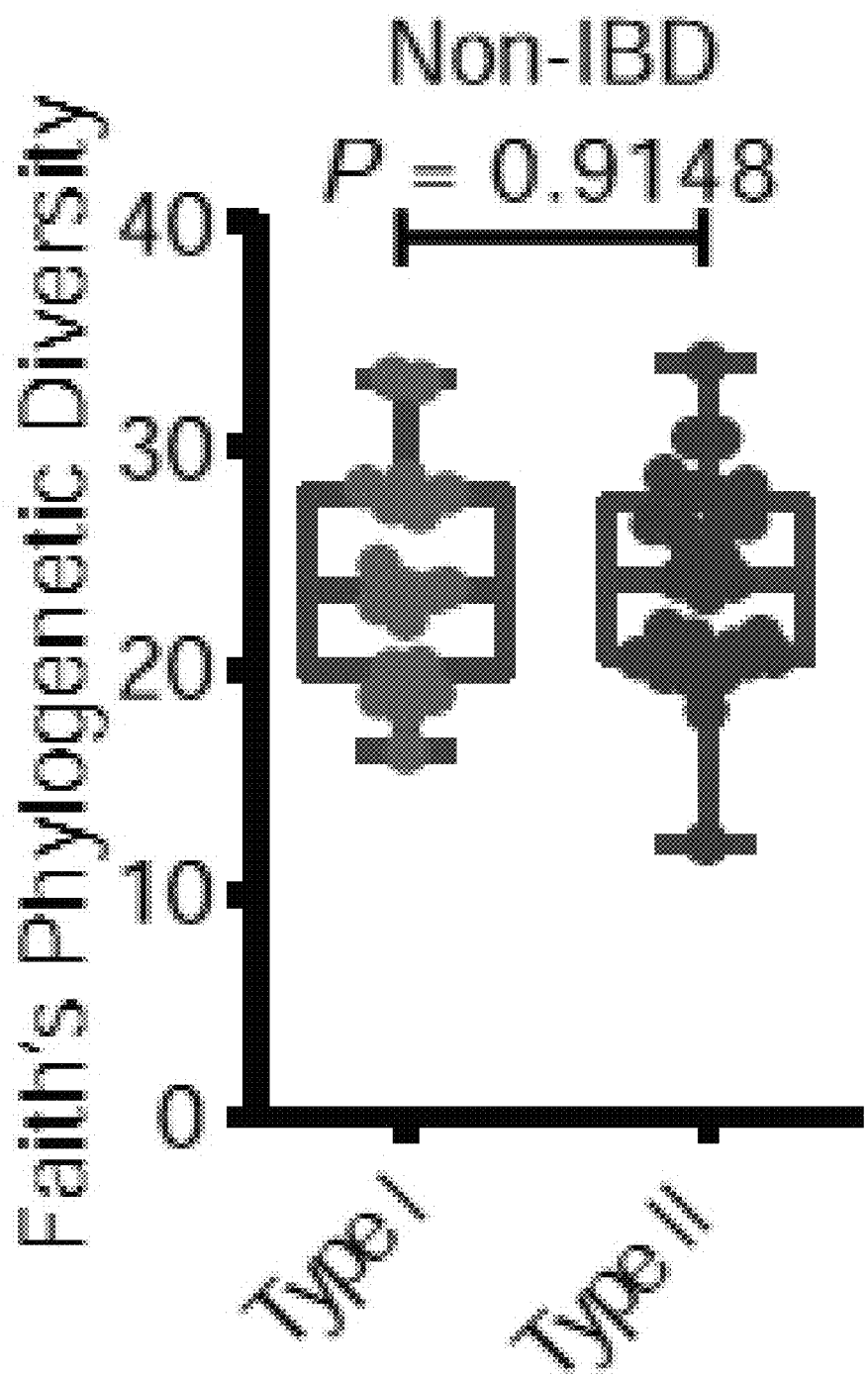
Figure 3E:
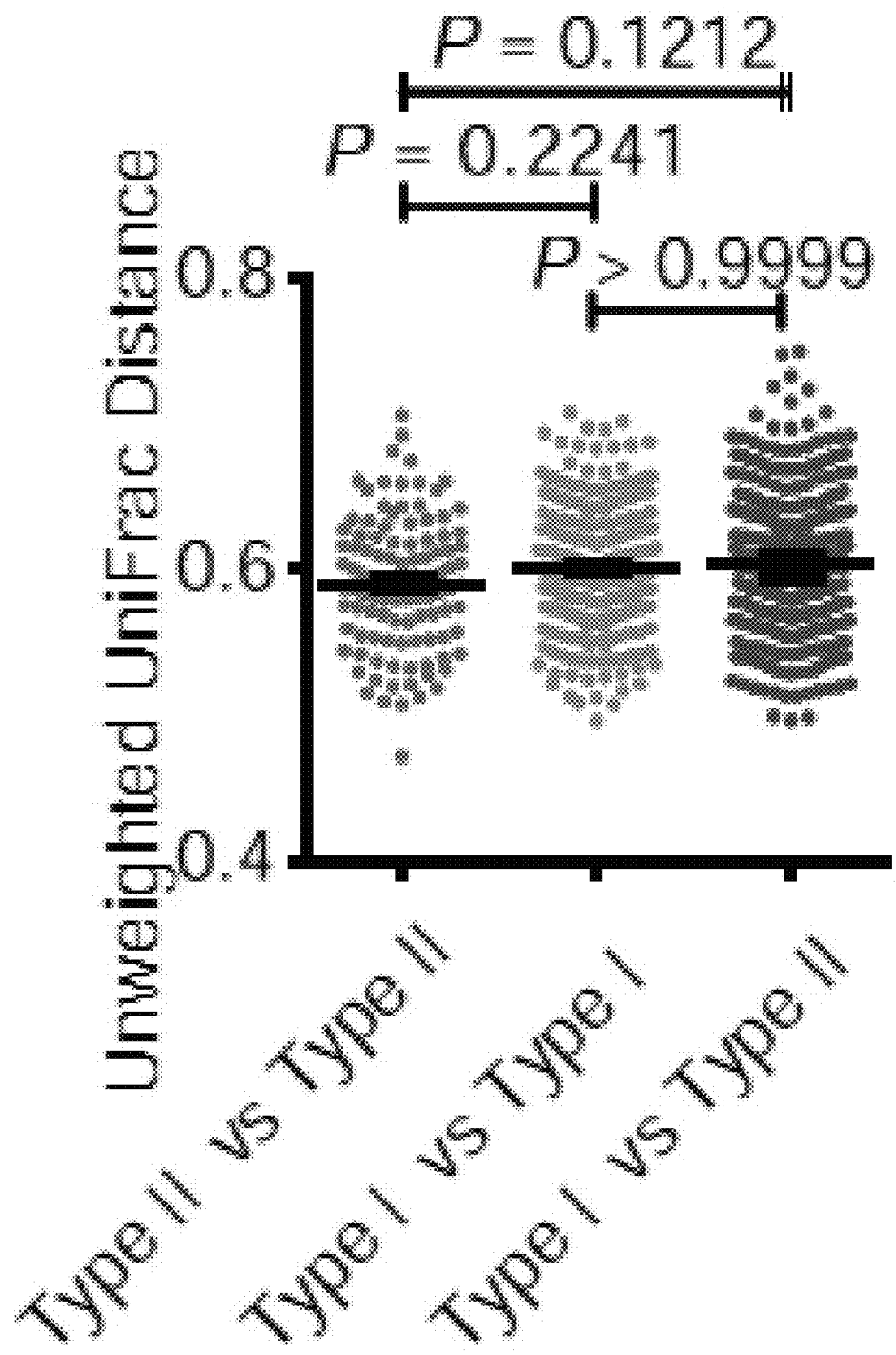
Figure 3F:
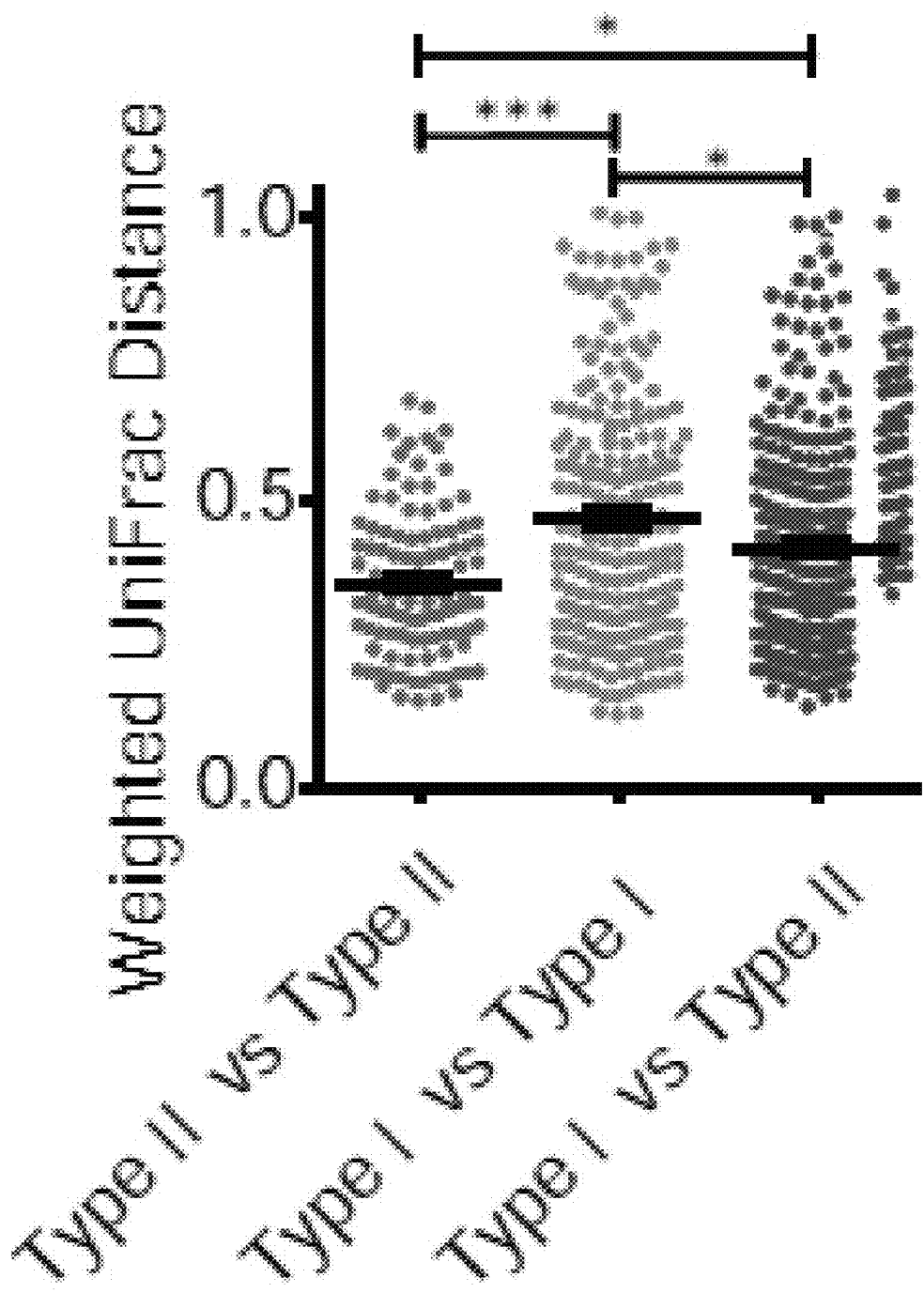
Figure 10A:
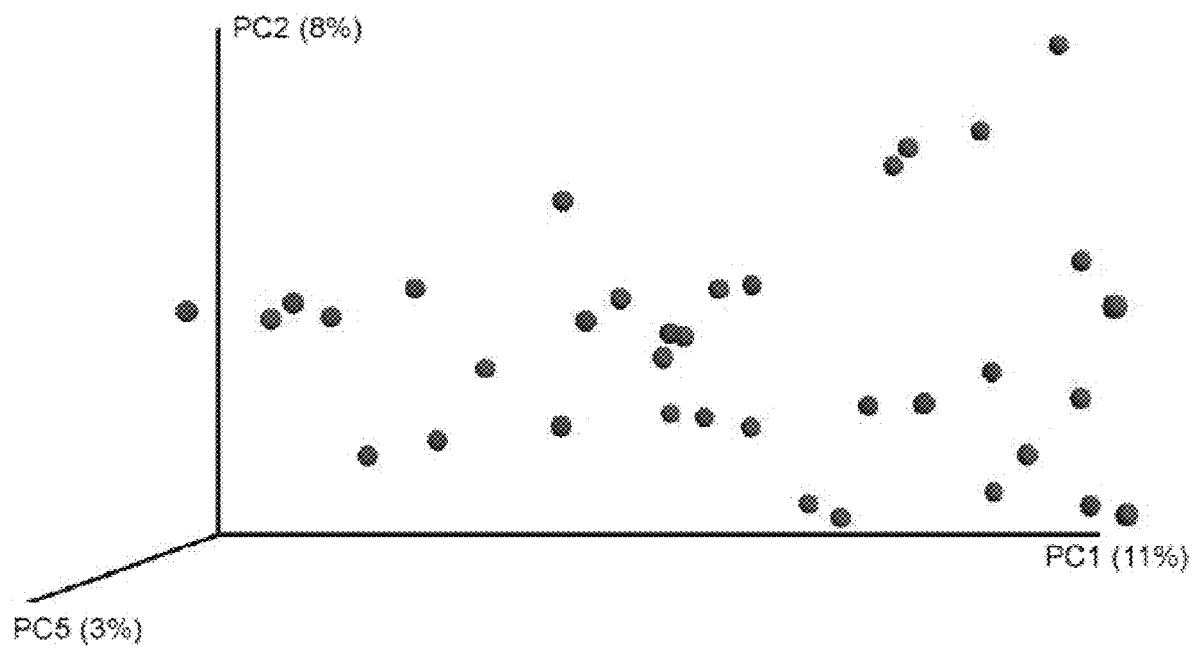
FIG. 10A and FIG. 10B depicts graphs showing that the mucosal microbiome of pediatric CD patients stratified by Paneth cell phenotype.
Figure 10B:
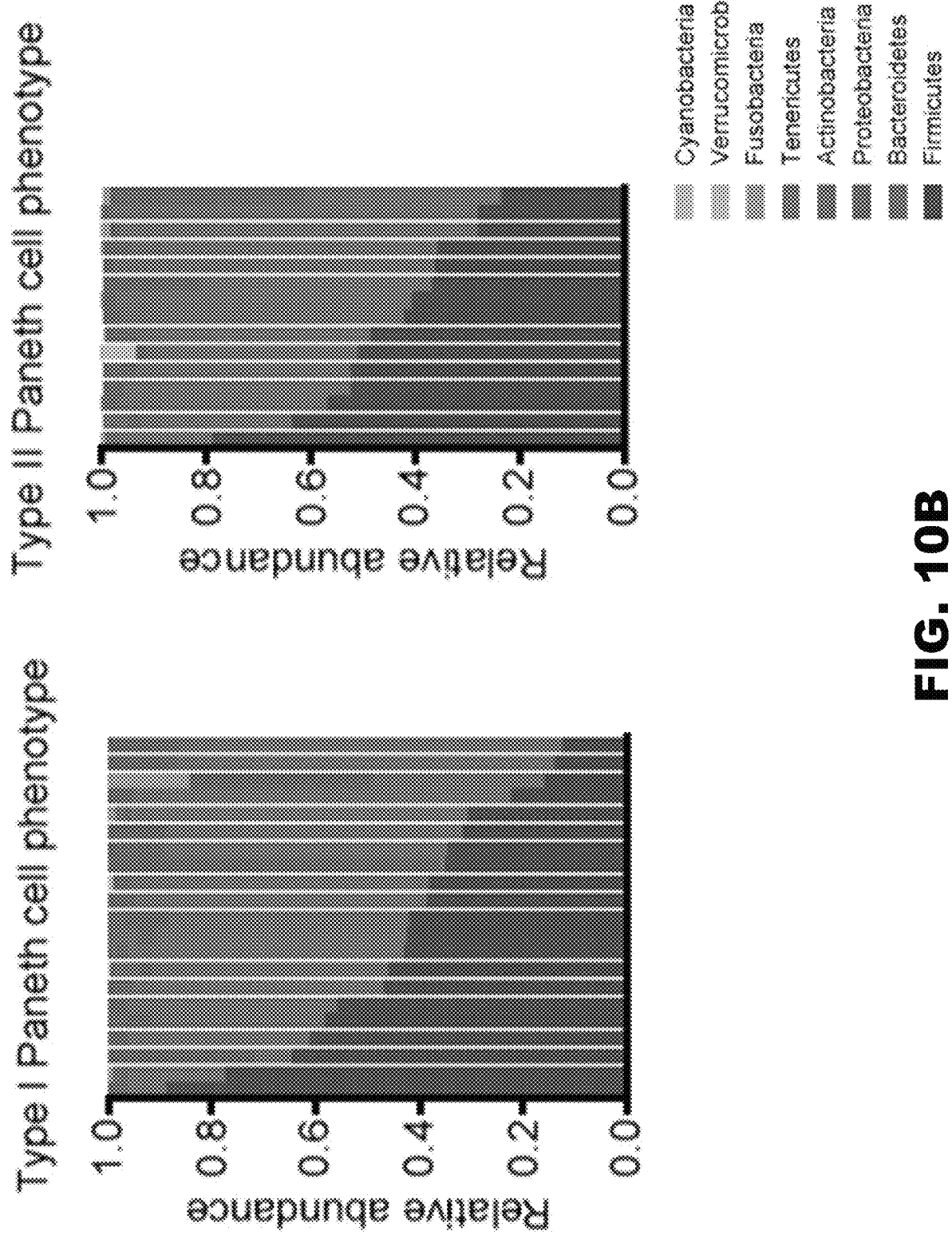
Figure 11A:
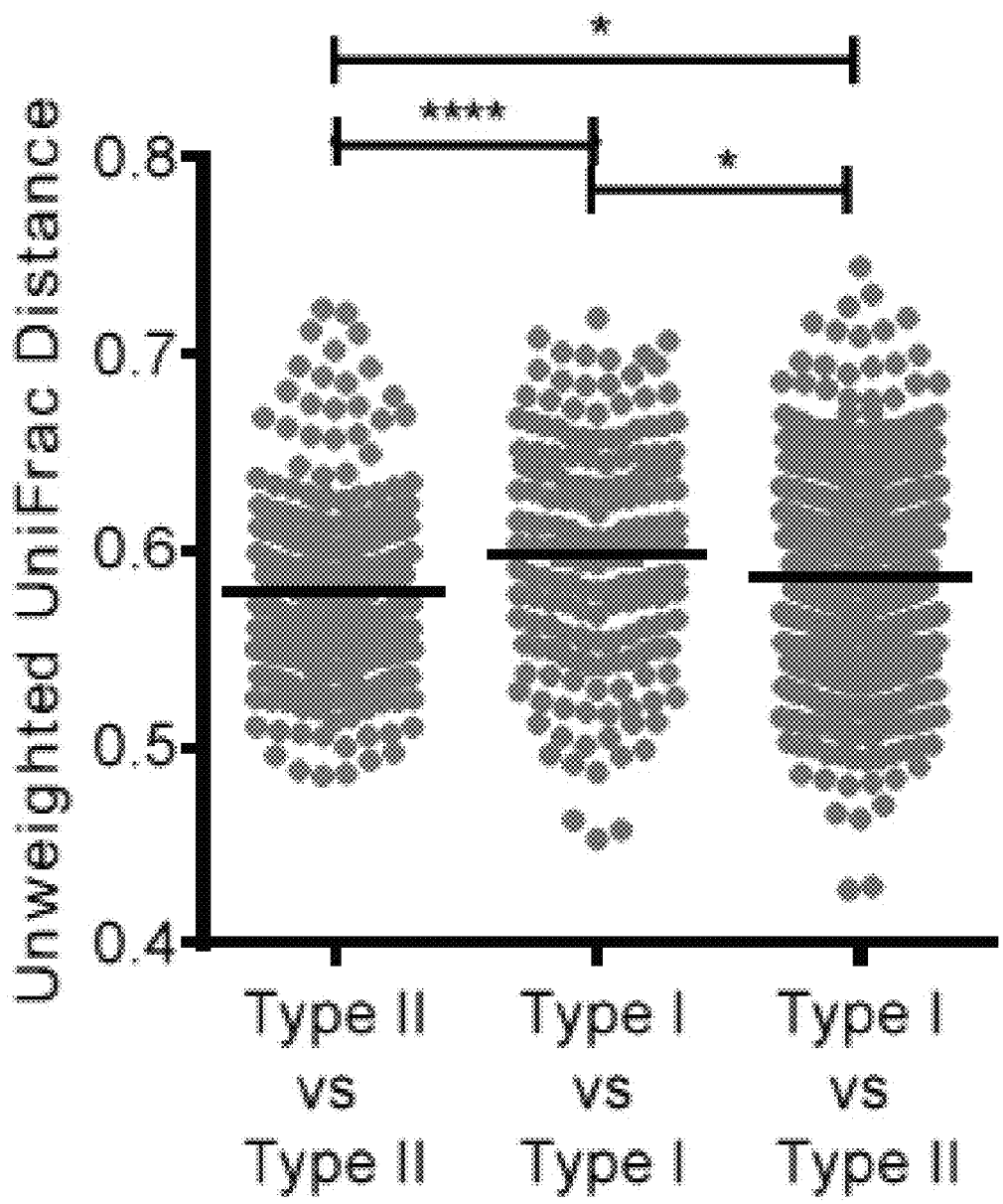
FIG. 11A, FIG. 11B, and FIG. 11C depict graphs and a cladogram showing that Type I Paneth cell phenotype in non-IBD patients is also associated with reduced beta-diversity in microbiome.
Figure 11B:
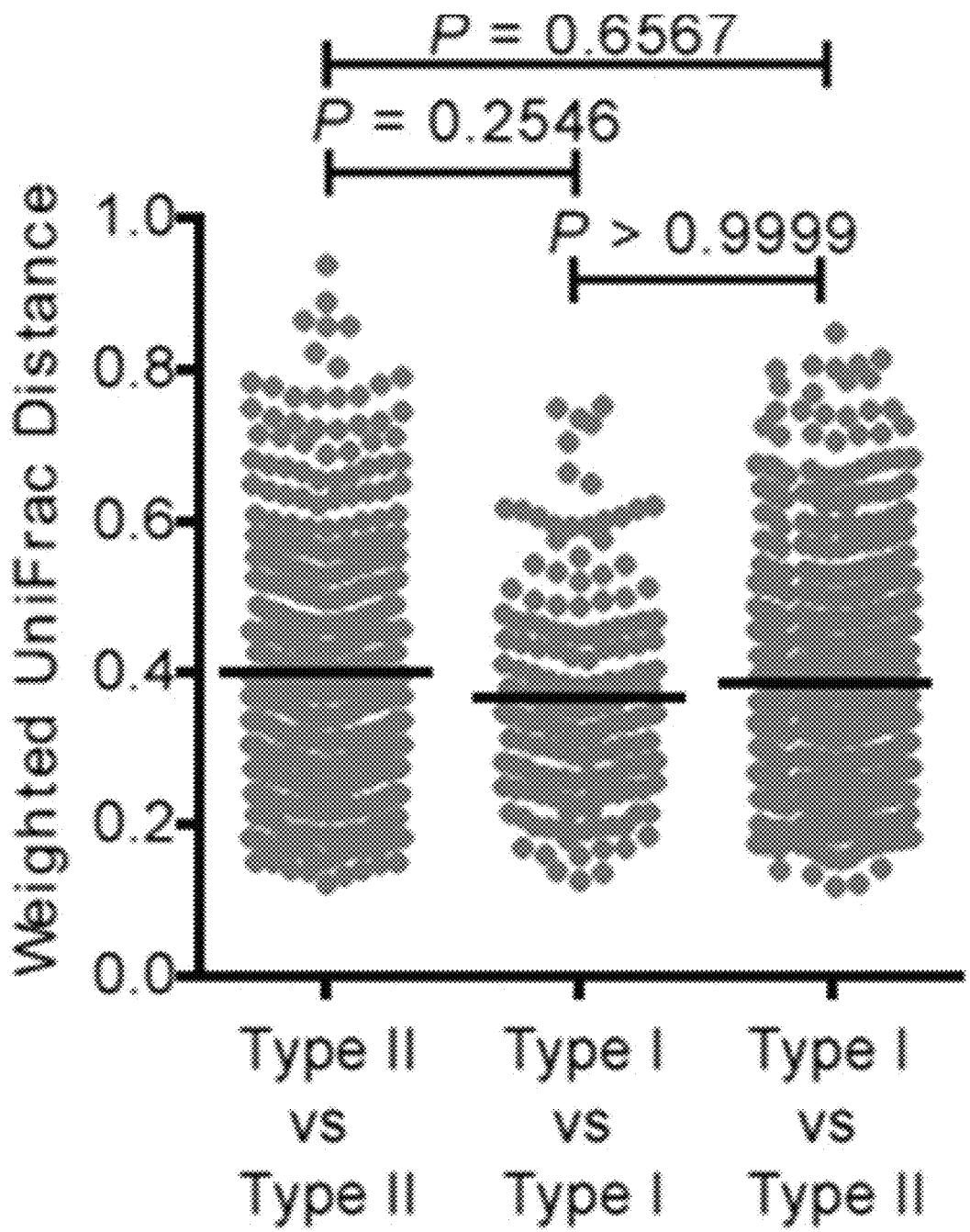
Figure 11C:
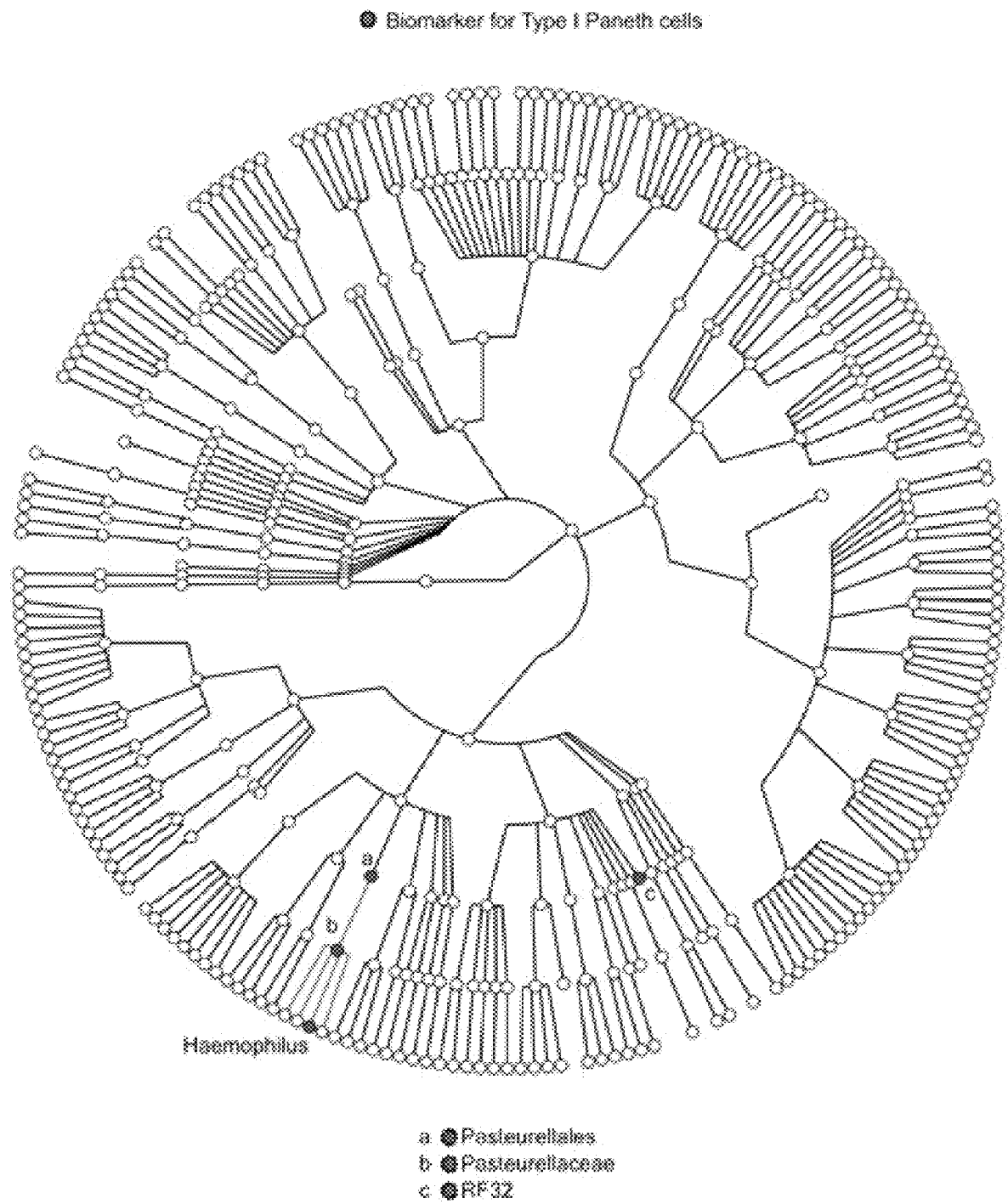

Example 4. Paneth Cell Phenotypes were Associated with Changes in a Subset of Bacterial Taxa Altered in Pediatric CD Patients We next examined the correlation of the Paneth cell phenotype with the composition of the mucosal microbiome. Amongst CD patients, the microbiome composition showed overlap in certain taxa when comparing Type I and II Paneth cell phenotypes (FIG. 10A and FIG. 10B). However, CD patients with the Type I Paneth cell phenotype showed significantly reduced alpha diversity compared to those with the Type II Paneth cell phenotype, a difference not observed in non-IBD patients (FIG. 3A, FIG. 3B, FIG. 3C, and FIG. 3D). CD patients with the Type I Paneth cell phenotype also showed significantly higher within-group beta-diversity than those with Type II Paneth cell phenotype (FIG. 3E and FIG. 3F), suggesting that CD patients with the Type I Paneth cell phenotype were a subset of patients whose microbial communities were more heterogeneous. This difference in beta-diversity was also observed in non-IBD patients in this cohort (FIG. 11A and FIG. 11B). A cladogram is shown in FIG. 11C.

Figure 4A:
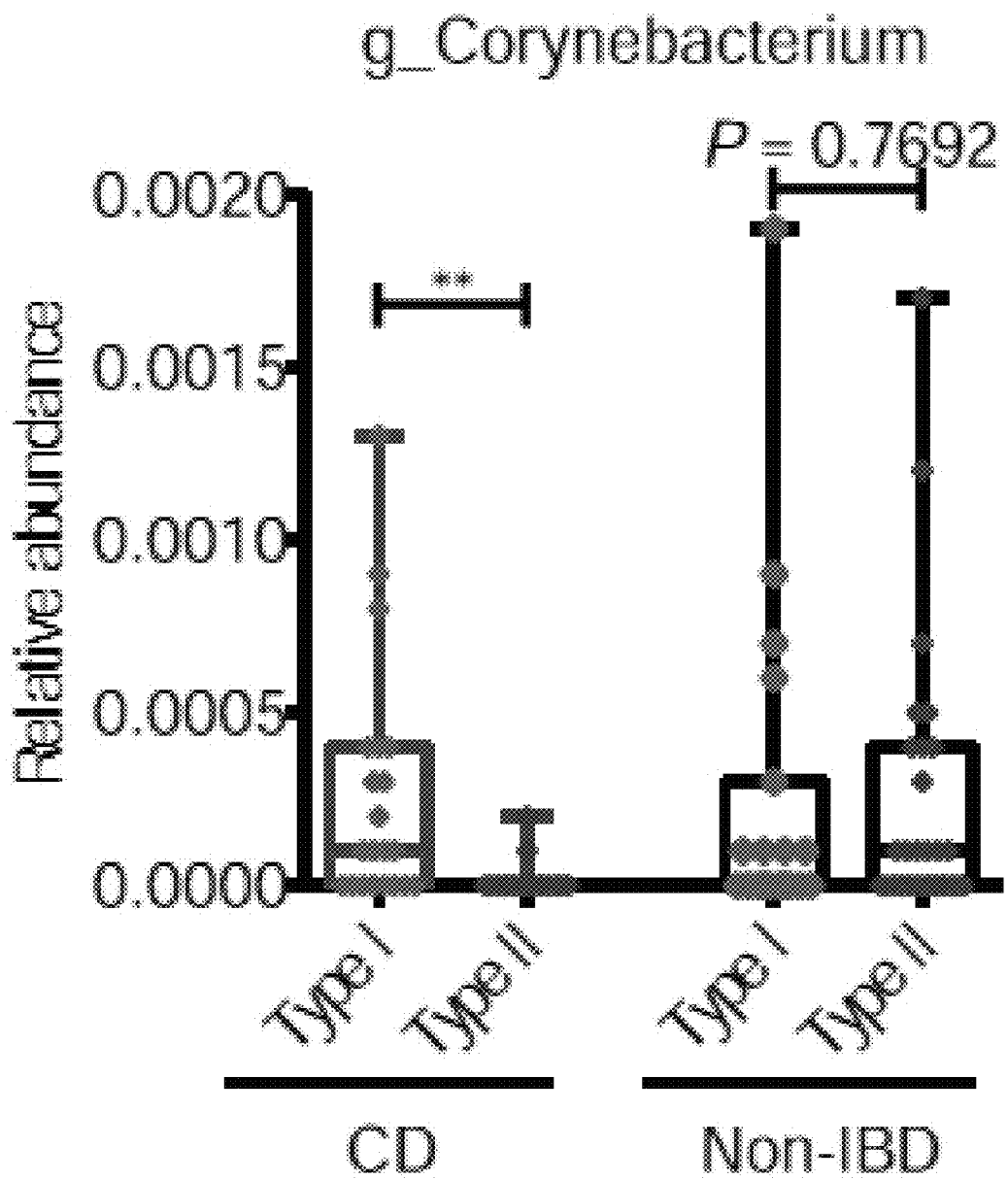
FIG. 4A, FIG. 4B, FIG. 4C, FIG. 4D, FIG. 4E, FIG. 4F, FIG. 4G, FIG. 4H, FIG. 4I, and FIG. 4J depicts graphs showing that stratifying pediatric CD patients by Paneth cell phenotype reveals taxonomic differences in CD patients.
Figure 4B:
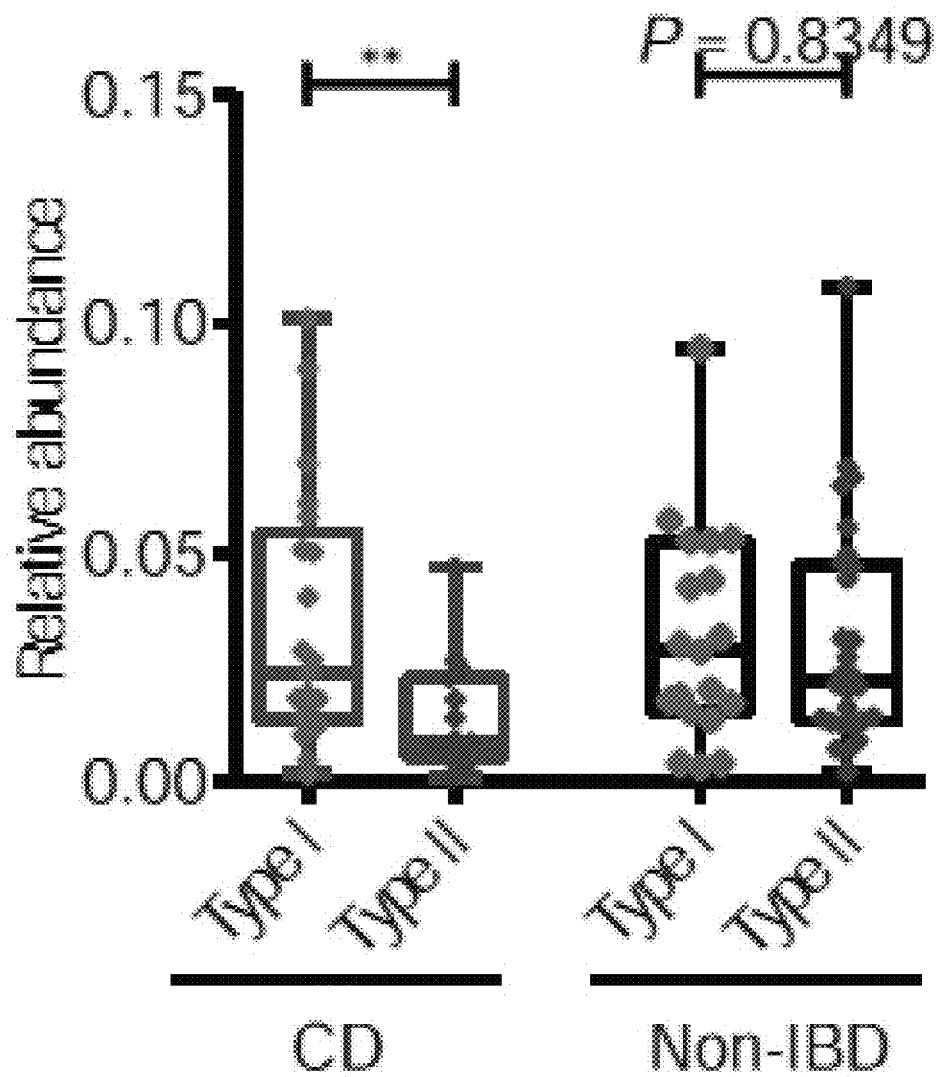
Figure 4C:
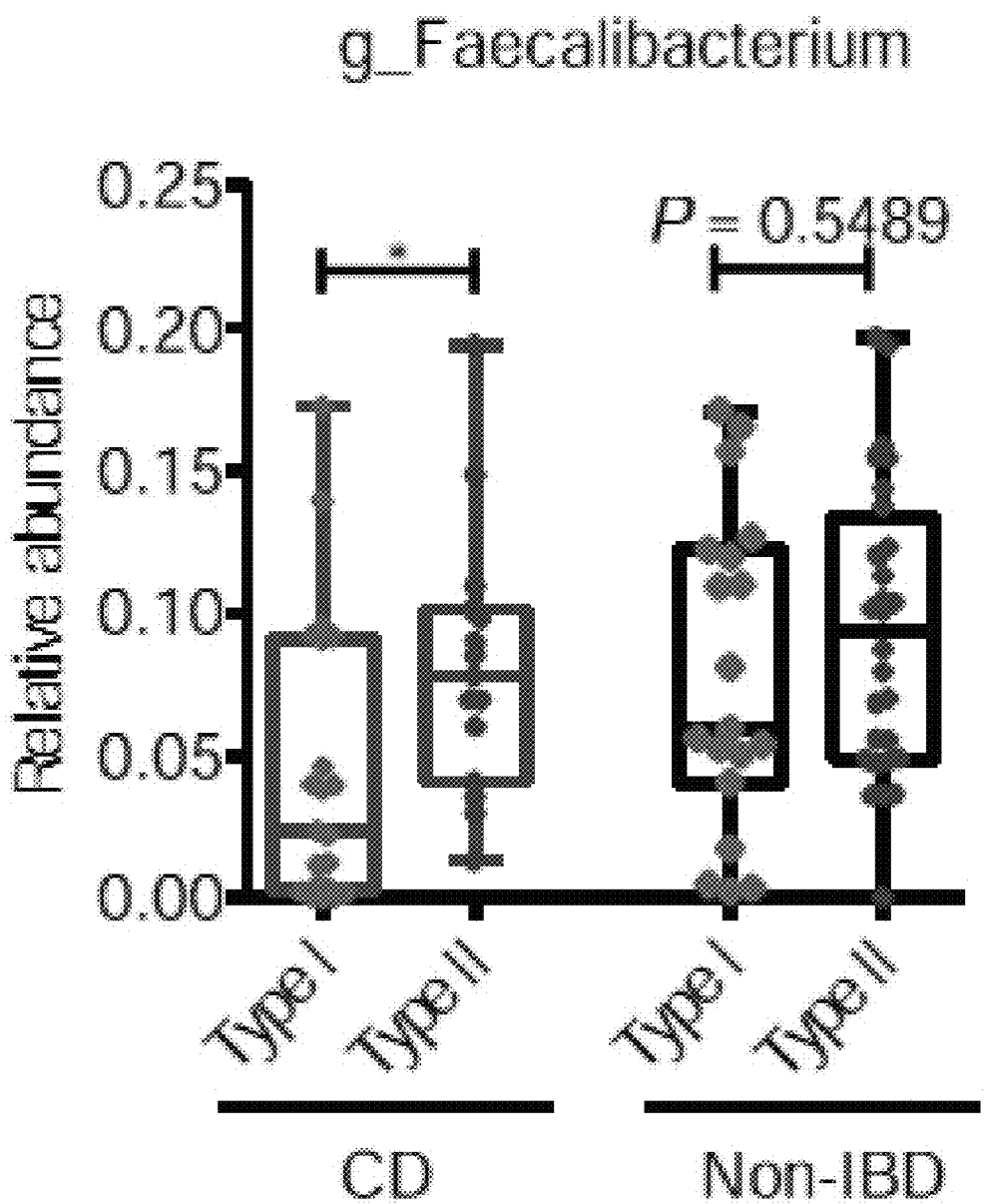
Figure 12A:
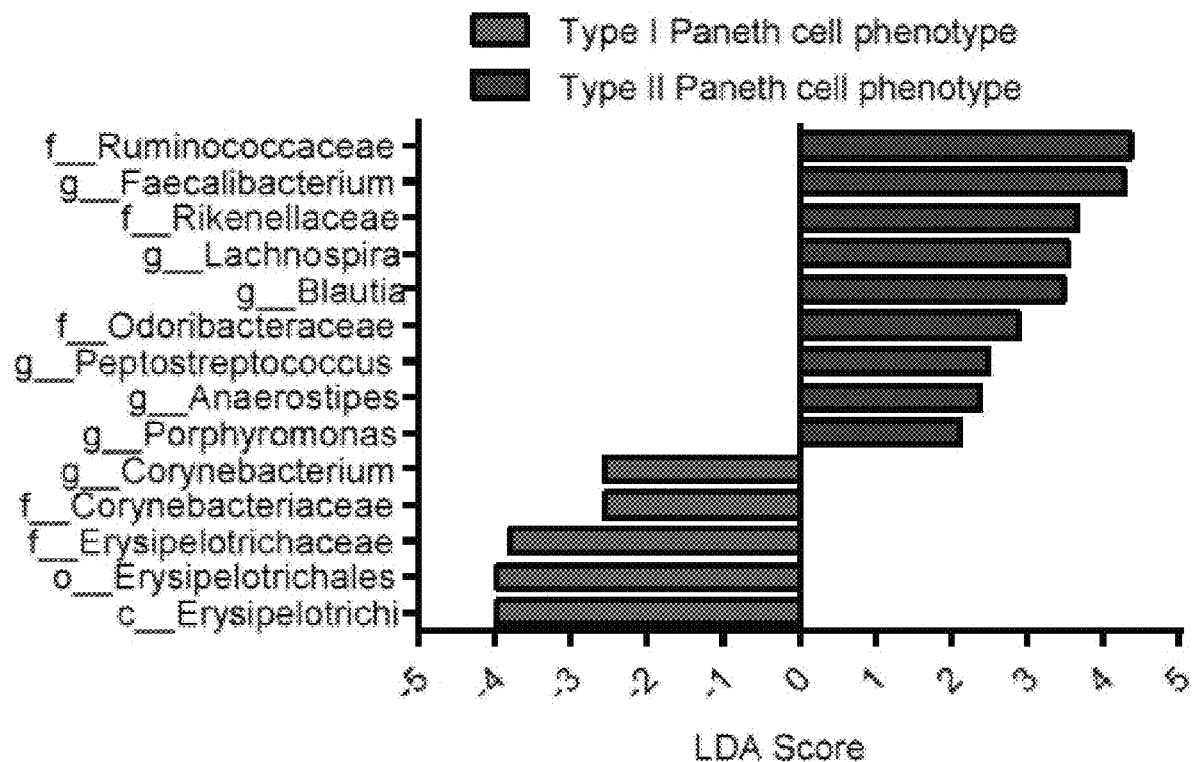
FIG. 12A and FIG. 12B depict a graph and a cladogram showing that Paneth cell phenotype correlates with different microbial taxa in CD patients.
Figure 12B:
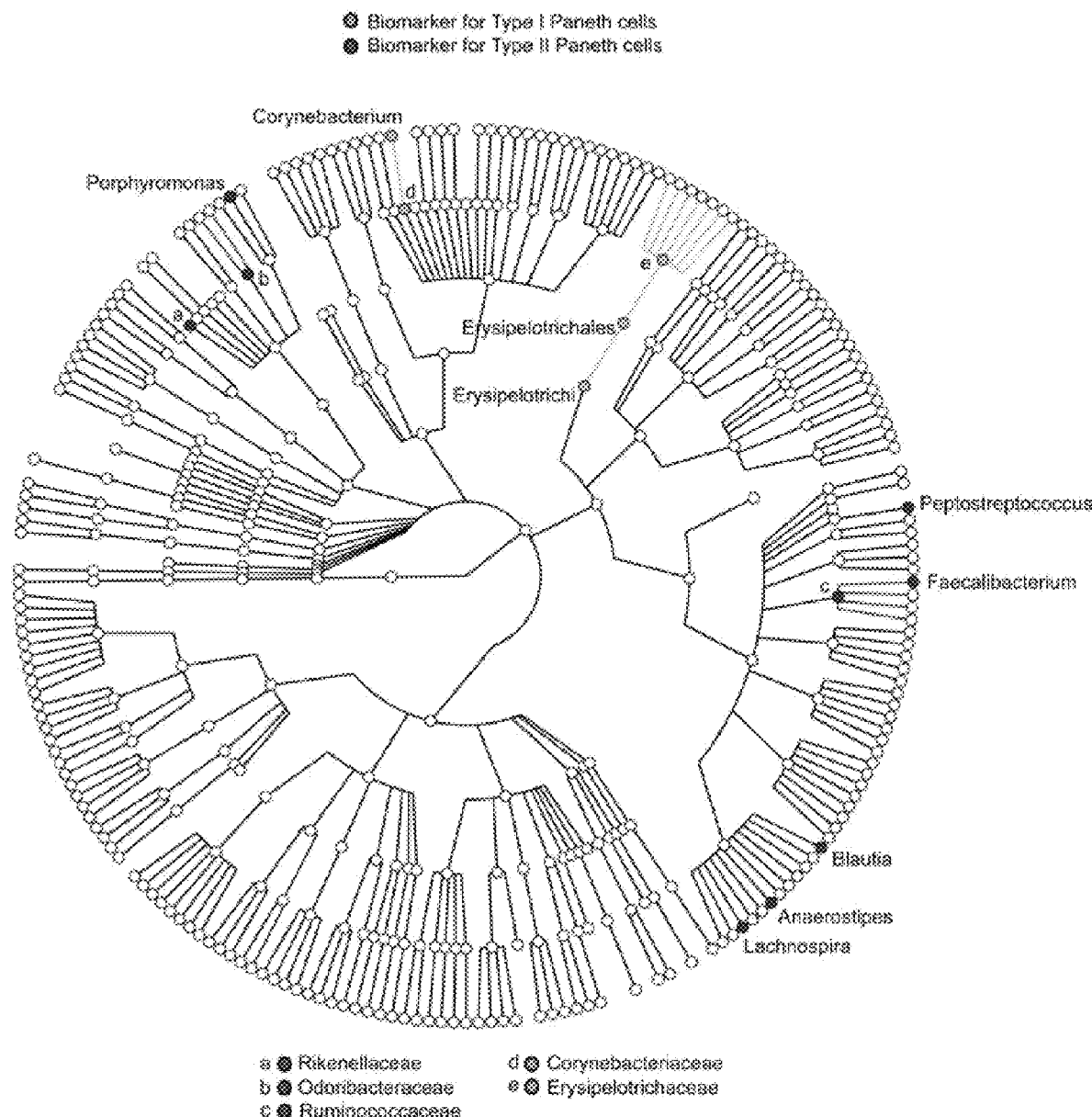

Detailed analysis on taxonomic differences between CD patients with Types I and II Paneth cell phenotypes (FIG. 12A and FIG. 12B) showed that *Corynebacterium* and Erysipelotrichaceae were more abundant in CD patients with the Type I Paneth cell phenotype (FIG. 4A and FIG. 4B), whereas *Faecalibacterium, Blautia, Ruminococcaceae, Porphyromonas, Lachnospira, Peptostreptococcus, Anaerostipes*, and *Odoribacteraceae* were more abundant in CD patients with the Type II Paneth cell phenotype (FIG. 4C, FIG. 4D, FIG. 4E, FIG. 4F, FIG. 4G, FIG. 4H, FIG. 4I, and FIG. 4J). Interestingly, whereas there was reduced abundance of *Faecalibacterium* and Lachnospriaceae in the ileal mucosa of pediatric CD patients in the RISK study, here these taxa were reduced only in CD patients with the Type I Paneth cell phenotype. *F. prausnitzii* is of interest as it possesses anti-inflammatory properties and is reduced in CD patients, in particular in those with ileal involvement. In addition, *Corynebacterium* and Erysipelotrichacea are considered to be pro-inflammatory, and the alteration of abundance of Erysipelotrichacea was also identified in the RISK cohort study. While we expected to find increased relative abundance of these microbes in CD patients with the Type I Paneth cell phenotype, the finding that these microbes are present in relative similar abundance in non-IBD patients (regardless of Paneth cell phenotype), was unexpected (FIG. 4A and FIG. 4B). Our findings suggest that CD patients with Type I Paneth cell phenotype contained reduced abundance of anti-inflammatory microbes while maintaining the abundance of pro-inflammatory microbes. In contrast, those with Type II Paneth cell phenotype contained a combination of reduced pro-inflammatory microbes while maintaining normal abundance of anti-inflammatory microbes.

Figure 5A:
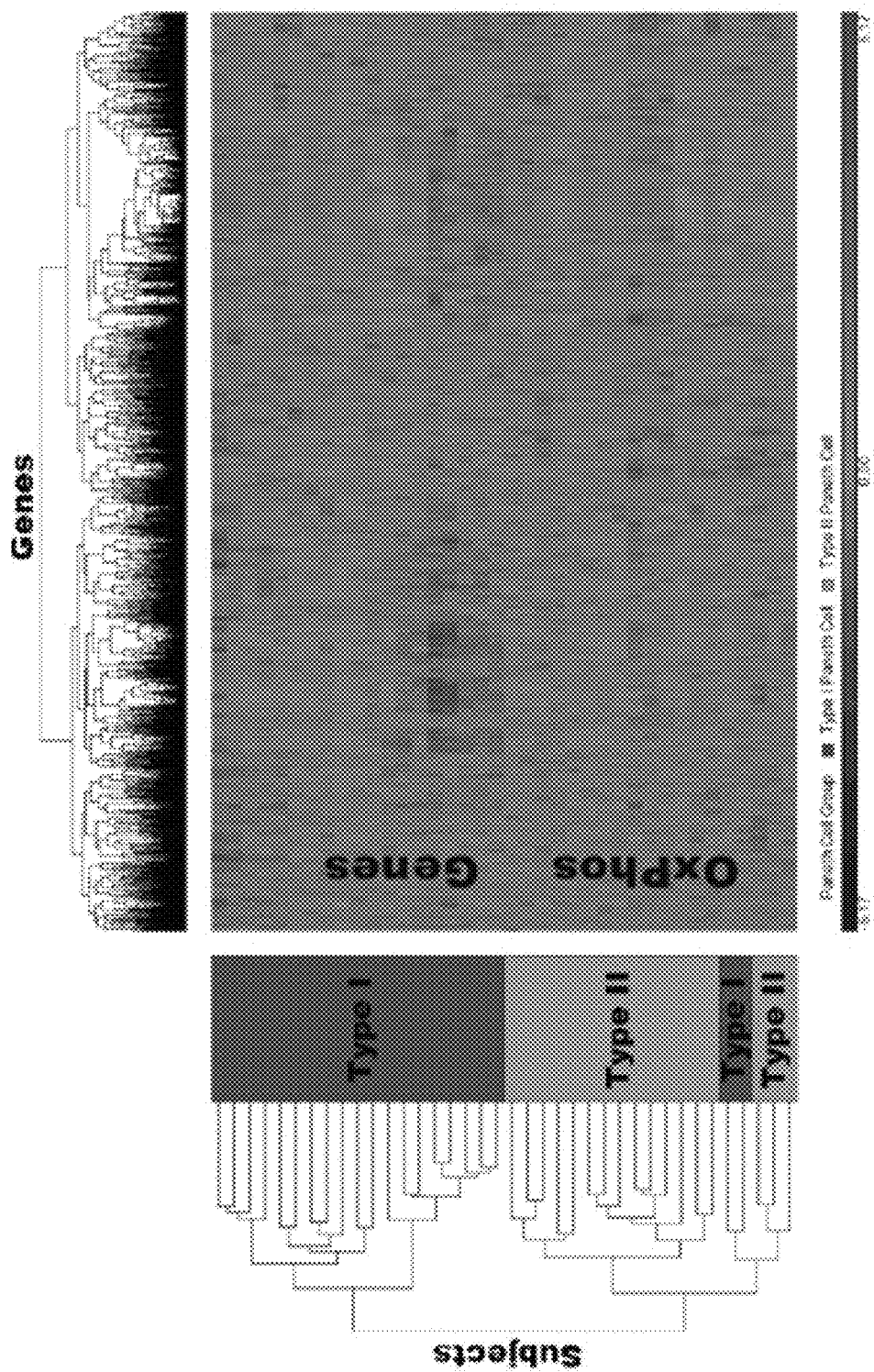
FIG. 5A, FIG. 5B, FIG. 5C, FIG. 5D, FIG. 5E, FIG. 5F and FIG. 5G depict a heatmap and graphs showing that the ileal mucosa of pediatric CD patients with Type I Paneth cell phenotype is associated with reduced expression of genes involved in oxidative phosphorylation.
Figure 5B:
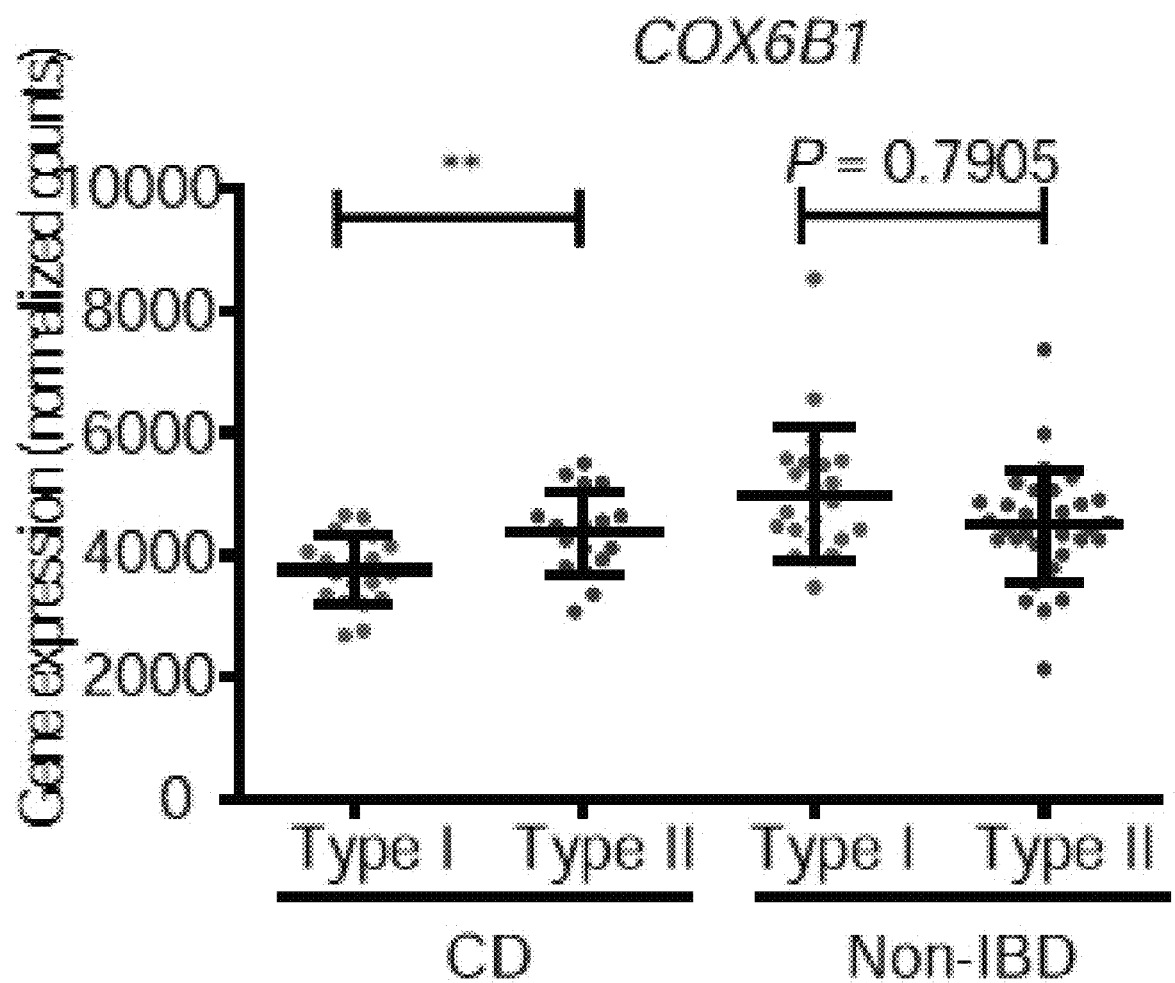
Figure 5C:
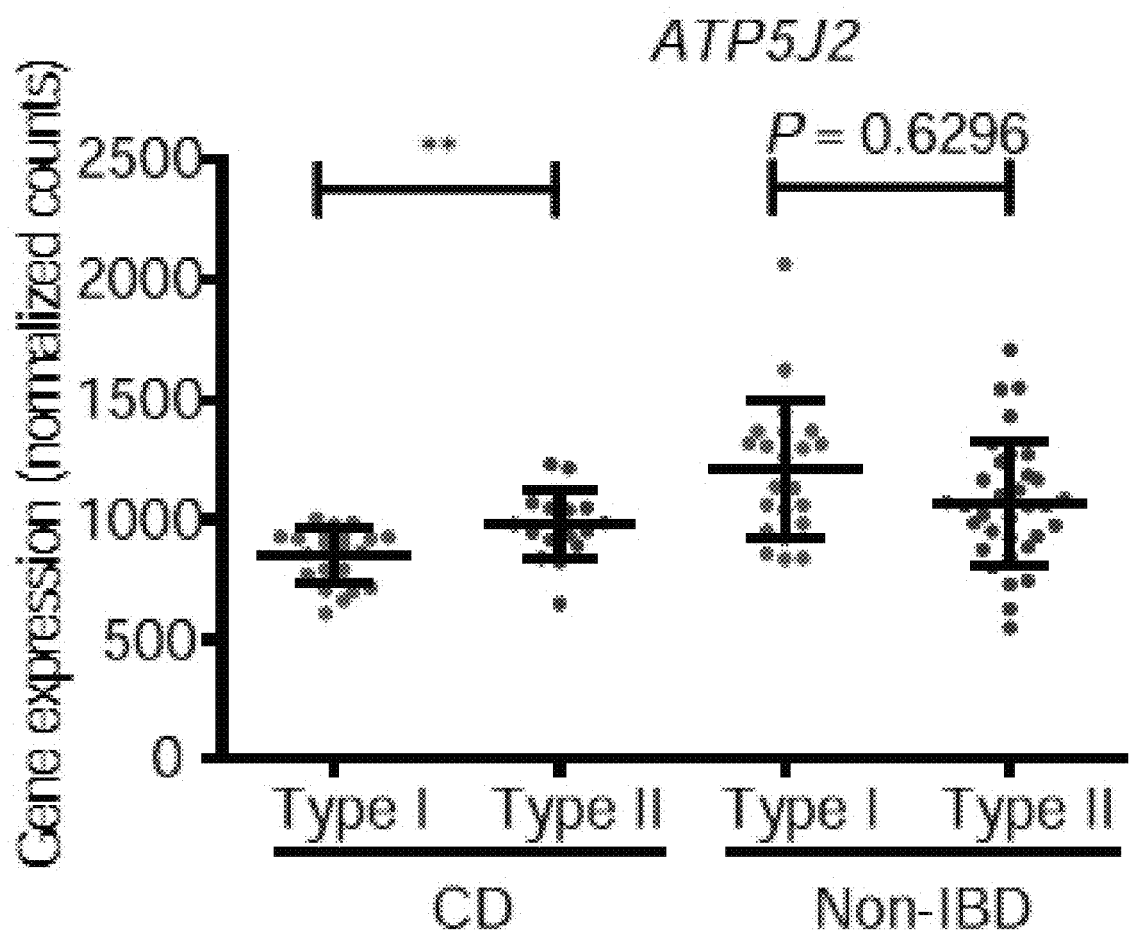
Figure 5D:
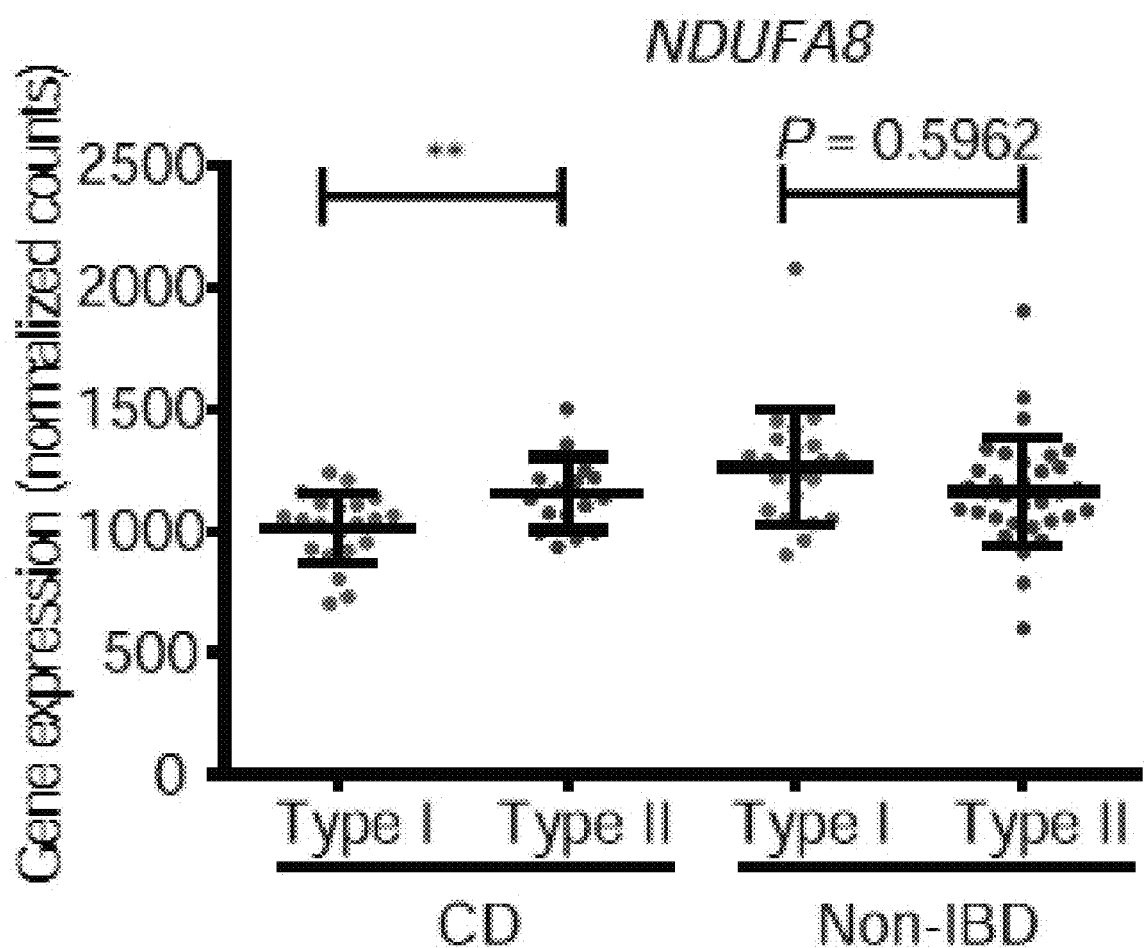
Figure 5E:
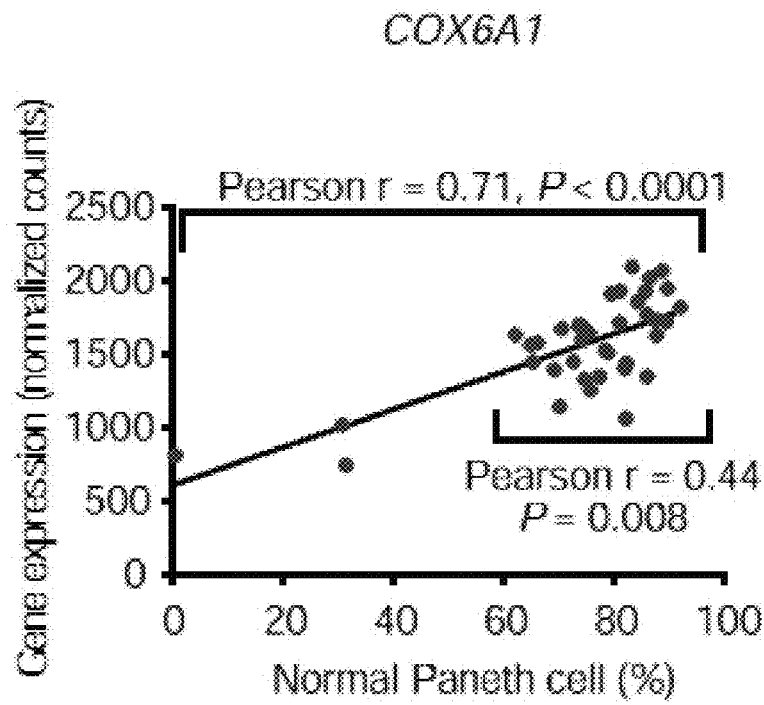
Figure 5F:
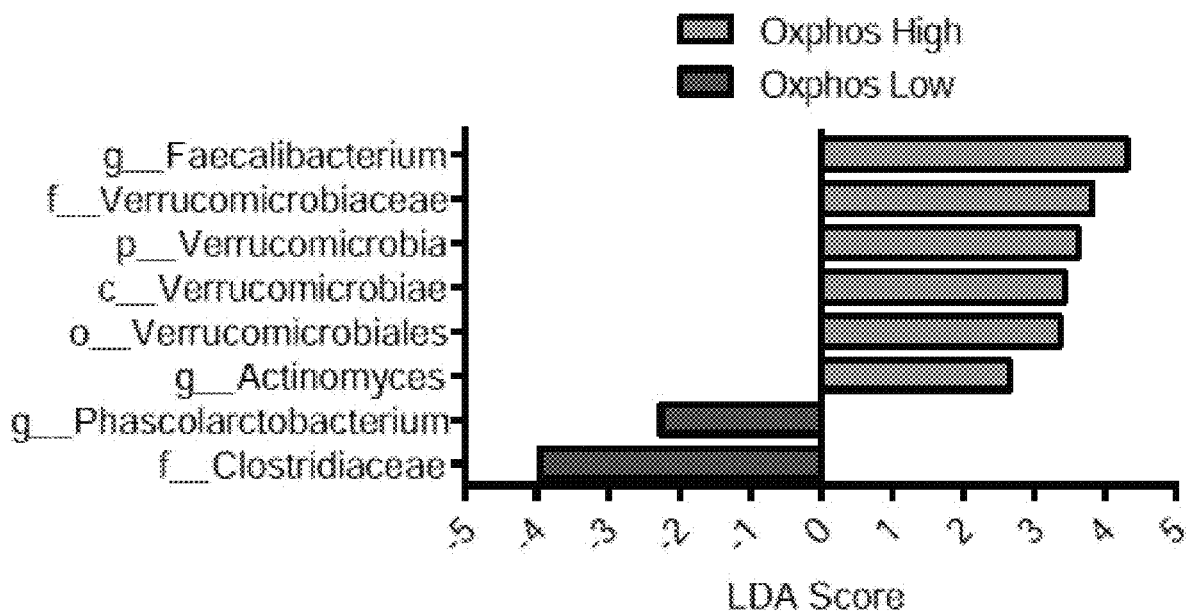
Figure 5G:
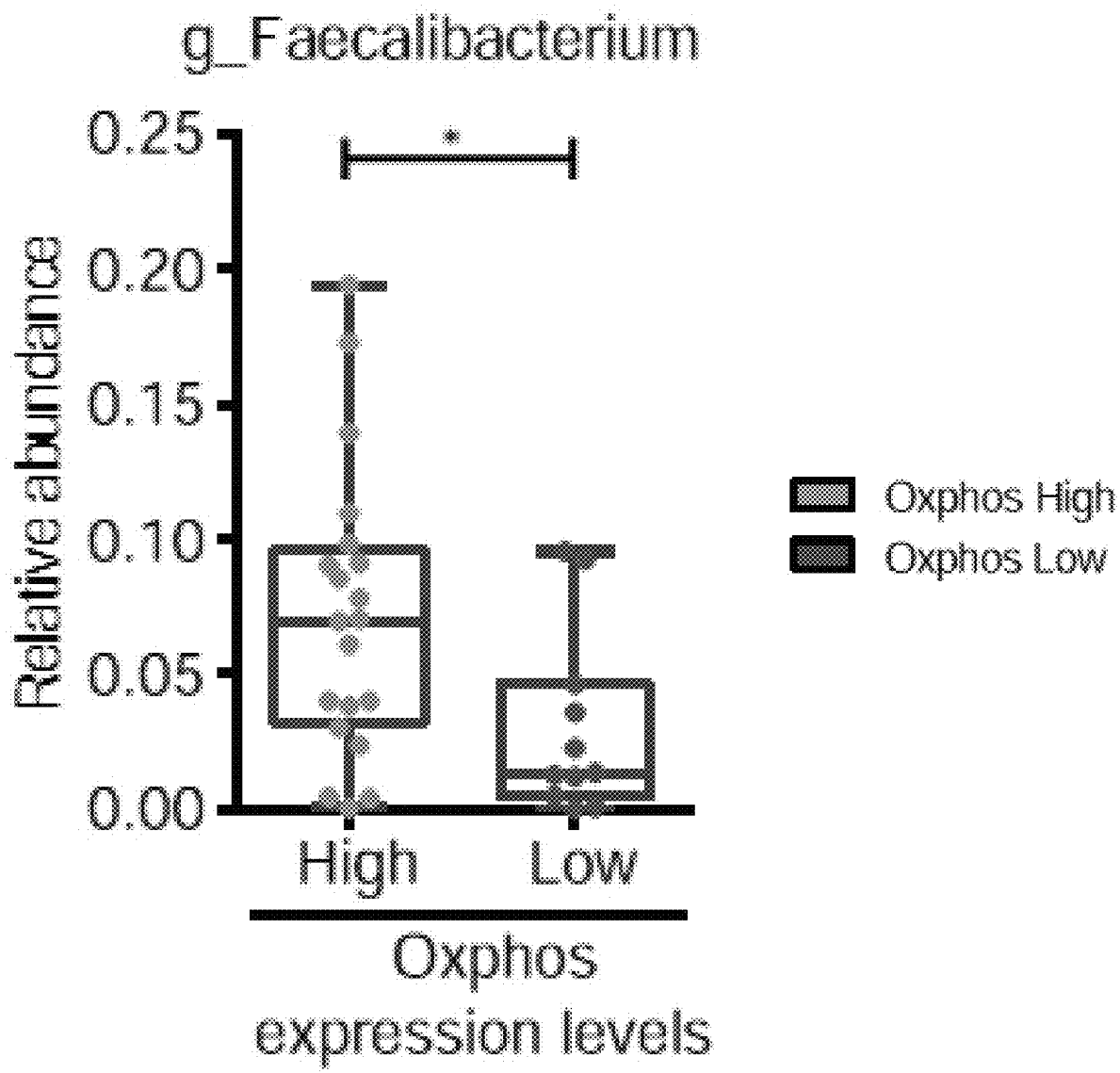
Figure 13:
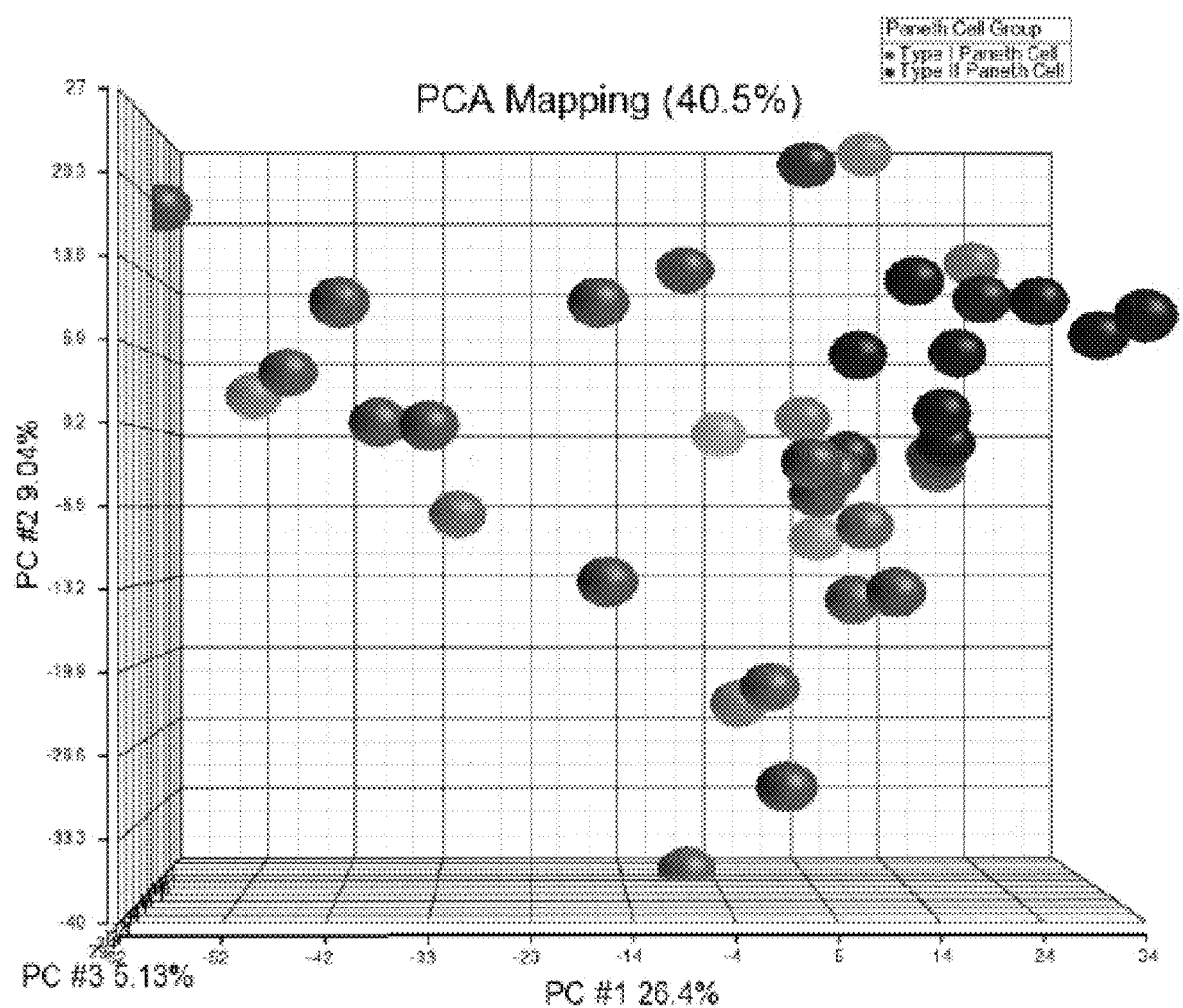
FIG. 13 depicts a graph showing the transcriptome profiles between Type I and II Paneth cell phenotypes. Principle Coordinate Analysis (PCA) of CD patients with either Type I (Red) or Type II (Blue) Paneth cell phenotypes based on gene expression data.
Figure 14A:
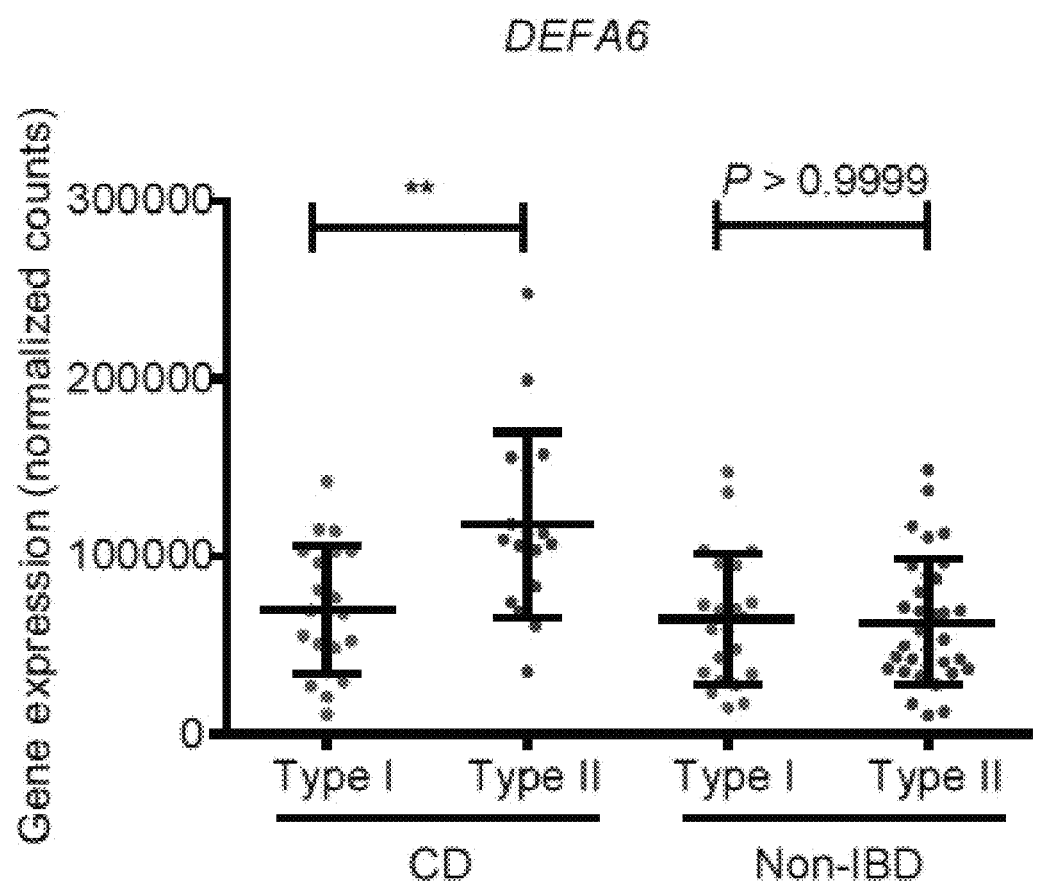
FIG. 14A, FIG. 14B, FIG. 14C, and FIG. 14D depict graphs showing that the expression of selected Paneth cell-specific genes is associated with Paneth cell phenotype in CD patients.
Figure 14B:
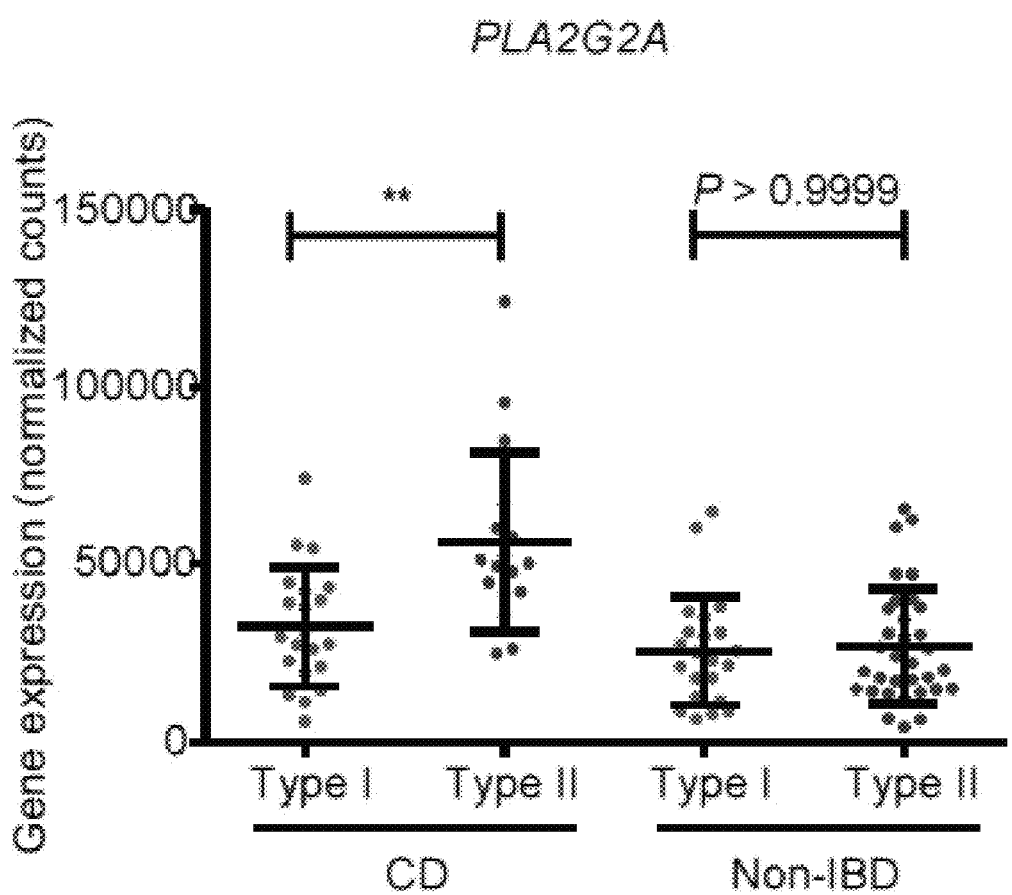
Figure 14C:
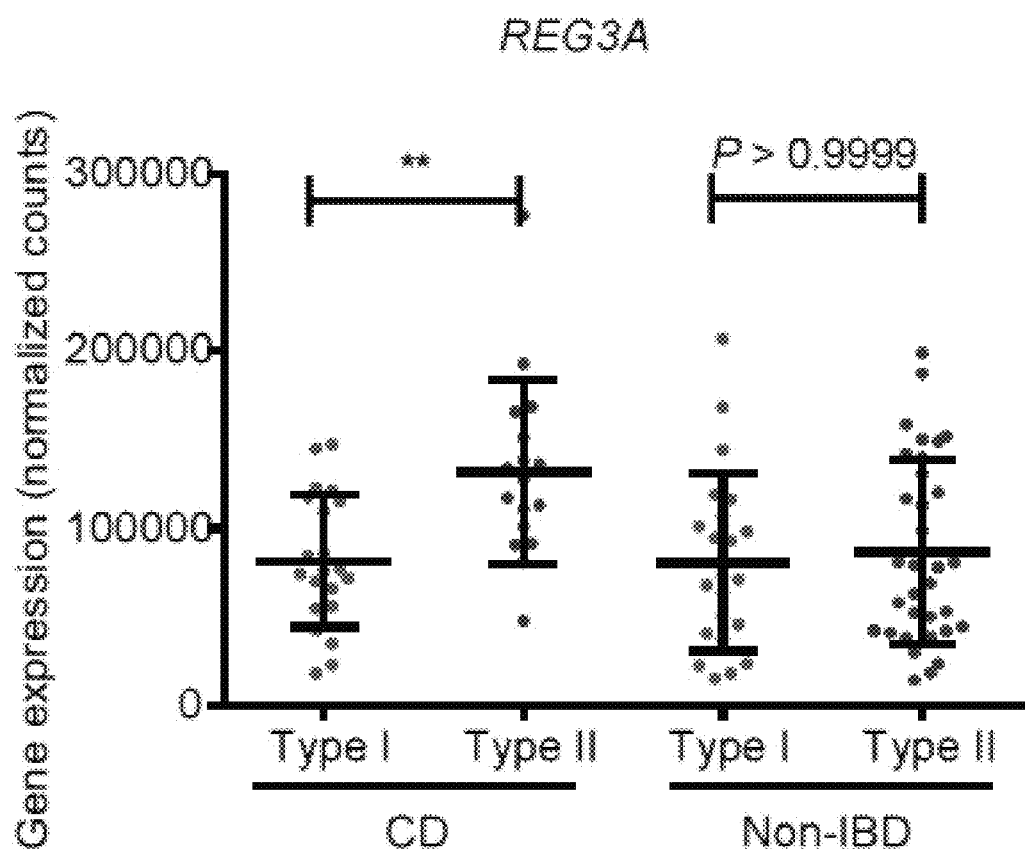
Figure 14D:
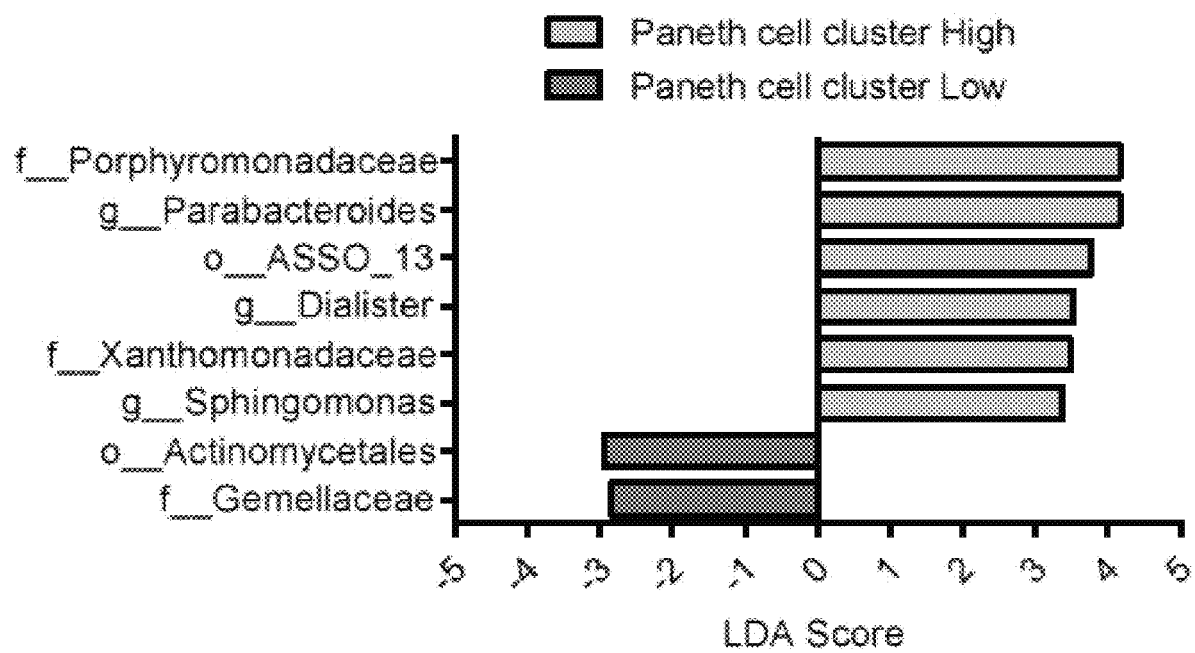

Example 5. Paneth Cell Phenotype was Associated with Unique Oxidative Phosphorylation Signature in CD Patients We next analyzed the ileal transcriptome and observed similar up- and downregulation of gene expression (including DUOXA2, APOA1, etc.) in our pediatric CD patients. We then correlated gene expression to Paneth cell phenotypes by principle coordinate analysis (FIG. 13) and clustering analysis (FIG. 5A) and found a strong association between Paneth cell phenotype and ileal gene expression. One striking finding was the association of reduced expression of a large cluster of oxidative phosphorylation genes (n=50) with the Type I Paneth cell phenotype in CD patients but not in non-IBD patients with the Type I Paneth cell phenotype (FIG. 5B, FIG. 5C, and FIG. 5D, see complete oxidative phosphorylation gene list in Table 2). Using COX6A1 as an example, we found that the expression of this gene correlated with the percentage of abnormal Paneth cells (FIG. 5E). Importantly, we found significant correlation between oxidative phosphorylation gene expression and specific taxa of the ileal microbiome (e.g. *Faecalibacterium*) that were dysregulated in CD patients with the Type I Paneth cell phenotype (FIG. 5F and FIG. 5G).

A second cluster of genes with diminished expression in CD patients with the Type I Paneth cell phenotype was associated with Paneth cells themselves (Table 3 and FIG. 14). The diminished expression of this Paneth cell cluster did not correlate with Paneth cell phenotypes in non-IBD patients (FIG. 14A, FIG. 14B, and FIG. 14C). In contrast to the oxidative phosphorylation gene cluster, using the Paneth cell gene cluster for microbiome stratification only showed differences in Porphyromonadaceae, a family under the phylum Bacteroidetes, previously linked to several metabolic parameters (FIG. 14D). However this was not further associated with Paneth cell phenotypes. Thus, the oxidative phosphorylation gene cluster showed a more robust correlation with microbiome and Paneth cell phenotype.

Discussion for Examples 1-5

Paneth cell phenotypes are a clinically relevant prognostic biomarker for post-operative CD and are associated with host genotype, pathologic hallmark, and immune-activation gene expression. We showed that pediatric CD patients, in contrast to adult CD patients, had a higher prevalence of the Type I (abnormal) Paneth cell phenotype. We further showed that the Type I Paneth cell phenotype was associated with taxonomic differences in the mucosal microbiome in CD but not in non-IBD patients. Finally, the relative abundance of specific taxa correlated with Paneth cell phenotypes was associated with alterations in oxidative phosphorylation gene expression.

CD patients have been suggested to possess reduced alpha-defensins in the ileum raising the possibility that defects in Paneth cells could lead to dysbiosis and IBD. Interestingly, whereas there was reduced abundance of barrier-associated microbes *Faecalibacterium* and Lachnospriaceae in the ileal mucosa of pediatric CD patients in the RISK study, who were not analyzed on the basis of Paneth, cell phenotype, in our study these taxa were reduced predominantly in CD patients with the Type I Paneth cell phenotype. Thus, one possible scenario is that the reduction of *F. prausnitzii* creates an additional stress for Paneth cells to produce and secrete antimicrobial peptides to combat potential invasive microbes, which eventually leads to the dysfunction of Paneth cells. Alternatively, dysmorphic Paneth cells, which are associated with reduced antimicrobial peptides, may allow pro-inflammatory microbes to out compete the barrier-associated microbes such as *F. prausnitzii*.

A second main finding in our microbiome analysis is that the abundance of Erysipelotrichaceae is reduced predominately in CD patients with the Type II Paneth cell phenotype. This alteration was also identified in CD patients compared to non-IBD in the RISK cohort. Our findings suggest that normal Paneth cell function may be crucial in the defense/clearance of these pro-inflammatory microbes in the context of CD. In contrast, Enterobacteriaceae, another family of pro-inflammatory microbes found to have increased relative abundance in CD patients in both our cohort and the RISK study, did not correlate with Paneth cell phenotype, suggesting the presence of inflammation may play a more important role than Paneth cell phenotype for Enterobacteriaceae colonization in CD. Together, our study and other previous reports suggest multiple mechanisms for how pro-inflammatory microbes become associated with CD patients.

Based on our previous findings in adult CD patients that Type I Paneth cell phenotype was associated with the patients' genetics (in particular CD-associated single nucleotide polymorphisms [SNP] in autophagy-associated ATG16L1 and NOD2), the lack of correlation between ATG16L1 T300A SNP and Type I Paneth cell phenotype in the Milwaukee cohort was unexpected. While it is possible that the sample size was too small to detect a correlation, it is also possible that additional genes involved in the development of CD in these patients also affect the development of Type I Paneth cell phenotype. Compared to adult CD, genetics plays a more important pathogenic role in pediatric CD, in particular those with very early onset disease, although in mouse models the Paneth cell antimicrobial function is independent of Nod2. Thus, it is possible that additional CD-susceptible genes may cause the Paneth cell defect. An alternative/complementary explanation is that environmental factor(s) play a more important role than genetics in inducing Paneth cell defect in this population. This highlights the importance of using Paneth cell phenotype as a biomarker as it may provide greater value over genetics or microbiota signatures alone.

Although we cannot measure antimicrobial activity in the subjects' ileal biopsies, altered expression of Paneth cell-specific genes among CD patients with Types I and II Paneth cell phenotypes may reflect diminished Paneth cell function under stress. In contrast, the correlation of Paneth cell phenotypes and the expression of the oxidative phosphorylation gene cluster, and that these genes could be transcriptionally co-expressed and co-regulated, suggest that an alternative, central transcriptional regulation mechanism may be responsible. Future functional studies examining Paneth cells and oxidative phosphorylation will provide additional insight.

In addition, future studies that include longitudinal sampling would allow a more detailed understanding of the dynamics of the Paneth cell-microbiome-ileal transcriptome interaction, including the determination of temporal changes in Paneth cell phenotype, microbiome and their relationship with disease susceptibility, progression, and response to therapy. A recent in vivo study in mice has found that gut dysbiosis leads to chronic ileal inflammation with subsequent failure of Paneth cell function, suggesting an alternative "pathway" that could regulate both Paneth cell phenotype and CD development. Furthermore, another recent study examining a cohort of pediatric CD patients found that fecal microbiota composition is dynamic and can be affected by diet, antibiotics, and the presence of inflammation. Our previous finding suggests that the Paneth cell phenotypes do not vary significantly over time. Thus, a longitudinal study will allow us to address the biologic and clinical relevance of such finding. Although it has been shown that the gut microbiome matures and stabilizes after 3 years of age, expansion of the current cohort to improve age matching of the CD and non-IBD cohorts will provide sufficient statistical power to interrogate multiple potential clinical confounding factors. However, it should be noted that it is not possible to ethically recruit asymptomatic healthy subjects for endoscopic biopsies in a pediatric population.

Figure 6:
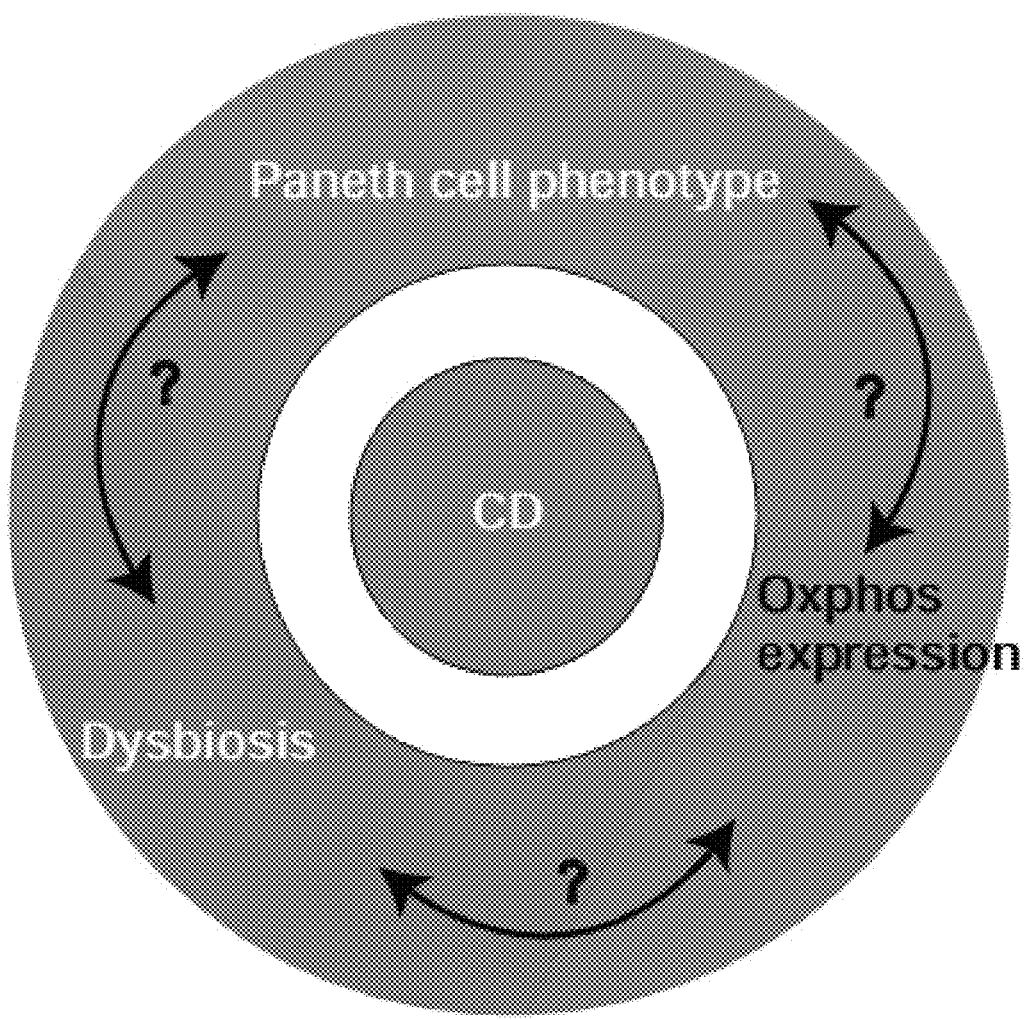
FIG. 6 depicts a schematic showing the proposed interactions between Paneth cell function, microbiota changes, and oxidative phosphorylation status in CD patients.

Importantly, our study suggests a potential complex interplay between Paneth cell phenotype and microbiome in CD, with oxidative phosphorylation being a potential mediator (FIG. 6). Of note, the microbiota has been proposed to play an important role in regulating host energy homeostasis through oxidative phosphorylation. Furthermore, a recent mouse study showed that alterations in diet can alter colonic microbial composition as well as down-regulation of oxidative phosphorylation genes. Further investigation is needed to reveal the mechanistic insight between Paneth cell function, microbiota changes, and oxidative phosphorylation status in the context of CD.

In summary, we have shown for the first time that a Paneth cell defect in CD patients correlates with changes in the mucosal microbiota, and identified the oxidative phosphorylation pathway as a potential mechanism. The imbalance of pro-inflammatory/barrier-associated microbial profiles associated with Paneth cell phenotypes and alterations in cellular metabolism provides us further insight into the disease pathogenesis. Future studies that include longitudinal sampling would allow a more detailed understanding of the temporal dynamics of the Paneth cell-microbiome-ileal transcriptome interaction, and their relationship with disease susceptibility, progression, and response to therapy.

Methods for Examples 1-5

Patients and Study Approval:

Patient samples were collected from Washington University School of Medicine (St. Louis), Cedars-Sinai Medical Center (Los Angeles), and Medical College of Wisconsin (Milwaukee), with approvals from each individual Institutional Review Board.

For the Washington University and Cedars-Sinai cohorts, CD patients who underwent ileocolectomy between 1999 and 2013 were identified through medical records. De-identified tissue samples from proximal (ileal) resection margins were used for Paneth cell phenotype analysis.

For the Milwaukee cohort, written informed consent was obtained from subjects or their parents/legal guardians. CD was defined and classified according to standard criteria (50, 51). A total of 70 CD patients were prospectively recruited from Medical College of Wisconsin, Milwaukee (Milwaukee cohort) from January 2011 to December 2013. After excluding those with inadequate biopsy samples for Paneth cell phenotyping (i.e., 40 or more crypts free of biopsy/processing artifact), 44 CD patients with Paneth cell phenotype and microbiome analyses remained. 6 of these patients' specimens failed quality control for transcriptome analysis. In parallel, a cohort of 83 symptomatic, non-IBD patients (not healthy volunteers) who underwent endoscopy for nonspecific gastrointestinal symptoms and without clinical or endoscopic evidence of CD were also recruited. Five with endoscopic inflammation (but otherwise did not meet diagnostic criteria for CD) and 16 with inadequate biopsy material for Paneth cell phenotype analysis were excluded. Therefore, only 62 patients with Paneth cell phenotype and microbiome analyses were included, of which 6 had failed quality control for transcriptome analysis. The detailed demographic and clinical information for these patients were shown in Table 1. Due to the exclusion of many samples due to quality control, the final cohorts of CD and non-IBD groups used for further analyses differ in age (P<0.0001; Table 1). Biopsies were taken from the terminal ileum using standard endoscopy forceps and placed in a sterile cryovial with RNAlater (QIAGEN; Valencia, Calif.) on ice in the endoscopy suite. Biopsy specimens were used for ileal microbiome and transcriptome studies, and Paneth cell phenotype analysis (see supplemental methods). The non-IBD controls underwent screening endoscopy for underlying gastrointestinal symptoms, but lacked macroscopic and microscopic inflammation. All subjects were free of any known infection at the time of sample collection.

Paneth Cell Phenotype Analysis:

Lysozyme and defensin 5 immunofluorescence was performed by T.C.L. Only samples with 40 or more well-oriented crypts that were free of biopsy artifact (and thus staining could be interpretable) were included for correlation analysis. For the Milwaukee cohort, the interpreter (T.C.L.) was blinded with the identity of the patients (CD vs. non-IBD) at the time of analysis. Classification of Type I and II Paneth cell phenotype was performed. In brief, each Paneth cell can be classified into normal (previously designated D0) or one of the 5 abnormal categories, including: disordered (abnormal distribution and size of the granules; previously designated D1), diminished (≤10 granules; previously designated D2), diffuse (smear of lysozyme or defensin within the cytoplasm with no recognizable granules; previously designated D3), excluded (majority of the granules do not contain stainable material; previously designated D4), and enlarged (rare, megagranules; previously designated D5)(25, 28). The Paneth cell phenotype of each patient is then defined by the percentage of total abnormal Paneth cells in the sample. Type I Paneth cell phenotype is defined as 20% of total Paneth cells showing morphologic defects, whereas Type II Paneth cell phenotype is defined as <20% of total Paneth cells showing morphologic defects.

Microbiome Analysis:

Genomic DNA was extracted from ileal biopsies using the MO BIO POWERLYZER POWERSOIL DNA Isolation kit (MO BIO, Carlsbad, Calif.) with slight modification in the protocol. After addition of C1 solution and heating the samples at 65° C. for 10 minutes, the sample was further subjected to heating at 95° C. for 10 minutes followed by vigorous bead beating using POWERLYZER (MO BIO). The 16S gene dataset consists of ILLUMINA MISEQ sequences targeting the V4 variable region. Detailed protocols used for 16S amplification and sequencing are as described before (52). In brief, genomic DNA was subjected to 16S amplifications using primers designed incorporating the ILLUMINA adapters and a sample barcode sequence, allowing directional sequencing covering variable region V4 (Primers: 515F [GTGCCAGCMGCCGCGGTAA] (SEQ ID NO:1) and 806R [GGACTACHVGGGTWTCTAAT] (SEQ ID NO:2)). PCR mixtures contained 10 µL of diluted template (1:50), 10 µL of HotMasterMix with the HotMaster Taq DNA Polymerase (5 Prime), and 5 µl of primer mix (2 µM of each primer). The cycling conditions consisted of an initial denaturation of 94° C. for 3 minutes, followed by 30 cycles of denaturation at 94° C. for 45 seconds, annealing at 50° C. for 60 seconds, extension at 72° C. for 5 minutes, and a final extension at 72° C. for 10 minutes. Amplicons were quantified on the Caliper LABCHIP GX (PerkinElmer, Waltham, Mass.), pooled in equimolar concentrations, size selected (375-425 bp) on the Pippin Prep (Sage Sciences, Beverly, Mass.) to reduce non-specific amplification products from host DNA, and a final library size and quantification was done on an Agilent Bioanalyzer 2100 DNA 1000 chips (Agilent Technologies, Santa Clara, Calif.). Sequencing was performed on the ILLUMINA MISEQ v2 platform, according to the manufacturer's specifications with addition of 5% PhiX, and generating paired-end reads of 175b in length in each direction. The overlapping paired-end reads were stitched together (approximately 97 bp overlap), size selected to reduce non-specific amplification products from host DNA (225-275 bp), and further processed in a data curation pipeline implemented in QIIME 1.5.0 as pick_reference_otus.py (53). In brief, this pipeline will pick operational taxonomic units (OTUs) using a reference-based method and constructs an OTU table. Taxonomy is assigned using the Greengenes predefined taxonomy map of reference sequence OTUs to taxonomy (54). The resulting OTU tables are checked for mislabeling (55) and contamination (56), and further microbial community analysis and visualizations. A mean sequence depth of 29,914/sample was obtained, and samples with less than 3,000 filtered sequences were excluded from analysis.

All samples were rarefied to a depth of 10000 sequences. Analysis of alpha diversity, including Faith's phylogenetic diversity (57) and Shannon diversity, was performed using alpha_diversity.py in QIIME on rarefied data. Beta-diversity was determined in QIIME using beta_diversity_through plots.py to determine both weighted and unweighted UniFrac distances and to generate principal coordinate analysis plots through Emperor (58).

RNA-Seq Data Quality Control and Processing:

RNA-seq reads were aligned to the GRCm38.76 assembly from Ensembl with STAR version 2.0.4b. Gene counts were derived from the number of uniquely aligned unambiguous reads by Subread:featureCount version 1.4.5. Sequencing performance was assessed for total number of aligned reads, total number of uniquely aligned reads, genes detected, ribosomal fraction known junction saturation and read distribution over known gene models with RSeQC version 2.3. All gene counts were subsequently normalized utilizing a generalized normalization package IRON version 2.1.5 (59) with RNA-Seq options.

Statistics:

Descriptive characteristics of the sample were summarized by median and interquartile range (IQR). A non-parametric Mann-Whitney-Wilcoxon test was used to compare continuous variables and a Chi-square test or Fisher's test was used to calculate the associations between categorical variables. Comparison of more than two groups was performed using the Kruskal-Wallis test followed by Dunn's multiple comparisons adjustment. Principle coordinate analysis was performed using ANOSIM with 999 permutations. Relative OTU abundance data were input into LEfSe to determine biomarkers with significant linear discriminant analysis effect size (60). Biomarkers for CD or non-IBD were identified by comparison of all samples. Biomarkers for Type I or II Paneth cell phenotypes were identified by within-group comparison of samples from CD patients or from non-IBD patients. After Kruskal-Wallis analysis (a value=0.05) of all features, a linear discriminant analysis model was used to rank discriminant features by the effect size with which they differentiated classes. The threshold for logarithmic linear discriminant analysis score for discriminative features was set at 2.0. Biomarkers were graphically annotated on a taxonomic tree with GraPhlAn (publicly available at <https://huttenhower.sph.harvard.edu/graphlan>). For transcriptome analysis, comparison between gene expression in each group stratified by patient group (CD vs. non-IBD) and Paneth cell phenotype was performed by one-way Analysis of Variance (ANOVA) followed by Tukey's multiple comparison adjustment. Pearson's correlation coefficient was used to calculate the correlations between gene expression level and percentage of normal Paneth cells (25). All tests were two-sided and a P value of <0.05 was considered significant. Data were plotted and analyzed using GRAPHPAD Prism (version 6.05) and SAS version 9.4 (SAS Institute, Cary, N.C.).

Genotyping of the Milwaukee Cohort:

DNA samples were genotyped for 196,524 markers using the Human Immuno_BeadChip_1149691 (Illumina Inc., San Diego, Calif., USA) according to the manufacture's protocol. Briefly, 200 ng of DNA (4 µL at 50 ng/µL) was independently amplified, labeled, and hybridized to Bead-Chip microarrays then scanned with default settings using the ILLUMINA ISCAN. Analysis was performed using Illumina's GenomeStudio Genotyping Module software v.2011. Genotype calls were initially generated using the ILLUMINA-provided genotype cluster definitions file (ImmunoChip_Gentrain_June2010, generated using HapMap project DNA samples) with a Gencall cutoff of 0.15. This was followed by manual inspection of approximately 5,000 low call SNPs and SNPs with AB frequency greater than 0.55. Genotype calls for six specific SNPs were examined for correlation with Paneth cell morphology: ATG16L1 SNPs rs12994997 and rs2241880 (T300A); and NOD2 SNPs rs2066844 (R702W), rs2066845 (G908R), rs5743289, and rs5743293 (L1007x, SNP13).

cDNA Library Construction:

Total RNA was isolated from ileal biopsy tissue using QIAGEN RNEASY Minikit, according to the kit protocol. Total RNA was quantified using the Quant-iT™ RIBOGREEN RNA Assay Kit and normalized to 4 ng/μL. An aliquot of 200 ng for each sample was transferred into library preparation, which was an automated variant of the ILLUMINA TRUSEQ mRNA Sample Preparation Kit. This method preserves strand orientation of the RNA transcript. It uses oligo dT beads to select mRNA from the total RNA sample. It is followed by heat fragmentation and cDNA synthesis from the RNA template. The resultant cDNA then goes through library preparation (end repair, base 'A' addition, adapter ligation, and enrichment) using Broad Institute designed indexed adapters substituted in for multiplexing. After enrichment the libraries were quantified with qPCR using the KAPA Library Quantification Kit for Illumina Sequencing Platforms and then pooled equimolarly. The entire process is in 96-well format and all pipetting is done by either Agilent Bravo or Hamilton Starlet.

Illumine Sequencing: Pooled libraries were normalized to 2 nM and denatured using 0.2N NaOH prior to sequencing. Flowcell cluster amplification and sequencing were performed according to the manufacturer's protocols using either the HiSeq 2000 v3 or HiSeq 2500. Each run was a 76 bp paired-end with an eight-base index barcode read. Data was analyzed using the Broad Picard Pipeline, which includes de-multiplexing and data aggregation.

TABLE 1

Basic information of the pediatric CD and non-IBD patients with mucosal microbiome, transcriptome, and Paneth cell phenotype analysis.

| Characteristic | Crohn's disease | Non-IBD controls | P value |
|---|---|---|---|
| Number | 44 | 62 | N/A |
| Median age (IQR)-yr | 15.5 (12.5-17) | 12 (9-14) | <0.0001 |
| Male sex (%) | 28 (64) | 33 (53) | 0.29 |
| Race | 4 | 5 | 0.30 |
| White | 2 | 5 | |
| Other | 2 | 7 | |
| Antibiotic exposure at the time of biopsy collection | 0 | 0 | N/A |
| CD Paris Classification* | L1-3 (7) | N/A | N/A |
| | L2-16 (36) | | |
| | L3-23 (52) | | |
| | Isolated small bowel disease-1 (2) | | |
| | Upper tract disease in combination with L1, L2, L3-25 (57) | | |
| | U/A-1 (2) | | |
| | B1-40 (91) | | |
| | B2-1 (2) | | |
| | B3-1 (2) | | |
| | B2/B3-1 (2) | | |
| Perianal disease (%) | 14 (32) | N/A | N/A |
| Granulomas (%) | 26 (60) | N/A | N/A |
| | U/A-1 (2) | | |
| IBD treatment at biopsy (%) | 33 (75) | N/A | N/A |

*L1: Distal 1/3 ileum ± limited cecal disease, L2: colonic, L3: ileocolonic, L4b-upper disease distal to ligament of Treitz.
B1: non-stricturing and non-penetrating, B2: stricturing, B3: penetrating.
N/A—not applicable.
U/A—unavailable.

TABLE 2

Mitochondrial oxidative phosphorylation gene cluster that is associated with Paneth cell phenotype.

| Gene | Description |
|---|---|
| UQCRHL | ubiquinol-cytochrome c reductase hinge protein-like |
| NDUFB3 | NADH dehydrogenase (ubiquinone) 1 beta subcomplex, 3, 12 kDa |
| NDUFS5 | NADH dehydrogenase (ubiquinone) Fe—S protein 5, 15 kDa (NADH-coenzyme Q reductase) |
| NDUFB1 | NADH dehydrogenase (ubiquinone) 1 beta subcomplex, 1, 7 kDa |
| NDUFA1 | NADH dehydrogenase (ubiquinone) 1 alpha subcomplex, 1, 7.5 kDa |
| COA3 | cytochrome c oxidase assembly factor 3 |
| NDUFS6 | NADH dehydrogenase (ubiquinone) Fe—S protein 6, 13 kDa (NADH-coenzyme Q reductase) |
| ATP5G1 | ATP synthase, H+ transporting, mitochondrial Fo complex, subunit C1 (subunit 9) |
| NDUFA9 | NADH dehydrogenase (ubiquinone) 1 alpha subcomplex, 9, 39 kDa |
| COX5A | cytochrome c oxidase subunit Va |
| COX6A1 | cytochrome c oxidase subunit VIa polypeptide 1 |
| UQCRH | ubiquinol-cytochrome c reductase hinge protein |
| UQCRQ | ubiquinol-cytochrome c reductase, complex III subunit VII, 9.5 kDa |
| UQCR10 | ubiquinol-cytochrome c reductase, complex III subunit X |
| ATP5I | ATP synthase, H+ transporting, mitochondrial Fo complex, subunit E |

TABLE 2-continued

Mitochondrial oxidative phosphorylation gene cluster that is associated with Paneth cell phenotype.

| Gene | Description |
| --- | --- |
| NDUFAF2 | NADH dehydrogenase (ubiquinone) complex I, assembly factor 2 |
| ATP5G3 | ATP synthase, H+ transporting, mitochondrial Fo complex, subunit C3 (subunit 9) |
| ATP5J2 | ATP synthase, H+ transporting, mitochondrial Fo complex, subunit F2 |
| COX7B | cytochrome c oxidase subunit VIIb |
| ATP5H | ATP synthase, H+ transporting, mitochondrial Fo complex, subunit d |
| COX6B1 | cytochrome c oxidase subunit VIb polypeptide 1 (ubiquitous) |
| NDUFA8 | NADH dehydrogenase (ubiquinone) 1 alpha subcomplex, 8, 19 kDa |
| NDUFB9 | NADH dehydrogenase (ubiquinone) 1 beta subcomplex, 9, 22 kDa |
| UQCRFS1 | ubiquinol-cytochrome c reductase, Rieske iron-sulfur polypeptide 1 |
| ATP5J | ATP synthase, H+ transporting, mitochondrial Fo complex, subunit F6 |
| NDUFB7 | NADH dehydrogenase (ubiquinone) 1 beta subcomplex, 7, 18 kDa |
| COQ5 | coenzyme Q5 homolog, methyltransferase (S. cerevisiae) |
| COX7A2 | cytochrome c oxidase subunit VIIa polypeptide 2 (liver) |
| NDUFB2 | NADH dehydrogenase (ubiquinone) 1 beta subcomplex, 2, 8 kDa |
| NDUFV3 | NADH dehydrogenase (ubiquinone) flavoprotein 3, 10 kDa |
| COX7C | cytochrome c oxidase subunit VIIc |
| COX5B | cytochrome c oxidase subunit Vb |
| COX6C | cytochrome c oxidase subunit VIc |
| NDUFA12 | NADH dehydrogenase (ubiquinone) 1 alpha subcomplex, 12 |
| NDUFB10 | NADH dehydrogenase (ubiquinone) 1 beta subcomplex, 10, 22 kDa |
| COX8A | cytochrome c oxidase subunit VIIIA (ubiquitous) |
| ATP5O | ATP synthase, H+ transporting, mitochondrial F1 complex, O subunit |
| COX4I1 | cytochrome c oxidase subunit IV isoform 1 |
| NDUFS4 | NADH dehydrogenase (ubiquinone) Fe—S protein 4, 18 kDa (NADH-coenzyme Q reductase) |
| ATP5L | ATP synthase, H+ transporting, mitochondrial Fo complex, subunit G |
| UQCRC1 | ubiquinol-cytochrome c reductase core protein I |
| NDUFS3 | NADH dehydrogenase (ubiquinone) Fe—S protein 3, 30 kDa (NADH-coenzyme Q reductase) |
| ATP5F1 | ATP synthase, H+ transporting, mitochondrial Fo complex, subunit B1 |
| NDUFA2 | NADH dehydrogenase (ubiquinone) 1 alpha subcomplex, 2, 8 kDa |
| COX7A1 | cytochrome c oxidase subunit VIIa polypeptide 1 (muscle) |
| NDUFB5 | NADH dehydrogenase (ubiquinone) 1 beta subcomplex, 5, 16 kDa |
| ATP5E | ATP synthase, H+ transporting, mitochondrial F1 complex, epsilon subunit |
| ATP5C1 | ATP synthase, H+ transporting, mitochondrial F1 complex, gamma polypeptide 1 |
| NDUFB11 | NADH dehydrogenase (ubiquinone) 1 beta subcomplex, 11, 17.3 kDa |
| ATP5B | ATP synthase, H+ transporting, mitochondrial F1 complex, beta polypeptide |

TABLE 3

Paneth cell gene cluster that is associated with Paneth cell phenotype.

| Gene name | Description |
| --- | --- |
| MSI1 | musashi RNA-binding protein 1 |
| PLA2G2A | phospholipase A2, group IIA (platelets, synovial fluid) |
| CARD16 | caspase recruitment domain family, member 16 |
| REG3A | regenerating islet-derived 3 alpha |
| DEFA6 | defensin, alpha 6, Paneth cell-specific |
| EMP2 | epithelial membrane protein 2 |
| EPHB2 | EPH receptor B2 |
| DEFA5 | defensin, alpha 5, Paneth cell-specific |
| LYZ | lysozyme |
| SPINK1 | serine peptidase inhibitor, Kazal type 1 |
| LCN2 | lipocalin 2 |
| REG1A | regenerating islet-derived 1 alpha |
| PIGR | polymeric immunoglobulin receptor |

REFERENCES FOR EXAMPLES 1-5

1. Jostins, L., et al. 2012. Host-microbe interactions have shaped the genetic architecture of inflammatory bowel disease. *Nature* 491:119-124.
2. Rogler, G., and Vavricka, S. 2015. Exposome in IBD: recent insights in environmental factors that influence the onset and course of IBD. *Inflamm Bowel Dis* 21:400-408.
3. Bloom, S. M., et al. 2011. Commensal *Bacteroides* species induce colitis in host-genotype-specific fashion in a mouse model of inflammatory bowel disease. *Cell Host Microbe* 9:390-403.
4. Bevins, C. L., and Salzman, N. H. 2011. Paneth cells, antimicrobial peptides and maintenance of intestinal homeostasis. *Nat Rev Microbiol* 9:356-368.
5. Kaser, A., et al. 2008. XBP1 links ER stress to intestinal inflammation and confers genetic risk for human inflammatory bowel disease. *Cell* 134:743-756.
6. Adolph, T. E., et al. 2013. Paneth cells as a site of origin for intestinal inflammation. *Nature* 503:272-276.

7. Salzman, N. H., et al. 2010. Enteric defensins are essential regulators of intestinal microbial ecology. *Nat Immunol* 11:76-83.
8. Wilson, C. L., et al. 1999. Regulation of intestinal alpha-defensin activation by the metalloproteinase matrilysin in innate host defense. *Science* 286:113-117.
9. Salzman, N. H., Ghosh, D., Huttner, K. M., Paterson, Y., and Bevins, C. L. 2003. Protection against enteric salmonellosis in transgenic mice expressing a human intestinal defensin. *Nature* 422:522-526.
10. Wehkamp, J., et al. 2005. Reduced Paneth cell alpha-defensins in ileal Crohn's disease. *Proc Natl Acad Sci USA* 102:18129-18134.
11. Perminow, G., et al. 2010. Defective paneth cell-mediated host defense in pediatric ileal Crohn's disease. *Am J Gastroenterol* 105:452-459.
12. Belkaid, Y., and Hand, T. W. 2014. Role of the microbiota in immunity and inflammation. *Cell* 157:121-141.
13. Kostic, A. D., Xavier, R. J., and Gevers, D. 2014. The microbiome in inflammatory bowel disease: current status and the future ahead. *Gastroenterology* 146:1489-1499.
14. Deuring, J. J., et al. 2014. Genomic ATG16L1 risk allele-restricted Paneth cell ER stress in quiescent Crohn's disease. *Gut* 63:1081-1091.
15. Willing, B., et al. 2009. Twin studies reveal specific imbalances in the mucosa-associated microbiota of patients with ileal Crohn's disease. *Inflamm Bowel Dis* 15:653-660.
16. Kolho, K. L., et al. 2015. Fecal Microbiota in Pediatric Inflammatory Bowel Disease and Its Relation to Inflammation. *Am J Gastroenterol* 110:921-930.
17. Hansen, R., et al. 2012. Microbiota of de-novo pediatric IBD: increased Faecalibacterium prausnitzii and reduced bacterial diversity in Crohn's but not in ulcerative colitis. *Am J Gastroenterol* 107:1913-1922.
18. Schwiertz, A., et al. 2010. Microbiota in pediatric inflammatory bowel disease. *J Pediatr* 157:240-244 e241.
19. Conte, M. P., et al. 2006. Gut-associated bacterial microbiota in paediatric patients with inflammatory bowel disease. *Gut* 55:1760-1767.
20. Manichanh, C., et al. 2006. Reduced diversity of faecal microbiota in Crohn's disease revealed by a metagenomic approach. *Gut* 55:205-211.
21. Lewis, J. D., et al. 2015. Inflammation, Antibiotics, and Diet as Environmental Stressors of the Gut Microbiome in Pediatric Crohn's Disease. *Cell Host Microbe* 18:489-500.
22. Gevers, D., et al. 2014. The treatment-naive microbiome in new-onset Crohn's disease. *Cell Host Microbe* 15:382-392.
23. Schaubeck, M., et al. 2015. Dysbiotic gut microbiota causes transmissible Crohn's disease-like ileitis independent of failure in antimicrobial defence. *Gut*.
24. Cadwell, K., et al. 2008. A key role for autophagy and the autophagy gene Atg16l1 in mouse and human intestinal Paneth cells. *Nature* 456:259-263.
25. VanDussen, K. L., et al. 2014. Genetic variants synthesize to produce paneth cell phenotypes that define subtypes of Crohn's disease. *Gastroenterology* 146:200-209.
26. Cadwell, K., et al. 2010. Virus-plus-susceptibility gene interaction determines Crohn's disease gene Atg16L1 phenotypes in intestine. *Cell* 141:1135-1145.
27. Liu, B., et al. 2013. Irgm1-deficient mice exhibit Paneth cell abnormalities and increased susceptibility to acute intestinal inflammation. *Am J Physiol Gastrointest Liver Physiol* 305: G573-584.
28. Liu, T. C., Gao, F., McGovern, D. P., and Stappenbeck, T. S. 2014. Spatial and temporal stability of paneth cell phenotypes in Crohn's disease: implications for prognostic cellular biomarker development. *Inflamm Bowel Dis* 20:646-651.
29. Haberman, Y., et al. 2014. Pediatric Crohn disease patients exhibit specific ileal transcriptome and microbiome signature. *J Clin Invest* 124:3617-3633.
30. Sokol, H., et al. 2008. Faecalibacterium prausnitzii is an anti-inflammatory commensal bacterium identified by gut microbiota analysis of Crohn disease patients. *Proc Natl Acad Sci USA* 105:16731-16736.
31. Kobayashi, T., et al. 2015. Dysbiosis and *Staphyloccus aureus* Colonization Drives Inflammation in Atopic Dermatitis. *Immunity* 42:756-766.
32. Dinh, D. M., et al. 2015. Intestinal microbiota, microbial translocation, and systemic inflammation in chronic HIV infection. *J Infect Dis* 211:19-27.
33. Virgin, H. W., and Todd, J. A. 2011. Metagenomics and personalized medicine. *Cell* 147:44-56.
34. Tschurtschenthaler, M., et al. 2014. Type I interferon signalling in the intestinal epithelium affects Paneth cells, microbial ecology and epithelial regeneration. *Gut* 63:1921-1931.
35. Palm, N. W., et al. 2014. Immunoglobulin A coating identifies colitogenic bacteria in inflammatory bowel disease. *Cell* 158:1000-1010.
36. Dalal, S. R., and Chang, E. B. 2014. The microbial basis of inflammatory bowel diseases. *J Clin Invest* 124:4190-4196.
37. Huttenhower, C., Kostic, A. D., and Xavier, R. J. 2014. Inflammatory bowel disease as a model for translating the microbiome. *Immunity* 40:843-854.
38. Albenberg, L. G., and Wu, G. D. 2014. Diet and the intestinal microbiome: associations, functions, and implications for health and disease. *Gastroenterology* 146:1564-1572.
39. Chassaing, B., and Darfeuille-Michaud, A. 2011. The commensal microbiota and enteropathogens in the pathogenesis of inflammatory bowel diseases. *Gastroenterology* 140:1720-1728.
40. Round, J. L., and Mazmanian, S. K. 2009. The gut microbiota shapes intestinal immune responses during health and disease. *Nat Rev Immunol* 9:313-323.
41. McGovern, D. P., Kugathasan, S., and Cho, J. H. 2015. Genetics of Inflammatory Bowel Diseases. *Gastroenterology* 149:1163-1176 e1162.
42. Avitzur, Y., et al. 2014. Mutations in tetratricopeptide repeat domain 7A result in a severe form of very early onset inflammatory bowel disease. *Gastroenterology* 146: 10281039.
43. Uhlig, H. H., et al. 2014. The diagnostic approach to monogenic very early onset inflammatory bowel disease. *Gastroenterology* 147:990-1007 e1003.
44. Shanahan, M. T., et al. 2014. Mouse Paneth cell antimicrobial function is independent of Nod2. *Gut* 63:903-910.
45. Hodin, C. M., et al. 2011. Reduced Paneth cell antimicrobial protein levels correlate with activation of the unfolded protein response in the gut of obese individuals. *J Pathol* 225:276-284.
46. van Waveren, C., and Moraes, C. T. 2008. Transcriptional co-expression and co-regulation of genes coding for components of the oxidative phosphorylation system. *BMC Genomics* 9:18.
47. Yatsunenko, T., et al. 2012. Human gut microbiome viewed across age and geography. *Nature* 486:222-227.

48. Donohoe, D. R., et al. 2011. The microbiome and butyrate regulate energy metabolism and autophagy in the mammalian colon. *Cell Metab* 13:517-526.
49. Mu, C., Yang, Y., Luo, Z., Guan, L., and Zhu, W. 2016. The Colonic Microbiome and Epithelial Transcriptome Are Altered in Rats Fed a High-Protein Diet Compared with a Normal-Protein Diet. *J Nutr.*
50. Bernstein, C. N., et al. 2010. World Gastroenterology Organization Practice Guidelines for the diagnosis and management of IBD in 2010. *Inflamm Bowel Dis* 16:112-124.
51. Levine, A., et al. 2011. Pediatric modification of the Montreal classification for inflammatory bowel disease: the Paris classification. *Inflamm Bowel Dis* 17:1314-1321.
52. Caporaso, J. G., et al. 2012. Ultra-high-throughput microbial community analysis on the Illumina HiSeq and MiSeq platforms. *ISME J* 6:1621-1624.
53. Caporaso, J. G., et al. 2010. QIIME allows analysis of high-throughput community sequencing data. *Nat Methods* 7:335-336.
54. McDonald, D., et al. 2012. An improved Greengenes taxonomy with explicit ranks for ecological and evolutionary analyses of bacteria and archaea. *ISME J* 6:610-618.
55. Knights, D., et al. 2011. Supervised classification of microbiota mitigates mislabeling errors. *ISME J* 5:570-573.
56. Knights, D., et al. 2011. Bayesian community-wide culture-independent microbial source tracking. *Nat Methods* 8:761-763.
57. Faith, D. P., and Baker, A. M. 2006. Phylogenetic diversity (PD) and biodiversity conservation: some bioinformatics challenges. *Evol Bioinform Online* 2:121-128.
58. Vazquez-Baeza, Y., Pirrung, M., Gonzalez, A., and Knight, R. 2013. EMPeror: a tool for visualizing high-throughput microbial community data. *Gigascience* 2:16.
59. Welsh, E. A., Eschrich, S. A., Berglund, A. E., and Fenstermacher, D. A. 2013. Iterative rank-order normalization of gene expression microarray data. *BMC Bioinformatics* 14:153.
60. Segata, N., et al. 2011. Metagenomic biomarker discovery and explanation. *Genome Biol* 12: R60.

Example 6. Morphologic Cytoplasmic Staining Patterns in Paneth Cells (as Determined by HD5 Immunofluorescence) Predict the Prognosis of Patients with Crohn's Disease Currently there is no reliable biomarker that could be used to predict the prognosis and/or response to treatment for patients with Crohn's disease. Paneth cell phenotype correlates with prognosis in Crohn's disease patients undergoing resection. Paneth cell phenotype is defined by categorizing each Paneth cell based on the distribution patterns of the antimicrobial protein into "normal" and "abnormal" Paneth cells. A minimum of 50 well-oriented crypts free of staining artifact are required for accurate phenotyping. Once each Paneth cell morphology pattern is categorized, the percentage of total Paneth cells with normal morphology is then determined. A cut off of 80% normal Paneth cells is used, and an abnormal Paneth cell phenotype is defined as <80% normal Paneth cells, whereas a normal Paneth cell phenotype is defined as 80% normal Paneth cells. Importantly, the morphology patterns of Paneth cells are best realized using immunofluorescence. Routine hematoxylin and eosin as well as immune-peroxidase staining do not offer the same resolution as immunofluorescence.

Previous findings were based solely on immunofluorescence staining using lysozyme antibody. However, in addition to Paneth cells, lysozyme is also expressed in myeloid-derived cells within the gastrointestinal (GI) tract, and this poses a technical limitation for developing an automated quantification system.

In the present disclosure, an HD5 antibody for immunofluorescence is used. HD5 is only expressed in Paneth cells and not in any other cell type within the GI tract, thus largely increasing the specificity of this test.

A second control marker using nuclear pore protein immunofluorescence may be used to determine the morphologic pattern of the nuclei of each Paneth cells. The use of DAPI as a nuclear stain shows no significant nuclear morphologic defect in Paneth cells with abnormal Paneth cell phenotype. A normal Paneth cell: normal nucleus ratio will be determined for each sample analyzed and a cut off of 80% will be used to stratify patients.

Figure 15:
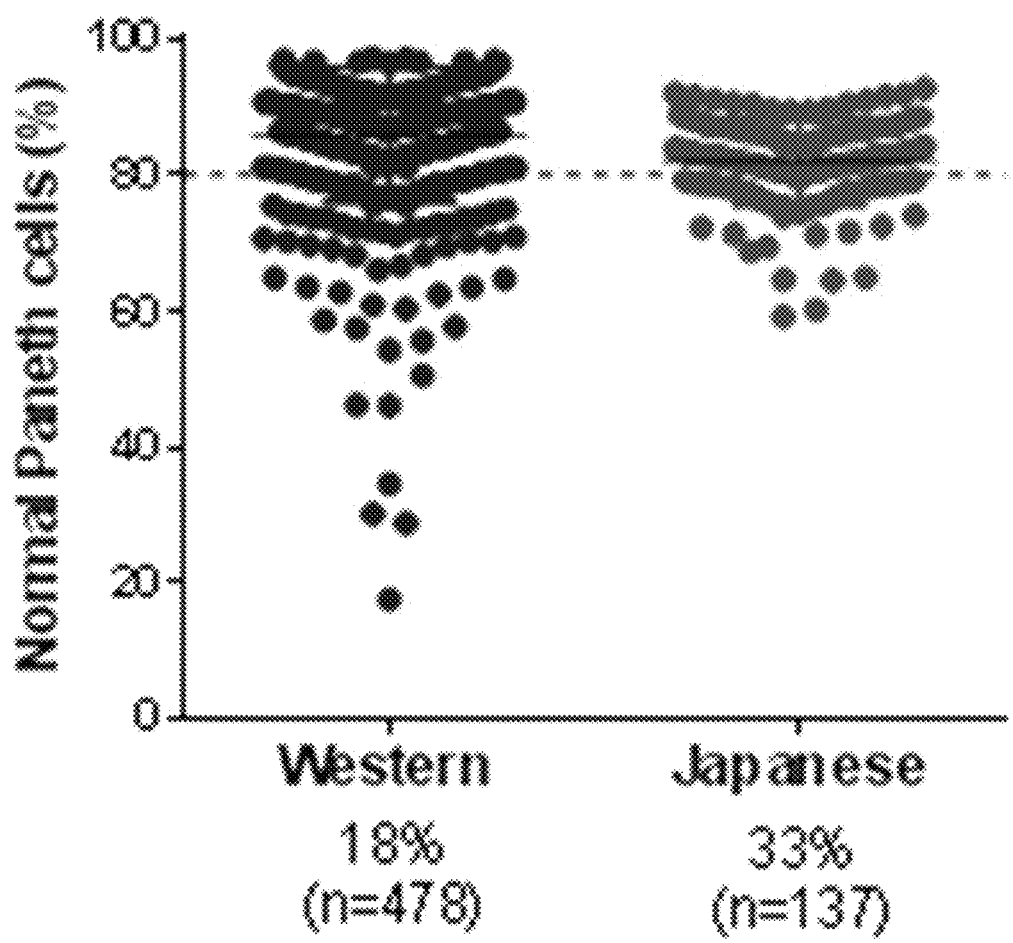
FIG. 15 depicts a graph showing that type I (abnormal) Paneth cell phenotype is prevalent in Western and Asian CD cohorts.
Figure 17:
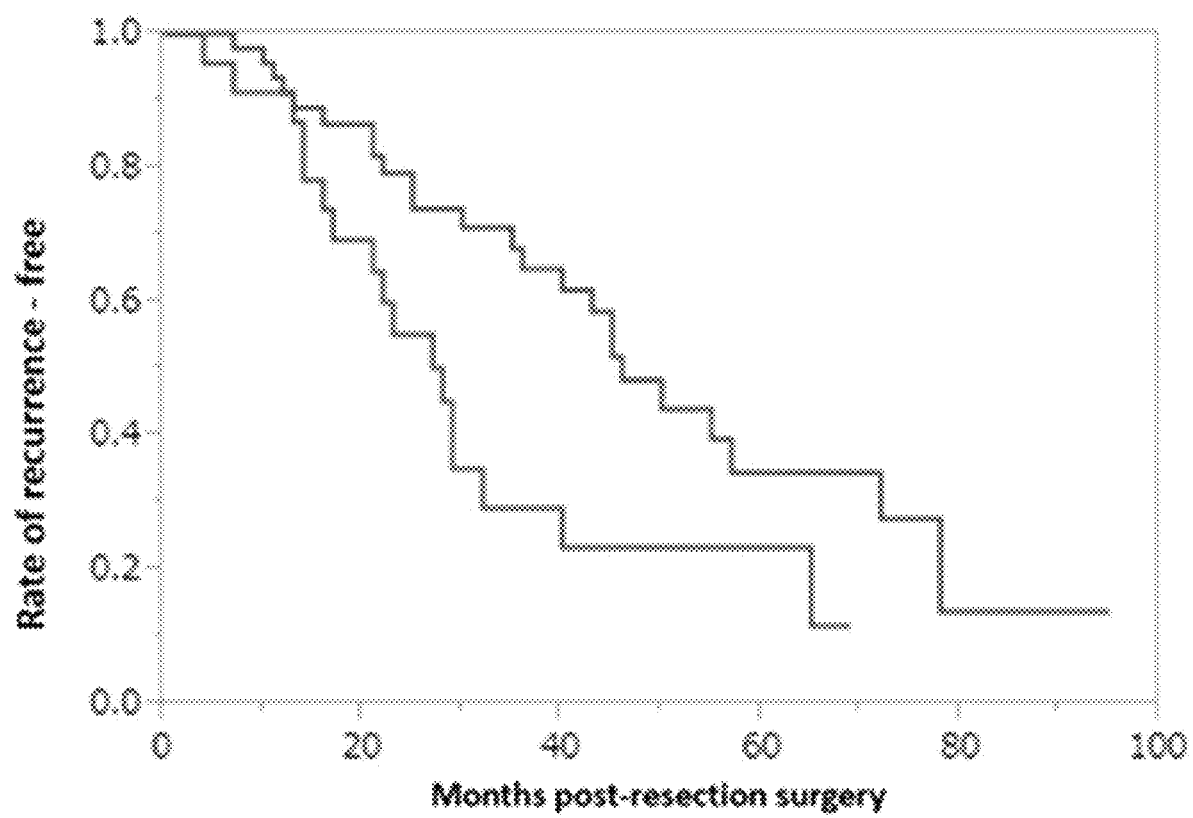
FIG. 17 depicts a graph showing that type I (abnormal) Paneth cell phenotype, as determined by HD5 IF, correlates with prognosis after surgery (P=0.0135).

Described herein is data correlating Paneth cell phenotype as defined by HD5 immunofluorescence, and prognosis of CD patients. Using a Japanese CD cohort, it was found that Type I (abnormal) Paneth cell phenotype (defined by 20% total Paneth cells with abnormal granule pattern) is prevalent in Japanese CD patients (FIG. 15), and that it correlates with time to disease recurrence after surgery. Type II (normal) Paneth cell phenotype, defined by <20% total Paneth cells with abnormal granule pattern, was associated with better prognosis in this cohort (P=0.013) (FIG. 17).

Example 7. Paneth Cell Phenotype is Associated with Novel Genetic Determinants and Clinical Outcome in Japanese Crohn's Disease Patients Background:
Morphology patterns of small intestinal Paneth cells (Paneth cell phenotypes) have emerged as a unique cellular biomarker for Western Crohn's disease (CD) patients. It integrates the effect of host genetics and environmental factors and is associated with pathology hallmark and clinical outcome. We previously showed that abnormal Paneth cells (PC) were associated with mutations in ATG16L1 and NOD2, both important in the pathogenesis of Western CD. To broaden the application of PC phenotype in CD, further understanding of the genetic determinants of PC phenotype and clinical validation is critical, in particular in other ethnic groups who possess a distinct spectrum of susceptibility genes than Caucasian CD. We hypothesized that novel genetic determinants exist in Asian CD, and that PC phenotype is also associated with poor outcome in these patients.

Methods
Subjects:
A total of 110 Japanese patients with CD were included in this study. All patients were diagnosed with CD and underwent ileal resection at Tohoku University Hospital (Sendai, Japan) between 2003 and 2014. The self-reported ethnicity of all patients was Japanese. The diagnosis of CD was made based on clinical symptoms and endoscopic, radiographic, and histological findings according to conventional criteria proposed by the Japanese Ministry of Health, Labour and Welfare (72). Demographics and clinical parameters (including clinical phenotype by Montreal classification, medication received prior to and after surgery, time to disease recurrence after resection) were extracted from the medical records blinded to Paneth cell phenotypes.

In addition, a total of 164 CD patients who underwent ileal resection were recruited at Washington University School of Medicine (St. Louis, Mo.) between 2005-2013, including a subset of patients (n=50) that were previously reported (19).

Paneth Cell Phenotype Analysis:

Ileal resection samples previously collected as part of standard diagnostic procedures and stored in Pathology Department archives at Tohoku University and Washington University were used for Paneth cell phenotype determination. The specimens were processed as formalin-fixed, paraffin-embedded tissue blocks as per routine surgical pathology practice. To be included in the study, the proximal margin tissue resection samples must have contained at least 50 well-oriented intestinal crypts (1) as determined by a pathologist (T.C.L.). Paneth cell phenotype was determined by Defensin-5 immunofluorescence, using Defensin-5 antibody (clone 8C8; dilution 1:2000; Novus Biologicals catalog number NB110) followed by donkey anti-mouse Alexa 488 antibody (dilution 1:500; ThermoFisher catalog number A-21202) as previously described (2). For a subset of cases, co-staining with lysozyme immunofluorescence was performed using lysozyme antibody (clone C-19; dilution 1:100; Santa Cruz catalog number sc-27958) followed by donkey anti-goat Alexa 594 antibody (dilution 1:500; ThermoFisher catalog number A-11058). Each Paneth cell was classified as normal or abnormal based on the morphology of the cytoplasmic granules (1-3). For prognostic correlation, the overall Paneth cell phenotype for each patient was then defined as following: Type I Paneth cell phenotype was defined as ≥20% abnormal Paneth cells, whereas Type II Paneth cell phenotype was defined as <20% abnormal Paneth cells (1-3). The cutoff of 20% was based on the analysis of 106 non-IBD cases, which showed that the mean percentage of normal Paneth cells was 80.63 (±1.17 SEM). Paneth cell phenotype analysis was performed by a pathologist (T.C.L.) who was blinded to the identification and clinical phenotype of the cases.

Definitions of Clinical Remission and Clinical Relapse:

Time from index ileal resection surgery of CD to relapse was calculated. Endoscopy and/or computed tomography were performed when the patients had symptoms indicating recurrence (i.e., abdominal pain, worsening of diarrhea, fever, body weight loss, nausea, and appetite loss), or at least once a year if the patients had no symptoms.

Definitions of recurrence were made by endoscopy and/or radiology. Endoscopic recurrence was defined as post-operative Rutgeert's score of i2 or more. Radiologic recurrence was defined by computed tomography showing bowel wall thickening (defined as a thickness >5 mm) or enhancement, fistulas, intra-abdominal abscess and bowel obstruction. All computed tomography scans were reviewed by two radiologists. Patients who received immunomodulators (thiopurines), biologics (infliximab or adalimumab), or elemental diet (more than 600 kcal/day) (4) post-resection were considered to have received postoperative prophylaxis.

Genotyping:

For Japanese CD patients, genomic DNA was obtained from peripheral blood leukocytes by standard phenol-chloroform extraction precipitation or by utilizing NA1000 Automated Nucleic Acid Extraction Machine (Kurabo, Osaka, Japan) or PAXgene DNA Kit (BD, New Jersey, USA). The genome-wide SNP genotypes of the Japanese CD patients were determined by the JAPONICA ARRAY, a SNP array designed specifically for the Japanese population (5). The array contains 659,253 SNPs, including tag SNPs for imputation, as well as SNPs related to phenotypes from previously reported GWAS and pharmacogenomics studies. As a part of quality control (QC) measures, SNPs with call rate less than 95% and samples with genotyping rates less than 95% were excluded from further analysis. Following SNP and sample QC, genotype data of 643,496 SNPs from 98 CD cases were available for further analysis. For North American CD patients, genomic DNA was extracted from whole blood (n=50) as described above or from formalin-fixed, paraffin-embedded (FFPE) tissue using QIAamp DNA FFPE Tissue kit (QIAGEN, Valencia, Calif.)(n=114). For cases where whole blood was used for genomic DNA extraction, genotyping was performed with Immunochip as previously described (3). For cases where FFPE tissue was used for genomic DNA extraction, genotyping was performed with TAQMAN SNP genotyping assays (Thermo Fisher; Waltham, Mass.).

Imputation:

Untyped genotypes were imputed in the GWAS samples using IMPUTE2 (version 2.3.2) and 1070 healthy individuals from Japan (1KJPN panel, which contain >20 million SNPs) (6) as a reference dataset. SNPs with low imputation quality (with a posterior probability score of <0.90), minor allele frequency <0.10 and Hardy-Weinberg equilibrium P value <1×10-5 were excluded. After exclusion, genotype data of 4,198,245 SNPs from 98 Japanese CD cases were used for further analysis.

Pathway and Network Analysis:

Gene enrichment and network analysis was performed on the top 288 annotated genes corresponding to the SNPs P 1×10-3 (from linear regression) using online bioinformatics tools (DAVID [<https://david.ncifcrf.gov/tools.jsp>]; STRING [<http://www.string-db.org/>]). Functional annotation clusters corresponding to the gene list were identified using DAVID. Protein-protein interaction (PPI) network for the 288 genes was extracted using STRING. An annotation network was constructed by combining function-based information with PPI network information and visualized using Cytoscape (<http://www.cytoscape.org>). Corresponding pathways (P<0.05) were annotated using the enrichment analysis tool in STRING. Core pathway analysis of the 17 candidate genes was performed using Ingenuity Pathway Analysis software (Qiagen; Redwood City, Calif.).

Figure 18:
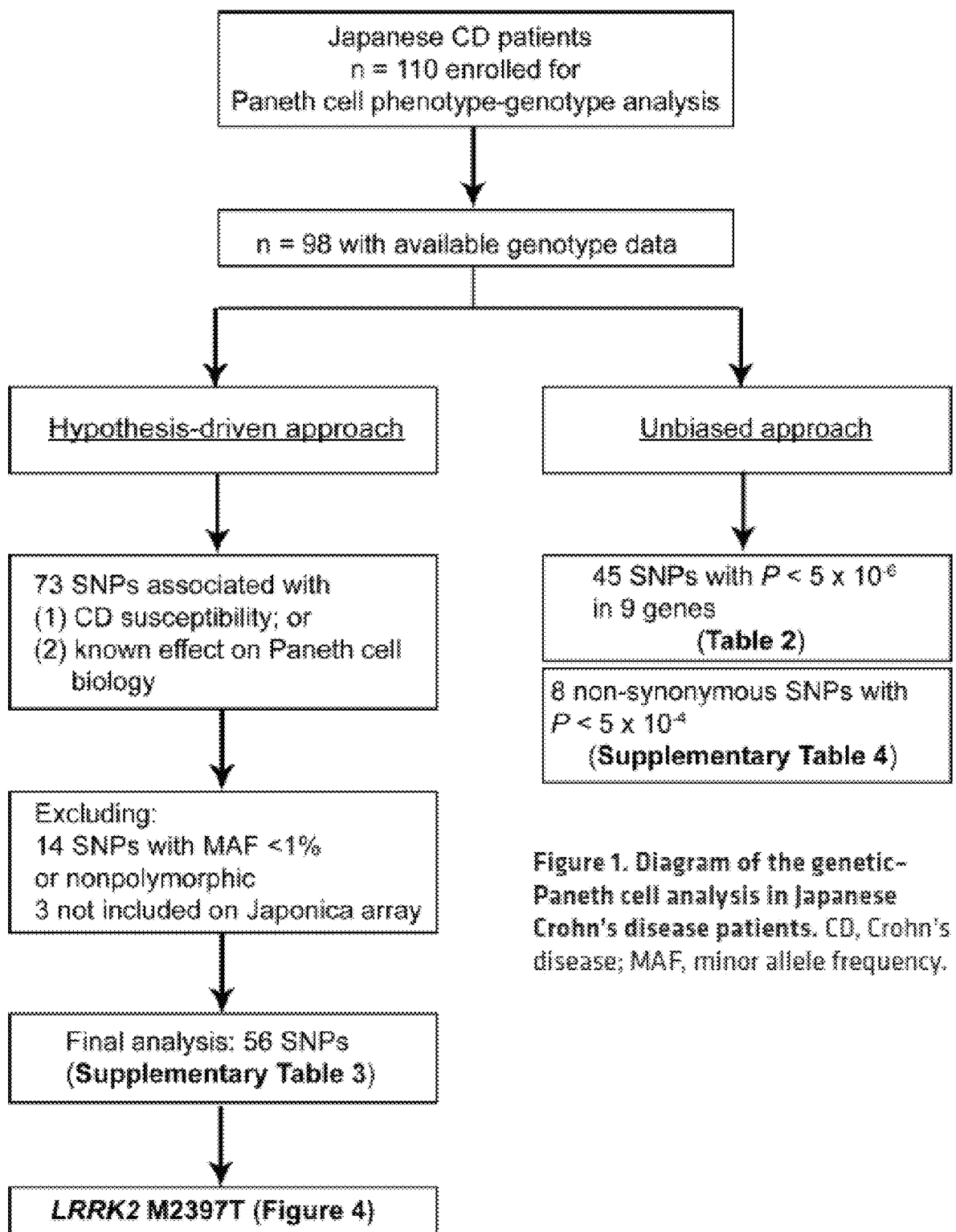
FIG. 18 depicts a flow chart of the genetic-Paneth cell analysis in Japanese Crohn's disease patients.

Statistical Analyses:

The percentages of normal Paneth cells between North American CD and Japanese CD were compared by unpaired T test, and the prevalence of Type I Paneth cell phenotype between the two groups were compared using Fisher exact test. For genotype-Paneth cell defect correlation, we first adopted a hypothesis-driven approach with selected SNPs (FIG. 18). These SNPs include: (1) 45 SNPs shown to be CD-specific susceptibility from ImmunoChip study examining European ancestry CD (7); (2) an additional 38 SNPs reported in European and East Asian ancestry CD (7); (3) 14 SNPs associated with East Asian (Japanese and/or Korean) CD through GWAS analyses (8-11) and deep-resequencing analysis (11); and (4) 2 functional CD-associated variants that were either reported to be associated with Paneth cell defect in our previous studies (13, 14), or whose genes involved had been implicated to be associated with Paneth cell biology in preclinical studies (15, 16). By excluding duplicates, a total of 73 SNPs were compiled as candidates. Among the 73 SNPs, 14 SNPs were very rare (MAF<1.0%) or non-polymorphic (i.e., NOD2 variants) in East Asian, and 3 SNPs were not constructed/included on the *Japonica* Array. After excluding these 17 SNPs, a final 56 SNPs were selected for hypothesis driven approach. After Bonferroni correction, SNPs with P-values <8.93×10-4 were considered significant. For hypothesis-driven analyses, we correlated the genotypes with the percentage of normal Paneth cells by linear regression.

For the subsequent unbiased, genome-wide association analysis (FIG. 18), linear regression was performed using PLINK v 1.07 software (16). SNPs with P-values $<5\times10^{-8}$ were considered genome-wide significant. SNPs with P-values $<5\times10^{-6}$ and non-synonymous SNPs with P-values $<5\times10^{-4}$ were considered candidates with nominal significance.

SNPs located within 100 kbp were considered to be in one region. Genes within 200 kbp of candidate SNPs were investigated. Correlation with time to disease recurrence after surgery was performed using the log-rank test and Cox-proportional hazards model. Manhattan plots were generated using the R package qqman, regional association plots were generated using LocusZoom application (17). All statistical analyses, except genome-wide linear regression, were performed using JMP 11 (SAS Institute Inc., Cary, N.C., USA), GraphPad Prism (version 6.5), or R software (version 3.1.3).

Power Calculation:

Using the software Quanto, we calculated the power of current study to detect genetic variants associated with the Paneth cell phenotype, and demonstrated that in the Japanese cohort, we have a power of 80.66% to detect a variant with variance contribution of 0.07 at 0.05 significance threshold for hypothesis-driven approach. In the Washington University cohort, we have a power of 82.65% to detect a variant with variance contribution of 0.05 with a significance threshold of 0.05. At genome-wide significance threshold ($5\times10^{-8}$), the Japanese cohort has a power of 56.91% to detect a variant with variance contribution of 0.247.

Study Approval:

The study was approved by the Ethics Committee of Tohoku University Graduate School of Medicine (Tohoku, Sendai, Japan) under protocol number 2013-1-539 and the Institution Review Board of Washington University School of Medicine (St. Louis, Mo., USA) under protocol number 201209047. Subjects provided informed consent prior to their participation in the study.

Data Depository:

The accession number for the genotyping data deposition at NCBI GEO repository is GSE90102.

Results

Figure 19:
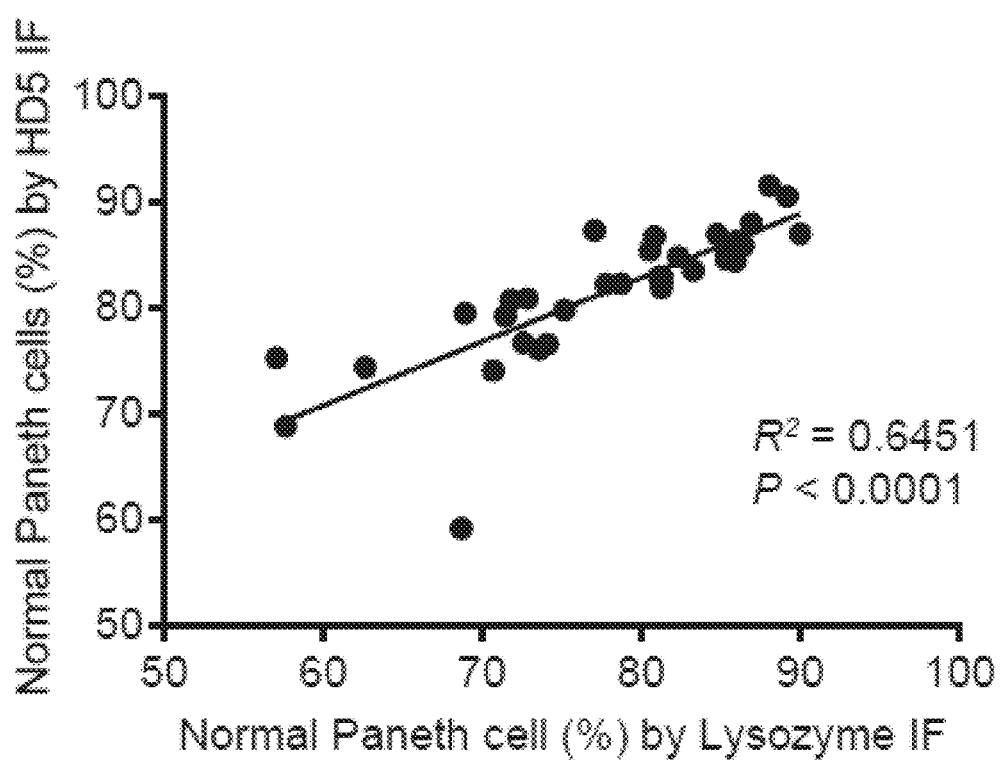
FIG. 19 depicts a graph showing the determination of percentage of normal Paneth cells obtained by Defensin-5 (HD5) immunofluorescence strongly correlated with that obtained by lysozyme immunofluorescence. A series of 33 Japanese Crohn's disease cases were co-stained with both HD5 and lysozyme immunofluorescence ($R^2=0.6451$; $P<0.0001$ by linear regression).
Figure 20A:
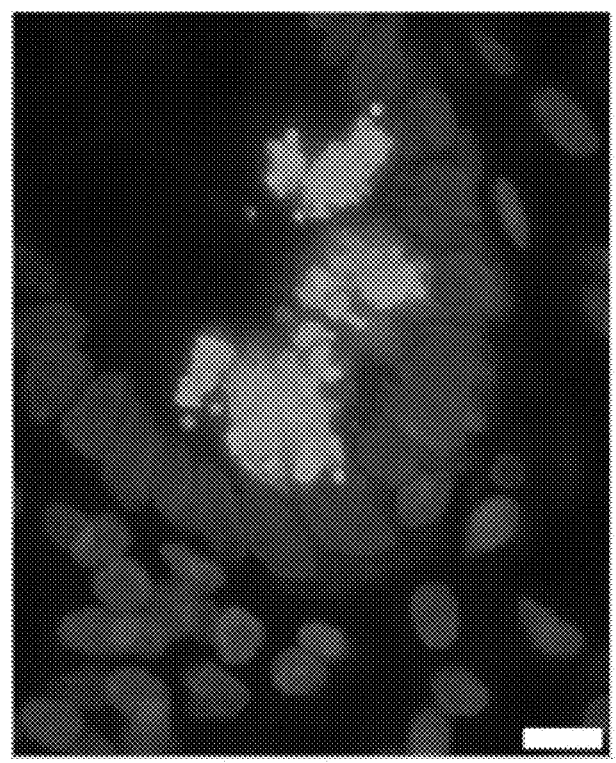
FIG. 20A and FIG. 20B depict graphs of Type I Paneth cell phenotype was prevalent in Japanese Crohn's disease (CD).
Figure 20B:
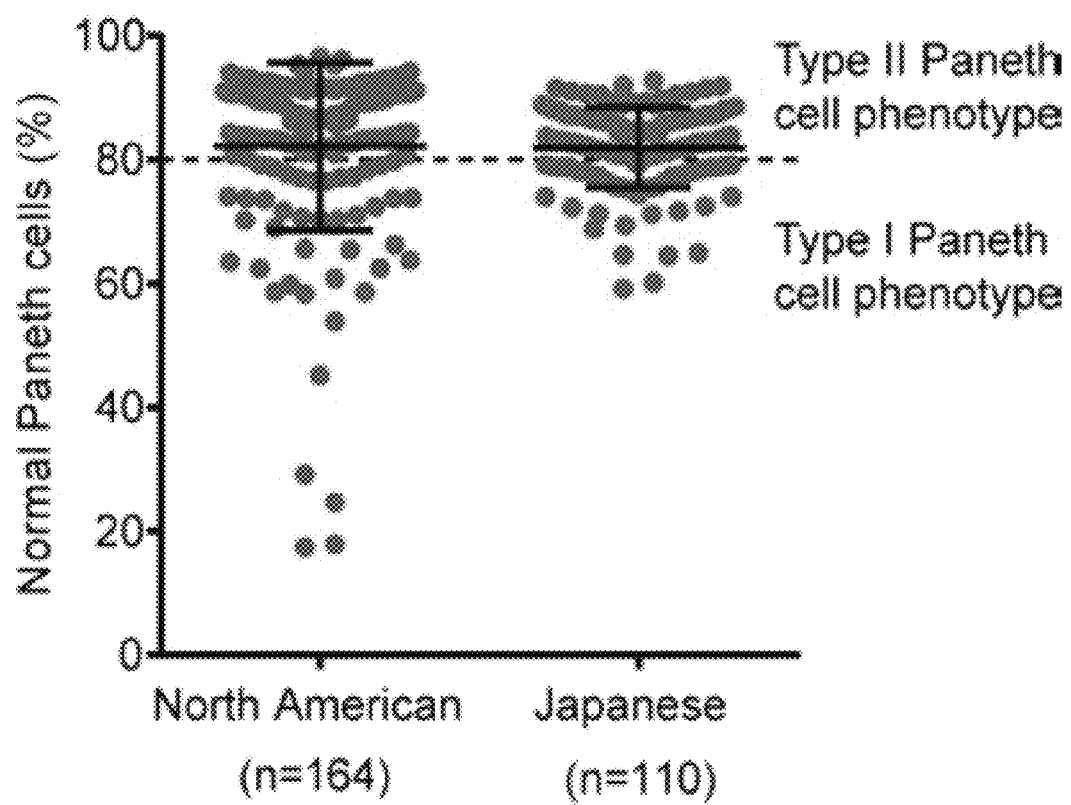
Figure 21A:
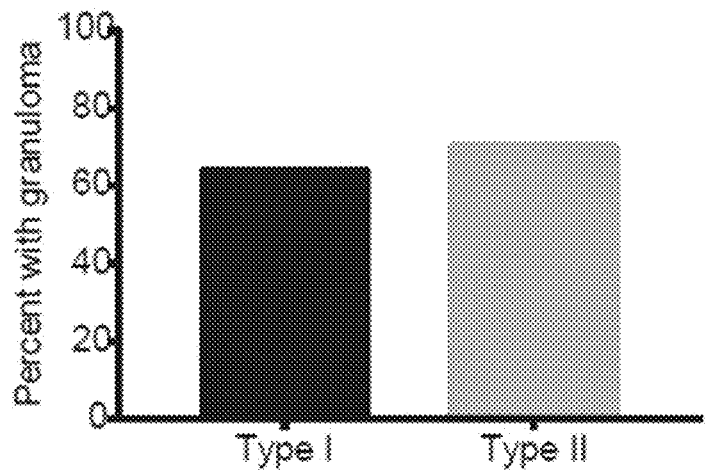
FIG. 21A, FIG. 21B, FIG. 21C, FIG. 21D, FIG. 21E, and FIG. 21F depict graphs showing the correlation of Paneth cell phenotype and presence of granuloma in the Japanese Crohn's disease cohort. No significant difference was seen when the presence of granuloma was correlated with (FIG. 21A) Type I vs. Type II Paneth cell phenotype (P=0.6469)
Figure 21B:
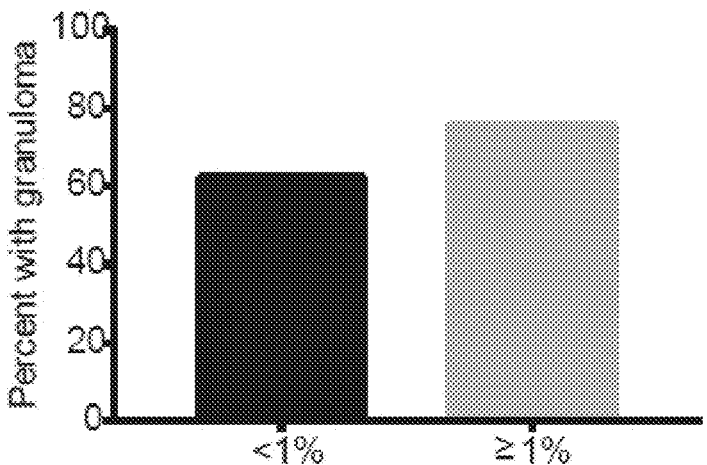
Figure 21C:
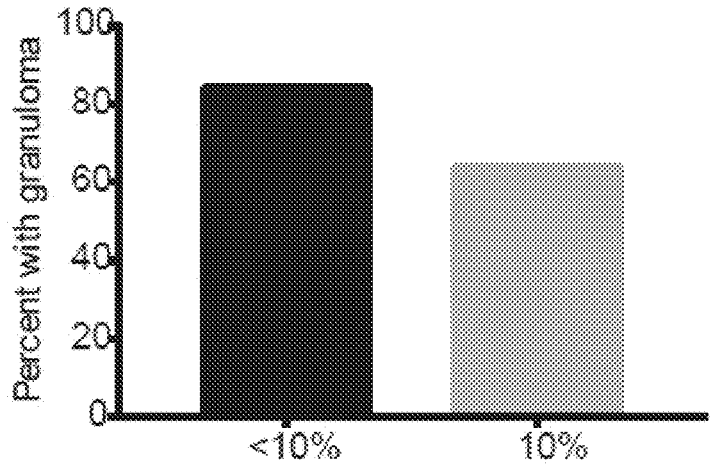
Figure 21D:
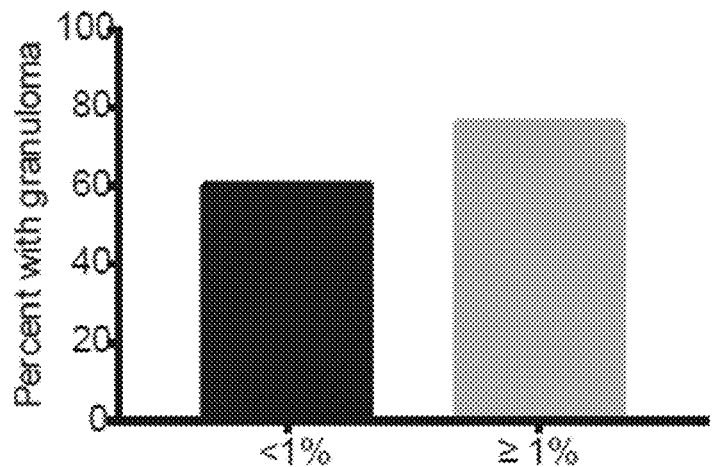
Figure 21E:
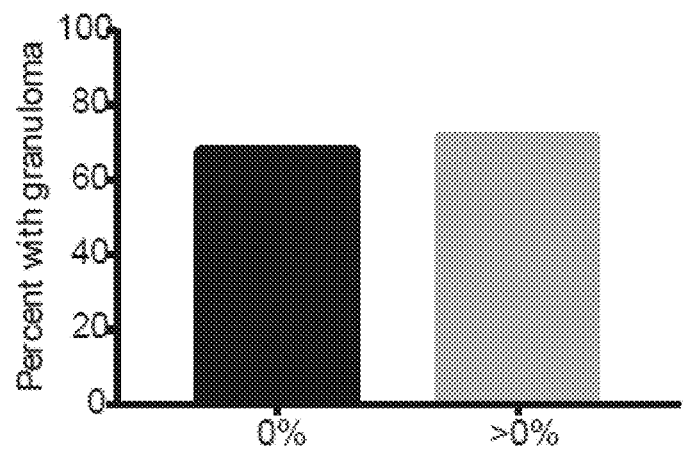
Figure 21F:
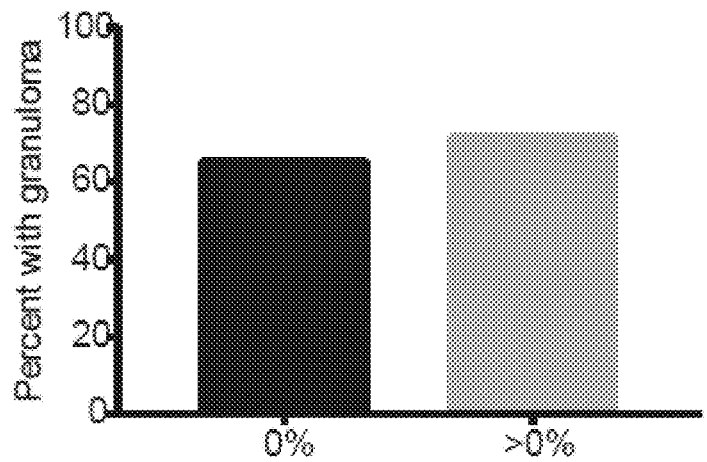

Paneth Cell Defects were Prevalent in Japanese CD Patients:

We first determined the percentage of normal Paneth cells in resection specimens of adult Japanese CD subjects using a previously reported method of immunofluorescence localization for Defensin-5 (2). The staining for Defensin-5 was specific for Paneth cells and the results were highly correlative to that obtained by lysozyme immunofluorescence ($R2=0.6451$; $P<0.0001$) (FIG. 19). There was a similar range of intracellular staining patterns to those previously observed in multiple North American CD cohorts (2, 3) (FIG. 20A). The average percentage of normal Paneth cells was similar between Japanese and North American CD subjects ($82.13\pm1.06$ vs. $81.9\pm0.55$; $P=0.87$) (FIG. 20B). As in previous studies, we utilized a cutoff of 20% (high abundance) abnormal Paneth cells to define a Type I Paneth cell phenotype (Type II is <20% abnormal Paneth cells). We found that the prevalence of Type I Paneth cell phenotype in Japanese CD subjects was similar to a North American cohort (33% vs. 26%; $P=0.26$) (FIG. 20B). We also examined potential correlations between the clinical data obtained for the Japanese CD subjects and Paneth cell phenotypes (Table 4). Of note, there was no significant difference in the demographics and clinical phenotype (Montreal classification) between patients with Type I and Type II Paneth cell phenotypes at time of resection. In addition, we also examined whether Paneth cell phenotype and/or individual morphology category correlated with the presence or absence of granuloma. We found that while there was a trend that the percentage of diminished Paneth cell morphology inversely correlated with the presence of granuloma as we have shown previously (3), overall there was no significant correlation between Paneth cell phenotype or each Paneth cell morphology category and granuloma (FIG. 21A, FIG. 21B, FIG. 21C, FIG. 21D, FIG. 21E, and FIG. 21F).

TABLE 4

Characteristics of all Japanese CD patients included in this study.

|  | Type I Paneth cell phenotype | Type II Paneth cell phenotype | P value |
|---|---|---|---|
| N | 31 | 79 |  |
| Sex (male) | 22 (71.0%) | 60 (76.0%) | 0.630 |
| Mean disease duration (years) | 17.5 (14.8-20.3) | 18.0 (16.2-19.7) | 0.786 |
| Mean age at onset | 23.8 (21.5-26.2) | 23.1 (21.7-24.6) | 0.612 |
| Disease Onset | | | |
| A1 | 4 (12.9%) | 11 (13.9%) | 1.000 |
| A2 | 26 (83.9%) | 67 (84.8%) | 1.000 |
| A3 | 1 (3.2%) | 1 (1.3%) | 0.486 |
| Disease Location | | | |
| L1 | 3 (9.7%) | 12 (15.2%) | 0.550 |
| L2 | 0 | 0 | NA |
| L3 | 28 (90.3%) | 67 (84.8%) | 0.550 |
| Disease Behavior | | | |
| B1 | 0 | 1 (1.3%) | 1.000 |
| B2 | 25 (80.7%) | 74 (93.6%) | 0.071 |
| B3 | 20 (64.5%) | 36 (45.6%) | 0.090 |
| Perianal disease | 24 (80%) | 59 (75.6%) | 0.800 |
| Current smoking | 9 (36%) | 16 (32%) | 0.798 |
| Treatment received prior to surgery | | | |
| Biologics (Bio) | 12 (38.7%) | 22 (27.9%) | 0.359 |
| Immunomodulator (IM) | 5 (16.1%) | 7 (8.9%) | 0.313 |
| Elemental diet (ED) | 12 (38.7%) | 18 (22.8%) | 0.102 |
| Treatment combination prior to surgery | | | |
| Only Bio | 5 (16.1%) | 13 (16.5%) | 1.000 |
| Only IM | 0 | 2 (2.5%) | 1.000 |
| Only ED | 6 (19.4%) | 13 (16.5%) | 0.781 |
| Bio + IM | 1 (3.2%) | 4 (5.1%) | 1.000 |
| Bio + ED | 2 (6.5%) | 4 (5.2%) | 1.000 |
| ED + IM | 0 | 0 | NA |
| Bio + IM+ ED | 4 (12.9%) | 1 (1.3%) | 0.022 |
| Postoperative therapy | | | |
| None | 7 (22.6%) | 27 (34.2%) | 0.262 |
| Bio | 16 (51.6%) | 35 (44.3%) | 0.529 |
| First use of Bio | 10 (32.3%) | 20 (25.3%) | 0.482 |
| IM | 6 (19.4%) | 12 (15.2%) | 0.579 |
| ED | 13 (41.9%) | 26 (32.9%) | 0.385 |
| Treatment combination | | | |
| Only Bio | 9 (29.0%) | 17 (21.5%) | 0.457 |
| Only IM | 1 (3.2%) | 2 (1.8%) | 1.000 |
| Only ED | 5 (16.1%) | 14 (17.7%) | 1.000 |
| Bio + IM | 1 (3.2%) | 7 (8.9%) | 0.437 |
| Bio + ED | 4 (12.9%) | 9 (11.4%) | 1.000 |
| ED + IM | 2 (6.5%) | 1 (1.3%) | 0.191 |
| Bio + IM + ED | 2 (6.5%) | 2 (2.5%) | 0.315 |

Figure 22:
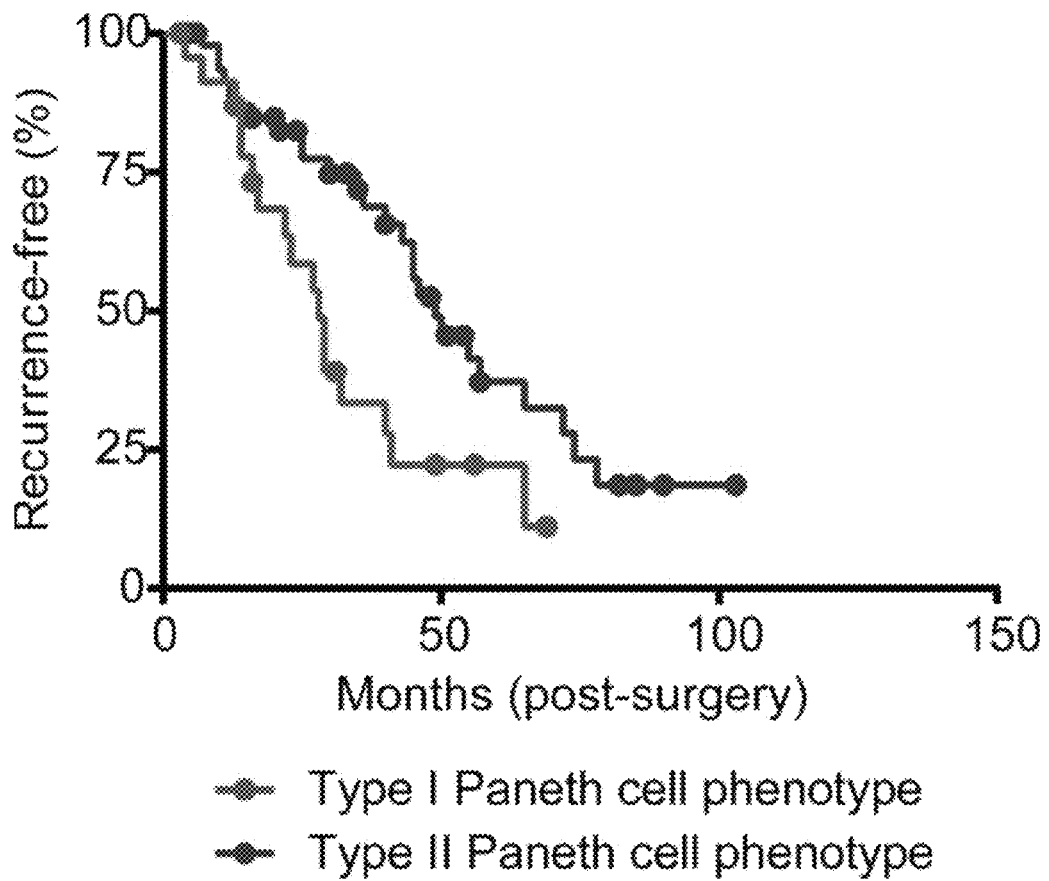
FIG. 22 depicts a graph of Paneth cell phenotypes correlated with time to disease recurrence after surgery in Japanese Crohn's disease (CD). The Kaplan-Meier curves of time to disease recurrence post-resection was determined in the CD cases that received prophylaxis post-surgery (n=76). Patients with Type I Paneth cell phenotype showed a significantly shorter time to disease recurrence (P=0.013 by Log-rank test).

Type I Paneth Cell Phenotype was Associated with Poor Clinical Outcome in Japanese CD:

To determine whether Paneth cell phenotype also correlated with clinical outcome in patients undergoing resections in Japanese CD, we analyzed the clinical outcome only for those patients who had received post-operative prophylactic therapy, as postoperative prophylaxis has been shown to be associated with outcome (18). We listed the characteristics of the patients that were included for outcome analysis in Table 5. We found that in Japanese CD patients, Type I Paneth cell phenotype was also associated with shorter time to disease recurrence after resection (P=0.013; HR=2.10, 95% CI=1.04-4.24) (FIG. 22). This association remained significant in multivariate analysis (Table 5), thus replicating the finding that we have previously shown in North American CD patients (3).

TABLE 5

Characteristics of Japanese CD patients who received prophylaxis.

| | Type I Paneth cell phenotype | Type II Paneth cell phenotype | P value |
|---|---|---|---|
| N | 24 | 52 | |
| Sex (male) | 18/24 (75.0%) | 38/52 (73.1%) | 1.000 |
| Mean disease duration (years) | 17.0 (13.7-20.3) | 17.1 (14.8-19.3) | 0.962 |
| Mean age at onset | 23.2 (20.7-25.6) | 23.1 (21.4-24.7) | 0.941 |
| Disease Onset | | | |
| A1 | 4/24 (16.7%) | 9/52 (17.3%) | 1.000 |
| A2 | 20/24 (83.3%) | 43/52 (82.7%) | 1.000 |
| A3 | 0 | 0 | NA |
| Disease Location | | | |
| L1 | 3/24 (12.5%) | 6/52 (11.5%) | 1.000 |
| L2 | 0 | 0 | NA |
| L3 | 21/24 (87.5%) | 46/52 (88.5%) | 1.000 |
| Disease Behavior | | | |
| B1 | 0 | 0 | NA |
| B2 | 21/24 (87.5%) | 50/52 (96.2%) | 0.318 |
| B3 | 14/24 (58.3%) | 21/52 (40.4%) | 0.216 |
| Perianal disease | 19/24 (79.2%) | 40/52 (78.4%) | 1.000 |
| Current smoking | 6/18 (33.3%) | 11/37 (29.7%) | 1.000 |
| Previous resection | 15/24 (62.5%) | 37/52 (71.2%) | 0.596 |
| Treatment received prior to surgery | | | |
| Biologics (Bio) | 9/24 (37.5%) | 19/52 (36.5%) | 1.000 |
| Immunomodulator (IM) | 5/24 (20.8%) | 5/52 (9.6%) | 0.272 |
| Elemental diet (ED) | 9/24 (37.5%) | 15/52 (28.9%) | 0.596 |
| Pre-surgery treatment combination | | | |
| Only Bio | 3/24 (12.5%) | 11/52 (21.2%) | 0.528 |
| Only IM | 0 | 0 | NA |
| Only ED | 4/24 (16.7%) | 11/52 (21.2%) | 0.763 |
| Bio + IM | 1/24 (4.2%) | 4/52 (7.7%) | 1.000 |
| Bio + ED | 1/24 (4.2%) | 3/52 (5.8%) | 1.000 |
| ED + IM | 0 | 0 | NA |
| Bio + IM + ED | 4/24 (16.7%) | 1/52 (1.3%) | 0.036 |
| Postoperative therapy | | | |
| Bio | 16/24 (66.7%) | 35/52 (67.3%) | 1.000 |
| First use of Bio | 10/24 (41.7%) | 20/52 (38.5%) | 0.806 |
| IM | 6/24 (25.0%) | 12/52 (23.1%) | 1.000 |
| ED | 13/24 (54.2%) | 26/52 (50.0%) | 0.808 |
| Postoperative treatment combination | | | |
| Only Bio | 9/24 (37.5%) | 17/52 (32.7%) | 0.796 |
| Only IM | 1/24 (4.2%) | 2/52 (3.9%) | 1.000 |
| Only ED | 5/24 (20.8%) | 14/52 (26.9%) | 0.777 |
| Bio + IM | 1/24 (4.2%) | 7/52 (13.5%) | 0.423 |
| Bio + ED | 4/24 (16.7%) | 9/52 (17.3%) | 1.000 |
| ED + IM | 2/24 (8.3%) | 1/52 (1.9%) | 0.233 |
| Bio + IM + ED | 2/24 (8.3%) | 2/52 (3.9%) | 0.587 |

Figure 23A:
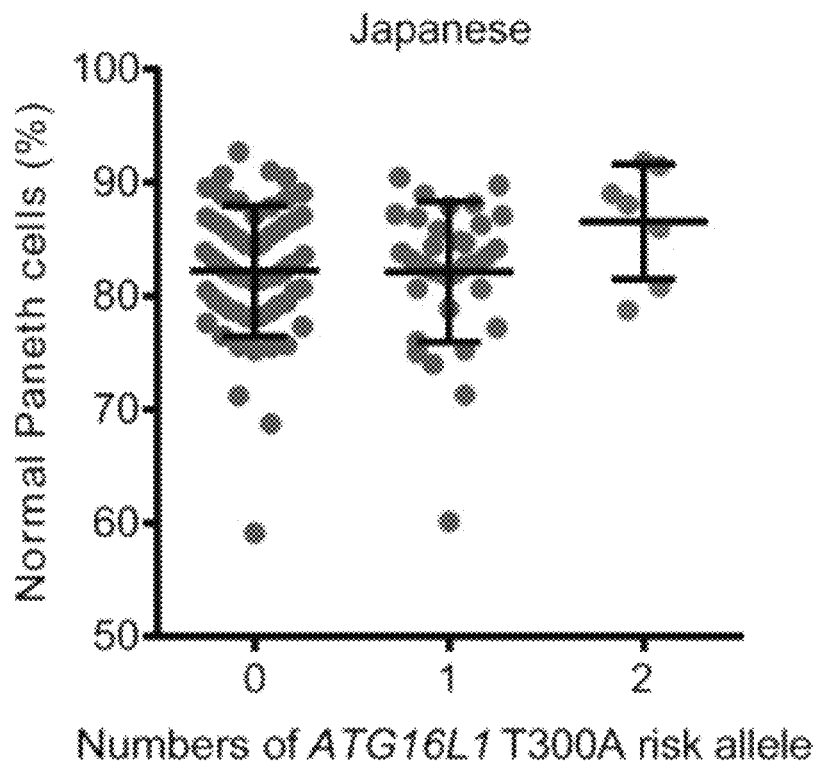
FIG. 23A, FIG. 23B, FIG. 23C, and FIG. 23D depict graphs of ATG16L1 T300A and LRRK2 M2397T genotypes showing dichotomous effects on Paneth cell defects in Japanese and North American Crohn's disease (CD) patients.
Figure 23B:
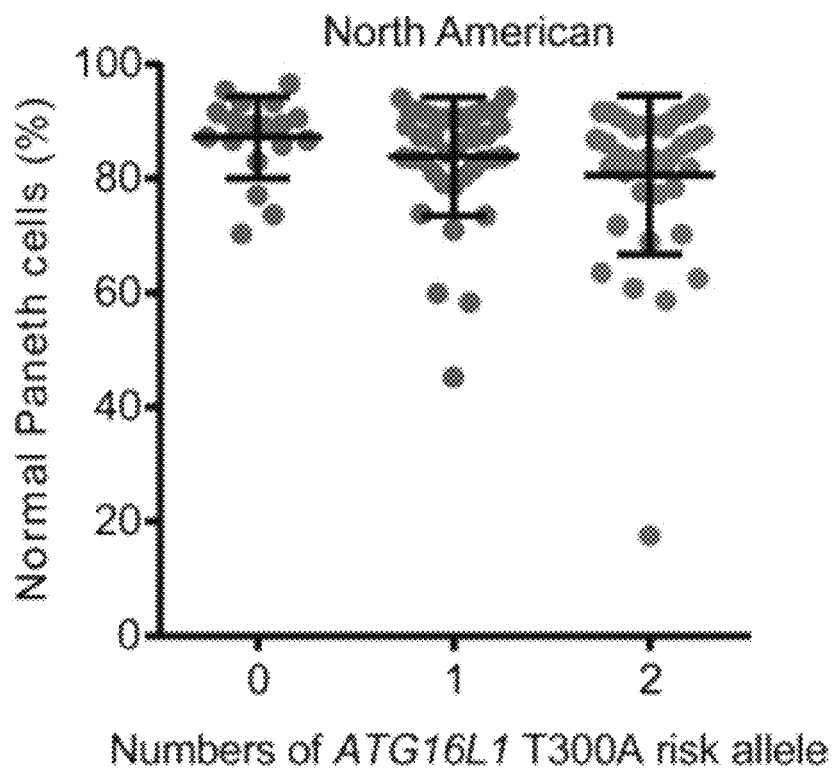

ATG T300A was not Associated with Paneth Cell Defect in Japanese CD:

We next examined the potential associations of Type I Paneth cell phenotype with 56 SNPs, selected based on known CD susceptibility associations (3, 5, 21-23, 27-29) or known association with Paneth cell function (14) (See Supplementary Table 3 of Liu, T. et al., *JCI Insight*, 2017, 2(6), e91917, which is herein incorporated by reference). These SNPs include coding variants for ATG16L1 (T300A) associated with Paneth cell defects in North American CD cohorts and in genetic mouse models (3, 13, 19). Among the Japanese CD patients with available genotype data (n=98), we found no significant difference between the numbers of ATG16L1 T300A risk alleles and the percentage of normal Paneth cells (R2=0.01717; P=0.20) (FIG. 23A). In contrast, in North American CD with wild type NOD2 (to eliminate potential confounding factors from NOD2; n=97), the numbers of ATG16L1 T300A risk allele correlated with the percentage of normal Paneth cells (R2=0.04387; P=0.0395) (FIG. 23B), a finding that we have shown previously with a smaller CD cohort (13). Of note, the allele frequency of ATG16L1 T300A in our Japanese CD cohort was 40%, a level comparable to what has been published (20). Therefore, in contrast to the North American CD, ATG16L1 T300A was not associated with the percentage of normal Paneth cells or Type I Paneth cell phenotype in Japanese CD. NOD2, another CD susceptible gene previously shown to be associated with Paneth cell defect in North American CD patients, is nonpolymophic in Japanese patients (21, 22), and thus was not included on the Japonica SNP array.

Figure 23C:
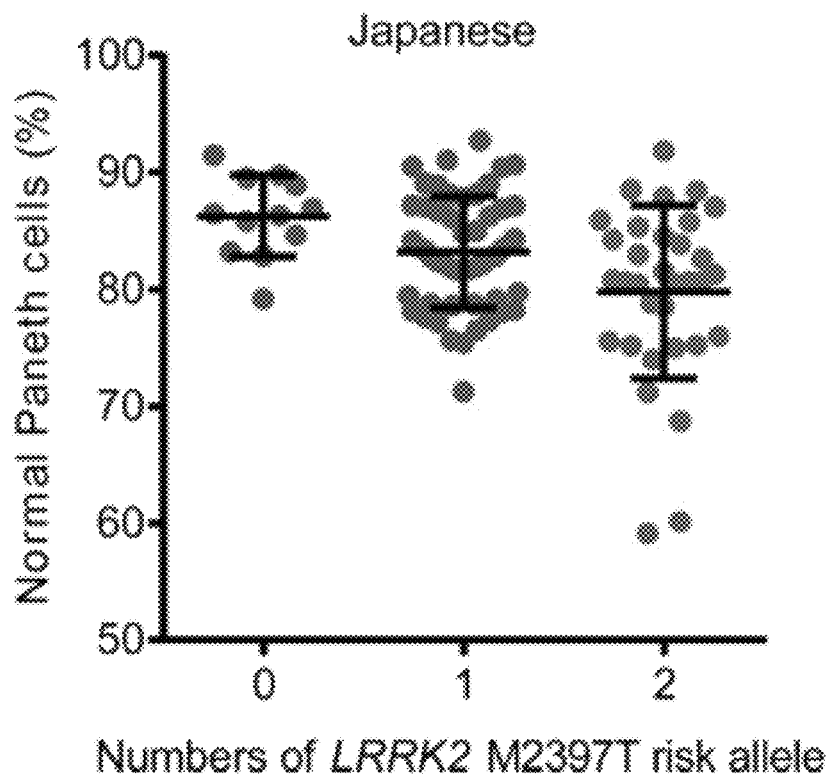
Figure 23D:
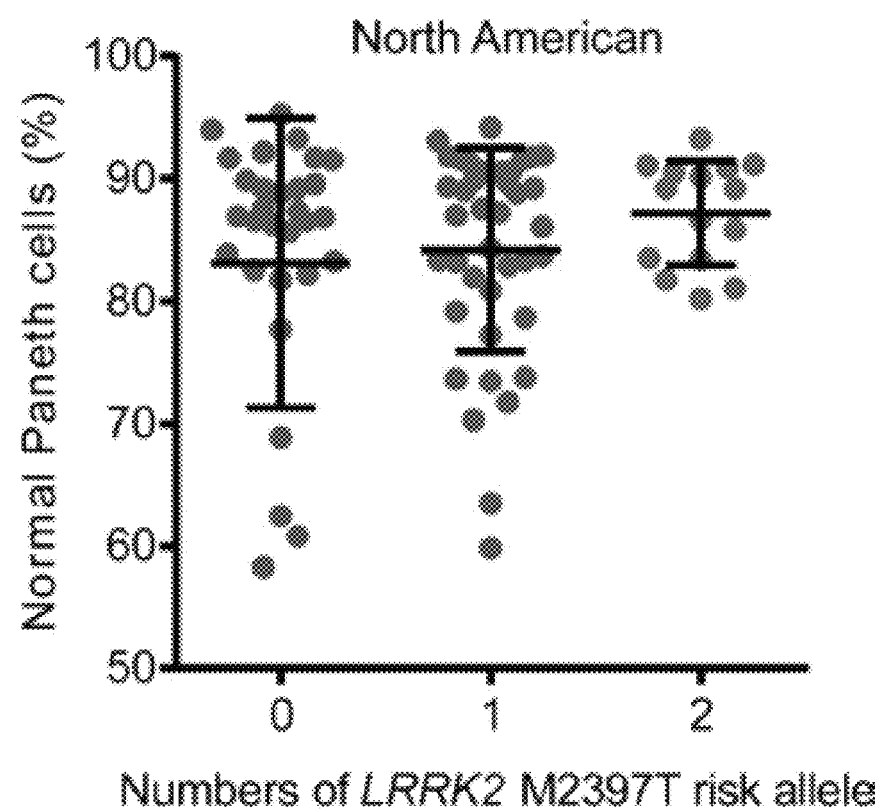

Western CD Susceptibility Allele LRRK2 M2397T was Associated with Paneth Cell Defect in Japanese CD:

Interestingly, the only SNP within the pool of 56 selected alleles for hypothesis-driven correlation analysis that showed significant association with Paneth cell defects in Japanese CD was LRRK2 M2397T (FIG. 23C). The LRRK2 M2397T SNP (rs3761863) is a missense susceptibility allele for European ancestry CD (23, 24), and Lrrk2 knockout mice have defective Paneth cells (25). In the Japanese CD cohort, we found that the number of T (risk) alleles of LRRK2 M2397T correlated with the percentage of normal Paneth cells (R2=0.247; P=3.62×10-4) (FIG. 23D). The results suggest that two defective copies of the LRRK2 gene product may be required to illicit Paneth cell defects in Japanese CD patients.

Figure 4D:
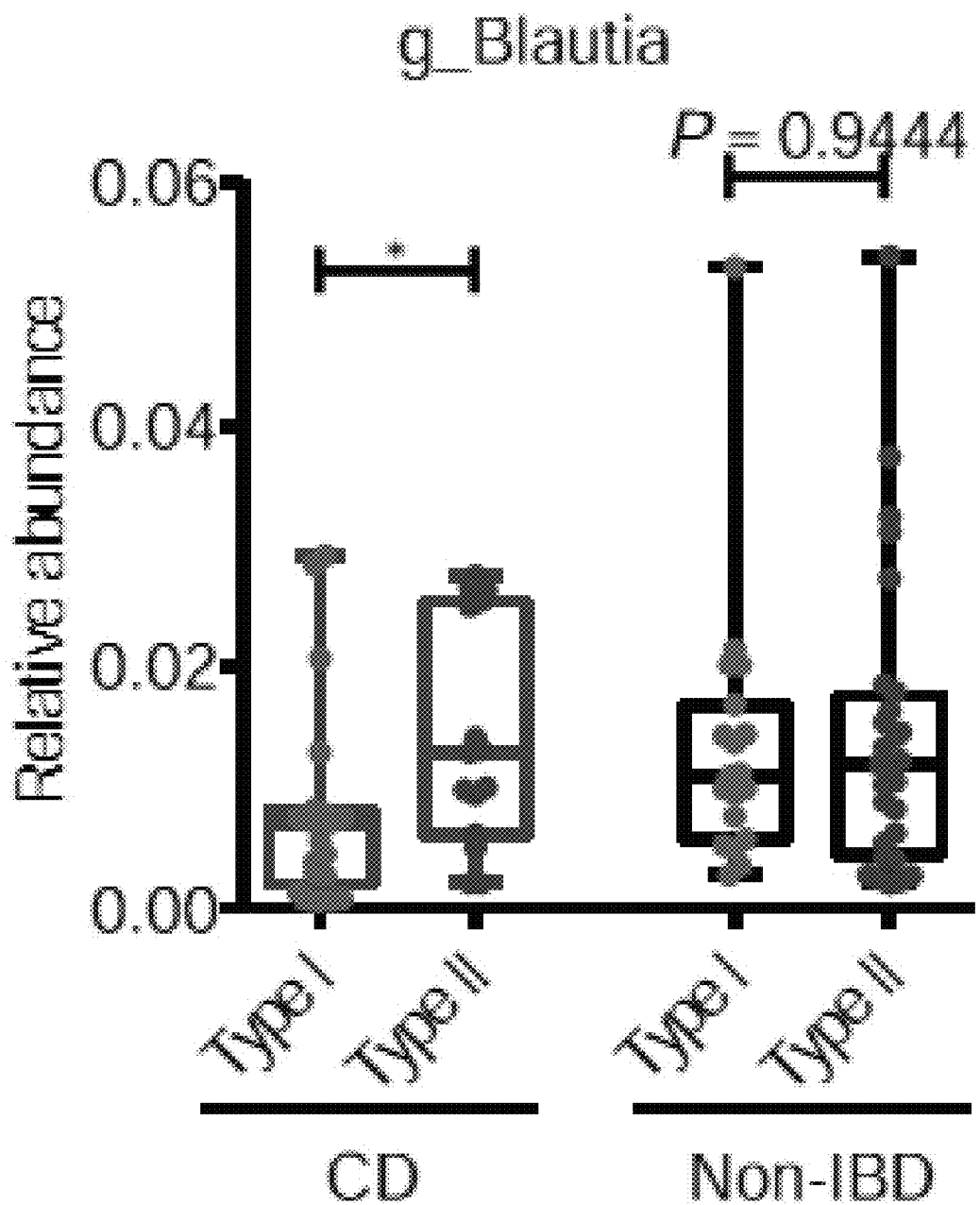
Figure 4E:
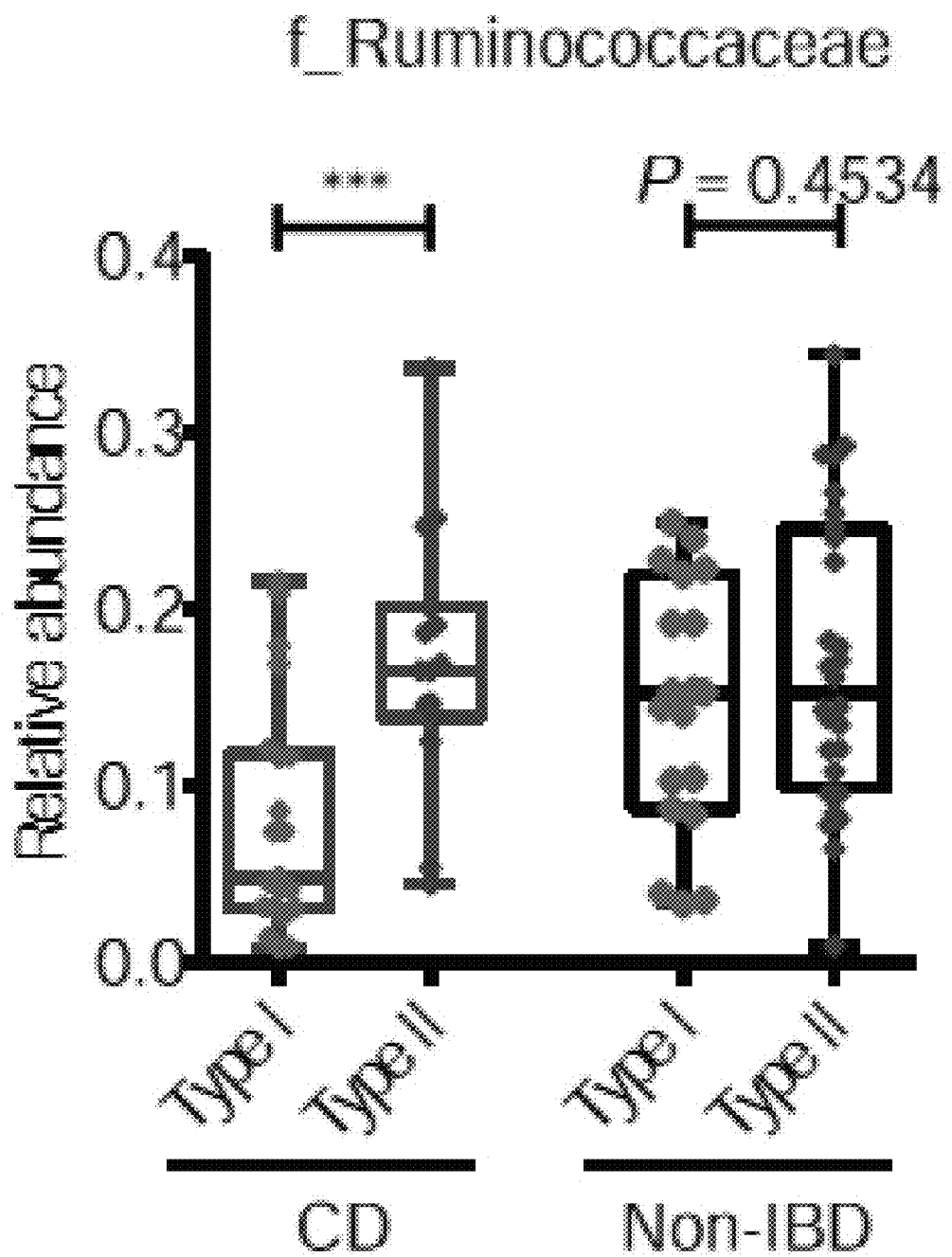
Figure 4F:
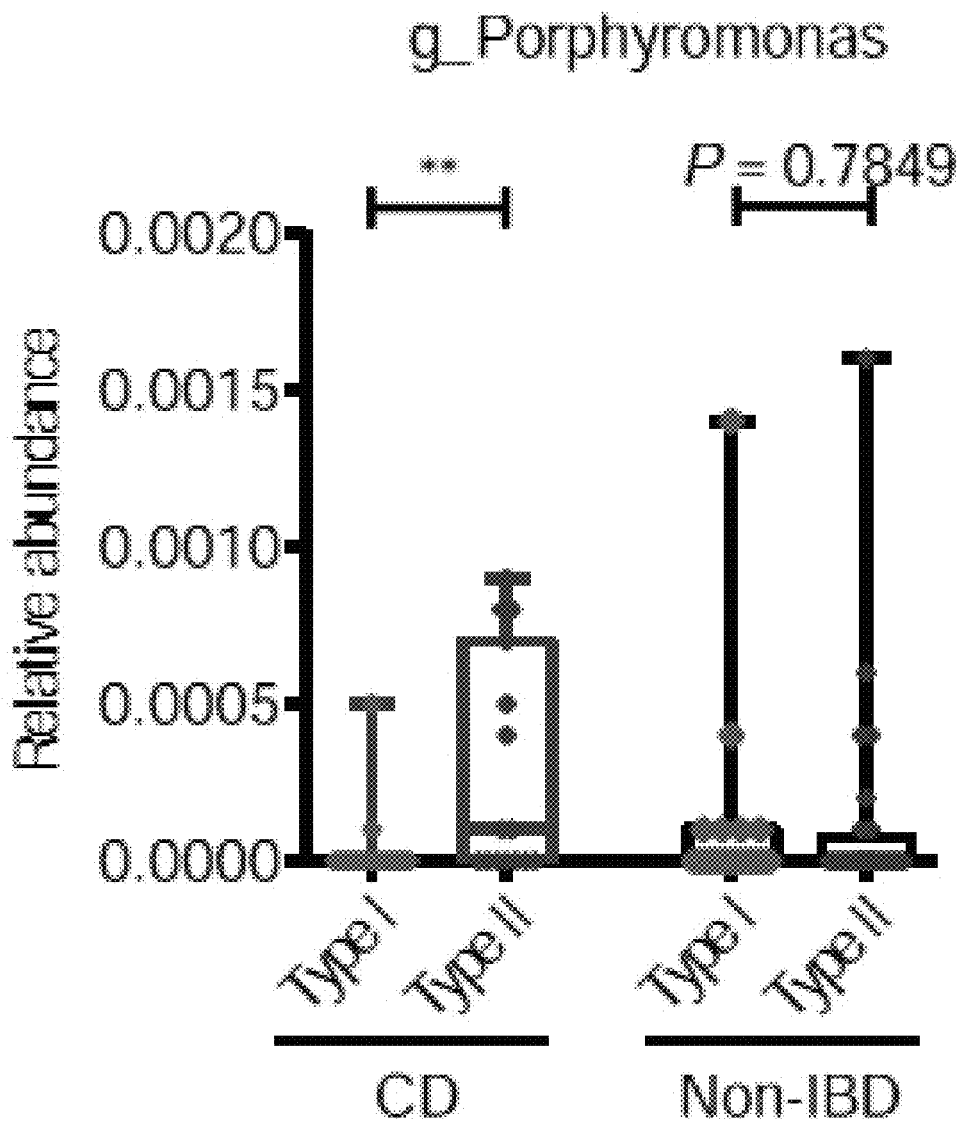
Figure 4G:
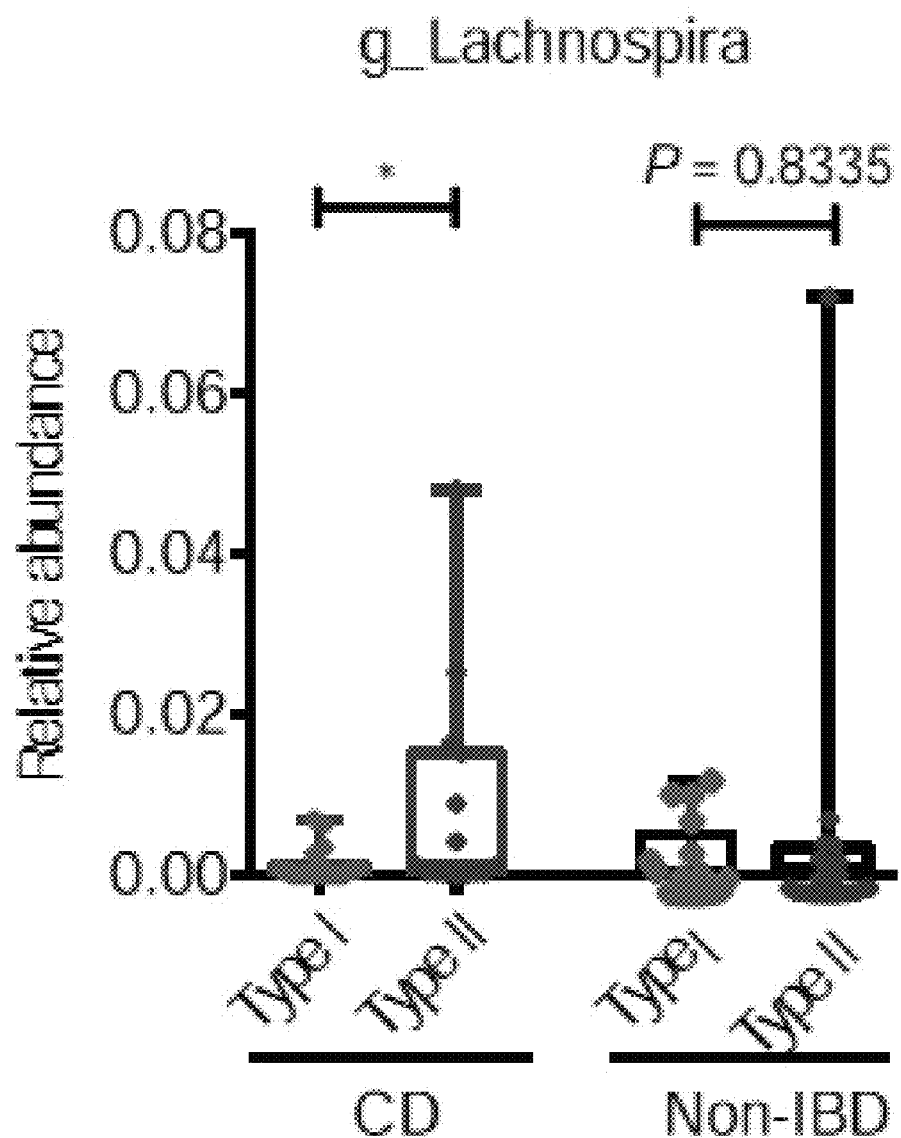
Figure 4H:
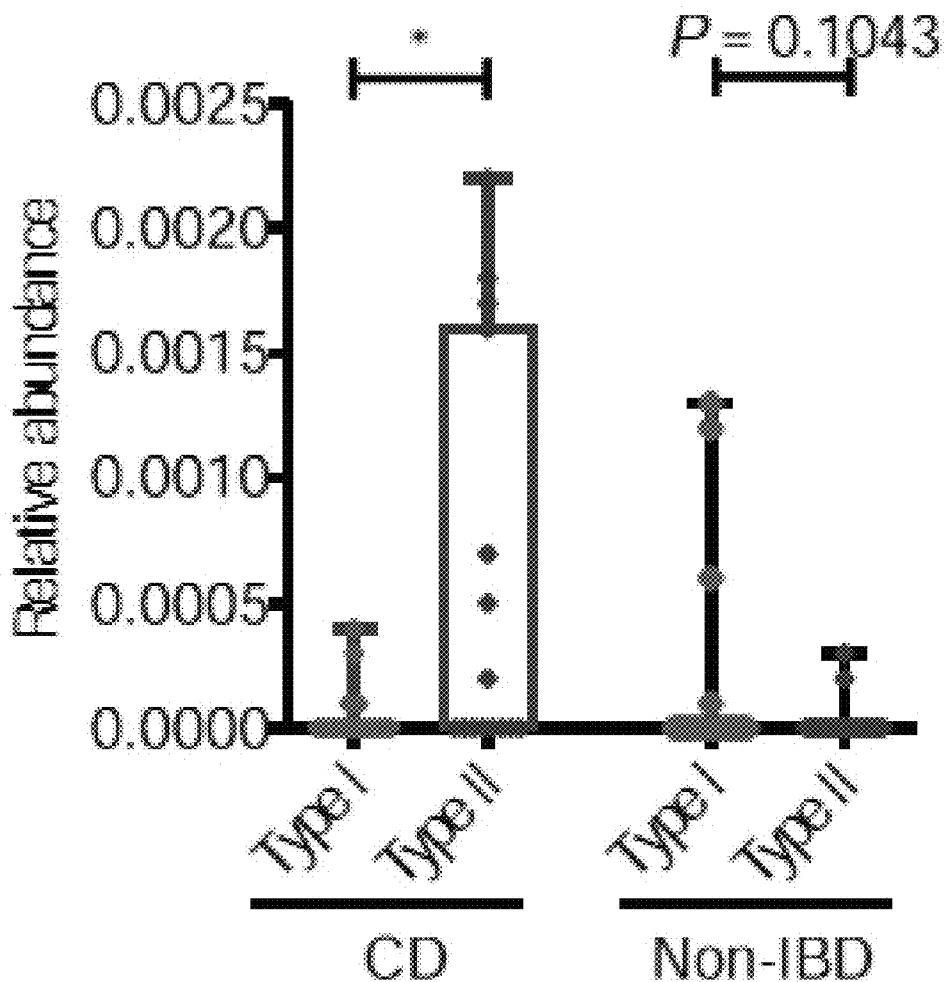
Figure 4I:
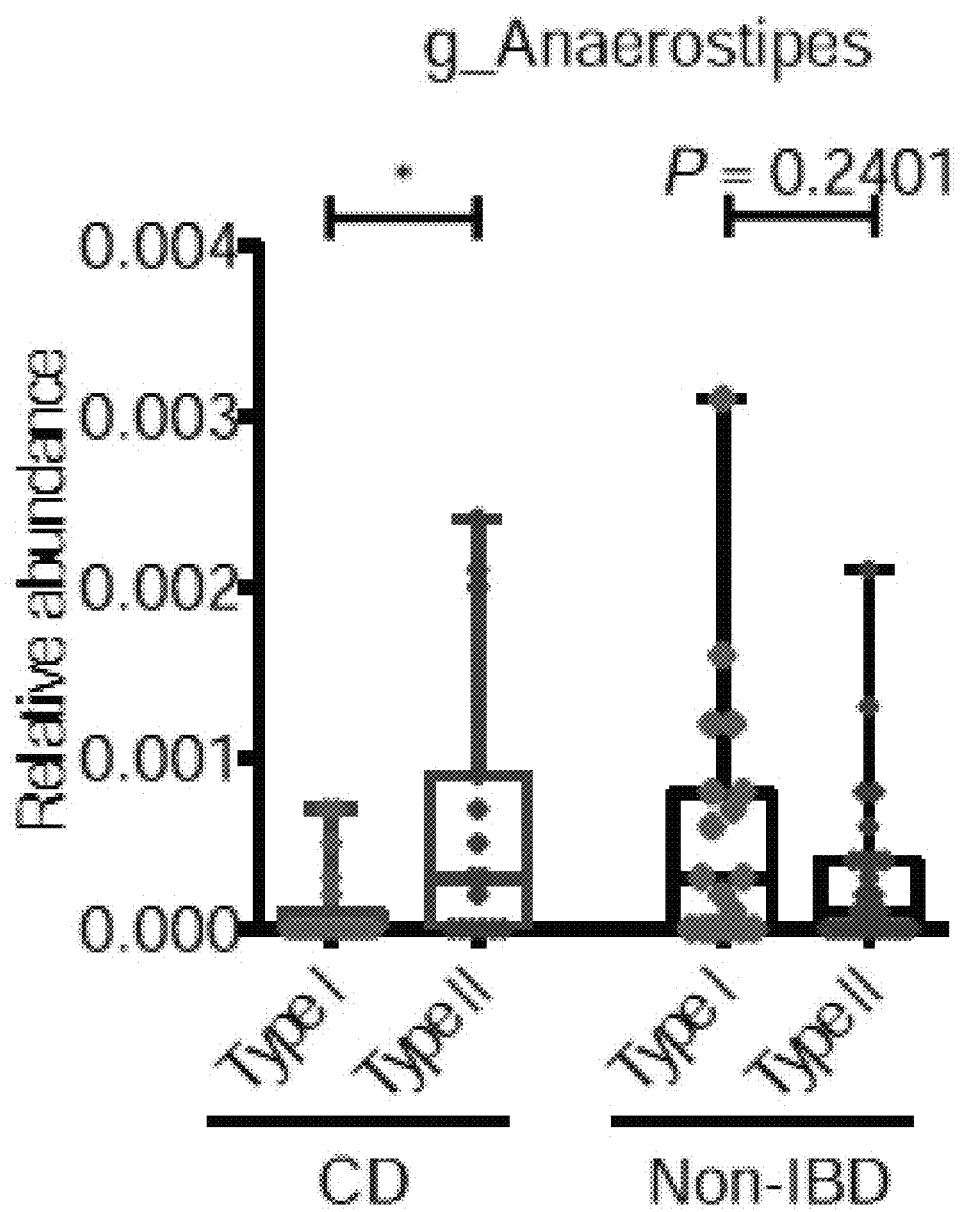
Figure 4J:
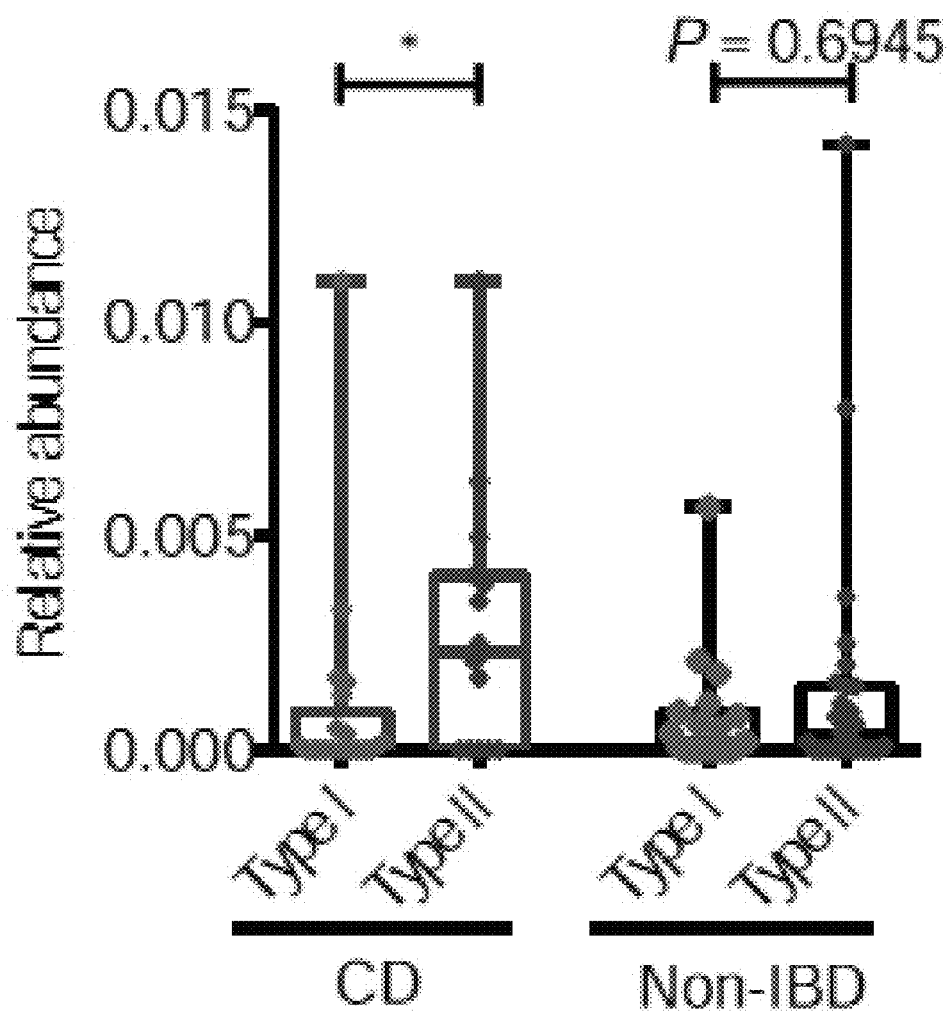
Figure 24A:
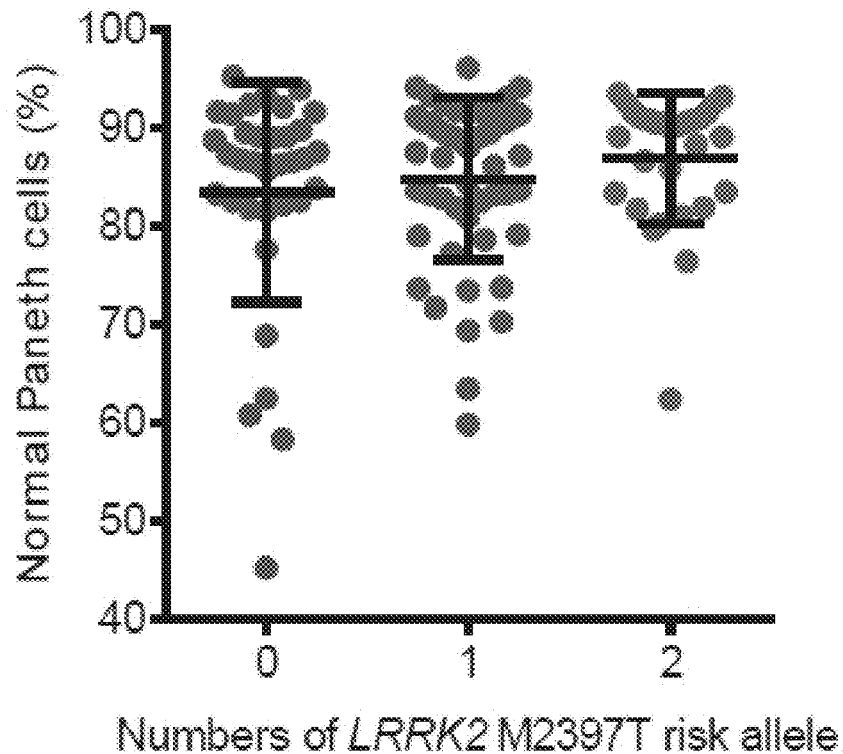
FIG. 24A and FIG. 24B depict graphs that show the numbers of LRRK2 M2397T allele did not correlate with the percentage of normal Paneth cells in North American Crohn's disease (CD) patients with (FIG. 24A) either ATG16L1 T300A or NOD2 risk alleles ($R^2=0.01998$ and $P=0.13$ by linear regression) or (FIG. 24B) no risk alleles for ATG16L1 T300A or NOD2 ($R^2=0.003903$ and $P=0.82$ by linear regression). Error bars represent ±SEM.
Figure 24B:
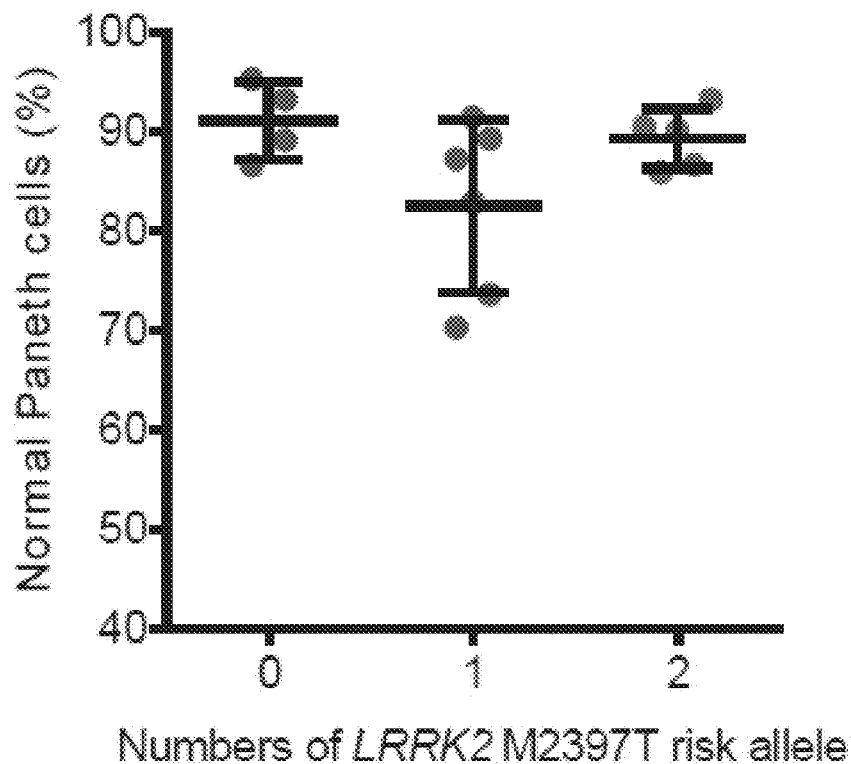

To determine whether this correlation was universal, we next analyzed the correlation of LRRK2 M2397T and Paneth cell defects in the North American CD cohort (with wild type NOD2 as described above). Surprisingly, there was no association between the numbers of LRRK2 M2397T risk allele and the degree of Paneth cell defect (R2=0.02054; P=0.76; FIG. 4D). As ATG16L1 T300A and NOD2 SNPs are known to be associated with Paneth cell defects in North American CD cohorts, we performed further analyses with the North American CD patients with ATG16L1 T300A and/or NOD2 risk alleles (n=116 with LRRK2 M2397T status available) as well as the patients without any risk alleles for ATG16L1 T300A or NOD2 (n=15 with LRRK2 M2397T status available). There was no association of LRRK2 M2397T and the percentage of normal Paneth cells when all patients (including ATG16L1 T300A and/or NOD2 risk alleles) were analyzed (P=0.13; FIG. 24A) or when only the subset of patients without ATG16L1 T300A and NOD2 risk alleles were analyzed (P=0.82; FIG. 24B). However, given the relatively small sample size with wild type ATG16L1 T300A and NOD2, further investigation with a greater sample size is needed.

Figure 26A:
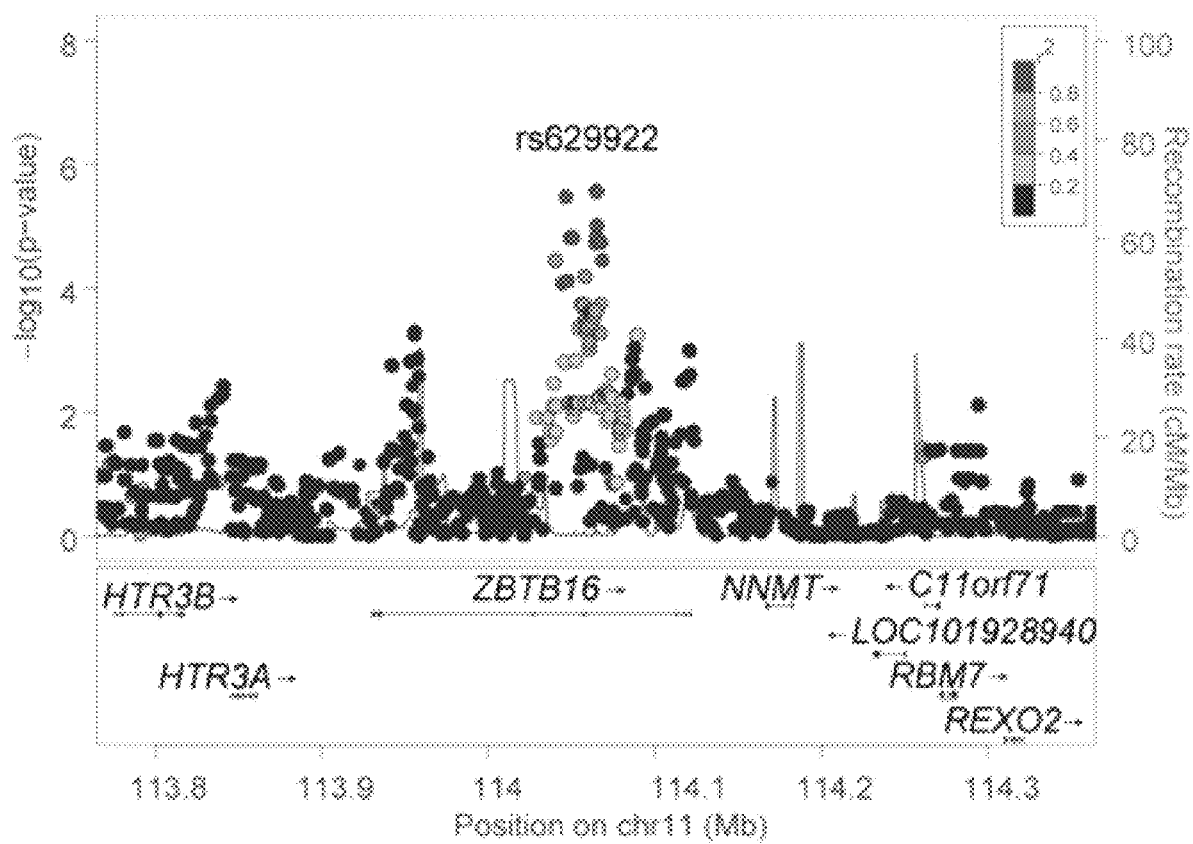
FIG. 26A, FIG. 26B, FIG. 26C, and FIG. 26D depict graphs of genome-wide association analysis results for Paneth cell defect in Japanese Crohn's disease (CD) patients. Locus zoom plots of P-values around selected top associated single nucleotide polymorphisms (SNPs) from Paneth cell phenotype regression analysis. The top associated SNPs for (FIG. 26A) ZBTB16, (FIG. 26C) MAFB, and (FIG. 26E) FER are shown as purple diamonds and the remaining SNPs are shown as circles, with color indicating the level of linkage disequilibrium ($R^2$) with lead SNP.
Figure 26B:
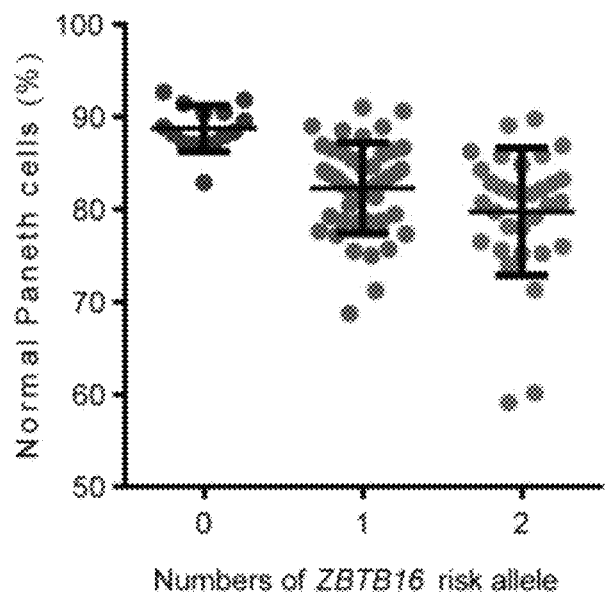
Figure 26C:
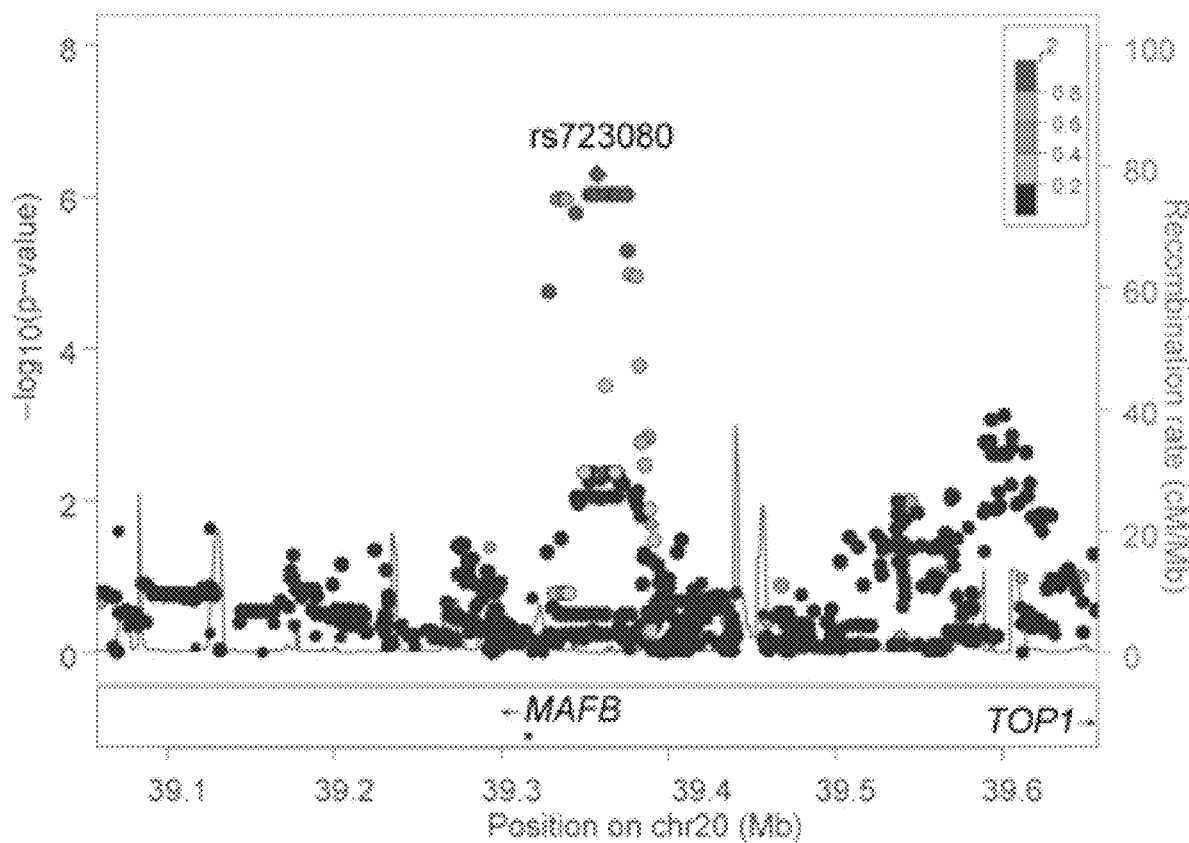
Figure 26D:
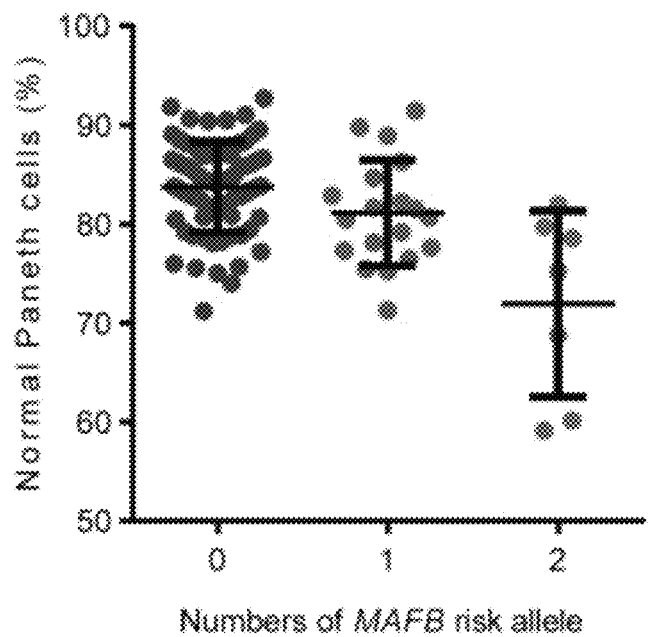
Figure 26E:
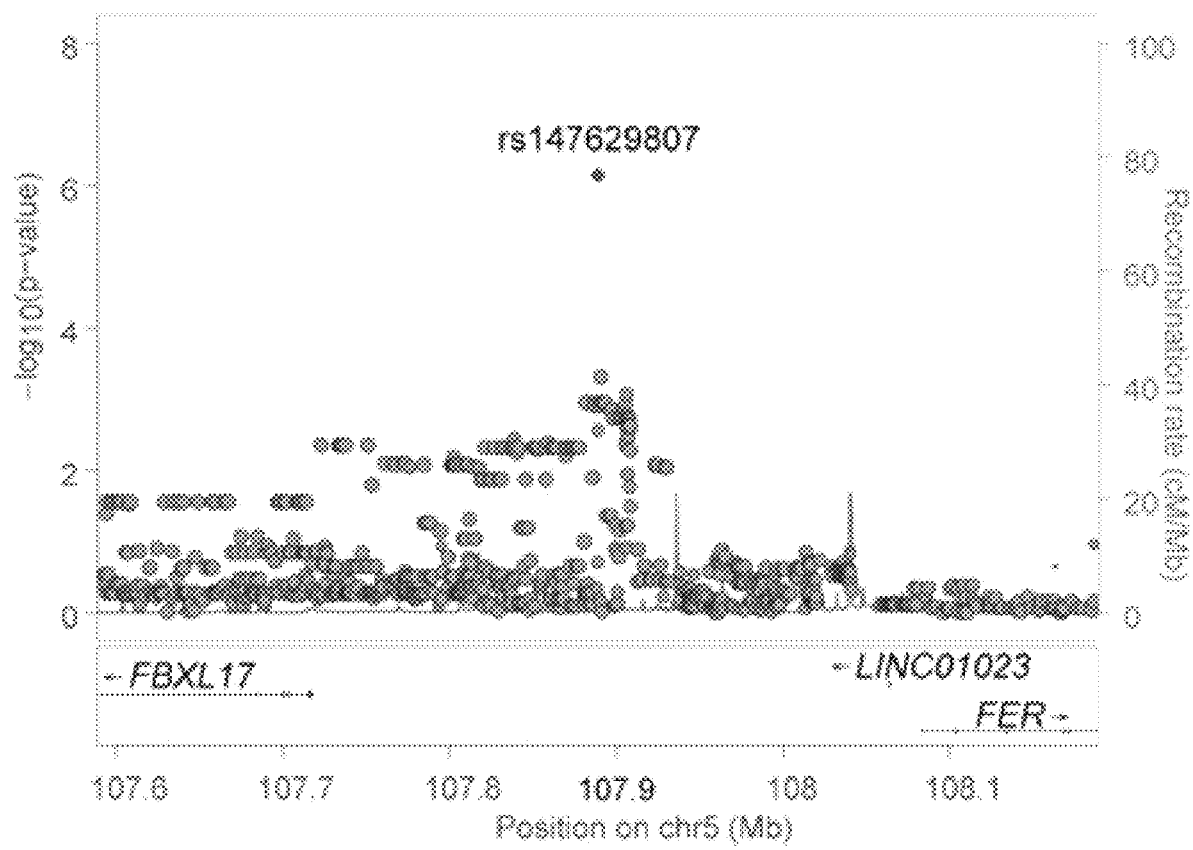
Figure 26F:
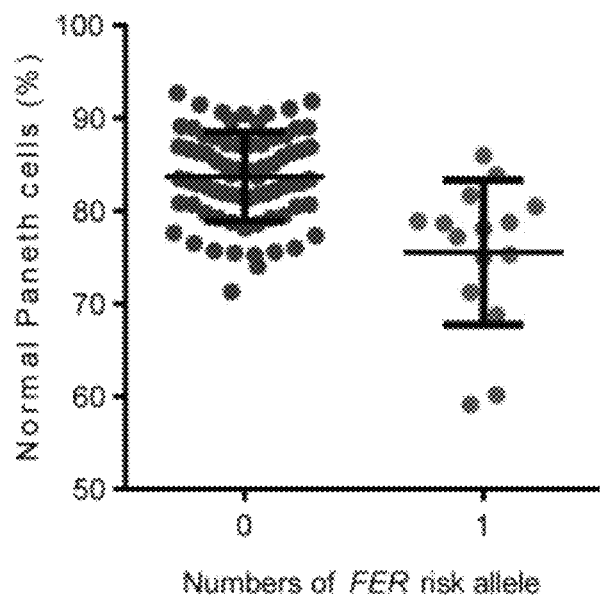

Therefore, our data suggest that there are dichotomous effects of the ATG16L1 and LRRK2 susceptibility alleles of on Paneth cell defects within Japanese and North American CD cohorts. Interestingly, the LRRK2 M2397T itself was not associated with outcome (P=0.5931) (Table 6).

candidate genes, ZBTB16 (FIG. 26A and FIG. 26B), MAFB (FIG. 26C and FIG. 26D), and FER (FIG. 26E and FIG. 26F) were of particular interest. ZBTB16 modulates autophagy by degrading Atg14 (35). MAFB is an important transcriptional factor for macrophage differentiation (36), and FER

TABLE 6

Univariate and multivariate association analyses of recurrence after surgery in Japanese CD cohort. Biologics incudes infliximab and adalimumab.

|  | N | Univariate | | Multivariate | |
|---|---|---|---|---|---|
|  |  | P value | hazard ratio | P value | hazard ratio |
| Disease Onset |  |  |  |  |  |
| A1 | 13/76 (17%) | 0.893 |  |  |  |
| A2 | 63/76 (83%) | 0.893 |  |  |  |
| A3 | 0 | NA |  |  |  |
| Disease Location |  |  |  |  |  |
| L1 | 9/76 (12%) | 0.173 |  |  |  |
| L2 | 0 | NA |  |  |  |
| L3 | 67/76 (88%) | 0.173 |  |  |  |
| Disease Behavior |  |  |  |  |  |
| B1 | 0 | NA |  |  |  |
| B2 | 71/76 (93%) | 0.463 |  |  |  |
| B3 | 35/76 (46%) | 0.611 |  |  |  |
| Perianal disease | 59/76 (78%) | 0.398 |  |  |  |
| Current smoker | 17/55 (31%) | 0.047 | 1.94 (0.91-2.14) |  |  |
| Previous resection | 52/76 (68%) | 0.600 | 1.22 (0.61-2.45) |  |  |
| Postoperative therapy |  |  |  |  |  |
| Elemental diet (ED) | 39/76 (51%) | 0.318 |  |  |  |
| Immunomodulator (IM) | 18/76 (24%) | 0.043 | 1.91 (0.88-4.12) | 0.108 |  |
| Biologics (Bio) | 51/76 (67%) | 0.463 |  |  |  |
| Bio + IM | 12/76 (16%) | 0.273 |  |  |  |
| First use of bio | 30/76 (39%) | 0.071 | 0.55 (0.30-1.02) | 0.028 | 0.47 (0.23-0.93) |
| LRRK2 M2397T (0 or 1, 2) | 8/67 (12%) | 0.100 | 0.44 (0.20-0.95) |  |  |
| Type I Paneth cell phenotype | 24/76 (32%) | 0.013 | 2.10 (1.04-4.24) | 0.007 | 2.56 (1.31-4.96) |

Figure 25:
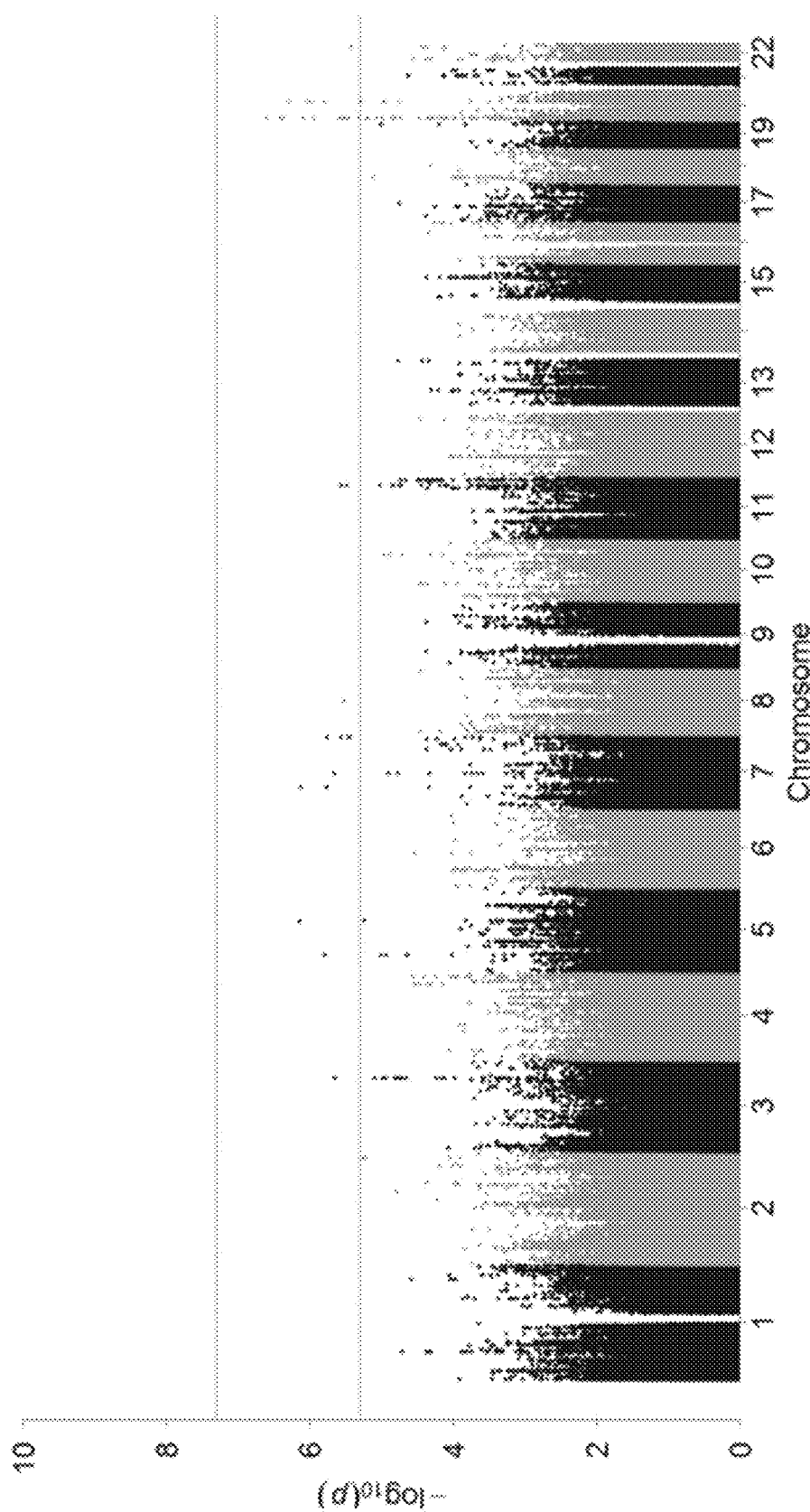
FIG. 25 depicts a Manhattan plot for 4,198,245 SNPs from the genome-wide association analysis for Paneth cell phenotype. Single nucleotide polymorphisms are plotted according to chromosomal location, with the −log 10(P) calculated by the linear regression test. The red line indicates the threshold for the genome-wide significance ($P=5\times10^{-8}$). The blue line indicates the threshold for the nominal significance ($P=5\times10^{-6}$).

Unbiased Genome-Wide Association Identified Additional Candidate Genes Associated with Paneth Cell Defect in Japanese CD:

We subsequently performed an unbiased genome-wide association scan to identify additional potential novel SNPs that could be associated with the degree of Paneth cell defects. Although no SNPs reached genome-wide significance ($<5\times10^{-8}$), 45 SNPs were identified as candidates (P $5\times10^{-6}$), as well as 8 non-synonymous SNPs that had P values $5\times10^{-4}$ (FIG. 25). The candidate SNPs were categorized into nine gene regions (Table 7 includes the nine top-associated SNPs in these regions). Among the nine plays a role in neutrophil chemotaxis (26), both of which are involved in innate immunity and plausibly act autophagy functions (27, 28). Therefore, genes involved in autophagy and innate immunity are candidates for the development of Paneth cell defect in Japanese CD. Further studies in additional cohorts are needed to confirm or refute these findings. Supplementary Table 4 shows the top functional or non-synonymous SNPs associated with Paneth cell defect (P $5\times10^{-4}$) (See Supplementary Table 4 of Liu, T. et al., *JCI Insight*, 2017, 2(6), e91917, which is herein incorporated by reference).

TABLE 7

Candidate SNPs and Genes (P < 5E−6).

| Chr | Top SNP ID | Allele 1/ Allele 2 | No of SNPs (P < 5E−6) | Min P | BETA | Genes of interest | Location |
|---|---|---|---|---|---|---|---|
| 20 | rs12481514 | A/G | 18 | 2.52E−07 | 4.469 | ADRA1D | intronic |
| 20 | rs723080 | C/T | 18 | 5.11E−07 | −4.754 | MAFB | upstream |
| 5 | rs147629807 | —/T | 1 | 7.22E−07 | −8.139 | FER | upstream |
| 5 | rs17318450 | A/G | 1 | 1.62E−06 | −5.826 | PRLR | upstream |
| 3 | rs12494894 | A/G | 2 | 2.25E−06 | −6.381 | MFSD1 | downstream |
| 11 | rs629922 | C/T | 2 | 2.74E−06 | 4.142 | ZBTB16 | intronic |

TABLE 7-continued

Candidate SNPs and Genes (P < 5E−6).

| Chr | Top SNP ID | Allele 1/ Allele 2 | No of SNPs (P < 5E−6) | Min P | BETA | Genes of interest | Location |
|---|---|---|---|---|---|---|---|
| 8 | rs72622838 | A/G | 1 | 3.04E−06 | −4.181 | EYA1 | downstream |
| 7 | rs11978753 | G/T | 1 | 3.65E−06 | −5.941 | ACTR3B | downstream |
| 22 | rs2238823 | A/G | 1 | 3.80E−06 | −5.626 | FBLN1 | downstream |

Figure 27:
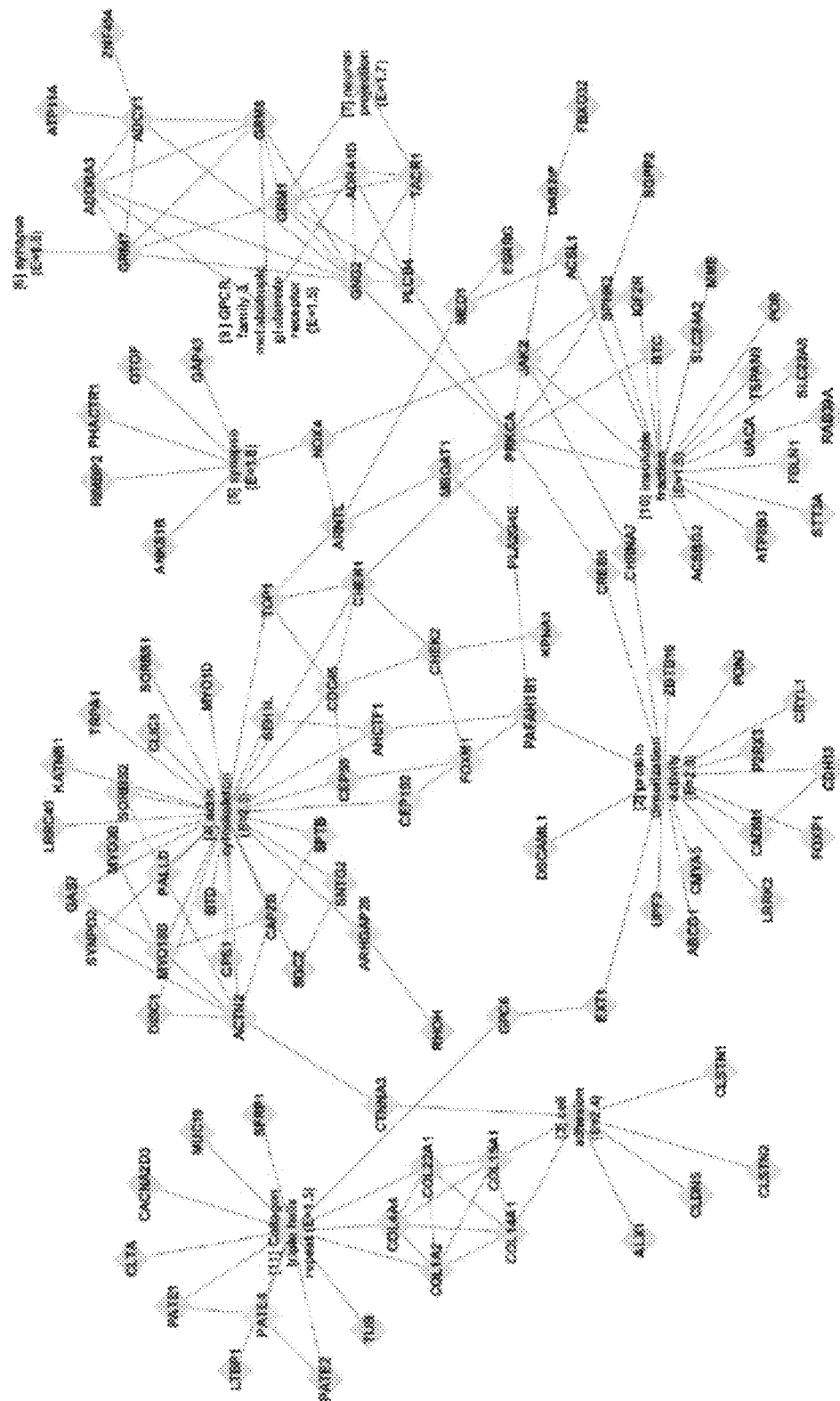
FIG. 27 depicts a network annotation of pathway analysis. Genes associated with the candidate single nucleotide polymorphismsare highlighted in yellow.

Pathway Analysis Revealed Association with Autophagy and Inflammatory Cytokines in Candidate Genes Associated with Paneth Cell Defect:

To determine the spectrum of pathways involved in the genes associated with Paneth cell defect in Japanese CD, we first performed gene enrichment, protein interaction and KEGG pathway analyses to explore the biological functions of the top annotated genes corresponding to SNPs associated with abnormal Paneth cells with P values≤1×10$^{-3}$ (n=288) to obtain an overview of these pathways. Our results demonstrate that the gene list was enriched for specific molecular functions and biological pathways that could be related to Paneth cell phenotype. Twelve functional annotation clusters with an enrichment score of E>1.4 (corresponding to unadjusted P value of 0.05) were identified for this gene set (See Supplementary Table 5 of Liu, T. et al., *JCI Insight*, 2017, 2(6), e91917, which is herein incorporated by reference). We also used the 288-gene list to generate a protein-protein interaction network (See Supplementary Table 6 of Liu, T. et al., *JCI Insight*, 2017, 2(6), e91917, which is herein incorporated by reference). The functional annotation of the network is shown in FIG. 27 and the KEGG pathways (P<0.05) for these genes are listed in Table 8. Many of the pathways and networks, such as cell adhesion and cytoskeletal remodeling, are known to be linked to IBD pathogenesis (4).

TABLE 8

Potential pathways associated with Paneth cell defect in Japanese CD.

| Term | Number of genes | P value | P value (FDR) |
|---|---|---|---|
| Protein digestion and absorption | 7 | $1.10 \times 10^{-4}$ | $3.14 \times 10^{-2}$ |
| Glutamatergic synapse | 7 | $5.48 \times 10^{-4}$ | $7.86 \times 10^{-2}$ |
| Calcium signaling pathway | 8 | $1.99 \times 10^{-3}$ | $1.91 \times 10^{-1}$ |
| Cholinergic synapse | 6 | $2.71 \times 10^{-3}$ | $1.95 \times 10^{-1}$ |
| Long-term depression | 4 | $6.75 \times 10^{-3}$ | $3.38 \times 10^{-1}$ |
| Inflammatory mediator regulation of TRP channels | 5 | $7.56 \times 10^{-3}$ | $3.38 \times 10^{-1}$ |
| Retrograde endocannabinoid signaling | 5 | $8.25 \times 10^{-3}$ | $3.38 \times 10^{-1}$ |
| Amoebiasis | 5 | $1.14 \times 10^{-2}$ | $4.10 \times 10^{-1}$ |
| Leukocyte transendothelial migration | 5 | $1.59 \times 10^{-2}$ | $4.73 \times 10^{-1}$ |
| Focal adhesion | 7 | $1.65 \times 10^{-2}$ | $4.73 \times 10^{-1}$ |
| Endocrine and other factor-regulated calcium reabsorption | 3 | $2.17 \times 10^{-2}$ | $5.05 \times 10^{-1}$ |
| Dopaminergic synapse | 5 | $2.28 \times 10^{-2}$ | $5.05 \times 10^{-1}$ |
| Neuroactive ligand-receptor interaction | 8 | $2.44 \times 10^{-2}$ | $5.05 \times 10^{-1}$ |
| ECM-receptor interaction | 4 | $2.46 \times 10^{-2}$ | $5.05 \times 10^{-1}$ |
| Adrenergic signaling in cardiomyocytes | 5 | $3.67 \times 10^{-2}$ | $7.03 \times 10^{-1}$ |
| VEGF signaling pathway | 3 | $4.11 \times 10^{-2}$ | $7.37 \times 10^{-1}$ |

Figure 28A:
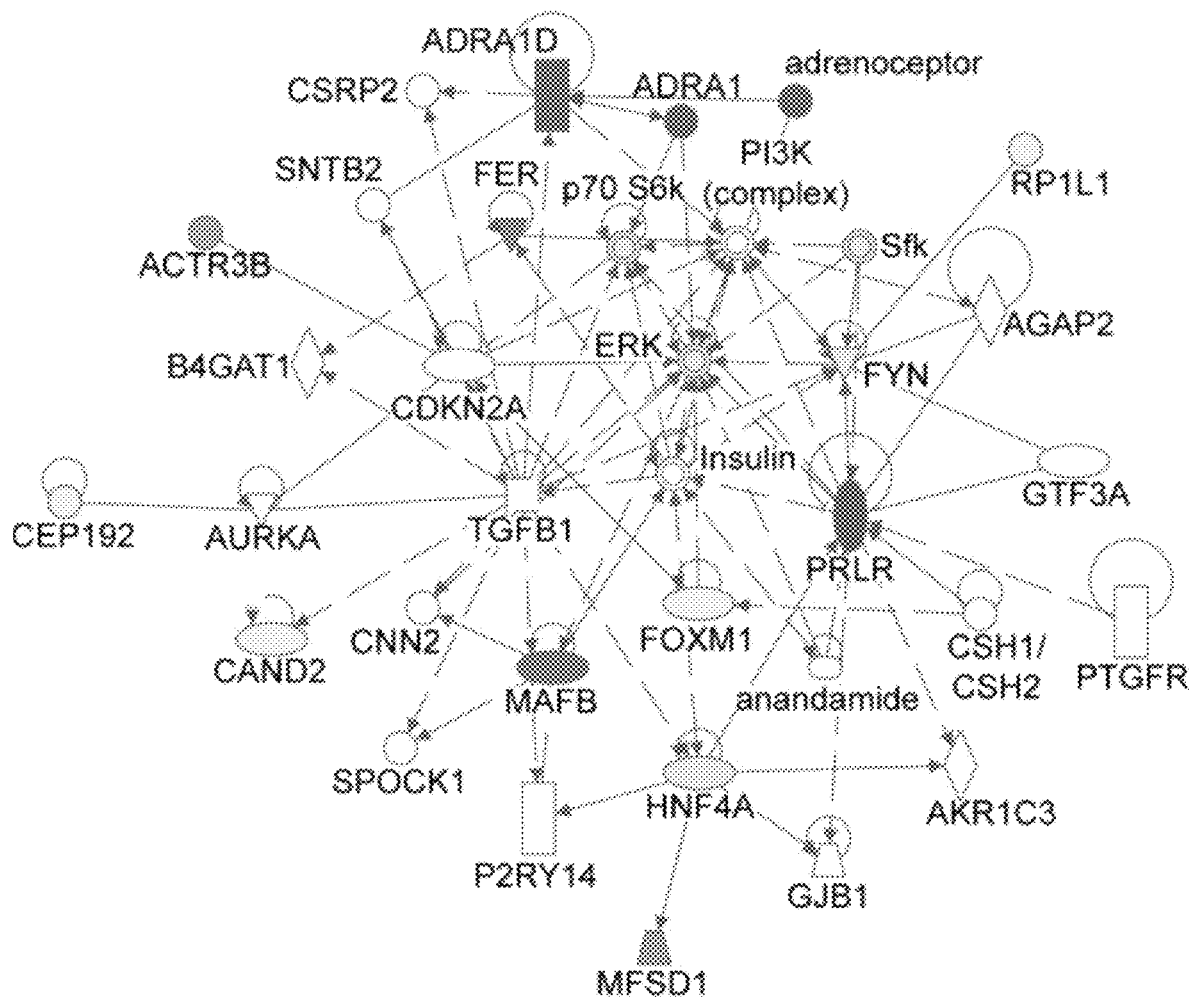
FIG. 28A and FIG. 28B depict graphs showing ingenuity pathway analysis of the genes associated with Paneth cell defect in Japanese Crohn's disease (CD) patients. The genes include LRRK2 and the candidate genes listed in Table 7 and Supplementary Table 4. The intensity of the color correlates with the P values. Solid lines indicate direct interactions, and dotted lines indicate indirect interactions. Red denotes genes associated with Paneth cell defect in Japanese CD (intensity positively correlates with P values). Blue denotes IBD susceptibility genes. The majority of the genes associated with Paneth cell defect are involved in (FIG. 28A) PI3K-mTOR pathway, which links to autophagy, whereas a minor subset of the genes are involved in (FIG. 28B) TNF signaling.
Figure 28B:
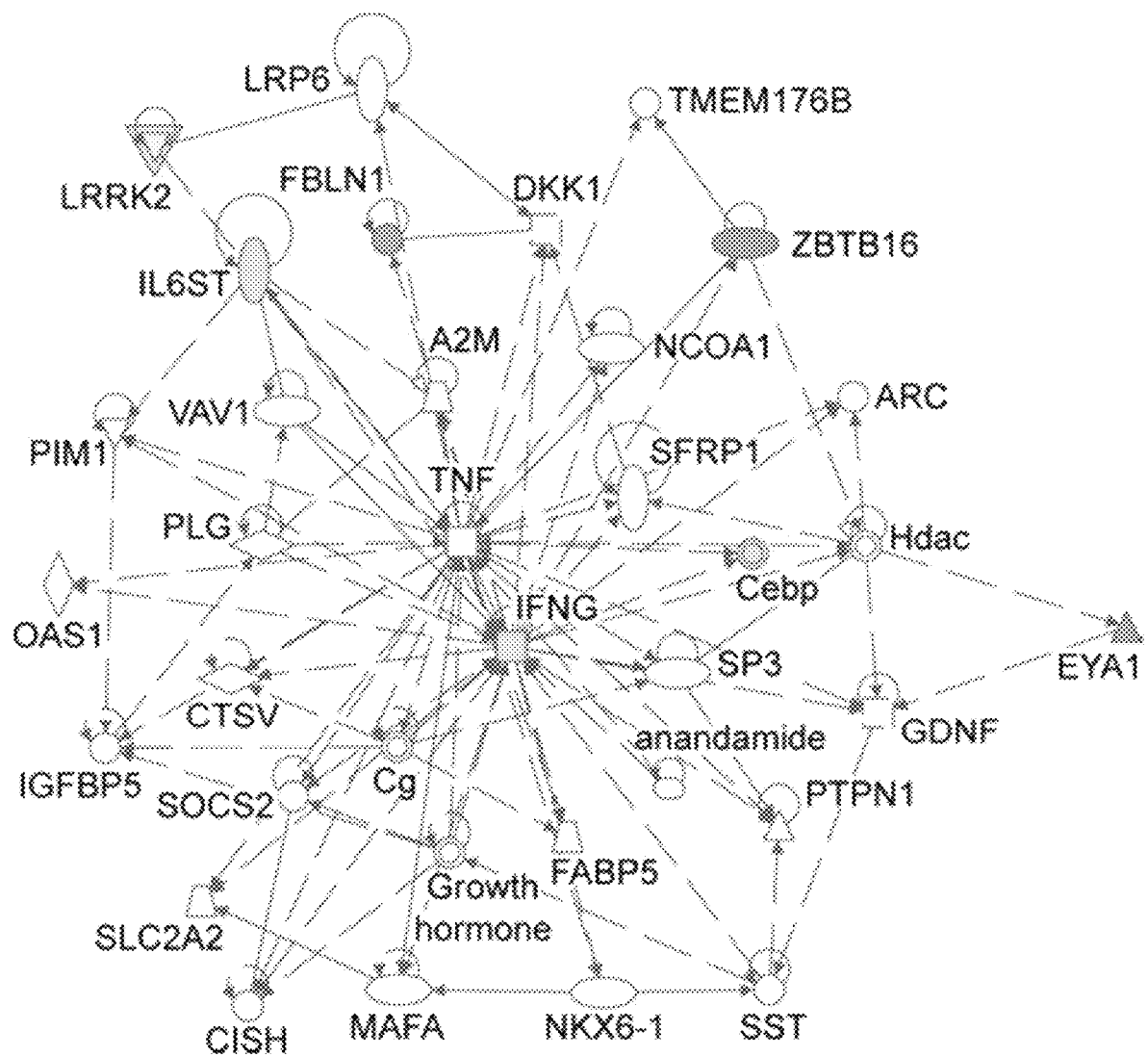

We next focused our analysis on the 17 identified candidate genes (LRRK2 and genes described in Table 7 and Supplementary Table 4 of Liu, T. et al., *JCI Insight*, 2017, 2(6), e91917, which is herein incorporated by reference). Ingenuity Pathway Analysis showed that the 17 genes identified can be connected in two distinct networks (FIG. 28A and FIG. 28B). The majority are involved in a gene network regulating PI3K and ERK signaling pathways (FIG. 28A). Both of these pathways can regulate the mTOR pathway, a known upstream regulator of autophagy (29, 30). Moreover, in previous studies, mTOR signaling has been linked to stem cell health and Paneth cell differentiation (31-33). A second subset of genes were linked to the TNF-α signaling pathway (FIG. 28B), consistent with the central role of TNF-α in IBD pathogenesis (34-36). TNF-α has also been implicated in the homeostasis of Paneth cell function (37-40). Therefore, the candidate genes for Paneth cell dysfunction in Japanese CD patients potentially act through modulating autophagy and TNF-α signaling. We also examined the potential interactions between the 17 identified genes and known CD susceptibility genes (35). We found interactions with several IBD susceptibility genes in both networks (35). For example, IBD susceptibility genes FYN, HCK, HNF4A, MAPK1, and RPS6KB1 were involved in the PI3K network, which included genes MAFB, ADRA1D, PRLR, ACTR3B, CEP192, CAND2, FOXM1, MFSD1, and RP1L1 that were identified in this study. Likewise, IBD susceptibility genes IFNG, IL6ST, LRRK2, and CEBPB, as well as genes identified in this study LRRK2, ZBTB16, FBLN1, and EYA1, were involved in the TNF-α network. Therefore, the genes identified in this study potentially act in concert with known IBD susceptibility genes in autophagy and TNF-α signaling networks in association with Paneth cell defect.

Discussion

In the current study, we first set out to determine the prevalence, and the genetic and clinical associations, of Paneth cell defect in Japanese CD, a population who possess a distinct spectrum of susceptibility genes compared to European ancestry CD. We demonstrated that not only was Paneth cell defect prevalent in the Japanese CD, clinically it also correlated with prognosis in Japanese CD patients after surgery. Surprisingly, there were dichotomous effects of ATG16L1 and LRRK2 between the two cohorts. We also identified several associated SNPs in genes linked to autophagy and TNF-α signaling as candidates for Paneth cell defect in the Japanese CD.

While ATG16L1 T300A was associated with defective Paneth cells in both mouse models and North American adult CD patient cohorts (13, 41, 42), this genetic association was not observed in Japanese CD. In contrast, we found that LRRK2 M2397T, a susceptibility allele for European ancestry but not for Japanese or Korean CD (9, 23, 24, 43, 44), was associated with Paneth cell defect in Japanese, but not North American CD. There are several important considerations when interpreting these findings. First, given the different allele frequencies of ATG16L1 T300A between European and Asian CD cohorts (7), it is possible that a larger sample size is required to achieve sufficient power to detect an association between ATG16L1 T300A with Paneth cell defect in Japanese CD. Second, while the LRRK2 M2397T is not a susceptibility allele for Japanese CD, it could also represent a power issue in the Japanese populations. In addition, it is possible that LRRK2 M2397T, a missense variant that could result in functional defect of LRRK2, may be associated with other aspects of CD manifestations. A recent study in leprosy (a granulomatous disease) showed that patients harboring the same LRRK2 M2397T alleles suffer from excessive pro-inflammatory responses (45). Interestingly, overlapping susceptibility loci between CD and mycobacterial infection (particularly leprosy) is established (23). A longitudinal study would provide additional insight into the clinical relevance of LRRK2 M2397T in Japanese CD. Additional advanced sequencing technologies such as fine mapping and deep sequencing of the LRRK2 gene and e-QTL analysis will be important to validate the association of the M2397T SNP with Paneth cell defect, as has been shown in other studies (12, 15).

Using mouse models, we previously showed that Paneth cell defect is the result of "Gene+Environment" interactions, suggesting that proper environmental triggers or genetic context may be required to illicit Paneth cell defect in CD patients. The sharp contrast of divergent correlations of ATG16L1 T300A and LRRK2 M2397T with Paneth cell defects in North American and Japanese CD cohorts suggests that the environmental factors that the North American and Japanese CD patients harboring these variants encountered could be distinct. Furthermore, based on our current understanding of the autophagy machinery, in complex biologic processes such as Paneth cell function and intestinal homeostasis, the functions of these autophagy-associated genes may need to be orchestrated in distinct fashions depending on the environmental insults unique to these populations (46). One important direction is to use Paneth cell phenotype analysis as a platform to identify potential environmental factors or additional genetic factors that interact with specific host mutants in triggering Paneth cell defect in CD patients and mouse models with LRRK2 deficiency. In addition, environmental and genetic factors that could exert "protective" effect of Paneth cell defect should be investigated through large-scale studies. Also of particular interest is to compare the Paneth cell phenotype in first- and second-generation Asian immigrants to North America (and vice versa), an approach that has yielded insight to disease pathogenesis in epidemiology studies (47-50). Based on our finding, we predict that while the genetic landscape of the second-generation immigrants will be similar to their parents, the genetic correlation to Paneth cell defects will trend more toward European ancestry North American CD. In addition, conducting genetic-Paneth cell defect analysis with focused ethnic groups (e.g., Ashkenazi Jewish) (51, 52) and with cross-ethnic groups (7) may provide additional insight into potential gene-gene interactions in triggering Paneth cell defect.

Among the candidate genes shown to be associated with Paneth cell defects by hypothesis-free association, ZBTB16, MAFB, and FER have been shown to be linked to autophagy and components of the innate immune response that could be modulated with autophagy. ZBTB has been shown to regulate autophagy by mediating the proteosomal degradation of Atg14L (25). ZBTB16 is also involved in type 2 innate lymphoid cell function (53), NKT cell differentiation (53), and regulation of inflammatory signaling (54). MAFB is associated with macrophage differentiation (55, 56). FER plays a role in leukocyte recruitment and intestinal barrier function in response to bacterial lipopolysaccharide recognition (57). Both macrophage differentiation and leukocyte recruitment are important elements of innate immunity and involves autophagy (27, 28). Thus, the observation that genes involved directly and indirectly in autophagy were candidates for Paneth cell defect supports the notion that autophagy is a central pathway that controls the intestinal homeostasis (58).

Importantly, although the SNPs for Paneth cell defect identified in this study were largely distinct from the known SNPs for European ancestry CD, Paneth cell phenotype still correlated with prognosis in Japanese CD patients undergoing surgery. These results indicate that Paneth cell phenotype, as an integrated readout for combinatorial effect of host genetics and environmental factors, could potentially be applied as a universal prognostic biomarker for CD patients of different ethnicity/genetic backgrounds undergoing resection. Of note, a recent study has highlighted that the genes associated with CD susceptibility and prognosis are distinct (59). Therefore, development of a potential gene score that predicts postoperative recurrence may be complementary to using Paneth cell phenotype as biomarker. In addition, while we did not observe the correlation between Paneth cell phenotype and the presence of granuloma, we did observe a trend between diminished Paneth cells and granuloma, a finding that was significant in our previous study in North American CD (3). Therefore, future studies with a larger sample size may provide more insight.

In summary, we demonstrated that Paneth cell defect was prevalent in Japanese CD, was associated with different spectrum of genes compared to North American CD, and was predictive of prognosis. The genes involved in Paneth cell defect in Japanese CD mainly affect autophagy and TNF signaling pathways. Paneth cell phenotype can be applied as a universal clinical and biological relevant biomarker for CD patients with diverse genetic backgrounds.

Conclusions:

We found dichotomous effects of ATG16L1 and LRRK2 on Paneth cell defect between Japanese and Western CD. Genes affecting Paneth cell phenotype in Japanese CD were also associated with autophagy. Paneth cell phenotype also predicted prognosis in Japanese CD.

References in Example 7

1. Liu, T. C., Gao, F., McGovern, D. P., and Stappenbeck, T. S. 2014. Spatial and temporal stability of paneth cell phenotypes in Crohn's disease: implications for prognostic cellular biomarker development. Inflamm Bowel Dis 20:646-651.
2. Liu, T. C., et al. 2016. Paneth cell defects in Crohn's disease promote dysbiosis. JCI Insight 1:e86907.
3. VanDussen, K. L., et al. 2014. Genetic variants synthesize to produce paneth cell phenotypes that define subtypes of Crohn's disease. Gastroenterology 146:200-209.
4. Takagi, S., et al. 2006. Effectiveness of an 'half elemental diet' as maintenance therapy for Crohn's disease: A randomized-controlled trial. Aliment Pharmacol Ther 24:1333-1340.
5. Kawai, Y., et al. 2015. Japonica array: improved genotype imputation by designing a population-specific SNP array with 1070 Japanese individuals. J Hum Genet 60:581-587.
6. Nagasaki, M., et al. 2015. Rare variant discovery by deep whole-genome sequencing of 1,070 Japanese individuals. Nat Commun 6:8018.

7. Liu, J. Z., et al. 2015. Association analyses identify 38 susceptibility loci for inflammatory bowel disease and highlight shared genetic risk across populations. Nat Genet 47:979-986.
8. Yamazaki, K., et al. 2013. A genome-wide association study identifies 2 susceptibility Loci for Crohn's disease in a Japanese population. Gastroenterology 144:781-788.
9. Yang, S. K., et al. 2014. Genome-wide association study of Crohn's disease in Koreans revealed three new susceptibility loci and common attributes of genetic susceptibility across ethnic populations. Gut 63:80-87.
10. Yang, S. K., et al. 2015. Immunochip analysis identification of 6 additional susceptibility loci for Crohn's disease in Koreans. Inflamm Bowel Dis 21:1-7.
11. Yamazaki, K., et al. 2005. Single nucleotide polymorphisms in TNFSF15 confersusceptibility to Crohn's disease. Hum Mol Genet 14:3499-3506.
12. Hong, S. N., et al. 2016. Deep resequencing of 131 Crohn's disease associated genes in pooled DNA confirmed three reported variants and identified eight novel variants. Gut 65:788-796.
13. Cadwell, K., et al. 2008. A key role for autophagy and the autophagy gene Atg16l1 in mouse and human intestinal Paneth cells. Nature 456:259-263.
14. Kaser, A., et al. 2008. XBP1 links ER stress to intestinal inflammation and confers genetic risk for human inflammatory bowel disease. Cell 134:743-756.
15. Trabzuni, D., et al. 2013. Fine-mapping, gene expression and splicing analysis of the disease associated LRRK2 locus. PLoS One 8:e70724.
16. Purcell, S., et al. 2007. PLINK: a tool set for whole-genome association and population-based linkage analyses. Am J Hum Genet 81:559-575.
17. Pruim, R. J., et al. 2010. LocusZoom: regional visualization of genome-wide association scan results. Bioinformatics 26:2336-2337.
18. Sorrentino, D. 2013. State-of-the-art medical prevention of postoperative recurrence of Crohn's disease. Nat Rev Gastroenterol Hepatol 10:413-422.
19. Cadwell, K., et al. 2010. Virus-plus-susceptibility gene interaction determines Crohn's disease gene Atg16L1 phenotypes in intestine. Cell 141:1135-1145.
20. Hampe, J., et al. 2007. A genome-wide association scan of nonsynonymous SNPs identifies a susceptibility variant for Crohn disease in ATG16L1. Nat Genet 39:207-211.
21. Inoue, N., et al. 2002. Lack of common NOD2 variants in Japanese patients with Crohn's disease. Gastroenterology 123:86-91.
22. Yamazaki, K., Takazoe, M., Tanaka, T., Kazumori, T., and Nakamura, Y. 2002.
Absence of mutation in the NOD2/CARD15 gene among 483 Japanese patients with Crohn's disease. J Hum Genet 47:469-472.
23. Jostins, L., et al. 2012. Host-microbe interactions have shaped the genetic architecture of inflammatory bowel disease. Nature 491:119-124.
24. Franke, A., et al. 2010. Genome-wide meta-analysis increases to 71 the number of confirmed Crohn's disease susceptibility loci. Nat Genet 42:1118-1125.
25. Zhang, Q., et al. 2015. Commensal bacteria direct selective cargo sorting to promote symbiosis. Nat Immunol 16:918-926.
26. Khajah, M., et al. 2013. Fer kinase limits neutrophil chemotaxis toward end target chemoattractants. J Immunol 190:2208-2216.
27. Chen, P., Cescon, M., and Bonaldo, P. 2014. Autophagy-mediated regulation of macrophages and its applications for cancer. Autophagy 10:192-200.
28. Kanayama, M., et al. 2015. Autophagy enhances NFkappaB activity in specific tissue macrophages by sequestering A20 to boost antifungal immunity. Nat Commun 6:5779.
29. Shanware, N. P., Bray, K., and Abraham, R. T. 2013. The PI3K, metabolic, and autophagy networks: interactive partners in cellular health and disease. Annu Rev Pharmacol Toxicol 53:89-106.
30. Jung, C. H., Ro, S. H., Cao, J., Otto, N. M., and Kim, D. H. 2010. mTOR regulation of autophagy. FEBS Lett 584:1287-1295.
31. Zhou, Y., Rychahou, P., Wang, Q., Weiss, H. L., and Evers, B. M. 2015. TSC2/mTORC1 signaling controls Paneth and goblet cell differentiation in the intestinal epithelium. Cell Death Dis 6:e1631.
32. Igarashi, M., and Guarente, L. 2016. mTORC1 and SIRT1 Cooperate to Foster Expansion of Gut Adult Stem Cells during Calorie Restriction. Cell 166:436-450.
33. Yilmaz, O. H., et al. 2012. mTORC1 in the Paneth cell niche couples intestinal stem-cell function to calorie intake. Nature 486:490-495.
34. Khor, B., Gardet, A., and Xavier, R. J. 2011. Genetics and pathogenesis of inflammatory bowel disease. Nature 474:307-317.
35. McGovern, D. P., Kugathasan, S., and Cho, J. H. 2015. Genetics of Inflammatory Bowel Diseases. Gastroenterology 149:1163-1176 e1162.
36. Gunther, C., et al. 2011. Caspase-8 regulates TNF-alpha-induced epithelial necroptosis and terminal ileitis. Nature 477:335-339.
37. Lu, W., and de Leeuw, E. 2014. Functional intersection of Human Defensin 5 with the TNF receptor pathway. FEBS Lett 588:1906-1912.
38. Van Hauwermeiren, F., et al. 2015. TNFR1-induced lethal inflammation is mediated by goblet and Paneth cell dysfunction. Mucosal Immunol 8:828-840.
39. Schaubeck, M., et al. 2016. Dysbiotic gut microbiota causes transmissible Crohn's disease-like ileitis independent of failure in antimicrobial defence. Gut 65:225-237.
40. Roulis, M., et al. 2016. Host and microbiota interactions are critical for development of murine Crohn's-like ileitis. Mucosal Immunol 9:787-797.
41. Lassen, K. G., et al. 2014. Atg16L1 T300A variant decreases selective autophagy resulting in altered cytokine signaling and decreased antibacterial defense. Proc Natl Acad Sci USA 111:7741-7746.
42. Murthy, A., et al. 2014. A Crohn's disease variant in Atg16l1 enhances its degradation by caspase 3. Nature 506:456-462.
43. Hirano, A., et al. 2013. Association study of 71 European Crohn's disease susceptibility loci in a Japanese population. Inflamm Bowel Dis 19:526-533.
44. Fuyuno, Y., et al. 2016. Genetic characteristics of inflammatory bowel disease in a Japanese population. J Gastroenterol 51:672-681.
45. Fava, V. M., et al. 2016. A Missense LRRK2 Variant Is a Risk Factor for Excessive Inflammatory Responses in Leprosy. PLoS Negl Trop Dis 10:e0004412.
46. Levine, B., Mizushima, N., and Virgin, H. W. 2011. Autophagy in immunity and inflammation. Nature 469:323-335.

47. Ko, Y., Butcher, R., and Leong, R. W. 2014. Epidemiological studies of migration and environmental risk factors in the inflammatory bowel diseases. World J Gastroenterol 20:1238-1247.
48. Probert, C. S., Jayanthi, V., Pinder, D., Wicks, A. C., and Mayberry, J. F. 1992. Epidemiological study of ulcerative proctocolitis in Indian migrants and the indigenous population of Leicestershire. Gut 33:687-693.
49. Carr, I., and Mayberry, J. F. 1999. The effects of migration on ulcerative colitis: a three-year prospective study among Europeans and first- and second-generation South Asians in Leicester (1991-1994). Am J Gastroenterol 94:2918-2922.
50. Li, X., Sundquist, J., Hemminki, K., and Sundquist, K. 2011. Risk of inflammatory bowel disease in first- and second-generation immigrants in Sweden: a nationwide follow-up study. Inflamm Bowel Dis 17:1784-1791.
51. Chuang, L. S., et al. 2016. A Frameshift in CSF2RB Predominant Among Ashkenazi Jews Increases Risk for Crohn's Disease and Reduces Monocyte Signaling via GM-CSF. Gastroenterology.
52. Vacic, V., et al. 2014. Genome-wide mapping of IBD segments in an Ashkenazi PD cohort identifies associated haplotypes. Hum Mol Genet 23:4693-4702.
53. Pobezinsky, L. A., et al. 2015. Let-7 microRNAs target the lineage-specific transcription factor PLZF to regulate terminal NKT cell differentiation and effector function. Nat Immunol 16:517-524.
54. Sadler, A. J., et al. 2015. BTB-ZF transcriptional regulator PLZF modifies chromatin to restrain inflammatory signaling programs. Proc Natl Acad Sci USA 112:1535-1540.
55. Aziz, A., Soucie, E., Sarrazin, S., and Sieweke, M. H. 2009. MafB/c-Maf deficiency enables self-renewal of differentiated functional macrophages. Science 326:867-871.
56. Soucie, E. L., et al. 2016. Lineage-specific enhancers activate self-renewal genes in macrophages and embryonic stem cells. Science 351:aad5510.
57. Qi, W., Ebbert, K. V., Craig, A. W., Greer, P. A., and McCafferty, D. M. 2005. Absence of Fer protein tyrosine kinase exacerbates endotoxin induced intestinal epithelial barrier dysfunction in vivo. Gut 54:1091-1097.
58. Baxt, L. A., and Xavier, R. J. 2015. Role of Autophagy in the Maintenance of Intestinal Homeostasis. Gastroenterology 149:553-562.
59. Lee, J. C., et al. 2017. Genome-wide association study identifies distinct genetic contributions to prognosis and susceptibility in Crohn's disease. Nat Genet.

Figure 29:
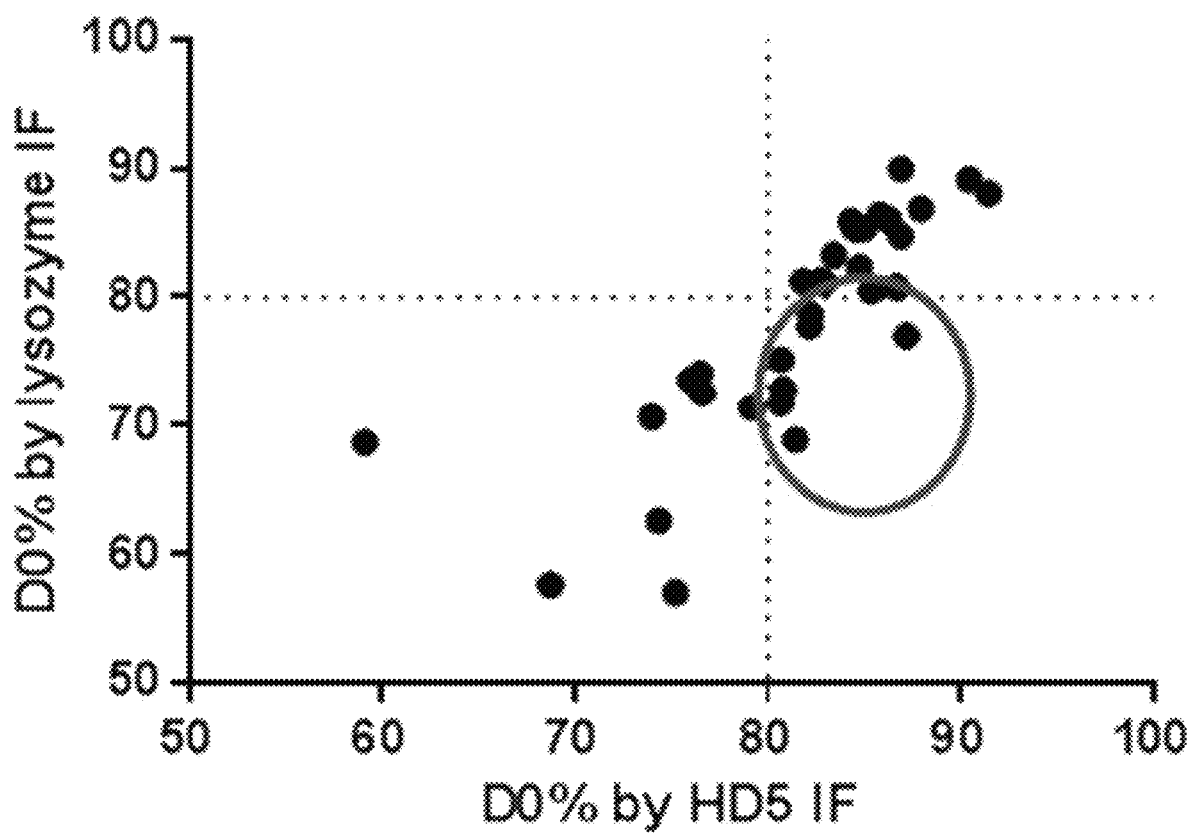
FIG. 29 depicts a graph showing the percentage of normal Paneth cells as examined by lysozyme and HD5 co-IF. The dot plot uses the same dataset as in Table 5. Dots in the circle represent cases where lysozyme IF underestimated the percentage of normal Paneth cells.
Figure 30A:
FIG. 30A, FIG. 30B, FIG. 30C, and FIG. 30D depict representative images of lysosome (FIG. 30A and FIG. 30C) and HD5 (FIG. 30B and FIG. 30D) immunofluorescence from the same sample. A,B: 200×; C, D: 400×.
Figure 30B:
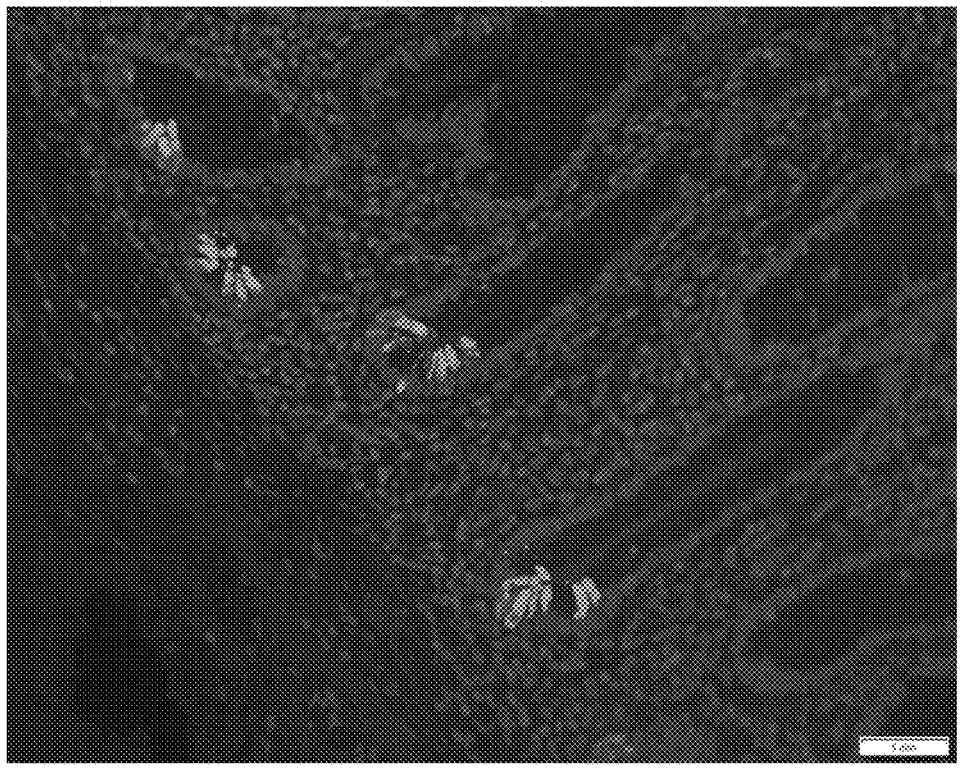
Figure 30C:
Figure 30D:
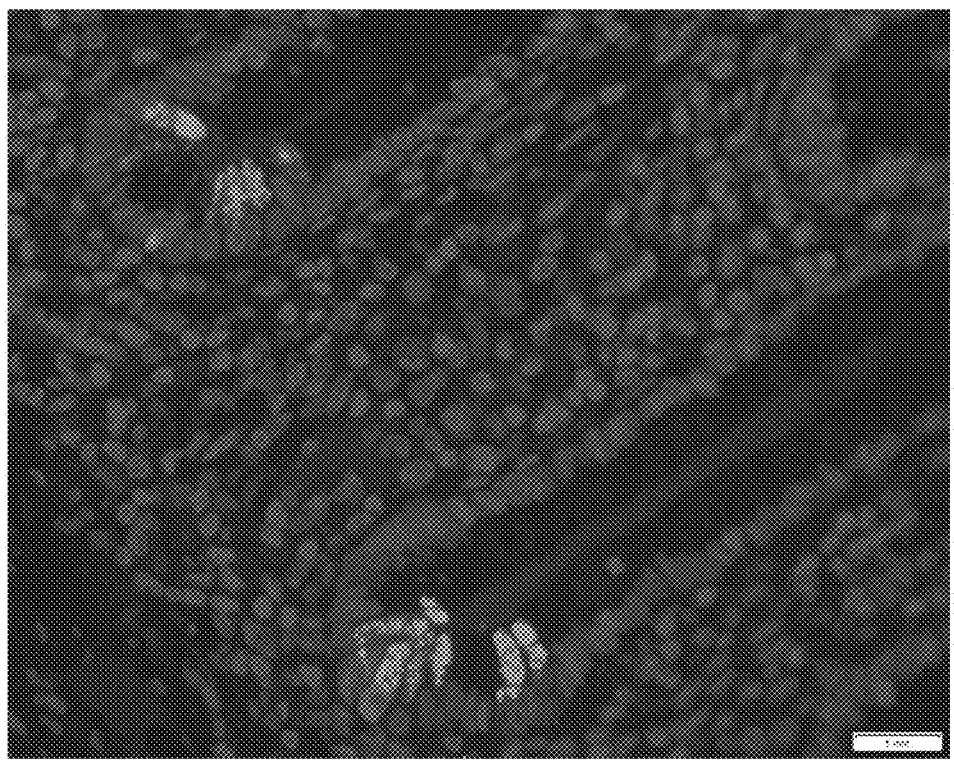
Figure 31A:
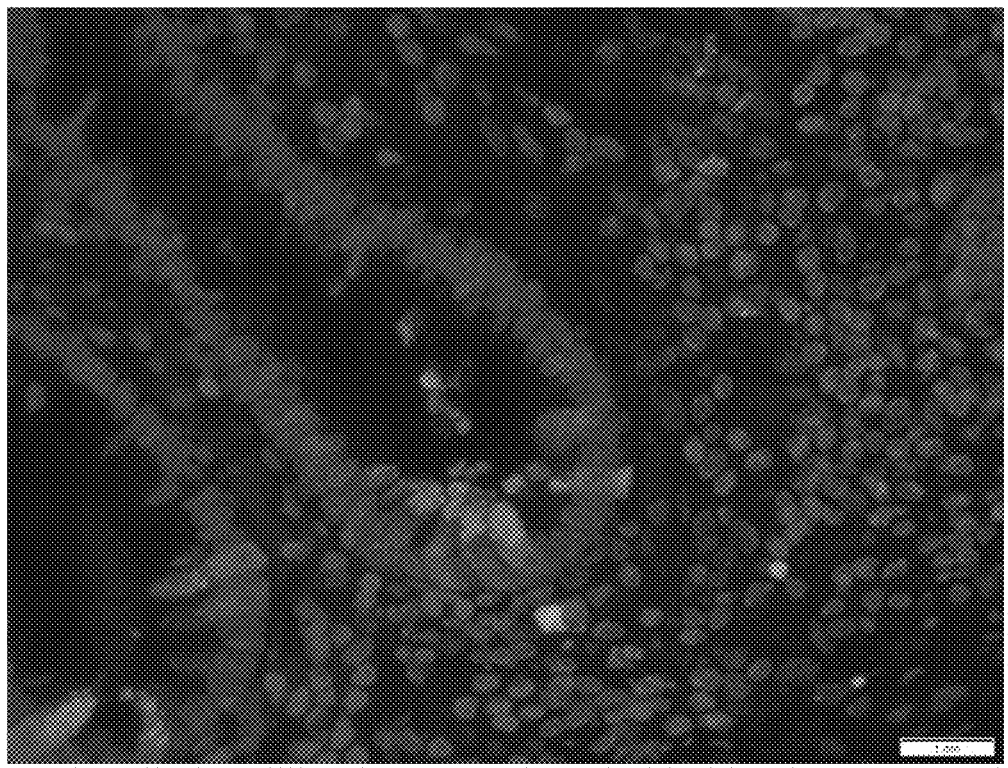
FIG. 31A and FIG. 31B depict representative images of lysozyme (FIG. 31A) and HD5 (FIG. 31B) immunofluorescence from the same sample (400×).
Figure 31B:

Example 8. HD5 Immunofluorescence is Superior to Lysozyme Immunofluorescence as Biomarker Thirty-three cases were co-stained with lysozyme and HD5 IF. Among the 33 cases, 26 of which showed concordance in Paneth cell phenotype (Type I vs. Type II) with the 2 stains. However, 7 cases (21%) showed discordance. All 7 cases showed lower percentages of normal Paneth cells (D0%) on lysozyme stain compared to HD5 stain (Table 5 and FIG. 29). Thus, HD5 IF can provide a more robust staining readout. As can be seen in the representative images of lysozyme and HD5 IF shown in FIG. 30A, FIG. 30B, FIG. 30C, FIG. 30D, FIG. 31A and FIG. 31B, in addition to the higher resolution of Paneth cell granule morphology by HD5 IF, there is also less background staining from the hematopoietic cells which express lysozyme but not HD5. This is an important feature for development of an automated Paneth cell quantification system.

TABLE 5

Percentage of normal Paneth cells as examined by lysozyme and HD5 co-IF. Bolded are the cases where readout from lysozyme IF underestimated the percentage of normal Paneth cells which resulted in different categorization of Paneth cell phenotype.

| Case number | HD5 | Lysozyme |
| --- | --- | --- |
| 1 | 59.15 | 68.67 |
| 2 | 68.76 | 57.63 |
| 3 | 74.01 | 70.69 |
| 4 | 74.37 | 62.62 |
| 5 | 75.23 | 57.03 |
| 6 | 76.00 | 73.58 |
| 7 | 76.50 | 74.07 |
| 8 | 76.63 | 72.57 |
| 9 | 79.17 | 71.43 |
| 10 | 81.86 | 81.27 |
| 11 | 82.75 | 81.32 |
| 12 | 82.89 | 81.15 |
| 13 | 83.46 | 83.25 |
| 14 | 84.35 | 85.90 |
| 15 | 84.53 | 85.32 |
| 16 | 84.77 | 82.33 |
| 17 | 85.02 | 85.34 |
| 18 | 85.37 | 80.54 |
| 19 | 85.83 | 86.39 |
| 20 | 86.28 | 86.03 |
| 21 | 86.68 | 80.81 |
| 22 | 86.90 | 84.76 |
| 23 | 86.92 | 89.98 |
| 24 | 87.95 | 86.89 |
| 25 | 90.46 | 89.15 |
| 26 | 91.46 | 88.07 |
| 27 | 81.45 | 68.90 |
| 28 | 80.72 | 75.16 |
| 29 | 80.67 | 71.79 |
| 30 | 80.82 | 72.81 |
| 31 | 82.18 | 77.75 |
| 32 | 82.21 | 78.71 |
| 33 | 87.22 | 77.03 |

Example 9: A Simple Stratification System Incorporating Key Clinical and Pathological Factors Predicts Outcome in Post-Operative Crohn's Disease Introduction:

Crohn's disease (CD), a main form of idiopathic inflammatory bowel disease (IBD), is difficult to cure. Many patients will require surgery during their life time, and despite the advances in therapies, approximately 40% of the patients who require surgery will need subsequent operations. However, there is still a lack of management guidelines for patients after surgery. In particular, as most of the medications are associated with rare but significant toxicities, identifying those patients that are at risk for early recurrence may allow development of individualized therapeutic strategies.

Paneth cells are secretory cells residing in the base of crypts in the small intestine (and to a less amount, first half of the large intestine). Paneth cells play important roles in innate immunity by packaging antimicrobial peptides lysozyme, defensin, and REG-3T, etc. into cytoplasmic granules, and secrete them into the lumen upon stimuli. We hypothesized that a simple stratification system integrating key clinical and pathological features that are easy to collect can be used to improve prognosis prediction and guide therapy in post-operative CD.

Background:

We have previously shown that significant Paneth cell defect (bad Paneth cell phenotype) correlates with certain Crohn's Disease (CD) susceptible genes, and is associated with pathology, distinct gene expression, and prognosis after surgery. While the results were promising, the study was performed in a cohort with enrichment in certain genotypes, and hence the predictive power of Paneth cell phenotype in a 'real life' setting remained untested. Moreover, the interplay of Paneth cell phenotype and other clinically validated prognostic factors in predicting the disease course is unknown. We hypothesized that an integrated risk stratification system incorporating Paneth cell phenotype and known clinical prognostic factor(s) may classify CD into clinically distinct subgroups.

Methods

Patients and Clinical Information:

All patients with CD that received ileal or ileocecal resection at Washington University School of Medicine between January 2011 and June 2013 were included. The following information was retrieved from the medical record: gender, age at operation, age at initial diagnosis, smoking history (never smoker vs. active and ex-smokers), clinical phenotype (per Montreal classification), treatment history, and endoscopic findings after surgery. The study protocol was approved by the Institutional Review Boards of Washington University School of Medicine.

Paneth Cell Phenotype Analysis:

Representative ileal sections from each resection specimen were selected by a pathologist (T.C.L) after reviewing the routine hematoxylin and eosin (H&E) stained slides for each case. Paneth cell granule distribution was classified using HD5 immunofluorescence as previously described (1,2). All sections used for Paneth cell phenotype analysis contained at least 50 well-oriented crypts (3). A case was classified as Type I Paneth cell phenotype if 20% of total Paneth cells contained abnormal cytoplasmic antimicrobial granule morphology, and Type II Paneth cell phenotype if it contained <20% abnormal cytoplasmic granules (4).

Clinical Endpoint:

The clinical end point was time to recurrence after resection. Recurrence was defined by endoscopy (Rutgeert's score≥i2) (5).

Statistical Analysis:

Time to disease recurrence was analyzed using Log-rank test (GraphPad; La Jolla, Calif.). For correlation of each clinical parameter or Paneth cell phenotype and recurrence, multivariate analysis was performed to identify independent prognosis indicator. A P value of 0.05 was considered significant. The statistical analyses were performed using SAS V9.2 (SAS Institutes, Cary, N.C.).

Results

Patient Characteristics:

The key patient characteristics are listed in Table 6. A total of 121 patients were enrolled, including 64 (53%) men and 57 (47%) women. The majority of patients (108; 89%) were Caucasians, followed by 11 (9%) African American, 1 (0.08%) Asian and 1 (0.08%) Native American. The average age at operation was 38 years old (y/o; range, 10-82 y/o), and the average age at diagnosis was 21 y/o (range, 9-59 y/o). By Paris criteria, the majority of the patients (80; 66%) had both small and large intestine involvement (L3), and only 4 cases were of colonic involvement only (L2). Most patients were of B2 and/or B3 clinical phenotype, with only 9% with B1 clinical phenotype. Forty-nine patients (41%) were active and/or ex-smokers. The mean follow up period is 15 months.

TABLE 6

Key patient characteristics.

| | |
|---|---|
| Total n | 121 |
| Male:Female | 64 (53%):57 (47%) |
| Ethnicity | Caucasian: 108 (89%) |
| | African American: 11 (9%) |
| | Asian: 1 (0.08%) |
| | Native American: 1 (0.08%) |
| Mean age at diagnosis | 21 years old (range, 9-59 years old) |
| Mean age at operation | 38 years old (range, 10-82 years old) |
| Location (Paris classification) | L1: 37 (31%) |
| | L2: 4 (3%) |
| | L3: 80 (66%) |
| Clinical phenotype (Paris classification) | B1: 11 (9%) |
| | B2: 64 (53%), B2p: 3 (2%) |
| | B3: 17 (14%), B3p: 4 (3%) |
| | B2B3: 18 (15%), B2B3p: 4 (3%) |
| Smoking history | 48/120 (40%) |
| Post-operative prophylaxis | 93/118 (79%) |

Figure 32:
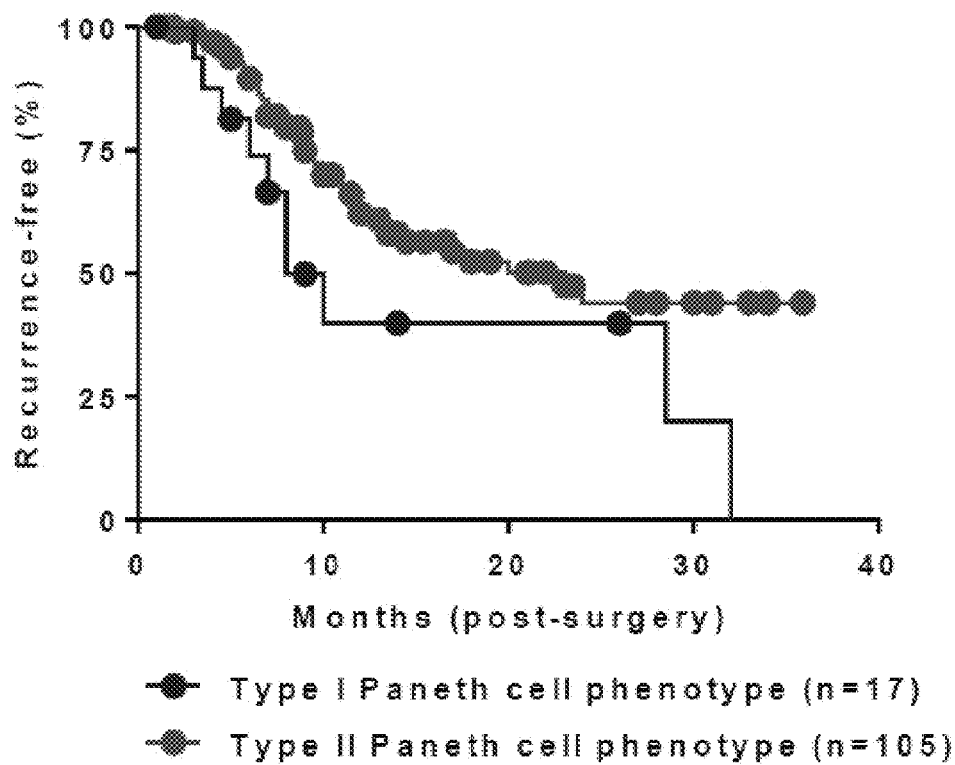
FIG. 32 depicts a graph showing Paneth cell phenotype predicts prognosis in post-operative CD. The median time to recurrence in Type II Paneth cell phenotype was 8 months, whereas that of the Type I Paneth cell phenotype was 23 months ($P=0.0476$).

Paneth Cell Phenotype Predicts Prognosis:

Our previous study suggests that among CD patients who underwent surgery, 15% were of the Type I Paneth cell phenotype, and these patients were associated with shorter time to recurrence after surgery.[4] In our current patient cohort, 17 patients (14%) had Paneth cell defects in ≥20% of the total Paneth cells and were classified as Type I Paneth cell phenotype. As shown in FIG. 32, Paneth cell phenotype was associated with prognosis in these patients. Whereas the median time to disease recurrence in patients with Type II Paneth cell phenotype was 23 months, it was significantly shorter in patients with Type I Paneth cell phenotype (8 months; P=0.0476).

Figure 33A:
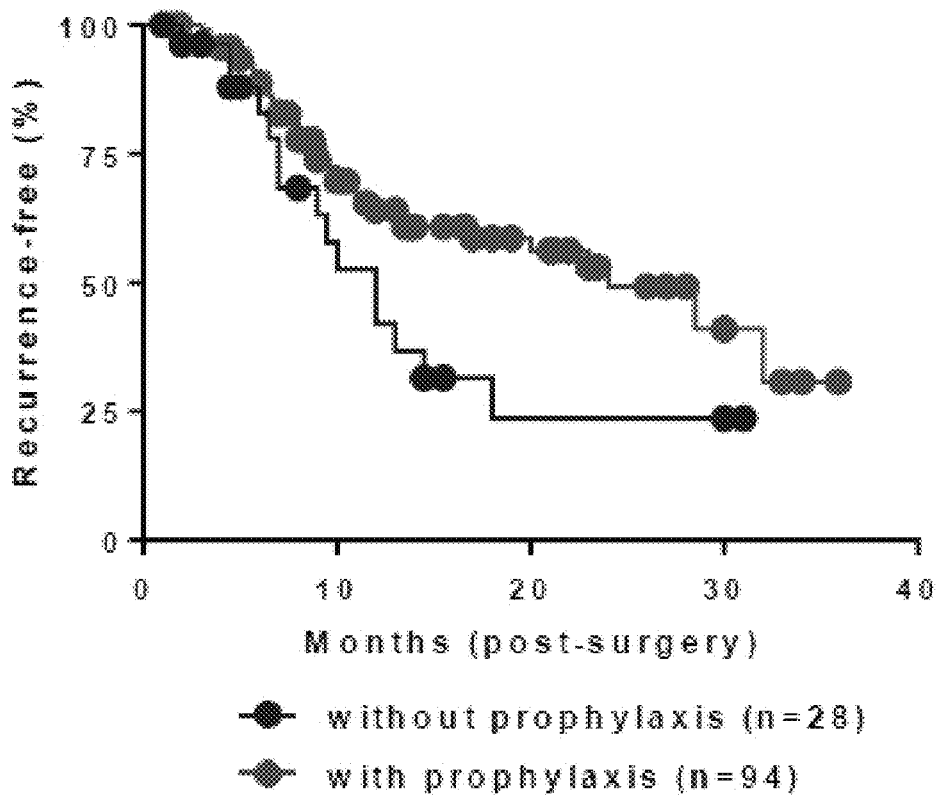
FIG. 33A and FIG. 33B depict graphs showing clinical factors that predict prognosis in post-operative CD.
Figure 33B:
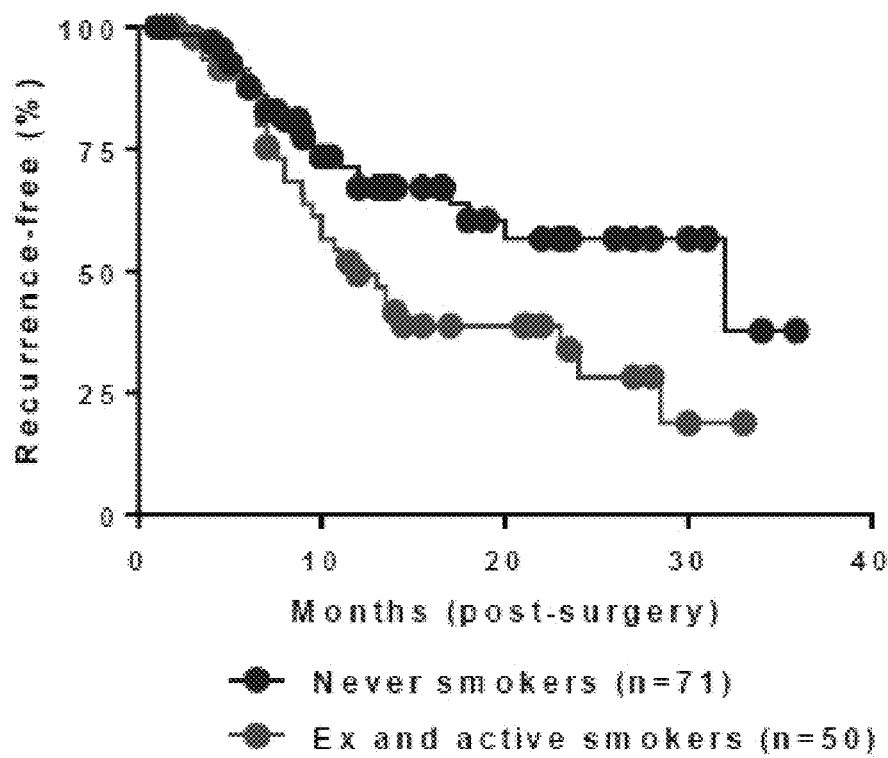

Clinical Factors that Predict Prognosis:

Previous studies have indicated that younger age at onset and smoking increase the likelihood of early recurrence after surgery, whereas postoperative prophylactic therapy delays/reduces recurrence. To determine if these could be potential confounding factors that may skew the analysis of Paneth cell phenotype, we tested whether these factors impact prognosis in our patient cohort. As shown in FIG. 33A, patients who received postoperative prophylaxis showed a significantly longer recurrence-free survival than those who did not (24 vs. 12 months; P=0.0369). Likewise, never smokers also have significantly longer recurrence-free survival than active/ex smokers (FIG. 33B; 32 vs. 12 months; P=0.0151). Of note, there was no significant difference between active and ex smokers (13 vs. 10.7 months; P=0.7070). In contrast, gender, ethnicity, anatomic location, clinical phenotype (per Paris classification), age at the time of diagnosis or surgery did not correlate with time to recurrence after surgery (P>0.05 for all; data not shown).

Figure 34:
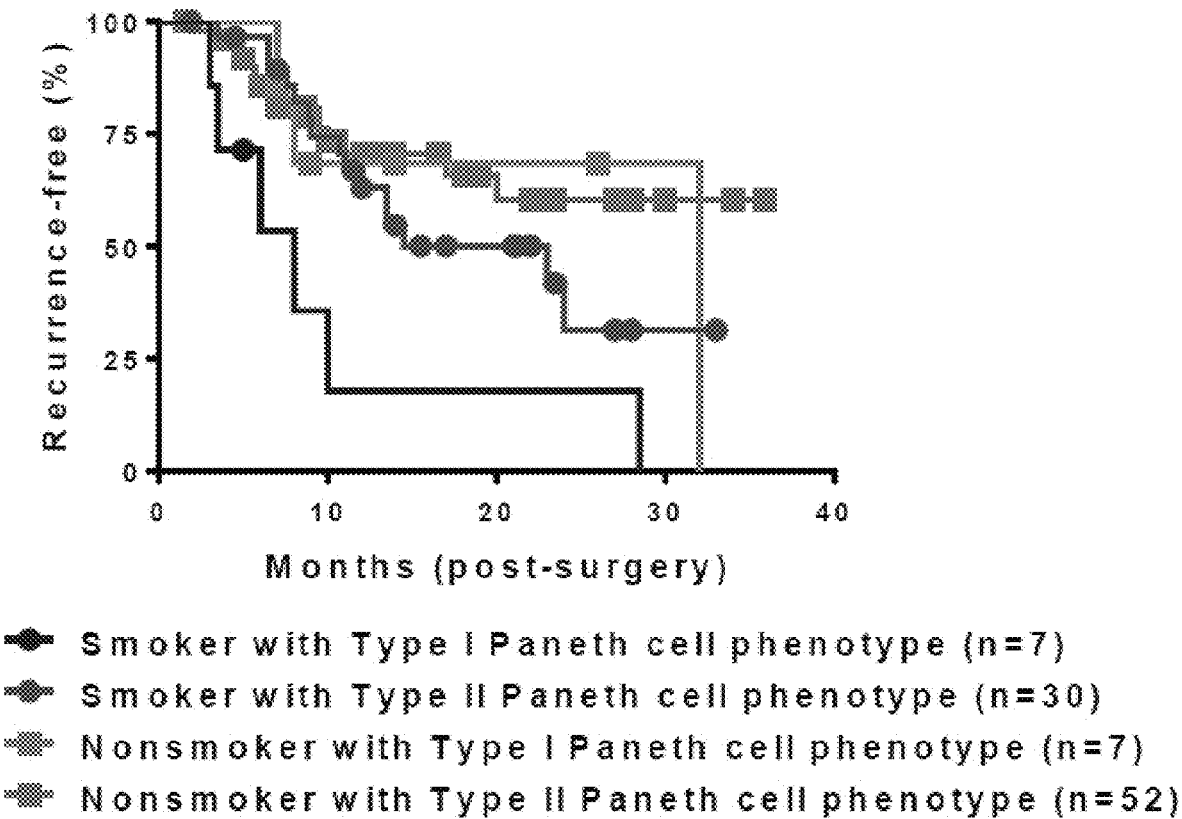
FIG. 34 depicts a graph showing patients who received post-operative prophylactic therapy, combination of Paneth cell phenotype and smoking further subclassifies CD prognosis. Smokers with Type I Paneth cell phenotype had the shortest time to disease recurrence ($P=0.0081$).

A Combined Clinical-Pathology Stratification System Predicts Post-Operative CD:

We then performed multivariate analysis to study whether there was interaction between the 3 identified prognosis predictors. There was no interaction between the three factors, and as such, these were independent predictors. We next sought to investigate whether factors that were directly associated with disease pathogenesis, namely smoking and Paneth cell phenotype, may provide further clinical utility with more precise stratification. We therefore examined the impact of smoking and Paneth cell phenotype in patients who received post-operative prophylactic therapy (n=98). As shown in FIG. 34, the combination of smoking history and Paneth cell phenotype stratifies patients into prognostically distinct subgoups (P=0.0081). Whereas the median time to recurrence for patients with Type I Paneth cell phenotype/smoker was 8 months, it was significantly longer in patients with Type I Paneth cell phenotype/never smoker (32 months) and in patients with Type II Paneth cell phenotype/smoker (23 months). Patients with Type II Paneth cell phenotype/never smoker had the best prognosis (median time to recurrence undefined). Therefore, a stratification system incorporating Paneth cell phenotype and smoking history can further stratifies CD patients after surgery.

Discussion:

We hypothesized that a stratification system based on pathogenesis-associated clinical and pathologic factors can predict prognosis in post-operative CD. We confirmed in our cohort that post-operative prophylaxis and smoking are associated with prognosis. We also validated our previous finding that Paneth cell phenotype can be used to predict prognosis in these patients. Furthermore, as a proof-of-principle study, we showed that a simple stratification system combining Paneth cell phenotype and smoking history can readily stratify patients into distinct subgroups.

There are several limitations to this study. As a retrospective analysis, not all patients were managed in an identical fashion, and hence, it was difficult to differentiate whether different prophylactic agents may further impact the analysis. In addition, while we have shown that both smoking and Paneth cell phenotype were important in determining prognosis, it is difficult to quantify the impact of each component. Likewise, as in many previous clinical studies have shown, the impact of smoking is difficult to quantify. Furthermore, the current study design did not allow us to investigate whether second hand smoking may also contribute to worse prognosis.

In summary, we have shown that combination of smoking and Paneth cell phenotype, representing the key clinical and pathological features, can stratify post-operative CD patients into prognostically distinct subgroups. Our study also highlights the importance of environmental factors in CD pathogenesis and progression. Future studies with increased sample size may allow the testing of a more quantifiable scoring system that integrates additional readout, such as microbiome and signaling pathway analysis. Finally, prospective studies using this stratification system are warranted to validate the clinical utility.

Conclusion:

Paneth cell phenotype and smoking history synergizes to predict prognosis in postoperative CD. Employment of an integrated stratification system incorporating key clinical and pathologic parameters can allow for more accurate prognosis prediction in CD patients undergoing surgery.

References for Examples 9

1. Liu T C, Gurram B, Baldridge M, et al. Paneth cell defects in Crohn's disease promote dysbiosis. JCI Insight. 2016; 1:e86907.
2. Liu T C, Naito T, Liu Z, et al. LRRK2 but not ATG16L1 is associated with Paneth cell defect in Japanese Crohn's disease patients. JCI Insight. 2017; 2:e91917.
3. Liu T C, Gao F, McGovern D, et al. Spatial and temporal stability of Paneth cell phenotypes in Crohn's Disease: implications for prognostic cellular biomarker development. Inflamm Bowel Dis. 2014; 146:200-209.
4. VanDussen K L, Liu T C, Li D, et al. Genetic variants synthesize to produce Paneth cell phenotypes that define subtypes of Crohn's Disease Gastroenterology. 2014; 146:200-209.
5. Rutgeerts P, Geboes K, Vantrappen G, et al. Predictability of the postoperative course of Crohn's disease. Gastroenterology. 1990; 99:956-963.

What is claimed is:

1. A method of determining treatment of a subject with Crohn's disease, the method comprising:
   a) detecting human defensin 5 (HD5) protein by immunostaining of HD5 in a biological sample obtained from the subject;
   b) identifying the number of HD5 positive cells in the biological sample with normal or abnormal HD5 localization and/or distribution, wherein abnormal includes disordered, diminished, diffuse, excluded and enlarged granule morphology;
   c) classifying the subject as having
      i) a Type II phenotype if <20% of cells have abnormal HD5 localization and/or distribution, or
      ii) a Type I phenotype if ≥20% of cells have abnormal HD5 localization and/or distribution and
   d) administering 5-aminosalicylate, corticosteroid, azathioprine, mercaptopurine, infliximab, adalimumab, certolizumab pegol, methotrexate, cyclosporine, tacrolimus, Natalizumab, vedolizumab, ustekinumab, antibiotics, anti-diarrheals, pain relievers, iron supplements, vitamin B-12 shots, calcium supplement, vitamin D supplement, or surgical procedure to the subject classified as Type II, or administering surgical procedure and one or more of 5-am inosalicylate, corticosteroid, azathioprine, mercaptopurine, infliximab, adalimumab, certolizumab pegol, methotrexate, cyclosporine, tacrolimus, Natalizumab, vedolizumab, ustekinumab, antibiotics, anti-diarrheals, pain relievers, iron supplements, vitamin B-12 shots, calcium supplement, and vitamin D supplement to the subject classified as Type I based on the classification of the subject as determined in step c).

2. The method of claim 1, wherein the cell is a Paneth cell.

3. The method of claim 1, wherein the HD5 protein is detected using immunofluorescence.

4. The method of claim 1, wherein the HD5 protein is detected with an autostainer.

5. The method of claim 1, wherein the biological sample is a tissue biopsy.

6. The method of claim 1, wherein:
   a) disordered is abnormal distribution and size of the HD5 granules;
   b) diminished is less than or equal to ten HD5 granules;
   c) diffuse is a smear of HD5 within the cytoplasm with no recognizable granules;
   d) excluded is the majority of HD5 granules do not contain stainable material; and
   e) enlarged is HD5 megagranules.

7. The method of claim 1, wherein the method further comprises detecting a nuclear pore protein in the biological sample.

* * * * *

SEQUENCE LISTING

<160> NUMBER OF SEQ ID NOS: 3

<210> SEQ ID NO 1
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 1

Gly Thr Gly Cys Cys Ala Gly Cys Met Gly Cys Cys Gly Cys Gly Gly
1               5                   10                  15

Thr Ala Ala

<210> SEQ ID NO 2
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 2

Gly Gly Ala Cys Thr Ala Cys His Val Gly Gly Gly Thr Trp Thr Cys
1               5                   10                  15

Thr Ala Ala Thr
            20

<210> SEQ ID NO 3
<211> LENGTH: 32

```
<212> TYPE: PRT
<213> ORGANISM: Homo sapiens

<400> SEQUENCE: 3

Ala Thr Cys Tyr Cys Arg His Gly Arg Cys Ala Thr Arg Glu Ser Leu
1               5                   10                  15

Ser Gly Val Cys Glu Ile Ser Gly Arg Leu Tyr Arg Leu Cys Cys Arg
            20                  25                  30
```